US012758610B2

(12) United States Patent
Khaled et al.

(10) Patent No.: US 12,758,610 B2
(45) **Date of Patent: *Oct. 13, 2026**

(54) METHODS AND COMPOSITIONS COMPRISING A CT20 PEPTIDE

(71) Applicant: UNIVERSITY OF CENTRAL FLORIDA RESEARCH FOUNDATION, INC., Orlando, FL (US)

(72) Inventors: Annette Khaled, Orlando, FL (US); Jesus Manuel Perez, Orlando, FL (US); Rania Bassiouni, Orlando, FL (US); Amanda Cox, Orlando, FL (US); Ana Martini, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 1115 days.

This patent is subject to a terminal disclaimer.

(21) Appl. No.: 17/687,635

(22) Filed: Mar. 5, 2022

(65) Prior Publication Data

US 2023/0035748 A1 Feb. 2, 2023

Related U.S. Application Data

(60) Continuation-in-part of application No. 17/486,432, filed on Sep. 27, 2021, now Pat. No. 12,178,840, which is a division of application No. 15/327,353, filed as application No. PCT/US2015/039806 on Jul. 9, 2015, now Pat. No. 11,129,868.

(60) Provisional application No. 62/026,564, filed on Jul. 18, 2014.

(51) Int. Cl.

*A61K 38/10* (2006.01)
*A61K 9/14* (2006.01)
*A61K 38/08* (2019.01)
*C12Q 1/02* (2006.01)

(52) U.S. Cl.

CPC ................ *A61K 38/10* (2013.01); *A61K 9/14* (2013.01); *A61K 38/08* (2013.01); *C12Q 1/025* (2013.01); *A61K 2121/00* (2013.01)

(58) Field of Classification Search

None

See application file for complete search history.

(56) References Cited

U.S. PATENT DOCUMENTS

| | | | | |
|---|---|---|---|---|
| 9,040,662 | B2 | 5/2015 | Khaled | |
| 11,129,868 | B2 * | 9/2021 | Khaled | C12Q 1/025 |
| 12,178,840 | B2 * | 12/2024 | Khaled | A61P 35/00 |
| 2002/0052316 | A1 * | 5/2002 | Shore | A61P 35/00 514/18.9 |
| 2003/0096367 | A1 | 5/2003 | Korsmeyer | |
| 2004/0191843 | A1 | 9/2004 | Wright et al. | |
| 2010/0099742 | A1 | 4/2010 | Stassi et al. | |
| 2011/0286919 | A1 | 11/2011 | Joshi et al. | |
| 2014/0178300 | A1 | 6/2014 | Pomper et al. | |
| 2014/0248210 | A1 | 9/2014 | Bradbury et al. | |
| 2014/0255299 | A1 | 9/2014 | Khaled et al. | |
| 2014/0349344 | A1 * | 11/2014 | Khaled | C07K 14/4747 435/320.1 |
| 2015/0004103 | A1 | 1/2015 | Csik et al. | |
| 2015/0104387 | A1 | 4/2015 | Ray et al. | |

FOREIGN PATENT DOCUMENTS

| | | | |
|---|---|---|---|
| EP | 15821541.8 | A1 | 5/2017 |
| WO | 2011103567 | A2 | 8/2011 |
| WO | 2013029011 | | 2/2013 |
| WO | 2013086430 | | 6/2013 |
| WO | 2016010826 | A1 | 1/2016 |

OTHER PUBLICATIONS

Lee, et al. The CT20 peptide causes detachment and death of metastatic breast cancer cells by promoting mitochondrial aggregation and cytoskeletal disruption. Cell Death Dis. May 22, 2014, 5:e1249.*

Vishnubhotla, et al. Chaperonin-containing T Complex (CCT) is a novel target for treatment of metastatic breast cancer. J Clin Oncol Jun. 2015, 33(suppl): abstr e13530 [the date is according to the posted 2015 ASCO Annual Meeting program web page [Retrieved from the Internet Aug. 27, 2015: ].*

Garg, Biophysical Characterization of the Membrane Binding Domain of the Pro-apoptotic Protein Bax, Summer Term 2011, pp. 1-78.

Carr, A.C. et al., Abstract 4895: CT20P as a Therapeutic for Lung Cancer with Elevated Chaperoning Containing TCP1 (CCT) Expression Levels, Cancer Research, 2017, p. 4895, 77 (13_Supplement).

Vishnubhotla, P. et al., CT20P as a Therapeutic for Lung Cancer with Elevated Chaperonin Containing TCP1 (CCT) Expression Levels, Journal of Clinical Oncology, 2017, 35 (15_suppl).

Carr, A.C. et al., Targeting Chaperonin Containing TCP1 (CCT) as a Molecular Therapeutic for Small Cell Lung Cancer, Oncotarget, 2017, p. 110273-110288, 8 (66).

EPO, Summons to attend oral proceedings in application EP15821541.8, Jul. 27, 2023.

New Zealand IPO, Examination Report in application 729191, Aug. 1, 2023.

Office Action issued in Canadian Application No. 2,962,062, mailed Jan. 30, 2024.

Antonsson, B., et al. "Bax is present as a high molecular weight oligomer/complex in the mitochondrial membrane of apoptotic-cells." J. Biol. Chem., vol. 276, pp. 11615-11623 (2001).

Ausili, A., et al. "The interaction of the bax c-terminal domain with negatively charged lipids modifies the secondary structure and changes its way of insertion into membranes." J. Struct. Biol., vol. 164, 146-152 (2008).

(Continued)

*Primary Examiner* — Maury A Audet

(74) *Attorney, Agent, or Firm* — Meunier Carlin & Curfman LLC

(57) ABSTRACT

Disclosed herein are compositions comprising a CT20 peptide and methods of using the disclosed compositions to treat cancers expressing chaperonin containing TCP (CCT).

18 Claims, 73 Drawing Sheets

Specification includes a Sequence Listing.

(56) References Cited

OTHER PUBLICATIONS

Barash, S., et al. "Human secretory signal peptide description by hidden markov model and generation of a strong 3 artificial signal peptide for secreted protein expression." Biochem. Biophys. Res. Commun., vol. 463, pp. 835-842 D (2002).
Basanez, G., et al. "Bax-type apoptotic proteins porate pure lipid bilayers through a mechanism sensitive to intrinsic monolayer curvature—" J. Biol. Chem., vol. 277, pp. 49360-49365 (2002).
Boohaker, R.J., et al. "Bax supports the mitochondrial network, promoting bioenergetics in nonapoptotic cells." Am. J. Physiol. Cell Physiol., vol. 300, pp. C1466-C1478 (2011).
Bovine serum albumin, from http://www.ncbi.nlm.nih.gov/protein/CAA76847.1, pp. 1-2, accessed May 5, 2016.
Brustovetsky, T., et al. "Bax insertion, oligomerization, and outer membrane permeabilization in brain mitochondria: role of permeability transition and SH-redox regulation—" Biochem. Biophys. Acta., vol. 1797, pp. 1795-1806 (2010).
Cartron, P.F., et al. "The first alpha helix of bax plays a necessary role in its ligand-induced activation by the BH3-only proteins bid and puma—" Mal. Cell, vol. 16(5), pp. 807-818 {2004).
Cartron, P.F., et al. "Distinct domains control the addressing and the insertion of bax into mitochondria." J. Biol. Chem., vol. 280, pp. 10587-10598 (2005).
Cartron, P.F., et al. "The expression of a new variant of the pro-apoptotic molecule bax, baxpsi, is correlated with an increased survival of glioblastoma multiforme patients—" Hum. Mal. Genet., vol. 11, pp. 675-687 (2002).
Cartron, P.F., et al. "Then-terminal end of bax contains a mitochondrial-targeting signal." J. Biol. Chem., vol. 278, pp. 11633-11641 (2003).
Deng, J., et al. "BH3 profiling identifies three distinct classes of apoptotic blocks to predict response to ABT-737 and conventional chemotherapeutic agents—" Cancer Cell, vol. 12, pp. 171-185 (2007).
Er, E., et al. "Control of bax homodimerization by its carboxyl terminus." J. Biol. Chem., vol. 282, pp. 24938-24947 (2007).
Eskes, R. , et al. "Bax-induced cytochrome c release from mitochondria is independent of the permeability transition pore but highly dependent on mg2+ ions—" J. Cell Biol., vol. 143, pp. 217-224 { 1998).
Garcia-Saez, A.J., et al. "Membrane-insertion fragments of bcl-xl, bax, and bid." Biochemistry, vol. 43, pp. 10930-10943 (2004).
Garcia-Saez, A.J., et al. "Peptides corresponding to helices 5 and 6 of bax can independently form large lipid pores." FEBS J., vol. 273, pp. 971-981 (2006).
Garcia-Saez, A.J., et al. "Peptides derived from apoptotic bax and bid reproduce the poration activity of the parent full-length proteins—" Biophys. J., vol. 88, pp. 3976-3990 (2005).
Garcia-Saez, A.J., et al. "Permeabilization of the outer mitochondrial membrane by bcl-2 proteins." Adv. Exp. Med. Biol., vol. 677, pp. 91-105 (2010).
Gavathiotis, E., et al. "Bax activation is initiated at a novel interaction site." Nature, vol. 455(7216), pp. 1076-10B1 (2008).
Geisse, S., et al. "Recombinant protein production by transient gene transfer into mammalian cells." Methods Enzymol., vol. 463, pp. 223-238 (2009).
George, N.M., et al. "Bax contains two functional mitochondrial targeting sequences and translocates to mitochondria in a conformational change- and homo-oligomerization-driven process—" J. Biol. Chem., vol. 2B5, pp. 13B4 (2010).
Ghibelli, L., et al. "Multistep and multitask bax activation." Mitochondrion, vol. 10, pp. 604-613 (2010).
Han, S-X, et al. "Secretory transactivating transcription-apoptin fusion protein induces apoptosis in hepatocellular carcinoma hepg2 cells—" World Journal of Gastroenterology, vol. 14(23), pp. 3642-3649 (2008).
Horie, C., et al. "Characterization of signal that directs c-tail-anchored proteins to mammalian mitochondrial outer membrane—" Mol. Biol. Cell, vol. 13.pp. 1615-1625 (2002).
International Search Report and Written Opinion issued in related International Application No. PCT/US2015/039806 on Dec. 4, 2015.
Jiang et al, Synthesis and Characterization of an Amphiphilic Hyperbranched Poly(amine-Ester)-co-D,L-lactide (HPAE-co-PLA) Copolymers and Their Nanoparticles for Protein Drug Delivery, Journal of Applied Polymer Science, 2010, 117, pp. 1156-1167.
Kaufmann, T., et al. "Characterization of the signal that directs bcl-x(I), but not bcl-2, to the mitochondrial outer membrane—" J. Cell Biol., vol. 160, pp. 53-64 (2003).
Kelekar, A., et al. "Bcl-2-family proteins: the role of the bh3 domain in apoptosis." Trends Cell Biol., vol. 8(8), pp. 324-330 (1998).
Krauson et al, Determining the mechanism of membrane permeabilizing peptides: Identification of potent, equilibrium poreformers, Biochimica et Biophysica Acta, 2012, pp. 1625-1632.
Leber, B., et al. "Embedded together: the life and death consequences of interaction of the bcl-2 family with membranes—" Apoptosis, vol. 12, pp. 897-911 {2007).
Lee et al, The CT20 peptide causes detachment and death of metastatic breast cancer cells by promoting mitochondrial aggregating and cytoskeletal disruption, Cell Death Dis, May 22, 2014, 5:e1249, p. 6, col. 2; p. 7, col. 1; p. 10, col. 2.
Li et al, Interaction of procyanidin 83 with bovine serum albumin, RSC Adv., 2014, 4, pp. 7301-7312.
Lu et al, Alkaloids Isolated from Natural Herbs as the Anticancer Agents, Evidence-Based Complementary and Alternative Medicine, 2012, pp. 1-12.
Del Martinez-Senac, M., et al. "Conformation of the c-terminal domain of the pro-apoptotic protein bax and mutants and its interaction with membranes—" Biochemistry, vol. 40, pp. 9983-9992 {2001).
Nechushtan, A., et al. "Conformation of the bax c-terminus regulates subcellular location and cell death." EMBO J., vol. 18, pp. 2330-2341 (1999).
Oltersdorf, T., et al. "An inhibitor of bcl-2 family proteins induces regression of solid tumours." Nature, vol. 435, pp. 677-681 {2005).
Oltvai, Z.N., et al. "Bcl-2 heterodimerizes in vivo with a conserved homolog, bax, that accelerates programmed cell death—" Cell, vol. 74, pp. 609-619 {1993).
Putcha, G.V., et al. "Bax translocation is a critical event in neuronal apoptosis: regulation by neuroprotectants, BCL-2, and caspases—" J. Neurosci., vol. 19, pp. 7476-7485 {1999).
Robertson, J.D., et al. "Outer mitochondrial membrane permeabilization: an open-and-shut case?" Cell Death Differ., vol. 10, pp. 485-487 (2003).
Roucou, X., et al. "Bax oligomerization in mitochondrial membranes requires tbid {caspase-8-cleaved bid) and a mitochondrial protein—" Biochem. J., vol. 368, pp. 915-921 (2002).
Santra, S., et al. "Aliphatic hyperbranched polyester: a new building block in the construction of multifunctional nanoparticles and nanocomposites—" Langmuir, vol. 26, pp. 5364 (2010).
Schinzel, A., et al. "Conformational control of bax localization and apoptotic activity by pro168." J. Cell Biol., vol. 164, pp. 1021-1032 (2004).
Schlesinger, P.H., et al. "The bax pore in liposomes." Biophysics, Cell Death Differ., vol. 13, pp. 1403-1408 (2006).
Singh et al, Nanoparticle-based targeted drug delivery, Experimental and Molecular Pathology, 2009, 86, pp. 215-223.
Suzuki, M., et al. "Structure of bax: coregulation of dimer formation and intracellular localization." cell, vol. 103, pp. 645-654 {2000).
Tait, S.W., et al. "Mitochondria and cell death: outer membrane permeabilization and beyond." Nat. Rev. Mol. Cell. Biol., vol. 11, pp. 621-632 {2010).
Valero, J.G., et al. "Bax-derived membrane-active peptides act as potent and direct inducers of apoptosis in cancer cells—" J. Cell Sci., vol. 124, pp. 556-564 (2011).
Vishnubhotla et al., Chaperonin-containing T Complex (CCT) is a novel target for treatment of metastatic breast cancer, J Clin Oncol, Abstract, Jun. 2015.
Water, from http://www.biology-online.org/dictionary/Water, pp. 1-3, accessed Apr. 24, 2014.

(56) References Cited

OTHER PUBLICATIONS

Westphal, D., et al. "Molecular biology of bax and bak activation and action." Biochim. Biophys. Acta, vol. 1813, pp. 521-531 {2011).
Wolter, K.G., et al. "Movement of bax from the cytosol to mitochondria during apoptosis." J. Cell Biol., vol. 139, pp. 1281-1292 (1997).
Youle, R.J., et al. "The bcl-2 protein family: opposing activities that mediate cell death." Nat. Rev. Mol. Cell. Biol., vol. 9, pp. 47-59 (2008).
Zhang, L., et al. "Role of bax in the apoptotic response to anticancer agents." Science, vol. 290, pp. 989 (2000).
Zhou, L., et al. "Dynamics and structure of the bax-bak complex responsible for releasing mitochondrial proteins during apoptosis—" J. Cell Sci., vol. 121, pp. 2186-2196 (2008).
Extended European Search Report issued in European Application No. 15821541.8, mailed Feb. 23, 2018.
Summary of Office Action issued in related application IL250209, mailed Aug. 4, 2019.
First Examination Report issued in Australian Application No. 2015290058 dated Mar. 6, 2020, 4 pages.
Boohaker et al, Development of a cytotoxic peptide based on the C-terminal domain of Bax, Abstract for the 103rd Annual Meeting of the American Association for Cancer Research held on Mar. 31-Apr. 4, 2012, pp. 1-2.
Tschammer, Helical Packing Regulates Structural Transitions in Bax, 2007, pp. 1-136.
Emi et al, Targeted therapy against Bcl-2-related proteins in breast cancer cells, Breast Cancer Research, 2005, 7, pp. R940-R952.
Mierzwa et al, Recent Advances in Combined Modality Therapy, The Oncologist, 2010, 15, pp. 372-381.
Cohen, Optimization of Dose-Time Factors for a Tumor and Multiple Associated Normal Tissues, Int. J. Radiat. Oneal. Biol. Phys., 1987, 13, pp. 251-258.
Office Action issued for U.S. Appl. No. 16/224,004, dated Jun. 8, 2020.
Office Action issued for Canadian Application No. 2962062, dated Jul. 30, 2021.
Office Action issued for Canadian Application No. 2962062, dated Jul. 28, 2022.
Office Action issued for Australian Application No. 2021204560, dated Jul. 30, 2022.
Blanco et al, "Targeted Nanoparticles for Cancer Therapy, Recent Advances in Novel Drug Carrier Systems", Oct. 31, 2012, Ali Demir Sezer, IntechOpen, DOI: 10.5772/51382. <URL: https://www.intechopen.com/books/recent-advances-in-novel-drug-carrier-systems/targeted-nanoparticles-for-cancer-therapy> Last retrieved Feb. 3, 2021.
Abd El-Rehim DM, Pinder SE, Paish CE, Bell J, Blamey R, Robertson JF, Nicholson RI, Ellis IO (2004) Expression of luminal and basal cytokeratins in human breast carcinoma. The Journal of Pathology: A Journal of the Pathological Society of Great Britain and Ireland 203 (2):661-671.
Albakova Z, Siam MKS, Sacitharan PK, Ziganshin RH, Ryazantsev DY, Sapozhnikov AM (2021) Extracellular heat shock proteins and cancer: New perspectives. Translational Oncology 14 (2):100995.
Alix-Panabières C, Pantel K (2016) Clinical Applications of Circulating Tumor Cells and Circulating Tumor DNA as Liquid Biopsy. Cancer Discovery 6 (5):479-491. doi:10.1158/2159-8290.cd-15-1483.
Bassiouni R, Nemec KN, Iketani A, Flores O, Showalter A, Khaled AS, Vishnubhotla P, Sprung RW, Kaittanis C, Perez JM, Khaled AR (2016) Chaperonin Containing TCP-1 Protein Level in Breast Cancer Cells Predicts Therapeutic Application of a Cytotoxic Peptide. 22 (17):4366-4379. doi:10.1158/1078-0432.ccr-15-2502.
Breuninger S, Stangl S, Werner C, Sievert W, Lobinger D, Foulds GA, Wagner S, Pickhard A, Piontek G, Kokowski K, Pockley AG, Multhoff G (2018) Membrane Hsp70—A Novel Target for the Isolation of Circulating Tumor Cells After Epithelial-to-Mesenchymal Transition. Frontiers in oncology 8:497. doi:10.3389/fonc.2018.00497.
Camasses A, Bogdanova A, Shevchenko A, Zachariae W (2003) The CCT Chaperonin Promotes Activation of the Anaphase-Promoting Complex through the Generation of Functional Cdc20. Molecular Cell 12 (1):87-100. doi:https://doi.org/10.1016/S1097-2765(03)00244-2.
Carr AC, Khaled AS, Bassiouni R, Flores O, Nierenberg D, Bhatti H, Vishnubhotla P, Perez JM, Santra S, Khaled AR (2017) Targeting chaperonin containing TCP1 (CCT) as a molecular therapeutic for small cell lung cancer. Oncotarget 8 (66). doi:10.18632/oncotarget.22681.
Chang Y-X, Lin Y-F, Chen C-L, Huang M-S, Hsiao M, Liang P-H (2020) Chaperonin-Containing TCP-1 Promotes Cancer Chemoresistance and Metastasis through the AKT-GSK3β-β-Catenin and XIAP-Survivin Pathways. Cancers 12 (12):3865.
Chi KN, Fleming MT, Sunderland K, Albany C, Gingerich J, Saad F, North SA, Starodub A, Lauer RC, Ruether JD, Sgroi MM, Scholz MC, Sweeney C (2017) Pacific trial: A randomized phase II study of apatorsen and abiraterone in patients (Pts) with metastatic castration-resistant prostate cancer (mCRPC) who have had PSA progression while receiving abiraterone (ABI). Journal of Clinical Oncology 35 (6_suppl):146-146. doi:10.1200/JCO.2017.35.6_suppl.146.
Ciocca DR, Calderwood SK (2005) Heat shock proteins in cancer: diagnostic, prognostic, predictive, and treatment implications. Cell stress & chaperones 10 (2):86.
Cohen SJ, Punt CJA, Iannotti N, Saidman BH, Sabbath KD, Gabrail NY, Picus J, Morse M, Mitchell E, Miller MC, Doyle GV, Tissing H, Terstappen LWMM, Meropol NJ (2008) Relationship of Circulating Tumor Cells to Tumor Response, Progression-Free Survival, and Overall Survival in Patients With Metastatic Colorectal Cancer. Journal of Clinical Oncology 26 (19):3213-3221. doi:10.1200/jco.2007.15.8923.
Coyne GOS, Monge C, Chen AP (2019) Role of HSP90 Inhibitors in the Treatment of Cancer. Heat Shock Protein 90 in Human Diseases and Disorders:125-143.
De Bono JS, Scher HI, Montgomery RB, Parker C, Miller MC, Tissing H, Doyle GV, Terstappen LWWM, Pienta KJ, Raghavan D (2008) Circulating Tumor Cells Predict Survival Benefit from Treatment in Metastatic Castration-Resistant Prostate Cancer. Clinical Cancer Research 14 (19):6302-6309. doi:10.1158/1078-0432.ccr-08-0872.
De Wit S, Manicone M, Rossi E, Lampignano R, Yang L, Zill B, Rengel-Puertas A, Ouhlen M, Crespo M, Berghuis AMS (2018a) EpCAMhigh and EpCAMlow circulating tumor cells in metastatic prostate and breast cancer patients. Oncotarget 9 (86):35705.
De Wit S, Van Dalum G, Lenferink AT, Tibbe AG, Hiltermann TJN, Groen HJ, Van Rijn CJ, Terstappen LW (2015) The detection of EpCAM+ and EpCAM-circulating tumor cells. Scientific Reports 5 (1):1-10.
De Wit S, Zeune LL, Hiltermann TJN, Groen HJM, Dalum GV, Terstappen L (2018b) Classification of Cells in CTC-Enriched Samples by Advanced Image Analysis. Cancers (Basel) 10 (10). doi:10.3390/cancers10100377.
Dietz MS, Sutton TL, Walker BS, Gast CE, Zarour L, Sengupta SK, Swain JR, Eng J, Parappilly M, Limbach K (2021) Relevance of Circulating Hybrid Cells as a Non-Invasive Biomarker for Myriad Solid Tumors. bioRxiv.
Eisenhauer EA, Therasse P, Bogaerts J, Schwartz LH, Sargent D, Ford R, Dancey J, Arbuck S, Gwyther S, Mooney M (2009) New response evaluation criteria in solid tumours: revised RECIST guideline (version 1.1). European journal of cancer 45 (2):228-247.
Flores O, Santra S, Kaittanis C, Bassiouni R, Khaled AS, Khaled AR, Grimm J, Perez JM (2017) PSMA-Targeted Theranostic Nanocarrier for Prostate Cancer. Theranostics 7 (9):2477-2494. doi:10.7150/thno.18879.
Ghozlan H, Showalter A, Lee E, Zhu X, Khaled AR (2021) Chaperonin-Containing TCP1 Complex (CCT) Promotes Breast Cancer Growth Through Correlations With Key Cell Cycle Regulators. Frontiers in Oncology 11 (1264). doi:10.3389/fonc.2021.663877.

(56) References Cited

OTHER PUBLICATIONS

Goldman M, Craft B, Hastie M, Repečka K, McDade F, Kamath A, Banerjee A, Luo Y, Rogers D, Brooks AN, Zhu J, Haussler D (2019) The UCSC Xena platform for public and private cancer genomics data visualization and interpretation. bioRxiv:326470. doi:10.1101/326470.
Gomez CR (2021) Role of heat shock proteins in aging and chronic inflammatory diseases. GeroScience. doi:10.1007/s11357-021-00394-2.
Guest ST, Kratche ZR, Bollig-Fischer A, Haddad R, Ethier SP (2015) Two members of the TRIC chaperonin complex, CCT2 and TCP1 are essential for survival of breast cancer cells and are linked to driving oncogenes. Experimental Cell Research 332 (2):223-235. doi:10.1016/j.yexcr.2015.02.005.
Hayes DF (2006) Circulating Tumor Cells at Each Follow-up Time Point during Therapy of Metastatic Breast Cancer Patients Predict Progression-Free and Overall Survival. Clinical Cancer Research 12 (14):4218-4224. doi:10.1158/1078-0432.ccr-05-2821.
Ilie M, Hofman V, Long-Mira E, Selva E, Vignaud J-M, Padovani B, Mouroux J, Marquette C-H, Hofman P (2014) "Sentinel" circulating tumor cells allow early diagnosis of lung cancer in patients with chronic obstructive pulmonary disease. PloS one 9 (10):e111597.
Jego G, Hazoumé A, Seigneuric R, Garrido C (2013) Targeting heat shock proteins in cancer. Cancer letters 332 (2):275-285.
Kasembeli M, Lau WCY, Roh S-H, Eckols TK, Frydman J, Chiu W, Tweardy DJ (2014) Modulation of STAT3 Folding and Function by TRiC/CCT Chaperonin. PLoS Biology 12 (4):e1001844. doi:10.1371/journal.pbio.1001844.
Khalil AA, Kabapy NF, Deraz SF, Smith C (2011) Heat shock proteins in oncology: diagnostic biomarkers or therapeutic targets? Biochimica et Biophysica Acta (BBA)—Reviews on Cancer 1816 (2):89-104.
Ko AH, Murphy PB, Peyton JD, Shipley D, Al-Hazzouri A, Rodriguez FA, Womack MS, Xiong HQ, Waterhouse DM, Tempero MA, Bendell JC (2016) RAINIER: A randomized, double-blinded, placebo-controlled phase II trial of gemcitabine (gem) plus nab-paclitaxel (nab-P) combined with apatorsen (A) or placebo (P1) in patients (pts) with metastatic pancreatic cancer (mPC). Journal of Clinical Oncology 34 (4_suppl):419-419. doi:10.1200/jco.2016.34.4_suppl.419.
Korsching E, Packeisen J, Agelopoulos K, Eisenacher M, Voss R, Isola J, Van Diest PJ, Brandt B, Boecker W, Buerger H (2002) Cytogenetic alterations and cytokeratin expression patterns in breast cancer: integrating a new model of breast differentiation into cytogenetic pathways of breast carcinogenesis. Laboratory investigation 82 (11):1525-1533.
Leitner A, Joachimiak LA, Bracher A, Mönkemeyer L, Walzthoeni T, Chen B, Pechmann S, Holmes S, Cong Y, Ma B, Ludtke S, Chiu W, Hartl FU, Aebersold R, Frydman J (2012) The molecular architecture of the eukaryotic chaperonin TRiC/CCT. Structure 20 (5):814-825. doi:10.1016/j.str.2012.03.007.
Lindsay CR, Le Moulec S, Billiot F, Loriot Y, Ngo-Camus M, Vielh P, Fizazi K, Massard C, Farace F (2016) Vimentin and Ki67 expression in circulating tumour cells derived from castrate-resistant prostate cancer. BMC Cancer 16 (1):168. doi:10.1186/s12885-016-2192-6.
Liu D, Wang Z, Korantzopoulos P, Liu T (2020a) Heat Shock Proteins in Atrial Fibrillation. 2021, 141-150.
Liu Q, Qi Y, Wang X, Kong X, Fang Y, Wang J (2020b) Molecular and clinical characterization of CCT2 expression at transcriptional level via 2994 samples of breast cancer.
Liu Y-J, Chang Y-J, Kuo Y-T, Liang P-H (2020c) Targeting β-tubulin/CCT-β complex induces apoptosis and suppresses migration and invasion of highly metastatic lung adenocarcinoma. Carcinogenesis 41 (5):699-710.
Lowes LE, Hedley BD, Keeney M, Allan AL (2012) User-defined protein marker assay development for characterization of circulating tumor cells using the CellSearch® system. Cytometry Part A 81A (11):983-995. doi:10.1002/cyto.a.22158.
Lowes LE, Hedley BD, Keeney M, Allan AL (2014) Adaptation of semiautomated circulating tumor cell (CTC) assays for clinical and preclinical research applications. Journal of visualized experiments : JoVE (84):e51248. doi:10.3791/51248.
Mantej J, Polasik K, Piotrowska E, Tukaj S (2019) Autoantibodies to heat shock proteins 60, 70, and 90 in patients with rheumatoid arthritis. Cell Stress and Chaperones 24 (1):283-287.
Meng S (2004) Circulating Tumor Cells in Patients with Breast Cancer Dormancy. Clinical Cancer Research 10 (24):8152-8162. doi:10.1158/1078-0432.ccr-04-1110.
Narayanan A, Pullepu D, Kabir MA (2016) The interactome of CCT complex—A computational analysis. Comput Biol Chem 64:396-402. doi:10.1016/j.compbiolchem.2016.09.002.
Patteson AE, Vahabikashi A, Goldman RD, Janmey PA (2020) Mechanical and Non-Mechanical Functions of Filamentous and Non-Filamentous Vimentin. Bioessays 42 (11):2000078.
Rakha EA, El-Sayed ME, Green AR, Paish EC, Lee AH, Ellis IO (2007) Breast carcinoma with basal differentiation: a proposal for pathology definition based on basal cytokeratin expression. Histopathology 50 (4):434-438. doi:10.1111/j.1365-2559.2007.02638.x.
Riethdorf S, Fritsche H, Müller V, Rau T, Schindlbeck C, Rack B, Janni W, Coith C, Beck K, Jänicke F (2007) Detection of circulating tumor cells in peripheral blood of patients with metastatic breast cancer: a validation study of the CellSearch system. Clinical cancer research 13 (3):920-928.
Rink M, Chun FK, Dahlem R, Soave A, Minner S, Hansen J, Stoupiec M, Coith C, Kluth LA, Ahyai SA (2012) Prognostic role and HER2 expression of circulating tumor cells in peripheral blood of patients prior to radical cystectomy: a prospective study. European urology 61 (4):810-817.
Roh S-H, Kasembeli M, Bakthavatsalam D, Chiu W, Tweardy D (2015) Contribution of the Type II Chaperonin, TRiC/CCT, to Oncogenesis. International Journal of Molecular Sciences 16 (11):26706-26720. doi:10.3390/ijms161125975.
Romi F, Helgeland G, Gilhus NE (2011) Heat-shock proteins in clinical neurology. European neurology 66 (2):65-69.
Satelli A, Batth I, Brownlee Z, Mitra A, Zhou S, Noh H, Rojas CR, Li H, Meng QH, Li S (2017) EMT circulating tumor cells detected by cell-surface vimentin are associated with prostate cancer progression. Oncotarget 8 (30):49329.
Satelli A, Li S (2011) Vimentin in cancer and its potential as a molecular target for cancer therapy. Cellular and molecular life sciences 68 (18):3033-3046.
Shipley D, Waterhouse DM, Jones SF, Stults DM, Ward PJ, Shih KC, Hemphill MB, McCleod M, Whorf RC, Page RD, Stilwell J, Mekhail T, Anderson K, Jacobs C, Hainsworth JD, Spigel DR (2016) The Spruce clinical trial: Double-blind randomized phase II trial of carboplatin and pemetrexed +/- apatorsen in patients with previously untreated stage IV non-squamous non-small-cell lung cancer. Journal of Clinical Oncology 34 (15_suppl):9092-9092. doi:10.1200/JCO.2016.34.15_suppl.9092.
Showalter AE, Martini AC, Nierenberg D, Hosang K, Fahmi NA, Gopalan P, Khaled AS, Zhang W, Khaled AR (2020) Investigating Chaperonin-Containing TCP-1 subunit 2 as an essential component of the chaperonin complex for tumorigenesis. Scientific Reports 10 (1):1-14.
Solimini NL, Luo J, Elledge SJ (2007) Non-oncogene addiction and the stress phenotype of cancer cells. Cell 130 (6):986-988. doi:10.1016/j.cell.2007.09.007.
Swennenhuis JF, van Dalum G, Zeune LL, Terstappen LWMM (2016) Improving the CellSearch® system. Expert review of molecular diagnostics 16 (12):1291-1305.
Veridex I (2008) Guideline for the Use and Optimization of User Defined Markers: CellSearch® Epithelial Cell Kit and CellSearch® CXC Kit Life Science Research Application Note www.cellsearchruo.com/sites/default/files/Guideline-for-Use-and-Optimization-of-User-Defined-Markers.pdf.
Wax MB, Tezel G, Kawase K, Kitazawa Y (2001) Serum autoantibodies to heat shock proteins in glaucoma patients from Japan and the United States. Ophthalmology 108 (2):296-302.
Won K-A, Schumacher RJ, Farr GW, Horwich AL, Reed SI (1998) Maturation of Human Cyclin E Requires the Function of Eukaryotic

(56) References Cited

OTHER PUBLICATIONS

Chaperonin CCT. Molecular and Cellular Biology 18 (12):7584-7589. doi:10.1128/mcb.18.12.7584.
Wu J, Chen S, Liu Y, Liu Z, Wang D, Cheng Y (2020) Therapeutic perspectives of heat shock proteins and their protein-protein interactions in myocardial infarction. Pharmacological Research 160:105162. doi:https://doi.org/10.1016/j.phrs.2020.105162.
Xiang Y, Zhang L, Huang Y, Ling J, Zhuo W (2019) Microarray-based data mining reveals key genes and potential therapeutic drugs for Cadmium-induced prostate cell malignant transformation. Environmental toxicology and pharmacology 68:141-147.
Xu H, Niu M, Yuan X, Wu K, Liu A (2020) CD44 as a tumor biomarker and therapeutic target. Experimental Hematology & Oncology 9 (1):36. doi:10.1186/s40164-020-00192-0.
Yokota S-I, Yamamoto Y, Shimizu K, Momoi H, Kamikawa T, Yamaoka Y, Yanagi H, Yura T, Kubota H (2001) Increased expression of cytosolic chaperonin CCT in human hepatocellular and colonic carcinoma. 6 (4):345. doi:10.1379/1466-1268(2001)006<0345:ieoccc>2.0.co;2.
Yuno A, Lee M-J, Lee S, Tomita Y, Rekhtman D, Moore B, Trepel JB (2018) Clinical evaluation and biomarker profiling of Hsp90 inhibitors. Chaperones:423-441.
Zeune L (2019) Automated CTC Classification, Enumeration and Phenotyping: where math meets biology. doi:10.3990/1.9789036547130.
Zeune L, Van Dalum G, Decraene C, Proudhon C, Fehm T, Neubauer H, Rack B, Alunni-Fabbroni M, Terstappen LWMM, Van Gils SA, Brune C (2017) Quantifying HER-2 expression on circulating tumor cells by ACCEPT. PLOS One 12 (10):e0186562. doi:10.1371/journal.pone.0186562.
Zhang Z, Ramnath N, Nagrath S (2015) Current Status of CTCs as Liquid Biopsy in Lung Cancer and Future Directions. Frontiers in oncology 5:209. doi:10.3389/fonc.2015.00209.
Zou Q, Yang Z-l, Yuan Y, Li J-h, Liang L-f, Zeng G-x, Chen S-l (2013) Clinicopathological features and CCT2 and PDIA2 expression in gallbladder squamous/adenosquamous carcinoma and gallbladder adenocarcinoma. World Journal of Surgical Oncology 11 (1):143. doi:10.1186/1477-7819-11-143.

* cited by examiner

| | CCT | Pull-down probe |
|---|---|---|
| 1- | 0.1 nmol | ---- |
| 2- | 0.1 nmol | Biotin |
| 3- | 0.1 nmol | 0.1 nmol CT20-Biotin |
| 4- | 0.1 nmol | 1 nmol CT20-Biotin |
| 5- | 0.1 nmol | 4 nmol CT20-Biotin |

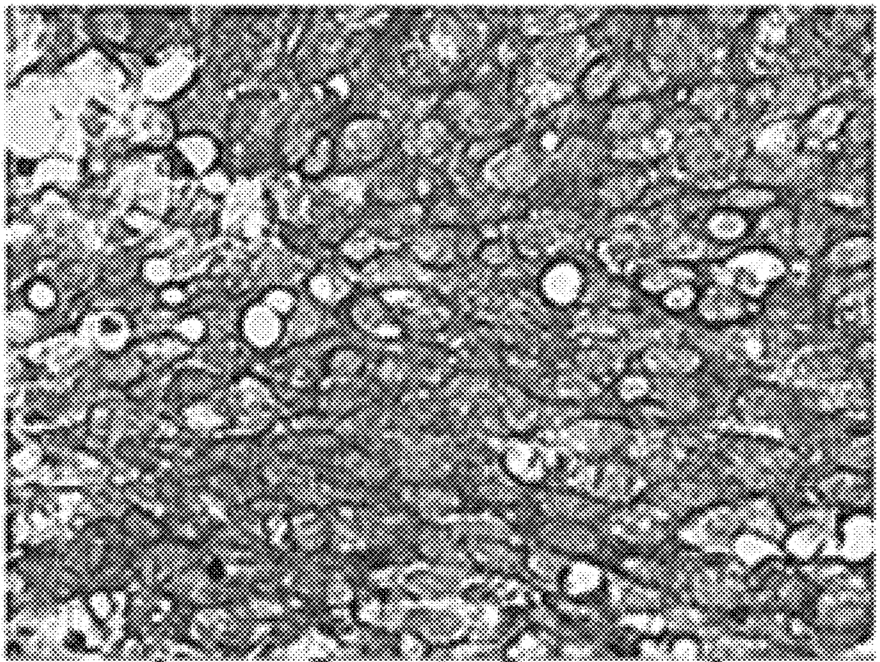
Invasive ductal carcinoma
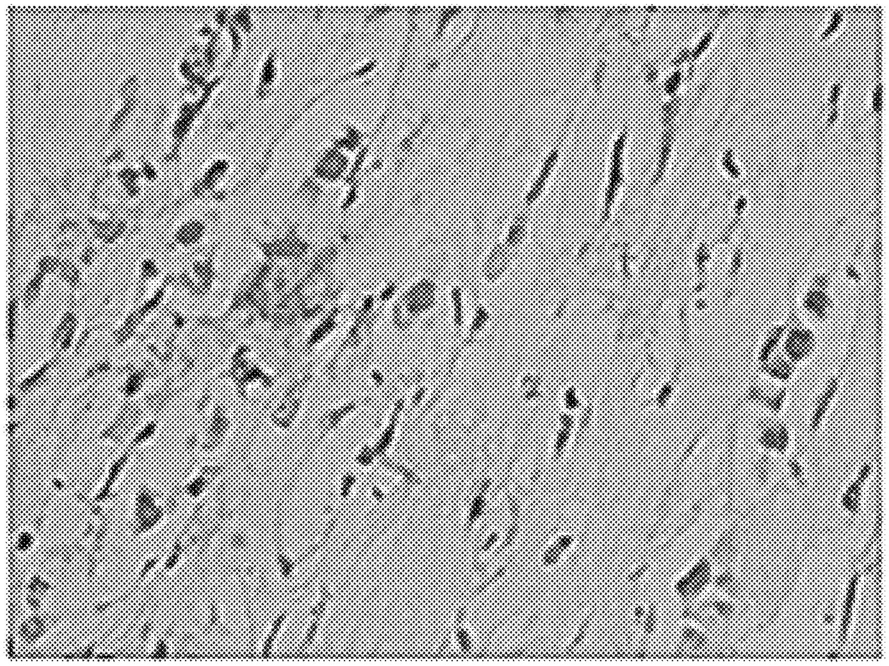
Medullary carcinoma
*Fig. 14B*

Normal lung tissue (score 0)

Squamous cell carcinoma (score 2)

Small cell carcinoma (score 4)

SCLC - T1
(score 4)

SCLC – T3
(score 4)

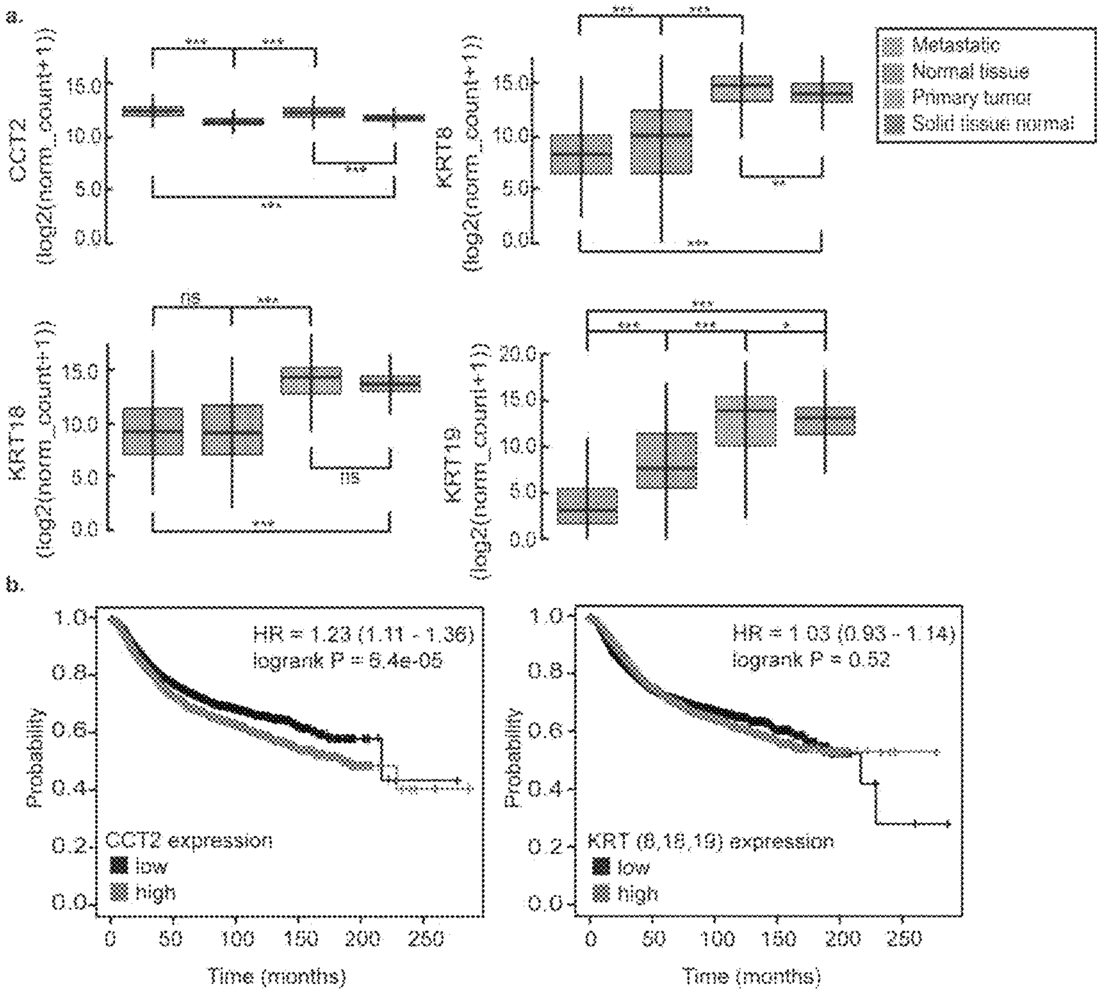
Median survival (months)
| Lower expression cohort | High expression cohort |
|---|---|
| 216.66 | 185.16 |
Upper Quartile survival (months)
| Lower expression cohort | High expression cohort |
|---|---|
| 48 | 51 |
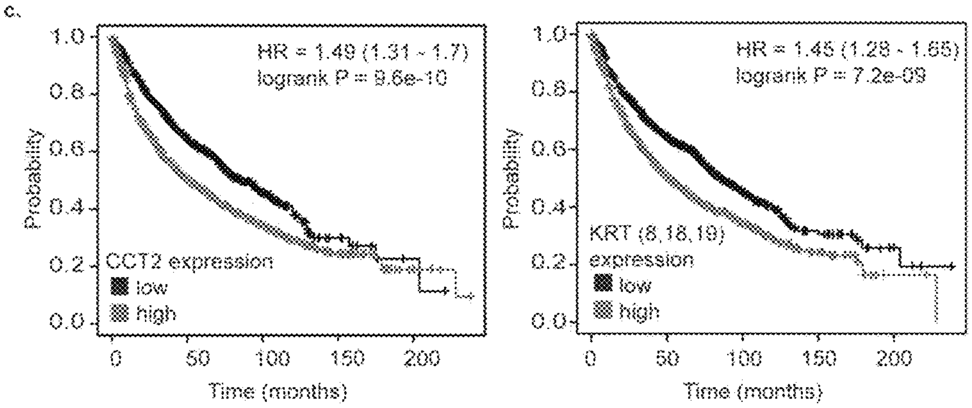
Median survival (months)
| Lower expression cohort | High expression cohort |
|---|---|
| 70.6 | 68 |
Upper quartile survival (months)
| Lower expression cohort | High expression cohort |
|---|---|
| 85.65 | 52 |
Fig. 23a, Fig. 23b, Fig. 23c

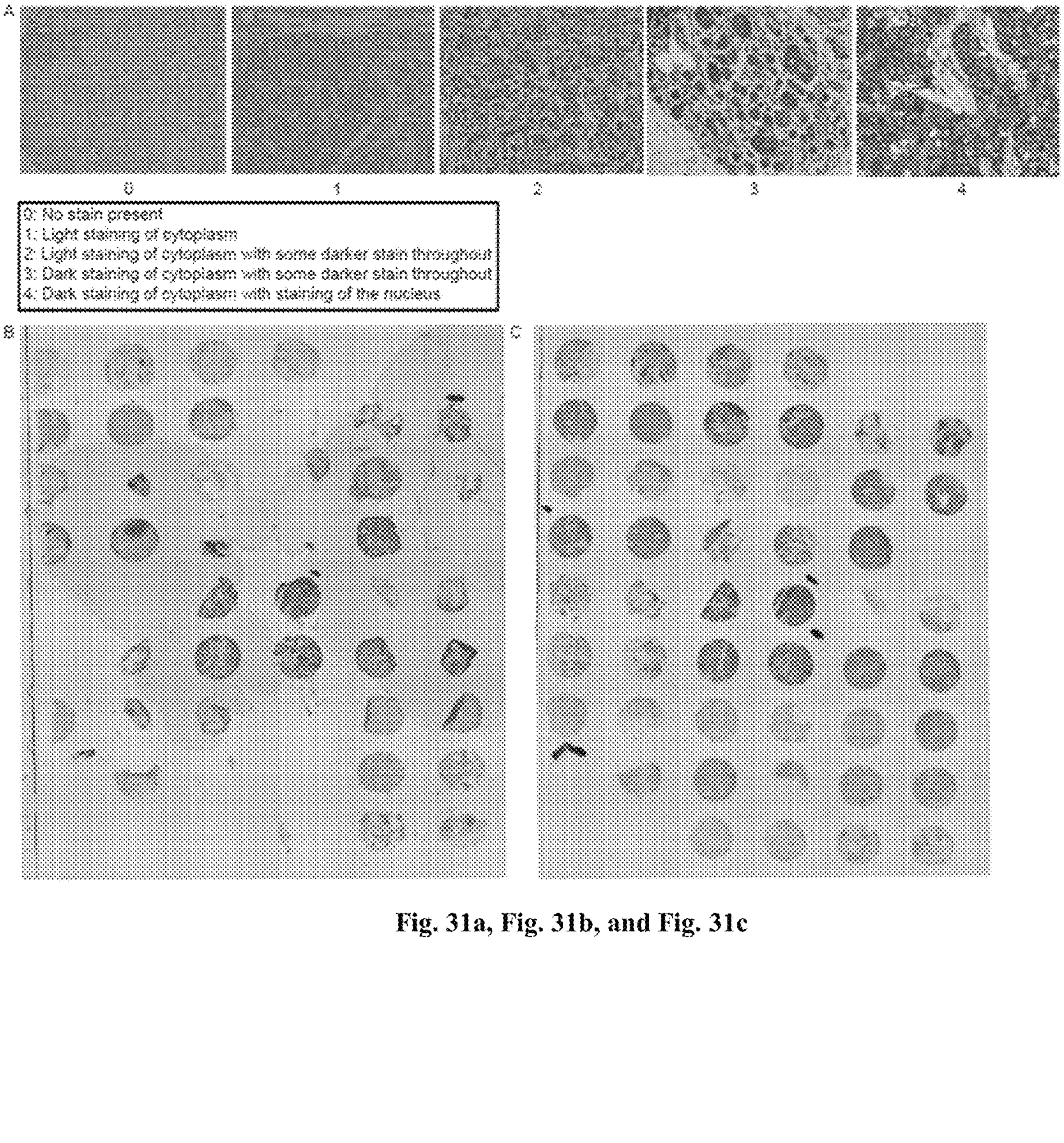
Fig. 31a, Fig. 31b, and Fig. 31c

SEQUENCE LISTING

```
<160> NUMBER OF SEQ ID NOS: 23

<210> SEQ ID NO 1
<211> LENGTH: 20
<212> TYPE: PRT
<213> ORGANISM: Artificial Sequence
<220> FEATURE:
<223> OTHER INFORMATION: Synthetic Construct

<400> SEQUENCE: 1

Val Thr Ile Phe Val Ala Gly Val Leu Thr Ala Ser Leu Thr Ile Trp
1               5                   10                  15

Lys Lys Met Gly
            20


<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Ala Ser Leu Thr Ile Trp Lys Lys Met Gly
1               5                   10


<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Val Thr Ile Phe Val Ala Gly Val Leu Thr
1               5                   10


<210> SEQ ID NO 4
<211> LENGTH: 7
<212> TYPE: PRT
```

<213> ORGANISM: Artificial Sequence
<220> FEATURE:
<223> OTHER INFORMATION: Synthetic Construct

<400> SEQUENCE: 4

Val Thr Ile Phe Val Ala Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Ile Phe Val Ala Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Construct

<400> SEQUENCE: 6

Ile Trp Lys Lys Met Gly
1               5

<210> SEQ ID NO 7
<211> LENGTH: 15
<212> TYPE: PRT
<213> ORGANISM: Artificial Sequence
<220> FEATURE:
<223> OTHER INFORMATION: Synthetic Construct

<400> SEQUENCE: 7

Gly Arg Pro Arg His Gln Gly Val Met Val Gly Met Gly Gln Lys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Construct

<400> SEQUENCE: 8

Asp Asn Gly Ser Gly Met Cys Lys Ala Gly Phe Ala Gly Asp Asp
1               5                   10                  15

<210> SEQ ID NO 9
<211> LENGTH: 20
<212> TYPE: PRT
<213> ORGANISM: Artificial Sequence
<220> FEATURE:
<223> OTHER INFORMATION: Synthetic Construct

<400> SEQUENCE: 9

Ala Thr Ala Ala Ala Ala Ala Ala Ala Thr Ala Ser Leu Thr Ile Gln
1               5                   10                  15

Asp Asp Met Gly
            20

<210> SEQ ID NO 10

<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
ggagtccgca gtcttacgag 20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
tctggaggac ctggtagagg 20

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
tcggaagcct aactacagcg a 21

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
agatgagcat tggcagcgag 20

<210> SEQ ID NO 14
<211> LENGTH: 24
<212> TYPE: DNA
<213> ORGANISM: Artificial Sequence
<220> FEATURE:
<223> OTHER INFORMATION: Synthetic Construct

<400> SEQUENCE: 14
gtgaatccag attagtttcc ctca 24

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15
caagacctgc tcaatgttaa g 21

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
gtctgtcatg gaaggtgctc 20

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
ctgaggatgg tgtaagcgat g 21

<210> SEQ ID NO 18
<211> LENGTH: 17
<212> TYPE: DNA
<213> ORGANISM: Artificial Sequence
<220> FEATURE:
<223> OTHER INFORMATION: Synthetic Construct

<400> SEQUENCE: 18
gtttgccagt gactcca 17

<210> SEQ ID NO 19
<211> LENGTH: 23
<212> TYPE: DNA
<213> ORGANISM: Artificial Sequence
<220> FEATURE:
<223> OTHER INFORMATION: Synthetic Construct

<400> SEQUENCE: 19
cataccacaa acatcagcac aag 23

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
tgttgctgga attgttgtgc 20

<210> SEQ ID NO 21
<211> LENGTH: 21
<212> TYPE: DNA
<213> ORGANISM: Artificial Sequence
<220> FEATURE:
<223> OTHER INFORMATION: Synthetic Construct

<400> SEQUENCE: 21
cctatgcatc tcacccatct c 21

<210> SEQ ID NO 22
<211> LENGTH: 22
<212> TYPE: DNA
<213> ORGANISM: Artificial Sequence
<220> FEATURE:
<223> OTHER INFORMATION: Synthetic Construct

<400> SEQUENCE: 22
gaaggtgaag gtcggagtca ac 22

<210> SEQ ID NO 23
<211> LENGTH: 22
<212> TYPE: DNA

-continued

```
<213> ORGANISM: Artificial Sequence
<220> FEATURE:
<223> OTHER INFORMATION: Synthetic Construct

<400> SEQUENCE: 23

tggaagatgg tgatgggatt tc                                           22
```

METHODS AND COMPOSITIONS COMPRISING A CT20 PEPTIDE

CROSS-REFERENCE TO RELATED APPLICATIONS

This application is a continuation in part of application Ser. No. 17/486,432, filed Sep. 27, 2021, which is a division of application Ser. No. 15/327,353, filed Jan. 18, 2017, now U.S. Pat. No. 11,129,868, which is a United States National Phase Patent Application of International Patent Application Number PCT/US2015/039806, filed on Jul. 9, 2015, which claims the benefit of U.S. Provisional Application 62/026,564, filed Jul. 18, 2014, which hereby incorporated herein by reference in their entireties.

INCORPORATION-BY-REFERENCE OF MATERIAL SUBMITTED ELECTRONICALLY

Incorporated by reference in its entirety herein is a computer readable sequence listing submitted concurrently herewith and identified as follows: One 5,102 bytes ASCII (Text) file named "10613-036US3_2022_07_05 Sequence Listing.txt," created on Jul. 5, 2022.

BACKGROUND

Breast cancer that metastasizes is one of the leading causes of death in women (U.S. Cancer Statistics Working Group. 2013). Certain subtypes of breast cancer have a higher incidence of developing metastasis. One such example is triple-negative breast cancer (TNBC), which lacks the estrogen receptor (ER), progesterone receptor (PR), and HER2 (ErbB2, Neu) (De Laurentiis, M., et al. 2010). Another aggressive form of breast cancer is HER2 amplification. While the early stage disease is treatable, advanced stage breast cancer is untreatable and survival rates are low (Fiszma G L, et al. 2011).

Metastatic breast cancers, especially the forms that arise from TNBC, are incurable and standard treatments are usually palliative. Although combinations of chemotherapy and molecular-targeted biological agents have the potential to be effective therapies, a recent survey of current clinical trials reported no improvement in overall survival in patients that underwent combination treatments (Bramati A, et al. 2014). This is due in part to the fact that the molecular basis for TNBC is unknown.

However, despite advances in the understanding of the pathology of metastatic cancer, there is still a need for compositions and methods that prevent or amerliroate metastases, and specifically compostions and methods that target CSCs or cells undergoing EMT. These needs and other needs are satisfied by the disclosed embodiments.

SUMMARY

Disclosed herein is a method of treating a subject suspected of having cancer. The method includes obtaining a sample from a subject, measuring the amount of chaperonin containing TCP (CCT) in the sample, comparing the amount of CCT in the sample to a pre-determined threshold CCT level, and initiating a therapeutic regimen if the amount of CCT in the sample is above the pre-determined threshold CCT level. The therapeutic regimen can include administering to a subject an effective amount of a composition including a CT20 peptide. The CT20 peptide of the therapeutic regimen includes an amino acid sequence having at least 60% sequence identity to SEQ ID NO:1, SEQ ID NO:2, SEQ ID NO:3, SEQ ID NO:4, SEQ ID NO:5, SEQ ID NO:6, or a combination thereof, such that the CT20 peptide is able to bind directly with CCT, which can include hydrophobic interactions. SEQ ID NOS 1-6 are shown in Table 5. In some embodiments, the CT20 peptide includes a biotin label.

The therapeutic regimen can include administering a therapeutic agent, an anti-cancer agent, an anti-neoplastic agent, a radiosensitizer, or a chemotherapeutic agent.

In some embodiments, the CT20 peptide of the therapeutic regimen may be delivered via nanoparticles suitable for delivery of the CT20 peptide into a cancer cell. The nanoparticles may also include at least one type of targeting moiety, for example, a ligand for a receptor expressed by cancer cells. In some embodiments, the receptor expressed by cancer cells is an EGF, HER2, or folate receptor. In some embodiments, the CT20 peptide is linked to an internalization domain suitable for delivery of the CT20 peptide into a cancer cell.

The cancer treated in the disclosed methods may include at least one of breast cancer, lung cancer, prostate cancer, liver cancer, colon cancer, lymphoma, melanoma, head cancers, neck cancers, or a cancer derived from a mesenchymal stem-like cancer. The sample obtained from the subject may be a blood sample, a cellular sample, or a biopsy.

Measuring the amount of CCT in the sample includes determining the amount of one or more subunits of CCT, for example, CCT$\alpha$, CCT$\beta$, CCT$\gamma$, CCT$\varepsilon$, CCT$\zeta$, CCT$\eta$, CCT$\theta$, and CCT1-8. A CT20 peptide may be used to measure the amount of CCT in the sample. The CT20 peptide used for measuring the amount of CCT in the sample may include SEQ ID NO: 1, SEQ ID NO: 2, SEQ ID NO: 3, SEQ ID NO: 4, SEQ ID NO: 5, or SEQ ID NO: 6. The CT20 peptide used for measuring the amount of CCT in the sample may interact directly with CCT, for example, via hydrophobic interactions. In some embodiments, the CT20 peptide used for measuring the amount of CCT in the sample includes a biotin label. CCT may be bound by the biotin-labeled CT20 peptide. In some embodiments, the bound CCT may be isolated using streptavidin beads. Measuring the amount of CCT in the sample may include quantifying the amount of CCT protein in the sample, quantifying the amount of CCT mRNA in the sample, or both.

Methods of treating a subject suspected of having cancer may also include comparing the amount of CCT in the sample to the amount of CCT in a sample obtained from one or more control subjects. The one or more control subjects can include subjects having been diagnosed with metastatic cancer and subjects without metastatic cancer. The methods may also include comparing the amount of CCT in the sample to a pre-determined range of CCT amounts. The pre-determined range of CCT amounts can include CCT amounts obtained from subjects having been diagnosed with metastatic cancer and from subjects without metastatic cancer.

The methods of treating a subject suspected of having a cancer may include treating a primary tumor, treating a secondary, metastasized tumor, and/or preventing cancer cell metastases. Some embodiments include inducing the death of cancer cells. In some embodiments, non-cancerous cells do not die.

In some embodiments, the CT20 peptide causes immunogenic cell death of the cancer, effectively cause the cancer to become a cancer vaccine. Therefore, the methods may also include initiating an immunotherapy regimen to promote a cancer vaccine response. For example, the immunotherapy regimen may include administration of checkpoint inhibitors.

Disclosed herein are methods of treating a cancer. The methods may include administering to a subject an effective amount of a composition including a CT20 peptide delivered via nanoparticles including at least one type of targeting moiety. The CT20 peptide may include SEQ ID NO: 1, SEQ ID NO: 2, SEQ ID NO: 3, SEQ ID NO: 4, SEQ ID NO: 5, SEQ ID NO: 6, any variant of SEQ ID NO:1-6 having at least 60% sequence identity to SEQ ID NO: 1, or a combination of two or more of the above. The CT20 peptide may include a biotin label.

In some embodiments, the targeting moiety includes a ligand for a receptor expressed by cancer cells, for example, EGF, HER2, or folate receptor. In some embodiments, the CT20 peptide is linked to an internalization domain.

In the disclosed methods of treating cancer, the CT20 peptide binds binds chaperonin containing TCP (CCT). The binding of CT20 to CCT may induce disruption or inhibition of one or more of the functions of CCT. For example, the binding of CT20 to CCT may disrupt the cytoskeleton. In some embodiments, the CT20 peptide directly interacts with chaperonin containing TCP (CCT), for example, by a hydrophobic interaction.

In some embodiments of the methods of treating cancer, the composition is administered directly to the cancer cells. In some embodiments, the composition is administered systemically to the subject. Some embodiments of the method include repeating the administration of the composition to the subject.

Some embodiments of the methods of treating cancer further include measuring the amount of chaperonin containing TCP (CCT) in the sample using a CT20 peptide, comparing the amount of CCT in the sample to a pre-determined threshold CCT level, and administering an effective amount of a composition including CT20 peptide if the amount of CCT in the sample is above the pre-determined threshold CCT level. The methods may further include evaluating the efficacy of the composition to treat the cancer cells.

Also disclosed herein are methods for capturing circulating tumors cells from liquid biological samples and the uses thereof for diagnosing/treating metastatic cancers and/or monitoring cancer metastasis or recurrences. Said methods comprise contacting the liquid biological sample with a chaperonin-containing TCP1(CCT)-targeting affinity reagent.

The details of one or more embodiments of the invention are set forth in the accompanying drawings and the description below. Other features, objects, and advantages of the invention will be apparent from the description and drawings, and from the claims.

In some aspects, disclosed herein is a method for capturing a circulating tumor cell from a liquid biological sample, comprising a) contacting the liquid biological sample with one or more chaperonin-containing TCP1(CCT)-targeting affinity reagents, and
b) capturing the cells retained in step a) thereby capturing the circulating tumor cell from the sample.

The one or more CCT targeting affinity reagents of any preceding aspect can be a CCT1 targeting affinity reagent, a CCT2 targeting affinity reagent, a CCT3 targeting affinity reagent, a CCT4 targeting affinity reagent, a CCT5 targeting affinity reagent, a CCT6 targeting affinity reagent, a CCT7 targeting affinity reagent, or a CCT8 targeting affinity reagent. In some embodiments, the CCT targeting affinity reagent is a CCT2 targeting reagent. In some embodiments, the CCT-targeting affinity reagent is an antibody.

In some examples, step a) of the method of any preceding aspect further comprises contacting the liquid biological sample with one or more mesenchymal-epithelial biomarkers.

In some examples, the circulating tumor cell of any preceding aspect does not have an increased level of a mesenchymal-epithelial biomarker. In some examples, the circulating tumor cell of any preceding aspect has an increased level of one or more mesenchymal-epithelial biomarkers.

In some examples, the method further comprises a step of detecting one or more mesenchymal-epithelial biomarkers in the circulating tumor cell.

In some examples, the one or more mesenchymal-epithelial biomarkers of any preceding aspect are selected from the group consisting of vimentin, HER2, EpCAM, E-cadherin, N-cadherin, CK5, CK6, CK7, CK8, CK14, CK18, and CK19. In some examples, the method further comprises a step of detecting one or more markers such as CD44 and/or CD45.

In some examples, the liquid biological sample of any preceding aspect comprises a whole blood sample, a urine sample, a plasma sample, a serum sample, or a lymphatic fluid sample.

Also disclosed herein is a method of diagnosing a metastatic cancer in a subject comprising a) obtaining a liquid biological sample from the subject,
b) capturing cells from the liquid biological sample of step a) using the method of any preceding aspect;
c) determining if the captured cells of step b) comprise circulating tumor cells; and
d) determining that the subject as having a metastatic cancer if two or more circulating tumor cells are captured.

In some examples, the method further comprises administering to the subject a therapeutically effective amount of a cancer therapeutic agent if two or more circulating tumor cells are captured.

Also disclosed herein is a method of treating a cancer in a subject, comprising a) obtaining a liquid biological sample from the subject,
b) contacting the liquid biological sample with one or more CCT-targeting affinity reagents,
c) determining if the captured cells of step b) comprise circulating tumor cells, and
d) administering to the subject a therapeutically effective amount of a cancer therapeutic agent if two or more circulating tumor cells are captured.

In some examples, step b) of the method of any preceding aspect further comprises contacting the liquid biological sample with one or more mesenchymal-epithelial biomarkers.

In some examples, the circulating tumor cell of any preceding aspect does not have an increased level of a mesenchymal-epithelial biomarker. In some examples, the circulating tumor cell of any preceding aspect has an increased level of one or more mesenchymal-epithelial biomarkers.

In some examples, the method further comprises a step of detecting one or more mesenchymal-epithelial biomarkers in the circulating tumor cell.

In some examples, the one or more mesenchymal-epithelial biomarkers of any preceding aspect are selected from the group consisting of vimentin, HER2, EpCAM, E-cadherin, N-cadherin, CK5, CK6, CK7, CK8, CK14, CK18, and CK19. In some examples, the method further comprises a step of detecting one or more markers such as CD44 and/or CD45.

In some examples, the liquid biological sample of any preceding aspect comprises a whole blood sample, a urine sample, a plasma sample, a serum sample, or a lymphatic fluid sample.

In some examples, the method of any preceding aspect further comprises determining the level of CCT2 expression in the captured cell. In some examples, the method of any preceding aspect further comprises staining a CCT2 polypeptide in the captured cell with one or more affinity reagents targeting the CCT2 polypeptide. In some examples, the method of any preceding aspect further comprises contacting the captured cells with a stain that binds DNA. In some embodiments, an increased level of CCT2 in the nucleus of the captured cells indicates that the captured cells are circulating tumor cells. Accordingly, in some embodiments, detection of a fully or partially overlap between the nucleus of the capture cell (e.g., as indicted by DNA staining) and the CCT2 polypeptide (e.g., as indicated by CCT2 staining) indicates that the captured cells are circulating tumor cells. In some embodiments, staining of the CCT2 polypeptide in the capture cells has no overlap or minimal overlap with the staining of CD45.

In some examples, the liquid biological sample has a volume of about 7.5 ml.

In some examples, the cancer is selected from the group consisting of breast cancer, lung cancer, melanoma, pancreatic cancer, brain cancer, and colon cancer.

BRIEF DESCRIPTION OF THE FIGURES

The accompanying figures, which are incorporated in and constitute a part of this specification, illustrate several embodiments.

Referring to FIG. 2A, the graph summarizes the results with FOL-NPs that were empty, contained Doxorubicin (DOX), or CT20, and are compared to COOH-NPs with CT20. Referring to FIG. 2B, representative ultrasound data is shown from mice treated with PBS or FOL-CT20-NPs. Arrows indicate treatment times. *$p<0.05$.

FIGS. 3A-3J show a representative timeline of CT20 peptide activities in breast cancer cells. CT20 peptide impaired mitochondrial movement (mitotracker green) (FIG. 3A) leading to clustering (JC-1 probe) (FIG. 3B) and reduced F-actin (green) polymerization (nucleus, DAPI, blue (FIG. 3C). Referring to FIG. 3D, the viability of cells was determined by measuring membrane permeability (Sytox) and membrane asymmetry (violet ratiometric dye). Gates are: N, necrotic; V, viable; A, apoptotic. Percentages are V (black) and N+A (red). Referring to FIG. 3E, by 6 hours, cells detach from substrate (fibronectin). Referring to FIG. 3F, membrane levels of β1 integrin decrease. Referring to FIGS. 3G-3I, post-cell detachment events include caspase activation, autophagy, and increased ROS production. Referring to FIG. 3J, apoptosis/anoikis was detected between 24-48 hours as described for FIG. 3D.

Referring to FIG. 4C, minimal cell death was detected.

(FIG. 5A) Several triple negative breast cancer (TNBC) cell lines and one control breast epithelial line (MCF-10A) were treated with CT20p at increasing doses for 48 hours, and adhesion was determined using a crystal violet adhesion assay. The percentage of adhesion relative to dose 0 is displayed. (FIG. 5B) CT20p was delivered to several breast cancer cell lines for the length of time indicated in the figure. Cell viability was assessed by staining with Sytox AADvanced and F2N12S dyes, which are indicator of membrane permeability and asymmetry, respectively. Quadrants are displayed to divide cell populations, and the percentage of viable cells in the lower right quadrant is indicated in as a percentage in the lower right corner of the scatter plot. As cells undergo apoptosis and necrosis, the population will lose membrane symmetry and increase permeability, shifting to the left and up. (FIG. 5C) A graph of the viability data of the MDA-MB-231, MDA-MB-436, MDA-MB-468, BT-549, and MCF-10A over 48 hours, as measured by the method described for 5B.

(FIG. 6A) The glycolytic profiles of the TNBC cell lines were determined using a Seahorse XF24 analyzer. The dotted lines represent injection points of compounds used to induce a metabolic response: glucose, oligomycin, and 2-DG. Glycolysis is represented by extracellular acidification rate (ECAR). Referring to FIG. 6B, the oxidative phosphorylation profiles of the cell lines were obtained by measuring oxygen consumption rate (OCR) after injection of oligomycin, FCCP, and rotenone/antimycinA. Referring to FIGS. 6C-6D, the glycolytic capacity (FIG. 6C) and mitochondrial coupling efficiency (FIG. 6D) of each cell line was calculated from the metabolic profile data. Referring to FIGS. 6E-6F, cells were treated with CT20p for 24 hours prior to performing the metabolic assays, and glycolytic capacity (FIG. 6E) and mitochondrial coupling efficiency (FIG. 6F) of untreated and CT20p-treated cells was determined.

(FIG. 8A) CT20p-Biotin (denoted CT20) was used to pull down interacting proteins in TNBC cell lysates as described in Materials & Methods. Biotin only (denoted B) was used as a control. Pull downs were analyzed by immunoblotting for CCM (FIG. 8B) An "in-cell" pull down was performed in MDA-MB-231 and MCF-10A cells as described in Materials and Methods. Briefly, CT20p-biotin encapsulated in HBPE-nanoparticles was delivered to viable cells, followed by cell lysis and recovery of interacting proteins. Pull downs, as well as whole cell lysate samples, were analyzed, and CCTβ and p38 were detected by Western blot. (FIG. 8C) As a control for the "in-cell" pull down, DiI dye encapsulated in HBPE-nanoparticles was delivered to viable MDA- MB-231 and MCF-10A cells, followed by cell lysis and recovery of bound proteins. CCTβ and p38 were detected by Western blot.

(FIG. 10A) Levels of three CCT subunits (beta, delta, and epsilon) were examined by western blot across TNBC cell lines. P38 is used as a loading control. (FIG. 10B) The protein levels of the subunits were quantified per total protein and normalized to the levels in MCF-10A cells. (FIG. 10C) Gene expression of the three subunits was analyzed by quantitative RT-PCR. The values were determined relative to MCF-10A gene expression of each subunit.

(FIG. 11A) MDA-MB-231 cells were fluorescently stained and seeded around stoppers in a 96-well plate. Cells were then treated with CT20p at 75 or 150 ug/mL for 24 hours. Removal of the stoppers created an exclusion zone, outlined in white. Control cells had stoppers removed immediately before data acquisition, and represent the pre-migration area. Remaining conditions were allowed to migrate into the exclusion zone for 10 hours before images were obtained with a Plate Runner HD. The leading edge of migrating cells after the migration period is outlined in black. (FIG. 11B) The migration areas were analyzed using Image J software, and the % closure of the exclusion zone was calculated.  $p<0.001$, * $p<0.0001$ (FIGS. 11C-11F) MDA-MB-231 cells (FIG. 11C) and MCF-10A cells (FIG. 11E) were stained with DAPI (blue), Mitotracker Red (red) and α-DM1a antibody to tubulin (green). Untreated cells were compared to cells that had been treated with CT20p for 24 hours. Tubulin architecture and mitochondrial distribution can be seen in the inset. Scale bars represent 50 μm and inset is magnified by a factor of 2.2×. The average amount of tubulin per cell in MDA-MB-231 (FIG. 11D) and MCF-10A (FIG. 11F) cells was determined. *** $P<0.0001$.

(FIG. 13A) Phase contrast images of MCF-10A and MCF-10A EMT cells illustrate differences in morphology. (FIG. 13B) MCF-10A and MCF-10A EMT cells were subjected to a migration assay for 20 hours as described in FIG. 11. The pre-migration area is defined in black. (FIG. 13C) MCF-10A cells were transfected to overexpress CCM The levels of CCT subunits were examined in these cells, as well as in MCF-10A and MCF-10A EMT cells. p38 is used as a loading control. (FIG. 13D) The level of CCTβ relative to total protein was quantified in the three MCF-10A variants. (FIG. 13E) The MCF-10A variants were treated with CT20p at a dose of 75 ug/mL for 24 hours. Viability was then assessed by staining with Sytox AADvanced and F2N12S, followed by flow cytometry as described in FIG. 5. The viable cells are in the lower-right quadrant, and their percentage is displayed in the lower right corner of the scatter plot.

FIG. 14B shows that breast cancer tissue array was examined for CCTβ levels by IHC. 40× magnification. CCTβ was detected in invasive breast cancer.

(FIG. 16A) Human breast cancer tissue arrays were analyzed by immunohistochemistry for CCM Tissue cores were scored by a pathologist based on intensity of staining. For analysis, tissues were characterized as cancer adjacent tissue (CAT) and invasive ductal carcinoma (IDC). IDC was furthermore divided by tumor severity as T1/T2 (less severe primary tumor) and T3/T4 (more severe primary tumor). CCTβ staining was compared between groups, with * indicating $p<0.05$ and * indicating $p<0.0001$. (FIG. 16**B) CCTβ staining was correlated to high levels of receptor expression. Displayed are estrogen receptor (ER++/+++), progesterone receptor (PR++/+++), Her2 (Her2 2+/3+), and TNBC. * indicates $p<0.05$ and  indicates $p<0.0001$. (FIG. 16**C) Representative images of CAT and IDC at various T grades are provided to illustrate varied levels of CCM Pathologist's score is indicated in parenthesis. Images are at 200× total magnification.

(FIG. 19A) CCTβ was detected in colon carcinoma tissue samples by immunohistochemistry. Samples were grouped by subtype. No subtypes of colon carcinoma were found to express more CCTβ than normal colon tissue. (FIG. 19B) Adenocarcinoma and mucinous adenocarcinoma samples were grouped by grade, a measure of cell differentiation, and CCTβ staining was compared among groups. No trends were revealed correlating CCTβ to tumor grade.

(FIG. 20A) Hepatic carcinoma and normal tissue samples were assessed for CCTβ expression by immunohistochemistry. Normal hepatic tissue was compared to two subtypes of carcinoma: cholangiocellular carcinoma and hepatocellular carcinoma. Significance indicated is in reference to normal hepatic tissue. (FIG. 20B) Hepatocellular carcinoma (HCC) samples were grouped according to TNM score, and T1/T2 samples were compared to T3/T4 samples. While both were significantly higher than normal hepatic tissue, there was no difference between progressive T scores. (FIG. 20C) HCC samples were grouped by grade, and CCTβ staining was compared among grades. Grade 3 HCC stained significantly higher for CCTβ than the other grades. (FIG. 20D) Representative photos indicate the difference between CCTβ expression in high grade and low grade HCC. *=p<0.05, ***=p<0.001.

(FIG. 21A) CCTβ was detected in prostate tissue samples by immunohistochemistry. Staining intensity was compared between normal prostate tissue and prostate adenocarcinoma. (FIGS. 21B-21D) Adenocarcinoma samples were grouped by TNM score FIG. 21B), Gleason grade (FIG. 21C), and stage (FIG. 21D) to examine whether CCTβ staining exhibited trends correlating to cancer severity. All indicated significance is in relation to normal prostate tissue. *=p<0.05, =p<0.01, *=p<0.001.

(FIG. 22A) CCTβ expression was examined in tissue samples of several different lung cancer subtypes by immunohistochemistry. Significance indicated is in reference to normal lung tissue. (FIG. 22B) Representative photos depict the low levels of CCTβ in normal lung tissue, compared to elevated levels in both squamous cell and small cell carcinomas. (FIG. 22C) Squamous cell lung cancer (SqCLC) samples were grouped according to TNM score. T1/2 samples were compared to T3/T4 samples. Significance indicated is in reference to normal lung tissue. (FIG. 22D) Small cell lung cancer (SCLC) samples were also grouped by TNM score, and the CCTβ staining the various groups was compared. Significance is in reference to normal lung tissue. (FIG. 22E) Representative photos portray the high levels of CCTβ present in SCLC, regardless of TNM score. *=p<0.05, =p<0.01, *=p<0.001, ****=p<0.0001.

FIGS. 23*a*-23*c* show bioinformatic and histological analysis of CCT2 in cancer patients. (a) UCSC Xena analysis from "TCGA, TARGET, GTEx" dataset (n=17,722) comparing mRNA expression of CCT2, KRT8, KRT18, and KRT19 in metastatic tissue (orange), normal tissues (green), primary tumor (blue), and primary solid tumor (purple). *=p<0.05, =p<0.005, *=p<0.0001. (b-c) KMplotter analysis of overall survival (OS) with low vs. high CCT2 mRNA expression and low vs high mRNA expression of the mean of KRT8, KRT18, and KRT19 combined in (b) breast cancer patients; n=4,929 and (c) lung cancer patients; n=1,925. Hazard ratios (HR) and log-rank p-values, as calculated by kmplot.com software, are listed on the KmPlots.

(FIG. 29*a*) Histological CCT2 staining in normal lung tissue. (FIG. 29*b*-29*d*) Histological CCT2 staining in cancerous lung tissue for (FIG. 29*b*) adenocarcinoma, (FIG. 29*c*) squamous cell carcinoma, and (FIG. 29*d*) small cell carcinoma.

(FIG. 30*a*) Overall cancer (n=17,200): the most significant differences were observed in the CCT2 and CCT3 genes, and the least difference was in the CCT6B gene. (FIG. 30*b*) Brain cancer (n=1,277): the most significant difference was seen in the CCT2 gene, and the least difference was in the CCT6B gene. (FIG. 30*c*) Breast cancer (n=1,660): the most significant differences were seen in the CCT3 and CCT8 genes and the least difference was in the CCT6B gene. (FIG. 30*d*) Colon cancer (n=598): the most significant difference was seen in the CCT2 gene, and the least difference was in the CCT6B gene. (FIG. 30*e*) Lung cancer (FIG. 8*n*=1,301): the most significant differences were seen in the CCT2 and CCT3 genes, and the least difference was in the CCT6B gene. $p<0.0001$ for all samples.

FIGS. 31A-31C show CCT2 score scale and histological analysis of CCT2 and STAT3 in cancerous breast tissue. (FIG. 31A) Representative images of breast cancer tissue at each CCT2 stain score 0-4 with an explanation for the stain score scale. Images are from 0: TMABRN801b sample E1, 1: patient 25, 2: patient 08, 3: patient 33, 4: patient 37. (FIG. 31B-31C) breast cancer TMA Core Matrix from Florida Hospital stained for (FIG. 31B) CCT2 and (FIG. 31C) STAT3.

(FIG. 32*a*) Normal breast tissue patient IDs: 2042 and 2259. (FIGS. 32*b*-32*c*) Twelve cancerous patients were stained for CCT2, and four representative images are shown here. (FIG. 32*b*) Ductal carcinoma patient IDs: 1874 and 1977. (FIG. 32*c*) Lobular carcinoma patient IDs: 2898 and 2199.

(FIGS. 33*a*-33*b*) Tested anti-CCT2-PE concentrations: 0 μg/ml (black), 5 μg/mL (blue), 10 μg/mL (purple), 20 μg/mL (green), and 25 μg/mL (yellow) in (FIG. 33*a*) MDA-MB-231 and (FIG. 33*b*) T47D-CCT2 cell lines with PE-isotype control (grey). (FIG. 33*c*) Tested various concentrations of MDA-MB-231 cells as indicated, with 10 μg/mL of anti-CCT2-PE (black/dark red/dark green) and PE-isotype control (light grey/red/green). (FIG. 33*d*) Tested 5× concentration of PE-isotype control (grey) with 70 min incubation in MDA-MD-231 cells with anti-CCT2-PE concentrations: 0 μg/mL (black), 5.5 μg/mL (purple), 11.0 μg/mL (green), 16.5 μg/mL (yellow), 22.0 μg/mL (blue), and 33.0 μg/mL (red).

(FIG. 34*a*) Representative images from CSS Analyzer II of spiked cancer cells stained with 0 μg/mL anti-CCT2-PE at three different exposure times: 0.2, 0.3, and 0.4 sec. (FIG. 34*b*) Images from CSS Analyzer II of spiked cancer cells at 0.2 seconds exposure stained with three different concentrations of anti-CCT2-PE: 4 μg/mL, 8 μg/mL, and 12 μg/mL as indicated. Column one: overlay of columns two and three. Column two: CK-FITC signal. Column three: DAPI signal. Column four: CD45-APC signal. Column five/"extra channel". This column was used to stain for anti-CCT2-PE. The experiment was completed in duplicate.

(FIG. 36*a*) An example image of ACCEPT opening screen with marker characterization mode (MC) selected. The image shows the location of input and output folders. The files are listed in red since they are not yet processed. (FIG. 36*b*) Representative image of ACCEPT visualization screen. Gate was applied with selected cells as shown by blue dots on the right panel. The full image scan from CSS magnets is represented by the top blue bar. Images of individual cells and their stain intensity are shown on the bottom in a layout similar to the CSS Analyzer II. (FIG. 36*c*) Example of the gate window under the "multiple gates" button, where different conditions can be applied to the various channels to isolate desired cells.

(FIG. 37A) Representative images of CTCs, based on standard CTC criteria, that were CCT2 positive at varying concentrations of the anti-CCT2-PE antibody. (FIG. 37B) Representative images of CTCs from each SCLC patient. Each image was taken from collections of relevant events that were analyzed using standard CTC criteria for the CSS CXC kits as above. (FIG. 37C) Representative images from CTCs collected using the CTC analysis algorithm (instead of CXC analysis algorithm) where the DAPI signal overlaps with CCT2-PE instead of CK-FLU ((Cytokeratin-fluorescein-conjugated) as in (FIG. 37A, FIG. 37B). Note that images that contain faint CD45 expression are a result of bleed-over from the signal in the PE channel.

Figure 1:
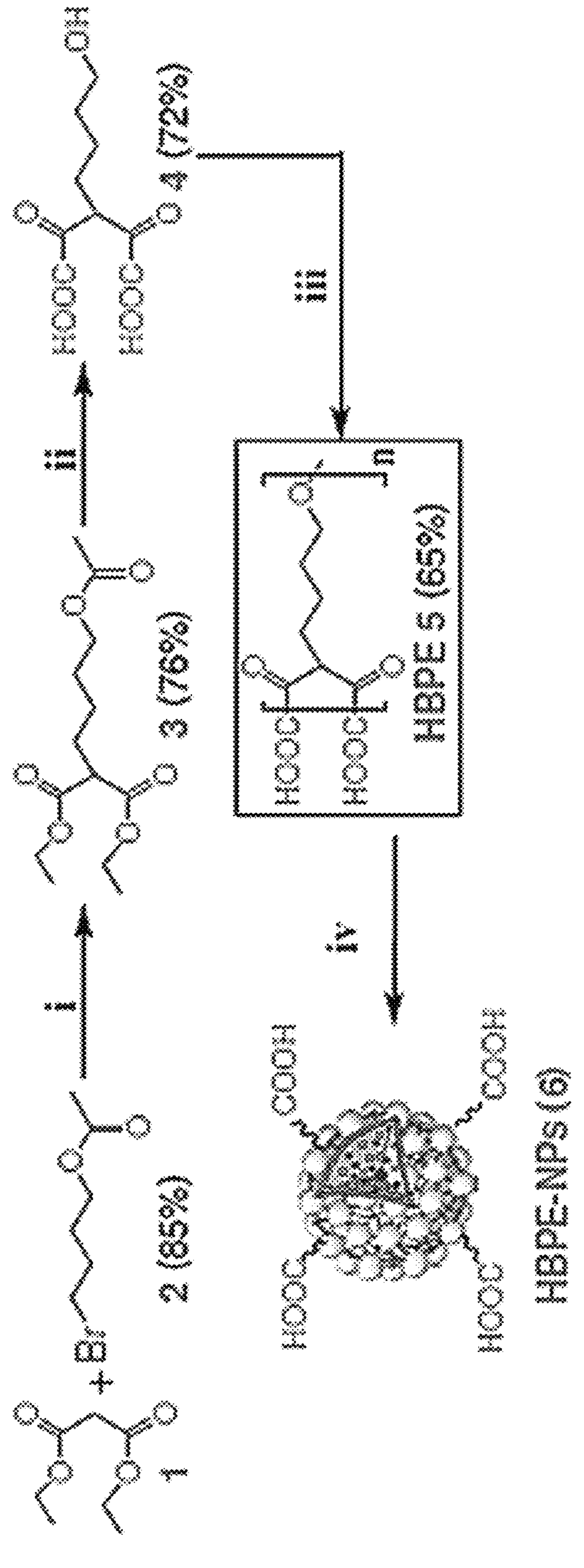
FIG. 1 shows a representative synthetic route towards the preparation of s hyperbranched polyester polymer and its cargo-encapsulating carboxylated polymeric NPs.

Additional advantages will be set forth in part in the description which follows, and in part will be obvious from the description. The advantages will be realized and attained by means of the elements and combinations particularly pointed out in the appended claims. It is to be understood that both the foregoing general description and the following detailed description are exemplary and explanatory only and are not restrictive, as claimed.

DETAILED DESCRIPTION

The disclosed embodiments can be understood more readily by reference to the following detailed description and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in practice or testing, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the disclosed embodiments are not entitled to antedate such publication by virtue of prior invention.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the amino acid abbreviations are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

"Peptide" as used herein refers to any peptide, oligopeptide, polypeptide, gene product, expression product, or protein. For example, a peptide can be a fragment of a full-length protein, such as, for example, the CT20 peptide. A peptide is comprised of consecutive amino acids. The term "peptide" encompasses naturally occurring or synthetic molecules.

In general, the biological activity or biological action of a peptide refers to any function exhibited or performed by the peptide that is ascribed to the naturally occurring form of the peptide as measured or observed in vivo (i.e., in the natural physiological environment of the protein) or in vitro (i.e., under laboratory conditions). For example, one biological activity of the CT20 peptide is the cytotoxic activity of the CT20 peptide. Another biological activity of the CT20 peptide is the ability to bind CCT.

The term "enzyme" as used herein refers to any peptide that catalyzes a chemical reaction of other substances without itself being destroyed or altered upon completion of the reaction. Typically, a peptide having enzymatic activity catalyzes the formation of one or more products from one or more substrates. Such peptides can have any type of enzymatic activity including, without limitation, the enzymatic activity or enzymatic activities associated with enzymes such as those disclosed herein.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the terms "transformation" and "transfection" mean the introduction of a nucleic acid, e.g., an expression vector, into a recipient cell including introduction of a nucleic acid to the chromosomal DNA of said cell. The art is familiar with various compositions, methods, techniques, etc. used to effect the introduction of a nucleic acid into a recipient cell. The art is familiar with such compositions, methods, techniques, etc. for both eukaryotic and prokaryotic cells. The art is familiar with such compositions, methods, techniques, etc. for the optimization of the introduction and expression of a nucleic acid into and within a recipient cell.

As used herein, "a CT20 peptide" or "CT20" may refer to one peptide or may refer one or more peptides (i.e., a C-terminal Bx peptide), such as molar concentrations of the peptide, as would be found in a composition. In an aspect, a CT20 peptide can comprise SEQ ID NO:1, SEQ ID NO:2, SEQ ID NO:3, SEQ ID NO:4, SEQ ID NO:5, or SEQ ID NO:6. In an aspect, a CT20 peptide can comprise a combination of two or more of SEQ ID NOs:1-6. In an aspect, the CT20 peptide may be a variant of SEQ ID NO:1, SEQ ID NO:2, SEQ ID NO:3, SEQ ID NO:4, SEQ ID NO:5, SEQ ID NO:6, or a combination thereof. The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 61%, 62%, 63%, 64%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to a reference sequence.

As used herein, "noncancerous cells" can refer to cells that are normal or cells that do not exhibit any metabolic or physiological characteristics associated with cancer. For example, noncancerous cells are healthy and normal cells.

As used herein, the term "subject" refers to the target of administration, e.g., an animal. Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a patient. A patient refers to a subject afflicted with a disease or disorder, such as, for example, cancer and/or aberrant cell growth. The term "patient" includes human and veterinary subjects. In an aspect, the subject has been diagnosed with a need for treatment for cancer and/or aberrant cell growth.

Therapeutic agents may include antimicrobial agents, such as antibiotics or antimycotic compounds, including but not limited to, active agents such as antifungal agents, antibacterial agents, anti-viral agents and antiparasitic agents, and metals. An antimicrobial agent can comprise a substance, compound or molecule, which kills or inhibits the growth of microorganisms such as bacteria, fungi, or protozoans. Antimicrobial agents may either kill microbes (microbiocidal) or prevent the growth of microbes (microbiostatic). Disinfectants are antimicrobial substances used on non-living objects or outside the body. Antimicrobial agents include those obtained from natural sources, such as Beta-lactam antibiotics (such as penicillins, cephalosporins), and protein synthesis inhibitors (such as aminoglycosides, macrolides, tetracyclines, chloramphenicol, polypeptides), and those from synthetic sources such as sulphonamides, cotrimoxazole, quinolones, anti-fungals, anti-cancer drugs, anti-malarials, anti-tuberculosis drugs, anti-leprotics, and anti-protozoals.

Examples of antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ainpicillin, amphotericin B, ketoconazole, fluconazole, pyrimethaniine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, heavy metals including, but not limited to, gold, platinum, silver, zinc and copper, and their combined forms including, salts, such as chloride, bromide, iodide and periodate, and complexes with carriers, and other forms. As used herein, the term metal includes all metal salts or metal compounds, including, but not limited to, metal chlorides, metal phosphates, metal sulfates, metal iodides or metal bromides. The active form of some metal salts is the ionic form. Other antimicrobial agents include, but are not limited to, polyene antifungals, Amphotericin B, Candicidin, Filipin, Hamycin, Natamycin, Nystatin, Rimocidin, Imidazoles, Bifonazole, Butoconazole, Clotrimazole, Econazole, Fenticonazole, Isoconazole, Ketoconazole, Miconazole, Omoconazole, Oxiconazole, Sertaconazole, Sulconazole, Tioconazole, Triazoles, Albaconazole, Fluconazole, Isavuconazole, Itraconazole, Posaconazole, Ravuconazole, Terconazole, Voriconazole, Thiazoles, Abafungin, Allylamines, Amorolfin, Butenafine, Naftifine, Terbinafine, Echinocandins, Anidulafungin, Caspofungin, Micafungin.

The terms "treating", "treatment", "therapy", and "therapeutic treatment" as used herein refer to curative therapy, prophylactic therapy, or preventative therapy. As used herein, the terms refers to the medical management of a subject or a patient with the intent to cure, ameliorate, stabilize, or prevent a disease, pathological condition, or disorder, such as, for example, cancer or a tumor. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In an aspect, the disease, pathological condition, or disorder is cancer, such as, for example, breast cancer, lung cancer, colorectal, liver cancer, or pancreatic cancer. In an aspect, cancer can be any cancer known to the art.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. For example, in an aspect, preventing can refer to the preventing of replication of cancer cells or the preventing of metastasis of cancer cells.

As used herein, the term "diagnosed" means having been subjected to a physical examination by a person of skill, for example, a physician or a researcher, and found to have a condition that can be diagnosed or treated by compositions or methods disclosed herein. For example, "diagnosed with cancer" means having been subjected to a physical examination by a person of skill, for example, a physician or a researcher, and found to have a condition that can be diagnosed or treated by a compound or composition that alleviates or ameliorates cancer and/or aberrant cell growth.

As used herein, the phrase "identified to be in need of treatment for a disorder," or the like, refers to selection of a subject based upon need for treatment of the disorder. For example, a subject can be identified as having a need for treatment of a disorder (e.g., a disorder related to cancer and/or aberrant cell growth) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a peptide (such as a CT20 peptide), or a composition (such as a composition comprising a CT20 peptide), or pharmaceutical preparation (such as a preparation comprising a CT20 peptide or a composition comprising a CT20 peptide) to a subject. Such methods are well known to those skilled in the art and include, but are not limited to, intracardiac administration, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed composition or peptide or pharmaceutical preparation and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the term "determining" can refer to measuring or ascertaining a quantity or an amount or a change in expression and/or activity level, e.g., of a nucleotide or transcript or polypeptide (e.g., CCT or a CCT subunit). For example, determining the amount of a disclosed transcript or polypeptide in a sample as used herein can refer to the steps that the skilled person would take to measure or ascertain some quantifiable value of the transcript or polypeptide in the sample. The art is familiar with the ways to measure an amount of the disclosed nucleotides, transcripts, polypeptides, etc. In an aspect, "determining" as used herein can refer to measuring or ascertaining the level of cell death or cell survival, for example, following administration of a CT20 peptide or a composition comprising an effective amount of a CT20 peptide. Methods of measuring or ascertaining cell survival and cell death are known to the art and include, but are not limited to, histochemical staining (e.g., TUNEL), cell proliferation assay, cell death assays, morphological examination, etc. In an aspect, the size of a tumor can be measured non-invasively through, for example, ultrasound or imaging.

As used herein, the term "level" refers to the amount of a target molecule in a sample, e.g., a sample from a subject. The amount of the molecule can be determined by any method known in the art and will depend in part on the nature of the molecule (i.e., gene, mRNA, cDNA, protein, enzyme, etc.). The art is familiar with quantification methods for nucleotides (e.g., genes, cDNA, mRNA, etc.) as well as proteins, polypeptides, enzymes, etc. It is understood that the amount or level of a molecule in a sample need not be determined in absolute terms, but can be determined in relative terms (e.g., when compare to a control or a sham or an untreated sample).

As used herein, the terms "effective amount" and "amount effective" refer to an amount that is sufficient to achieve the desired result or to have an effect on an undesired condition. For example, in an aspect, an effective amount of a CT20 peptide is an amount that kills and/or inhibits the growth of cells without causing extraneous damage to surrounding non-cancerous cells. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts.

By "modulate" is meant to alter, by increase or decrease. As used herein, a "modulator" can mean a composition that can either increase or decrease the expression level or activity level of a gene or gene product such as a peptide. Modulation in expression or activity does not have to be complete. For example, expression or activity can be modulated by about 10%, 20%, 30%, 40%, 50%, 60%, 70%, 80%, 90%, 95%, 99%, 100% or any percentage in between as compared to a control cell wherein the expression or activity of a gene or gene product has not been modulated by a composition.

As used herein, "$EC_{50}$," is intended to refer to the concentration or dose of a substance (e.g., a CT20 peptide or a disclosed composition comprising a CT20 peptide) that is required for 50% enhancement or activation of a biological process, or component of a process, including a protein, subunit, organelle, ribonucleoprotein, etc. $EC_{50}$ also refers to the concentration or dose of a substance that is required for 50% enhancement or activation in vivo, as further defined elsewhere herein. Alternatively, $EC_{50}$ can refer to the concentration or dose of compound that provokes a response halfway between the baseline and maximum response. The response can be measured in an in vitro or in vivo system as is convenient and appropriate for the biological response of interest. For example, the response can be measured in vitro using cultured cancer cells or in an ex vivo organ culture system with isolated cancer cells, e.g., pancreatic cancer cells, breast cancer cells, liver cancer cells, lung cancer cells, colorectal cancer cells, etc.). Alternatively, the response can be measured in vivo using an appropriate research model such as rodent, including mice and rats. The mouse or rat can be an inbred strain with phenotypic characteristics of interest such as, for example, cancer and/or aberrant cell growth. As appropriate, the response can be measured in a transgenic or knockout mouse or rat wherein a gene or genes has been introduced or knocked-out, as appropriate, to replicate a disease process.

As used herein, "$IC_{50}$," is intended to refer to the concentration or dose of a substance (e.g., a CT20 peptide or a disclosed composition comprising a CT20 peptide) that is required for 50% inhibition or diminution of a biological process, or component of a process, including a protein, subunit, organelle, ribonucleoprotein, etc. $IC_{50}$ also refers to the concentration or dose of a substance that is required for 50% inhibition or diminution in vivo, as further defined elsewhere herein. Alternatively, $IC_{50}$ also refers to the half maximal (50%) inhibitory concentration (IC) or inhibitory dose of a substance. The response can be measured in an in vitro or in vivo system as is convenient and appropriate for the biological response of interest. For example, the response can be measured in vitro using cultured cancer cells or in an ex vivo organ culture system with isolated cancer cells (e.g., breast cancer cells, pancreatic cancer cells, liver cancer cells, lung cancer cells, colorectal cancer cells, etc.). Alternatively, the response can be measured in vivo using an appropriate research model such as rodent, including mice and rats. The mouse or rat can be an inbred strain with phenotypic characteristics of interest such as, for example, cancer and/or aberrant cell growth. As appropriate, the response can be measured in a transgenic or knockout mouse or rat wherein a gene or genes has been introduced or knocked-out, as appropriate, to replicate a disease process.

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "cancer" refers to a proliferative disorder or disease caused or characterized by the proliferation of cells which have lost susceptibility to normal growth control. The term "cancer" includes tumors and any other proliferative disorders. Cancers of the same tissue type originate in the same tissue, and can be divided into different subtypes based on their biological characteristics. Cancer includes, but is not limited to, melanoma, leukemia, astrocytoma, glioblastoma, lymphoma, glioma, Hodgkin's lymphoma, and chronic lymphocyte leukemia. Cancer also includes, but is not limited to, cancer of the brain, bone, pancreas, lung, liver, breast, thyroid, ovary, uterus, testis, pituitary, kidney, stomach, esophagus, anus, and rectum.

As used herein, the term "metastasis" is meant to refer to the process in which cancer cells originating in one organ or part of the body, with or without transit by a body fluid, and relocate to another part of the body and continue to replicate. Metastasized cells can subsequently form tumors which may further metastasize. Metastasis thus refers to the spread of cancer, from the part of the body where it originally occurred, to other parts of the body.

The term "metastatic tumor" refers to a secondary tumor growing at the site different from the site of the cancer origin.

The term "circulating tumor cells" or "CTCs" refers to tumor cells found in circulation of a patient having a tumor. In some embodiments, the tumor is a solid tumor.

As used herein, the term "sensitizing" refers to an increased sensitivity of a cell or a subject to a treatment, such as a therapeutic treatment. The term "sensitizing" also refers to a reduction or decrease in the resistance of a cancer cell or a subject with cancer in responding to a therapeutic treatment. An increased sensitivity or a reduced sensitivity to a therapeutic treatment is measured according to a known method in the art for the particular treatment and methods including, but not limited to, cell proliferation assays and cell death assays. The sensitivity or resistance may also be measured in a subject by measuring the tumor size reduction over a period of time, such as, for example, every 1 to 3 to 6 month for a human subject and every 2 to 4 to 6 weeks for non-human subject (e.g., mouse or rat). The sensitivity of a cell or a subject to treatment can be measured or determined by comparing the sensitivity of a cell or a subject following administration of a CT20 peptide or a composition comprising an effective amount of a CT20 peptide to the sensitivity of a cell or subject that has not been administered a CT20 peptide or a composition comprising an effective amount of a CT20 peptide.

The terms "affinity reagent" refers to a reagent capable of specific binding to its target as defined herein.

In the present invention, "specific for" and "specificity" mean selective binding. Accordingly, an antibody that is specific for one antigen selectively binds that antigen and not other antigens or not other antigens lacking epitope look-alikes. The term "binding," and "specific binding" are used interchangeably to refer to the ability of a reagent to selectively bind its target. Typically, specificity is characterized by a dissociation constant of $10^4 M^{-1}$ to $10^{12} M^{-1}$. Empirical methods using appropriate controls may be employed to distinguish specific and non-specific binding in a particular case.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

An "increase" can refer to any change that results in a greater amount of a symptom, disease, composition, condition or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

The "fragments," whether attached to other sequences or not, can include insertions, deletions, substitutions, or other selected modifications of particular regions or specific amino acids residues, provided the activity of the fragment is not significantly altered or impaired compared to the nonmodified peptide or protein. These modifications can provide for some additional property, such as to remove or add amino acids capable of disulfide bonding, to increase its bio-longevity, to alter its secretory characteristics, etc. "Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels. "Inhibitors" of expression or of activity are used to refer to inhibitory molecules, respectively, identified using in vitro and in vivo assays for expression or activity of a described target protein, e.g., ligands, antagonists, and their homologs and mimetics. Inhibitors are agents that, e.g., inhibit expression or bind to, partially or totally block stimulation or protease activity, decrease, prevent, delay activation, inactivate, desensitize, or down regulate the activity of the described target protein, e.g., antagonists. A control sample (untreated with inhibitors) are assigned a relative activity value of 100%. Inhibition of a described target protein is achieved when the activity value relative to the control is about 80%, optionally 50% or 25, 10%, 5% or 1%.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

As used herein, the term "anti-cancer" or "anti-neoplastic" drug refers to one or more drugs that can be used in conjunction with a CT20 peptide or a composition comprising an effective amount of a CT20 peptide to treat cancer and/or aberrant cell growth. Examples of anti-cancer drugs or anti-neoplastic drugs include, but are not limited to, the following: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane;

atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

As used herein, radiosensitizers make a cancer cell more likely to be damaged. Radiosensitizers enhance the sensitivity of cancer cells and/or a tumor to ionizing radiation, thereby increasing the efficacy of radiotherapy. Examples of radiosensitizers include gemcitabine, 5-fluorouracil, pentoxifylline, and vinorelbine.

The majority of chemotherapeutic drugs can be divided in to: alkylating agents (e.g., cisplatin, carboplatin, oxaliplatin, mechloethamine, cyclophosphamide, chlorambucil), antimetabolites (e.g., azathioprine, mercaptopurine), anthracyclines, plant alkaloids and terpenoids (e.g., vinca alkaloids (e.g., vincristine, vinblastine, vinorelbine, vindesine, and podophyllotoxin) and taxanes (e.g., paclitaxel and docetaxel), topoisomerase inhibitors (e.g., irinotecan, topotecan, amsacrine, etoposide, etoposide phosphate, and teniposide), monoclonal antibodies (e.g., trastuzumab, cetuximab, rituximab, bevacizumab), other antitumour agents (e.g., dactinomycin), and hormonal therapy (e.g., steroids such as dexamethasone, finasteride, aromatase inhibitors, and gonadotropin-releasing hormone agonists).

Disclosed are the components to be used to prepare a composition of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed can be resorted to by those skilled in the art, and that such modifications and variations are considered to be within the scope of this invention as defined by the description and the appended claims.

Disclosed herein are cancer therapeutic compositions comprising a CT20 peptide. A CT20 peptide is a C-terminal Bax peptide, or a variant thereof. Bax is a 21 kD protein of 192 amino acids, comprised of nine alpha helices. Under non-apoptotic conditions, Bax predominantly resides in the cytosol, with a small percentage of the protein localized to the mitochondria (Boohaker et al., 2011). Bax peptides, Bax proteins, and Bax genes are known to those skilled in the art.

Disclosed herein is a composition for targeting CCT in cells comprising a CT20 peptide. The cells can be individual cells or cells that are on or in a subject. In an aspect, the cells can be eukaryotic or prokaryotic cells, including but not limited to bacteria and fungi. In an aspect, the cells can be in a subject. In an aspect, the cells can be on a surface, which can be inert or can be the surface of a subject. In an aspect, the cells are cancer cells or transformed cells. In an aspect, the cancer cells can comprise metastatic cancer cells. In an aspect, the cancer cells can comprise mesenchymal stem-like cancer cell. In an aspect, the cancer cell can be a cell from any type of cancer including, but not limited to, cancer of the head and neck cancer, esophagus, stomach, pancreas, kidney, bladder, bone, brain, and cervix. In an aspect, the cancer can be breast cancer. In an aspect, the cancer can be colorectal cancer. In an aspect, the cancer can be lung cancer. In an aspect, the cancer can be liver cancer. In an aspect, the cancer can be prostate cancer. In an aspect, the cancer can be melanoma. In an aspect, the cancer can be lymphoma. In an aspect, the cancer can be a drug resistant cancer. In an aspect, the cancer cell can be a drug resistant cancer cell. In an aspect, a disclosed composition comprising a CT20 peptide can be administered directly into a tumor. In an aspect, a disclosed composition comprising a CT20 peptide can be administered directly to the cancer cells. In an aspect, a disclosed composition induces death of cancer cells. In an aspect, noncancerous cells do not die.

In an aspect, binding CCT can comprise disruption or inhibition of one or more of the functions of CCT. In an aspect, disruption or inhibition of one or more of the functions of CCT results in accumulation of unfolded proteins, growth arrest, changes in cell morphology, loss of motility, and/or a combination thereof. In an aspect, the unfolded proteins can comprise actin and tubulin.

In an aspect, a disclosed composition for binding CCT in cells comprising a CT20 peptide can induce cell death. In an aspect, the cell death mimics necrosis. In an aspect, the cell death occurs independent of endogenous Bax activity. In an aspect, the cell death can occur independent of endogenous caspase activity. In an aspect, the cell death can be resistant to Bcl-2 over-expression.

In an aspect, a disclosed composition for binding CCT in cells comprising a CT20 peptide induces cell death, wherein (i) the cell death mimics necrosis, (ii) the cell death occurs independent of endogenous Bax activity, (iii) the cell death occurs independent of endogenous caspase activity, or (iv) the cell death is resistant to Bcl-2 over-expression, or (v) the cell death exhibits a combination thereof.

In an aspect, a disclosed CT20 peptide can comprise SEQ ID NO: 1, SEQ ID NO: 2, SEQ ID NO: 3, SEQ ID NO: 4, SEQ ID NO: 5, and/or SEQ ID NO: 6, or a combination of two or more of SEQ ID NOs: 1-6. For example, in an aspect, a disclosed CT20 peptide can be VTIFVAGVLTASLTIWKKMG (SEQ ID NO: 1). In an aspect, a disclosed CT20 peptide can be ASLTIWKKMG (SEQ ID NO: 2). In an aspect, a disclosed CT20 peptide can be VTIFVAGVLT (SEQ ID NO: 3). In an aspect, a disclosed CT20 peptide can be VTIFVAG (SEQ ID NO: 4). In an aspect, a disclosed CT20 peptide can be IFVAG (SEQ ID NO: 5). In an aspect, a disclosed CT20 peptide can be IWKKMG (SEQ ID NO: 6). In an aspect, a disclosed composition for binding CCT in cells can comprise one or more CT20 peptides, wherein the one or more CT20 peptides can comprise SEQ ID NO:1, SEQ NO: 2, SEQ ID NO: 3, SEQ ID NO: 4, SEQ ID NO: 5, or SEQ ID NO: 6, or a combination thereof.

In an aspect, a CT20 peptide of a disclosed composition for binding CCT in cells can be delivered via nanoparticles.

As used herein, "nanoparticle" may refer to any nanostructure capable of delivering pharmaceutical compounds, nucleic acids, peptides, or proteins. Nanoparticles may be naturally or synthetically derived. In some aspects, "nanoparticles" may include plasma vesicle particles, liposomes, exosomes, protein-based particles, albumin particles, nucleic acid-based particles, natural polymers, synthetic polymers, hydrogels, dendrimers, silicon-based materials, metal-based materials, carbon-based materials, calcium-based materials, or a combination of any of the above.

In an aspect, the nanoparticles are hyperbranched polyester polymeric nanoparticles. In an aspect, the nanoparticles are polymeric nanoparticles. In an aspect, the nanoparticles can comprise a targeting moiety. In an aspect, the targeting moiety can comprise a targeting ligand. In an aspect, the targeting ligand can be for a receptor expressed by cancer cells. In an aspect, the receptor expressed by cancer cells can be an EGF, HER2, or folate receptor. In an aspect, the receptor expressed by cancer cells can be any receptor known to the skilled person to be expressed by cancer cells. In some embodiments, the receptor may be know to be expressed by colon cancer cells, prostate cancer cells, lung cancer cells, liver cancer cells, and/or breast cancer cells.

In an aspect, the targeting ligand is a folate compound. In an aspect, the targeting ligand is a glutamate compound. In an aspect, the targeting ligand is a polyglutamated folate compound. In an aspect, the targeting ligand is glutamate azido urea. In an aspect, the targeting ligand is folate azido urea. In an aspect, the targeting ligand is glutamate azido urea. In an aspect, the targeting ligand is a bifunctional glutamate-folate hybridized compound. In an aspect, the targeting ligand is at high density. In an aspect, the targeting ligand is at low density. In an aspect, the targeting ligand is at high valency. In an aspect, the targeting ligand is at low valency. In an aspect, the targeting ligand is a substrate for a solid tumor-specific cell protein. In an aspect, the solid tumor-specific cell protein is prostate specific membrane antigen (PSMA).

In an aspect, a disclosed composition for binding CCT in cells comprising a CT20 peptide can comprise one or more therapeutic agents. In an aspect, the one or more therapeutic agents are selected from one or more antimicrobial compounds, one or more antibacterial compounds, one or more antifungal compounds, or one or more anti-cancer agents, or a combination thereof. In an aspect, a disclosed composition for binding CCT in cells comprising a CT20 peptide can comprise one or more anti-cancer agents. In an aspect, the one or more anti-cancer agents can comprise cisplatin. In an aspect, the one or more anti-cancer drugs induce apoptosis. In an aspect, a disclosed composition comprising a CT20 peptide can comprise one or more chemotherapeutic drugs. In an aspect, a disclosed composition comprising a CT20 peptide can comprise one or more radiosensitizers. In an aspect, a disclosed composition comprising a CT20 peptide can comprise a pharmaceutically acceptable carrier.

In an aspect, a disclosed composition for binding CCT in cells comprising a CT20 peptide can comprise (i) one or more therapeutic agents, (ii) one or more anti-cancer agents, (iii) one or more chemotherapeutic drugs, and (iv) one or more radiosensitizers. In an aspect, a disclosed composition can comprise one or more anti-cancer agents and one or more chemotherapeutic drugs. In an aspect, a disclosed composition can comprise one or more anti-cancer agents and one or more radiosensitizers. In an aspect, a disclosed composition can comprise one or more chemotherapeutic agents and one or more radiosensitizers.

In an aspect, a disclosed composition for binding CTT in cells can be administered systemically to a subject. In an aspect, the subject can be a mammal. In an aspect, the mammal can be a primate. In an aspect, the mammal can be a human. In an aspect, the human can be a patient.

In an aspect, a disclosed composition for binding CTT in cells comprising a CT20 peptide can be administered to a subject repeatedly. In an aspect, a disclosed composition can be administered to the subject at least two times. In an aspect, a disclosed composition can be administered to the subject two or more times. In an aspect, a disclosed composition can be administered at routine or regular intervals. For example, in an aspect, a disclosed composition can be administered to the subject one time per day, or two times per day, or three or more times per day. In an aspect, a disclosed composition can be administered to the subject daily, or one time per week, or two times per week, or three or more times per week, etc. In an aspect, a disclosed composition can be administered to the subject weekly, or every other week, or every third week, or every fourth week, etc. In an aspect, a disclosed composition can be administered to the subject monthly, or every other month, or every third month, or every fourth month, etc. In an aspect, the repeated administration of a disclosed composition occurs over a pre-determined or definite duration of time. In an aspect, the repeated administration of a disclosed composition occurs over an indefinite period of time.

In an aspect, following the administration of a disclosed composition for binding CCT in cells comprising a CT20 peptide, the cells are sensitized to treatment. In an aspect, following the administration of a disclosed composition comprising a CT20 peptide, a subject can be sensitized to treatment. In an aspect, an increased sensitivity or a reduced sensitivity to a treatment, such as a therapeutic treatment, can be measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a disclosed composition comprising a CT20 peptide to the sensitivity of a cell or subject that has not been administered a disclosed composition comprising a CT20 peptide.

For example, in an aspect, following the administration of a disclosed composition for binding CCT in cells comprising a CT20 peptide, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a disclosed composition comprising a CT20 peptide. In an aspect, following the administration of a disclosed composition comprising a CT20 peptide the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a disclosed composition comprising a CT20 peptide. The determination of a cell's or a subject's sensitivity or resistance can be routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a subject can be modified based on data regarding a cell's or a subject's sensitivity or resistance to treatment. For example, in an aspect, the treatment can modified by changing the dose of a disclosed compositions, the route of administration of a disclosed compositions, the frequency of administration of a disclosed composition, etc.

Disclosed herein is a composition for binding CCT in cells comprising a CT20 peptide and one or more anti-cancer drugs.

Disclosed herein is a composition for killing cells comprising a CT20 peptide. The cells can be individual cells, or cells that are on or in a subject. In an aspect, the cells are eukaryotic or prokaryotic cells, including but not limited to bacteria and fungi. In an aspect, the cells are in a subject. In an aspect, the cells are on a surface, which can be inert or can be the surface of a subject. In an aspect, the cells are cancer cells or transformed cells. In an aspect, the cancer cells can comprise metastatic cancer cells. In an aspect, the cancer cells can comprise mesenchymal stem-like cancer cell. In an aspect, the cancer cell can be a cell from any type of cancer including, but not limited to, cancer of the head and neck cancer, esophagus, stomach, pancreas, kidney, bladder, bone, brain, and cervix. In an aspect, the cancer can be breast cancer. In an aspect, the cancer can be colorectal cancer. In an aspect, the cancer can be lung cancer. In an aspect, the cancer can be liver cancer. In an aspect, the cancer can be prostate cancer. In an aspect, the cancer can be melanoma. In an aspect, the cancer can be lymphoma. In an aspect, the cancer can be a drug resistant cancer. In an aspect, the cancer cell can be a drug resistant cancer cell. In an aspect, a disclosed composition comprising a CT20 peptide can be administered directly into a tumor. In an aspect, a disclosed composition comprising a CT20 peptide can be administered directly to the cancer cells. In an aspect, a disclosed composition induces death of cancer cells. In an aspect, non-cancerous cells do not die.

In an aspect, a disclosed composition for killing cells comprising a CT20 peptide induces cell death. In an aspect, the cell death mimics necrosis. In an aspect, the cell death occurs independent of endogenous Bax activity. In an aspect, the cell death occurs independent of endogenous caspase activity. In an aspect, the cell death can be resistant to Bcl-2 over-expression.

In an aspect, a disclosed composition for killing cells comprising a CT20 peptide induces cell death, wherein (i) the cell death mimics necrosis, (ii) the cell death occurs independent of endogenous Bax activity, (iii) the cell death occurs independent of endogenous caspase activity, or (iv) the cell death can be resistant to Bcl-2 over-expression, or (v) the cell death exhibits a combination thereof.

In an aspect, a disclosed CT20 peptide can comprise SEQ ID NO: 1, SEQ ID NO: 2, SEQ ID NO: 3, SEQ ID NO: 4, SEQ ID NO: 5, and/or SEQ ID NO: 6, or a combination of two or more of SEQ ID NOs: 1-6. For example, in an aspect, a disclosed CT20 peptide can be VTIFVAGVL-TASLTIWKKMG (SEQ ID NO: 1). In an aspect, a disclosed CT20 peptide can be ASLTIWKKMG (SEQ ID NO: 2). In an aspect, a disclosed CT20 peptide can be VTIFVAGVLT (SEQ ID NO: 3). In an aspect, a disclosed CT20 peptide can be VTIFVAG (SEQ ID NO: 4). In an aspect, a disclosed CT20 peptide can be IFVAG (SEQ ID NO: 5). In an aspect, a disclosed CT20 peptide can be IWKKMG (SEQ ID NO: 6). In an aspect, a disclosed composition for binding CCT in cells can comprise one or more CT20 peptides, wherein the one or more CT20 peptides can comprise SEQ ID NO:1, SEQ NO: 2, SEQ ID NO: 3, SEQ ID NO: 4, SEQ ID NO: 5, or SEQ ID NO: 6.

In an aspect, a CT20 peptide of a disclosed composition for killing cells can be delivered via nanoparticles. As used herein, "nanoparticle" may refer to any nanostructure capable of delivering pharmaceutical compounds, nucleic acids, peptides, or proteins. Nanoparticles may be naturally or synthetically derived. In some aspects, "nanoparticles" may include plasma vesicle particles, liposomes, exosomes, protein-based particles, albumin particles, nucleic acid-based particles, natural polymers, synthetic polymers, hydrogels, dendrimers, silicon-based materials, metal-based materials, carbon-based materials, calcium-based materials, or a combination of any of the above.

In an aspect, the nanoparticles are hyperbranched polyester polymeric nanoparticles. In an aspect, the nanoparticles are polymeric nanoparticles. In an aspect, the nanoparticles can comprise a targeting moiety. In an aspect, the targeting moiety can comprise a ligand for a receptor expressed by cancer cells. In an aspect, the receptor expressed by cancer cells can be an EGF, HER2, or folate receptor. In an aspect, the receptor expressed by cancer cells can be any receptor known to the skilled person to be expressed by cancer cells.

In an aspect, the targeting ligand is a folate compound. In an aspect, the targeting ligand is a glutamate compound. In an aspect, the targeting ligand is a polyglutamated folate compound. In an aspect, the targeting ligand is glutamate azido urea. In an aspect, the targeting ligand is folate azido urea. In an aspect, the targeting ligand is glutamate azido urea. In an aspect, the targeting ligand is a bifunctional glutamate-folate hybridized compound. In an aspect, the targeting ligand is at high density. In an aspect, the targeting ligand is at low density. In an aspect, the targeting ligand is at high valency. In an aspect, the targeting ligand is at low valency. In an aspect, the targeting ligand is a substrate for a solid tumor-specific cell protein. In an aspect, the solid tumor-specific cell protein is prostate specific membrane antigen (PSMA).

In an aspect, a disclosed composition for killing cells comprising a CT20 peptide can comprise one or more therapeutic agents. In an aspect, the one or more therapeutic agents are selected from one or more antimicrobial compounds, one or more antibacterial compounds, one or more antifungal compounds, or one or more anti-cancer agents, or a combination thereof. In an aspect, a disclosed composition for binding CCT in cells comprising a CT20 peptide can comprise one or more anti-cancer agents. In an aspect, the one or more anti-cancer agents can comprise cisplatin. In an aspect, the one or more anti-cancer drugs induce apoptosis. In an aspect, a disclosed composition comprising a CT20 peptide can comprise one or more chemotherapeutic drugs. In an aspect, a disclosed composition comprising a CT20 peptide can comprise one or more radiosensitizers. In an aspect, a disclosed composition comprising a CT20 peptide can comprise a pharmaceutically acceptable carrier.

In an aspect, a disclosed composition for killing cells comprising a CT20 peptide can comprise (i) one or more therapeutic agents, (ii) one or more anti-cancer agents, (iii) one or more chemotherapeutic drugs, and (iv) one or more radiosensitizers. In an aspect, a disclosed composition can comprise one or more anti-cancer agents and one or more chemotherapeutic drugs. In an aspect, a disclosed composition can comprise one or more anti-cancer agents and one or more radiosensitizers. In an aspect, a disclosed composition can comprise one or more chemotherapeutic agents and one or more radiosensitizers.

In an aspect, a disclosed composition for killing cells can be administered systemically to a subject. In an aspect, the subject can be a mammal. In an aspect, the mammal can be a primate. In an aspect, the mammal can be a human. In an aspect, the human can be a patient.

In an aspect, a disclosed composition for killing cells comprising a CT20 peptide can be administered to a subject repeatedly. In an aspect, a disclosed composition can be administered to a subject at least two times. In an aspect, a disclosed composition can be administered to the subject two or more times. In an aspect, a disclosed composition can be administered at routine or regular intervals. For example, in an aspect, a disclosed composition can be administered to the subject one time per day, or two times per day, or three or more times per day. In an aspect, a disclosed composition can be administered to the subject daily, or one time per week, or two times per week, or three or more times per week, etc. In an aspect, a disclosed composition can be administered to the subject weekly, or every other week, or every third week, or every fourth week, etc. In an aspect, a disclosed composition can be administered to the subject monthly, or every other month, or every third month, or every fourth month, etc. In an aspect, the repeated administration of a disclosed composition occurs over a predetermined or definite duration of time. In an aspect, the repeated administration of a disclosed composition occurs over an indefinite period of time.

In an aspect, following the administration of a disclosed composition for killing cells comprising a CT20 peptide, the cells are sensitized to treatment. In an aspect, following the administration of a disclosed composition for killing cells comprising a CT20 peptide, a subject can be sensitized to treatment. In an aspect, an increased sensitivity or a reduced sensitivity to a treatment, such as a therapeutic treatment, can be measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a disclosed composition for killing cells comprising a CT20 peptide to the sensitivity of a cell or subject that has not been administered a disclosed composition for killing cells comprising a CT20 peptide.

For example, in an aspect, following the administration of a disclosed composition for killing cells comprising a CT20 peptide, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a disclosed composition for killing cells comprising a CT20 peptide. In an aspect, following the administration of a disclosed composition for killing cells comprising a CT20 peptide, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a disclosed composition for killing cells comprising a CT20 peptide. The determination of a cell's or a subject's sensitivity or resistance is routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a subject can be modified based on data regarding a cell's or a subject's sensitivity or resistance to treatment. For example, in an aspect, the treatment can modified by changing the dose of a disclosed compositions, the route of administration of a disclosed compositions, the frequency of administration of a disclosed composition, etc.

Disclosed herein is a composition for killing cells comprising a CT20 peptide and one or more anti-cancer drugs.

In an aspect, the disclosed embodiments relate to pharmaceutical compositions comprising a disclosed composition for binding CCT in cells. In an aspect, the disclosed embodiments relate to pharmaceutical compositions comprising a disclosed composition for killing cells. In an aspect, the disclosed compositions for binding CCT in cells and for killing cells can comprise a CT20 peptide. In an aspect, a pharmaceutical composition can be provided comprising a therapeutically effective amount of at least one disclosed composition and a pharmaceutically acceptable carrier.

Disclosed herein is a method of identifying a cellular target, comprising: contacting a cellular sample with a CT20 peptide, and isolating a candidate cellular target. In an aspect, the CT20 peptide can comprise a biotin label. In an aspect, the candidate cellular target can be bound to the biotin-labeled CT20 peptide. In an aspect, the candidate cellular target can be CCT.

In an aspect, a disclosed method of identifying a cellular target can comprise contacting to a cellular sample a CT20 peptide, wherein the cellular sample can comprise a lysate of cancer cells. The cells can be individual cells, or cells that are on or in a subject. In an aspect, the cells are eukaryotic or prokaryotic cells, including but not limited to bacteria and fungi. In an aspect, the cells are in a subject. In an aspect, the cells are on a surface, which can be inert or can be the surface of a subject. In an aspect, the cellular sample can comprise normal cells. In an aspect, the cellular sample can comprise a lysate of cancer cells. In an aspect, the cancer cells can comprise metastatic cancer cells. In an aspect, the cancer cells can comprise breast cancer cells. In an aspect, the cancer cells can comprise lung cancer cells. In an aspect, the cancer cells can comprise prostrate cancer cells. In an aspect, the cancer cells can comprise mesenchymal stem-like cancer cell. In an aspect, the cancer cell can be a cell from any type of cancer including, but not limited to, cancer of the head and neck cancer, esophagus, stomach, pancreas, kidney, bladder, bone, brain, and cervix. In an aspect, the cancer can be breast cancer. In an aspect, the cancer can be colorectal cancer. In an aspect, the cancer can be lung cancer. In an aspect, the cancer can be a drug resistant cancer. In an aspect, the cancer cell can be a drug resistant cancer cell. In an aspect, a disclosed composition comprising a CT20 peptide can be administered directly into a tumor. In an aspect, a disclosed composition comprising a CT20 peptide can be administered directly to the cancer cells. In an aspect, a disclosed composition induces death of cancer cells. In an aspect, noncancerous cells do not die.

In an aspect, a disclosed method of identifying a cellular target can comprise isolating a candidate cellular target, wherein isolating the candidate cellular target can comprise using streptavidin beads.

In an aspect, a disclosed CT20 peptide can comprise SEQ ID NO: 1, SEQ ID NO: 2, SEQ ID NO: 3, SEQ ID NO: 4, SEQ ID NO: 5, and/or SEQ ID NO: 6, or a combination of two or more of SEQ ID NOs: 1-6. For example, in an aspect, a disclosed CT20 peptide can be VTIFVAGVL-TASLTIWKKMG (SEQ ID NO: 1). In an aspect, a disclosed CT20 peptide can be ASLTIWKKMG (SEQ ID NO: 2). In an aspect, a disclosed CT20 peptide can be VTIFVAGVLT (SEQ ID NO: 3). In an aspect, a disclosed CT20 peptide can be VTIFVAG (SEQ ID NO: 4). In an aspect, a disclosed CT20 peptide can be IFVAG (SEQ ID NO: 5). In an aspect, a disclosed CT20 peptide can be IWKKMG (SEQ ID NO: 6). In an aspect, a disclosed composition for binding CCT in cells can comprise one or more CT20 peptides, wherein the one or more CT20 peptides can comprise SEQ ID NO:1, SEQ NO: 2, SEQ ID NO: 3, SEQ ID NO: 4, SEQ ID NO: 5, or SEQ ID NO: 6.

In an aspect, a disclosed CT20 peptide can be delivered via nanoparticles. As used herein, "nanoparticle" may refer to any nanostructure capable of delivering pharmaceutical compounds, nucleic acids, peptides, or proteins. Nanoparticles may be naturally or synthetically derived. In some aspects, "nanoparticles" may include plasma vesicle particles, liposomes, exosomes, protein-based particles, albumin particles, nucleic acid-based particles, natural polymers, synthetic polymers, hydrogels, dendrimers, silicon-based materials, metal-based materials, carbon-based materials, calcium-based materials, or a combination of any of the above.

In an aspect, the nanoparticles are polymeric nanoparticles. In an aspect, the nanoparticles are hyperbranched polyester polymeric nanoparticles. In an aspect, the nanoparticles can comprise a targeting moiety. In an aspect, the targeting moiety can comprise a ligand for a receptor expressed by cancer cells. In an aspect, the receptor expressed by cancer cells can be an EGF, HER2, or folate receptor. In an aspect, the receptor expressed by cancer cells can be any receptor known to the skilled person to be expressed by cancer cells.

In an aspect, the targeting ligand is a folate compound. In an aspect, the targeting ligand is a glutamate compound. In an aspect, the targeting ligand is a polyglutamated folate compound. In an aspect, the targeting ligand is glutamate azido urea. In an aspect, the targeting ligand is folate azido urea. In an aspect, the targeting ligand is glutamate azido urea. In an aspect, the targeting ligand is a bifunctional glutamate-folate hybridized compound. In an aspect, the targeting ligand is at high density. In an aspect, the targeting ligand is at low density. In an aspect, the targeting ligand is at high valency. In an aspect, the targeting ligand is at low valency. In an aspect, the targeting ligand is a substrate for a solid tumor-specific cell protein. In an aspect, the solid tumor-specific cell protein is prostate specific membrane antigen (PSMA).

In an aspect, a disclosed method of identifying a cellular target can comprise characterizing the candidate cellular target. In an aspect, characterizing the candidate cellular target can comprise mass spectrometry, immunoblotting, or both. In an aspect, characterizing the candidate cellular target can comprise mass spectrometry. In an aspect, characterizing the candidate cellular target can comprise immunoblotting. In an aspect, characterizing the candidate cellular target can comprise both mass spectrometry and immunoblotting.

Disclosed herein are methods of inhibiting replication of cancer cells. In an aspect, disclosed herein is a method of inhibiting replication of cancer cells, the method comprising administering to at least one cancer cell an effective amount of a composition comprising a CT20 peptide. The cells can be individual cells, or cells that are on or in a subject. In an aspect, the cells are eukaryotic or prokaryotic cells, including but not limited to bacteria and fungi. In an aspect, the cells are in a subject. In an aspect, the cells are on a surface, which can be inert or can be the surface of a subject. In an aspect, the cancer cells can comprise metastatic cancer cells. In an aspect, the cancer cells can comprise mesenchymal stem-like cancer cell. In an aspect, the cancer cell can comprise a breast cancer cell. In an aspect, the cancer cell can comprise a lung cancer cell. In an aspect, the cancer cell can comprise a prostrate cancer cell. In an aspect, the cancer cell can be a cell from any type of cancer including, but not limited to, cancer of the head and neck cancer, esophagus, stomach, pancreas, kidney, bladder, bone, brain, and cervix. In an aspect, the cancer can be breast cancer. In an aspect, the cancer can be colorectal cancer. In an aspect, the cancer can be lung cancer. In an aspect, the cancer can be liver cancer. In an aspect, the cancer can be prostate cancer. In an aspect, the cancer can be melanoma. In an aspect, the cancer can be lymphoma. In an aspect, the cancer cell can be a drug resistant cancer cell. In an aspect, a disclosed composition comprising a CT20 peptide can be administered directly into a tumor. In an aspect, a disclosed composition comprising a CT20 peptide can be administered directly to the cancer cells. In an aspect, a disclosed composition induces death of cancer cells. In an aspect, noncancerous cells do not die.

In an aspect, the CT20 peptide of a disclosed method of inhibiting replication of cancer cells, the CT20 peptide targets chaperonin containing TCP (CTT). In an aspect, binding CCT can comprise disruption or inhibition of one or more of the functions of CCT. In an aspect, disruption or inhibition of one or more of the functions of CCT results in accumulation of unfolded proteins, growth arrest, changes in cell morphology, loss of motility, and/or a combination thereof. In an aspect, the unfolded proteins can comprise actin and tubulin. In an aspect, the CT20 peptide disrupts the cytoskeleton.

In an aspect of a disclosed method of inhibiting replication of cancer cells, the cancer cells are sensitized to treatment. In an aspect, an increased sensitivity or a reduced sensitivity to a treatment, such as a therapeutic treatment, can be measured according to one or more methods as known in the art for the particular treatment. In an aspect, methods of measuring sensitivity to a treatment include, but not limited to, cell proliferation assays and cell death assays. In an aspect, the sensitivity of a cell to treatment can be measured or determined by comparing the sensitivity of a cell following administration of a CT20 peptide or a composition comprising a CT20 peptide to the sensitivity of a cell that has not been administered a CT20 peptide or a composition comprising a CT20 peptide.

For example, in an aspect, following the administration of a CT20 peptide or a composition comprising a CT20 peptide, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a CT20 peptide or a composition comprising a CT20 peptide. In an aspect, following the administration of a CT20 peptide or a composition comprising a CT20 peptide, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a CT20 peptide or a composition comprising a CT20 peptide. The determination of a cell's sensitivity or resistance can be routine in the art and within the skill of an ordinary clinician and/or researcher.

In an aspect, the determination of a cell's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than periodic times. In an aspect, treatment for a subject can be modified based on data regarding a cell's or a subject's sensitivity or resistance to treatment.

In an aspect, a disclosed method of inhibiting replication of cancer cells can comprise repeating the administration of a CT20 peptide or a composition comprising an effective amount of a CT20 peptide. In an aspect, a CT20 peptide or a composition comprising an effective amount of a CT20 peptide can be administered to the subject at least two times. In an aspect, a CT20 peptide or a composition comprising an effective amount of a CT20 peptide can be administered to the subject two or more times. In an aspect, a CT20 peptide or a composition comprising an effective amount of a CT20 peptide can be administered at routine or regular intervals. For example, in an aspect, a CT20 peptide or a composition comprising an effective amount of a CT20 peptide can be administered to the subject one time per day, or two times per day, or three or more times per day. In an aspect, a CT20 peptide or a composition comprising an effective amount of a CT20 peptide can be administered to the subject daily, or one time per week, or two times per week, or three or more times per week, etc. In an aspect, a CT20 peptide or a composition comprising an effective amount of a CT20 peptide can be administered to the subject weekly, or every other week, or every third week, or every fourth week, etc. In an aspect, a CT20 peptide or a composition comprising an effective amount of a CT20 peptide can be administered to the subject monthly, or every other month, or every third month, or every fourth month, etc. In an aspect, the repeated administration of a CT20 peptide or a composition comprising an effective amount of a CT20 peptide occurs over a pre-determined or definite duration of time. In an aspect, the repeated administration of a CT20 peptide or a composition comprising an effective amount of a CT20 peptide occurs over an indefinite period of time.

In an aspect, a disclosed method of inhibiting replication of cancer cells can comprise inducing death of the at least one cancer cell. In an aspect, the cell death mimics necrosis. In an aspect, cell death occurs independent of endogenous Bax activity. In an aspect, cell death occurs independent of endogenous caspase activity. In an aspect, cell death can be resistant to Bcl-2 over-expression. In an aspect, a disclosed method of killing cancer cells induces cell death, wherein (i) cell death mimics necrosis, (ii) cell death occurs independent of endogenous Bax activity, (iii) cell death occurs independent of endogenous caspase activity, or (iv) cell death can be resistant to Bcl-2 over-expression, or (v) cell death exhibits a combination thereof.

In an aspect, a CT20 peptide of a disclosed method of inhibiting replication of cancer cells can comprise SEQ ID NO: 1, SEQ ID NO: 2, SEQ ID NO: 3, SEQ ID NO: 4, SEQ ID NO: 5, and/or SEQ ID NO: 6, or a combination of two or more of SEQ ID NOs: 1-6. For example, in an aspect, a CT20 peptide of a disclosed method can be VTIFVAGVL-TASLTIWKKMG (SEQ ID NO: 1). In an aspect, a CT20 peptide of a disclosed method can be ASLTIWKKMG (SEQ ID NO: 2). In an aspect, a CT20 peptide of a disclosed method can be VTIFVAGVLT (SEQ ID NO: 3). In an aspect, a CT20 peptide of a disclosed method can be VTIFVAG (SEQ ID NO: 4). In an aspect, a CT20 peptide of a disclosed method can be IFVAG (SEQ ID NO: 5). In an aspect, a CT20 peptide of a disclosed method can be IWKKMG (SEQ ID NO: 6). In an aspect, a disclosed method for inhibiting replication of cancer cells can comprise one or more CT20 peptides, wherein the one or more CT20 peptides can comprise SEQ ID NO:1, SEQ NO: 2, SEQ ID NO: 3, SEQ ID NO: 4, SEQ ID NO: 5, or SEQ ID NO: 6.

In an aspect, a CT20 peptide of the disclosed method of inhibiting replication of cancer cells can comprise a biotin label. In an aspect, a CT20 peptide of a disclosed method can be delivered via nanoparticles. As used herein, "nanoparticle" may refer to any nanostructure capable of delivering pharmaceutical compounds, nucleic acids, peptides, or proteins. Nanoparticles may be naturally or synthetically derived. In some aspects, "nanoparticles" may include plasma vesicle particles, liposomes, exosomes, protein-based particles, albumin particles, nucleic acid-based particles, natural polymers, synthetic polymers, hydrogels, dendrimers, silicon-based materials, metal-based materials, carbon-based materials, calcium-based materials, or a combination of any of the above.

In an aspect, the nanoparticles are polymeric nanoparticles. In an aspect, the nanoparticles are hyperbranched polyester polymeric nanoparticles. In an aspect, the nanoparticles can comprise a targeting moiety. In an aspect, the targeting moiety can comprise a ligand for a receptor expressed by cancer cells. In an aspect, the receptor expressed by cancer cells can be an EGF, HER2, or folate receptor. In an aspect, the receptor expressed by cancer cells can be any receptor known to the skilled person to be expressed by cancer cells.

In an aspect, the targeting ligand is a folate compound. In an aspect, the targeting ligand is a glutamate compound. In an aspect, the targeting ligand is a polyglutamated folate compound. In an aspect, the targeting ligand is glutamate azido urea. In an aspect, the targeting ligand is folate azido urea. In an aspect, the targeting ligand is glutamate azido urea. In an aspect, the targeting ligand is a bifunctional glutamate-folate hybridized compound. In an aspect, the targeting ligand is at high density. In an aspect, the targeting ligand is at low density. In an aspect, the targeting ligand is at high valency. In an aspect, the targeting ligand is at low valency. In an aspect, the targeting ligand is a substrate for a solid tumor-specific cell protein. In an aspect, the solid tumor-specific cell protein is prostate specific membrane antigen (PSMA).

In an aspect, a disclosed method of inhibiting replication of cancer cells comprising administering a CT20 peptide or a composition comprising an effective amount of a CT20 peptide can comprise administering one or more anti-cancer drugs. In an aspect, the one or more anti-cancer drugs can comprise cisplatin. In an aspect, the one or more anti-cancer drugs induce apoptosis. In an aspect, a disclosed method of inhibiting replication of cancer cells comprising administering a CT20 peptide or a composition comprising an effective amount of a CT20 peptide can comprise administering one or more chemotherapeutic drugs. In an aspect, a disclosed method of inhibiting replication of cancer cells comprising administering a CT20 peptide or a composition comprising an effective amount of a CT20 peptide can comprise administering one or more radiosensitizers.

In an aspect, a disclosed composition for killing cells comprising a CT20 peptide can comprise (i) one or more therapeutic agents, (ii) one or more anti-cancer agents, (iii) one or more chemotherapeutic drugs, and (iv) one or more radiosensitizers. In an aspect, a disclosed composition can comprise one or more anti-cancer agents and one or more chemotherapeutic drugs. In an aspect, a disclosed composition can comprise one or more anti-cancer agents and one or more radiosensitizers. In an aspect, a disclosed composition can comprise one or more chemotherapeutic agents and one or more radiosensitizers.

Disclosed herein are methods of inhibiting replication of cancer cells in a subject. In an aspect, disclosed herein can be a method of inhibiting replication of cancer cells in a subject, the method comprising administering to a subject an effective amount of a composition comprising a CT20 peptide. The cells can be individual cells, or cells that are on or in a subject. In an aspect, the cells are eukaryotic or prokaryotic cells, including but not limited to bacteria and fungi. In an aspect, the cells are in a subject. In an aspect, the cells are on a surface, which can be inert or can be the surface of a subject. In an aspect, the cells are cancer cells or transformed cells. In an aspect, the cancer cells can comprise breast cancer cells. In an aspect, the cancer cells can comprise lung cancer cells. In an aspect, the cancer cells can comprise prostrate cancer cells. In an aspect, the cancer cells can comprise metastatic cancer cells. In an aspect, the cancer cells can comprise mesenchymal stem-like cancer cell. In an aspect, the cancer cell can be a cell from any type of cancer including, but not limited to, cancer of the head and neck cancer, esophagus, stomach, pancreas, kidney, bladder, bone, brain, and cervix. In an aspect, the cancer can be breast cancer. In an aspect, the cancer can be colorectal cancer. In an aspect, the cancer can be lung cancer. In an aspect, the cancer can be a drug resistant cancer. In an aspect, the cancer cell can be a drug resistant cancer cell. In an aspect, a disclosed composition comprising a CT20 peptide can be administered directly into a tumor. In an aspect, a disclosed composition comprising a CT20 peptide can be administered directly to the cancer cells. In an aspect, a disclosed composition induces death of cancer cells. In an aspect, noncancerous cells do not die. In an aspect, a CT20 peptide of a disclosed method of inhibiting replication of cancer cells in a subject targets chaperonin containing TCP (CCT). In an aspect, binding CCT can comprise disruption or inhibition of one or more of the functions of CCT. In an aspect, disruption or inhibition of one or more of the functions of CCT results in accumulation of unfolded proteins, growth arrest, changes in cell morphology, loss of motility, and/or a combination thereof. In an aspect, the unfolded proteins can comprise actin and tubulin.

In an aspect of a disclosed method of inhibiting replication of cancer cells in a subject, the cancer cells are sensitized to treatment. In an aspect of a disclosed method of inhibiting replication of cancer cells in a subject, the subject can be sensitized to treatment. In an aspect, an increased sensitivity or a reduced sensitivity to a treatment, such as a therapeutic treatment, can be measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a CT20 peptide or a composition comprising a CT20 peptide to the sensitivity of a cell or subject that has not been administered a CT20 peptide or a composition comprising a CT20 peptide.

For example, in an aspect, following the administration of a CT20 peptide or a composition comprising a CT20 peptide, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a CT20 peptide or a composition comprising a CT20 peptide. In an aspect, following the administration of a CT20 peptide or a composition comprising a CT20 peptide, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a CT20 peptide or a composition comprising a CT20 peptide. The determination of a cell's or a subject's sensitivity or resistance can be routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than periodic times. In an aspect, treatment for a subject can be modified based on data regarding a cell's or a subject's sensitivity or resistance to treatment.

In an aspect, a disclosed method of inhibiting replication of cancer cells in a subject can comprise repeating the administration of a CT20 peptide or a composition comprising an effective amount of a CT20 peptide. In an aspect, a CT20 peptide or a composition comprising an effective amount of a CT20 peptide can be administered systemically to the subject. In an aspect, a CT20 peptide or a composition comprising an effective amount of a CT20 peptide can be administered to the subject at least two times. In an aspect, a CT20 peptide or a composition comprising an effective amount of a CT20 peptide can be administered to the subject two or more times. In an aspect, a CT20 peptide or a composition comprising an effective amount of a CT20 peptide can be administered at routine or regular intervals. For example, in an aspect, a CT20 peptide or a composition comprising an effective amount of a CT20 peptide can be administered to the subject one time per day, or two times per day, or three or more times per day. In an aspect, a CT20 peptide or a composition comprising an effective amount of a CT20 peptide can be administered to the subject daily, or one time per week, or two times per week, or three or more times per week, etc. In an aspect, a CT20 peptide or a composition comprising an effective amount of a CT20 peptide can be administered to the subject weekly, or every other week, or every third week, or every fourth week, etc. In an aspect, a CT20 peptide or a composition comprising an effective amount of a CT20 peptide can be administered to the subject monthly, or every other month, or every third month, or every fourth month, etc. In an aspect, the repeated administration of a CT20 peptide or a composition comprising an effective amount of a CT20 peptide occurs over a pre-determined or definite duration of time. In an aspect, the repeated administration of a CT20 peptide or a composition comprising an effective amount of a CT20 peptide occurs over an indefinite period of time.

In an aspect, a disclosed method of inhibiting replication of cancer cells in a subject can comprise inducing death of cancer cells. In an aspect, noncancerous cells do not die. In an aspect, cell death mimics necrosis. In an aspect, cell death occurs independent of endogenous Bax activity. In an aspect, cell death occurs independent of endogenous caspase activity. In an aspect, cell death can be resistant to Bcl-2 over-expression. In an aspect, a disclosed method of killing cancer cells induces cell death, wherein (i) cell death mimics necrosis, (ii) cell death occurs independent of endogenous Bax activity, (iii) cell death occurs independent of endogenous caspase activity, or (iv) cell death can be resistant to Bcl-2 over-expression, or (v) cell death exhibits a combination thereof.

In an aspect, a CT20 peptide of a disclosed method of inhibiting replication of cancer cells in a subject can comprise SEQ ID NO: 1, SEQ ID NO: 2, SEQ ID NO: 3, SEQ ID NO: 4, SEQ ID NO: 5, and/or SEQ ID NO: 6, or a combination of two or more of SEQ ID NOs: 1-6. For example, in an aspect, a CT20 peptide of a disclosed method can be VTIFVAGVLTASLTIWKKMG (SEQ ID NO: 1). In an aspect, a CT20 peptide of a disclosed method can be ASLTIWKKMG (SEQ ID NO: 2). In an aspect, a CT20 peptide of a disclosed method can be VTIFVAGVLT (SEQ ID NO: 3). In an aspect, a CT20 peptide of a disclosed method can be VTIFVAG (SEQ ID NO: 4). In an aspect, a CT20 peptide of a disclosed method can be IFVAG (SEQ ID NO: 5). In an aspect, a CT20 peptide of a disclosed method can be IWKKMG (SEQ ID NO: 6). In an aspect, a disclosed method for inhibiting replication of cancer cells in a subject can comprise one or more CT20 peptides, wherein the one or more CT20 peptides can comprise SEQ ID NO:1, SEQ NO: 2, SEQ ID NO: 3, SEQ ID NO: 4, SEQ ID NO: 5, or SEQ ID NO: 6.

In an aspect, a CT20 peptide of a disclosed method of inhibiting replication of cancer cells in a subject can comprise a biotin-tag. In an aspect, a CT20 peptide of a disclosed method can be delivered via nanoparticles. As used herein, "nanoparticle" may refer to any nanostructure capable of delivering pharmaceutical compounds, nucleic acids, peptides, or proteins. Nanoparticles may be naturally or synthetically derived. In some aspects, "nanoparticles" may include plasma vesicle particles, liposomes, exosomes, protein-based particles, albumin particles, nucleic acid-based particles, natural polymers, synthetic polymers, hydrogels, dendrimers, silicon-based materials, metal-based materials, carbon-based materials, calcium-based materials, or a combination of any of the above.

In an aspect, the nanoparticles are polymeric nanoparticles. In an aspect, the nanoparticles are hyperbranched polyester polymeric nanoparticles. In an aspect, the nanoparticles can comprise a targeting moiety. In an aspect, the targeting moiety can comprise a ligand for a receptor expressed by cancer cells. In an aspect, the receptor expressed by cancer cells can be an EGF, HER2, or folate receptor. In an aspect, the receptor expressed by cancer cells can be any receptor known to the skilled person to be expressed by cancer cells.

In an aspect, the targeting ligand is a folate compound. In an aspect, the targeting ligand is a glutamate compound. In an aspect, the targeting ligand is a polyglutamated folate compound. In an aspect, the targeting ligand is glutamate azido urea. In an aspect, the targeting ligand is folate azido urea. In an aspect, the targeting ligand is glutamate azido urea. In an aspect, the targeting ligand is a bifunctional glutamate-folate hybridized compound. In an aspect, the targeting ligand is at high density. In an aspect, the targeting ligand is at low density. In an aspect, the targeting ligand is at high valency. In an aspect, the targeting ligand is at low valency. In an aspect, the targeting ligand is a substrate for a solid tumor-specific cell protein. In an aspect, the solid tumor-specific cell protein is prostate specific membrane antigen (PSMA).

In an aspect, a disclosed method of inhibiting replication of cancer cells in a subject comprising administering a CT20 peptide or a composition comprising an effective amount of a CT20 peptide can comprise administering one or more anti-cancer drugs. In an aspect, the one or more anti-cancer drugs can comprise cisplatin. In an aspect, the one or more anti-cancer drugs induce apoptosis. In an aspect, a disclosed method can comprise administering one or more therapeutic agents. In an aspect, a disclosed method can comprise administering one or more chemotherapeutic drugs. In an aspect, a disclosed method can comprise administering one or more radiosensitizers. In an aspect, a composition of a disclosed method can comprise a pharmaceutically acceptable carrier.

In an aspect, a CT20 peptide of a disclosed method of inhibiting replication of cancer cells in a subject can comprise (i) one or more therapeutic agents, (ii) one or more anti-cancer agents, (iii) one or more chemotherapeutic drugs, and (iv) one or more radiosensitizers. In an aspect, a CT20 peptide of a disclosed method can comprise one or more anti-cancer agents and one or more chemotherapeutic drugs. In an aspect, a CT20 peptide of a disclosed method can comprise one or more anti-cancer agents and one or more radiosensitizers. In an aspect, a CT20 peptide of a disclosed method can comprise one or more chemotherapeutic agents and one or more radiosensitizers.

In an aspect of a disclosed method of inhibiting replication of cancer cells in a subject, the subject can be a mammal. In an aspect, the mammal can be a primate. In an aspect, the mammal can be a human. In an aspect, the human can be a patient.

In an aspect, a disclosed method of inhibiting replication of cancer cells in a subject can comprise evaluating the efficacy of the composition. In an aspect, evaluating the efficacy of the composition can comprise determining whether the cancer cells have metastasized. In an aspect, evaluating the efficacy of the composition can comprise determining the size of the tumor or tumors formed by the cancer cells.

Disclosed herein is a method of treating a cancer. The cancer may be detected by an assay, or it may be suspected due to various symptoms being experienced by a subject. The method of treating a cancer includes obtaining a sample from a subject, and measuring the amount of chaperonin containing TCP (CCT) in the sample. In an aspect, the subject can have been diagnosed with cancer. In an aspect, the subject can be suspected of having cancer. In an aspect, the cancer can be breast cancer, lung cancer, prostate cancer, liver cancer, colon cancer, or any other cancer known to the art. In an aspect, the cancer can comprise a mesenchymal stem-like cancer. In an aspect of a disclosed method of treating a cancer, the sample can be a blood sample or a cellular sample. In an aspect, a cellular sample can be obtained via biopsy or by any other technique known to the art.

In an aspect, a disclosed method of treating a cancer can comprise isolating the bound CCT using streptavidin beads. A disclosed method of treating a cancer can comprise quantifying the amount of CCT protein in the sample or the amount of CCT mRNA in the sample, or both.

In an aspect of a disclosed method of treating a cancer, measuring the amount of CCT in the sample can comprise determining the amount of one or more subunits of CCT. In an aspect, one or more subunits of CCT can comprise CCTα, CCTβ, CCTγ, CCTε, CCTε, CCTζ, CCTη, CCTθ, and CCT1-8. In an aspect, CCT can comprise CCTα, CCTβ, CCTγ, CCTε, CCTε, CCTζ, CCTη, CCTθ, and/or CCT1-8.

In an aspect, measuring the amount of CCT in the sample can comprise using a CT20 peptide. The CT20 peptide used to measure the CCT can comprise SEQ ID NO: 1, SEQ ID NO: 2, SEQ ID NO: 3, SEQ ID NO: 4, SEQ ID NO: 5, and/or SEQ ID NO: 6, or a combination of two or more of SEQ ID NOs: 1-6. For example, in an aspect, a CT20 peptide can be VTIFVAGVLTASLTIWKKMG (SEQ ID NO: 1). In an aspect, a CT20 peptide can be ASLTIWKKMG (SEQ ID NO: 2). In an aspect, a CT20 peptide can be VTIFVAGVLT (SEQ ID NO: 3). In an aspect, a CT20 peptide can be VTIFVAG (SEQ ID NO: 4). In an aspect, a CT20 peptide can be IFVAG (SEQ ID NO: 5). In an aspect, a CT20 peptide of a disclosed method can be IWKKMG (SEQ ID NO: 6). In an aspect, a CT20 peptide can comprise one or more of SEQ ID NO:1, SEQ NO: 2, SEQ ID NO: 3, SEQ ID NO: 4, SEQ ID NO: 5, or SEQ ID NO: 6.

In an aspect, the CT20 peptide may be a variant of SEQ ID NO:1, SEQ ID NO:2, SEQ ID NO:3, SEQ ID NO:4, SEQ ID NO:5, SEQ ID NO:6, or a combination thereof. The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 61%, 62%, 63%, 64%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to a reference sequence.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction *W/Z*, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

In an aspect, the CT20 peptide used to measure the CCT may be delivered via nanoparticles. As used herein, "nanoparticle" may refer to any nanostructure capable of delivering pharmaceutical compounds, nucleic acids, peptides, or proteins. Nanoparticles may be naturally or synthetically derived. In some aspects, "nanoparticles" may include plasma vesicle particles, liposomes, exosomes, protein-based particles, albumin particles, nucleic acid-based particles, natural polymers, synthetic polymers, hydrogels, dendrimers, silicon-based materials, metal-based materials, carbon-based materials, calcium-based materials, or a combination of any of the above.

In an aspect, nanoparticles can be polymeric nanoparticles. In an aspect, nanoparticles can be hyperbranched polyester polymeric nanoparticles. In an aspect, the nanoparticles are hyperbranched polyester polymeric nanoparticles.

In an aspect of a disclosed method of treating cancer, a CT20 peptide is administered to a subject as part of a therapeutic regimen. The CT20 peptide can comprise SEQ ID NO: 1, SEQ ID NO: 2, SEQ ID NO: 3, SEQ ID NO: 4, SEQ ID NO: 5, and/or SEQ ID NO: 6, or a combination of two or more of SEQ ID NOs: 1-6. For example, in an aspect, a CT20 peptide can be VTIFVAGVLTASLTIWKKMG (SEQ ID NO: 1). In an aspect, a CT20 peptide can be ASLTIWKKMG (SEQ ID NO: 2). In an aspect, a CT20 peptide can be VTIFVAGVLT (SEQ ID NO: 3). In an aspect, a CT20 peptide can be VTIFVAG (SEQ ID NO: 4). In an aspect, a CT20 peptide can be IFVAG (SEQ ID NO: 5). In an aspect, a CT20 peptide of a disclosed method can be IWKKMG (SEQ ID NO: 6). In an aspect, a CT20 peptide can comprise one or more of SEQ ID NO:1, SEQ NO: 2, SEQ ID NO: 3, SEQ ID NO: 4, SEQ ID NO: 5, or SEQ ID NO: 6.

In an aspect, the CT20 peptide administered as part of a therapeutic regimen can be delivered via nanoparticles. As used herein, "nanoparticle" may refer to any nanostructure capable of delivering pharmaceutical compounds, nucleic acids, peptides, or proteins. Nanoparticles may be naturally or synthetically derived. In some aspects, "nanoparticles" may include plasma vesicle particles, liposomes, exosomes, protein-based particles, albumin particles, nucleic acid-based particles, natural polymers, synthetic polymers, hydrogels, dendrimers, silicon-based materials, metal-based materials, carbon-based materials, calcium-based materials, or a combination of any of the above.

In an aspect, nanoparticles can be polymeric nanoparticles. In an aspect, nanoparticles can be hyperbranched polyester polymeric nanoparticles. In an aspect, the nanoparticles are hyperbranched polyester polymeric nanoparticles. In an aspect, the nanoparticles can comprise a targeting moiety. In an aspect, the targeting moiety can comprise a ligand for a receptor expressed by cancer cells. In an aspect, the receptor expressed by cancer cells can be an EGF, HER2, or folate receptor. In an aspect, the receptor expressed by cancer cells can be any receptor known to the skilled person to be expressed by cancer cells.

In an aspect, the targeting ligand is a folate compound. In an aspect, the targeting ligand is a glutamate compound. In an aspect, the targeting ligand is a polyglutamated folate compound. In an aspect, the targeting ligand is glutamate azido urea. In an aspect, the targeting ligand is folate azido urea. In an aspect, the targeting ligand is glutamate azido urea. In an aspect, the targeting ligand is a bifunctional glutamate-folate hybridized compound. In an aspect, the targeting ligand is at high density. In an aspect, the targeting ligand is at low density. In an aspect, the targeting ligand is at high valency. In an aspect, the targeting ligand is at low valency. In an aspect, the targeting ligand is a substrate for a solid tumor-specific cell protein. In an aspect, the solid tumor-specific cell protein is prostate specific membrane antigen (PSMA).

In an aspect, an internalization domain may be linked to the CT20 peptide. The provided polypeptide can further constitute a fusion protein or otherwise have additional N-terminal, C-terminal, or intermediate amino acid sequences, e.g., linkers or tags. "Linker", as used herein, is an amino acid sequences or insertion that can be used to connect or separate two distinct polypeptides or polypeptide fragments, wherein the linker does not otherwise contribute to the essential function of the composition. A polypeptide provided herein, can have an amino acid linker comprising, for example, the amino acids GLS, ALS, or LLA. A "tag", as used herein, refers to a distinct amino acid sequence that can be used to detect or purify the provided polypeptide, wherein the tag does not otherwise contribute to the essential function of the composition. The provided polypeptide can further have deleted N-terminal, C-terminal or intermediate amino acids that do not contribute to the essential activity of the polypeptide.

The CT20 peptide can be linked to an internalization sequence or a protein transduction domain to effectively enter the cell. Recent studies have identified several cell penetrating peptides, including the TAT transactivation domain of the HIV virus, antennapedia, and transportan that can readily transport molecules and small peptides across the plasma membrane (Schwarze et al., Science. 1999 285 (5433):1569-72; Derossi et al. J Biol Chem. 1996 271(30): 18188-93; Yuan et al., Cancer Res. 2002 62(15):4186-90). More recently, polyarginine has shown an even greater efficiency of transporting peptides and proteins across the plasma, membrane making it an attractive tool for peptide mediated transport (Fuchs and Raines, Biochemistry. 2004 43(9):2438-44). Nonaarginine has been described as one of the most efficient polyarginine based protein transduction domains, with maximal uptake of significantly greater than TAT or antennapeadia. Peptide mediated cytotoxicity has also been shown to be less with polyarginine-based internalization sequences. R9 mediated membrane transport is facilitated through heparan sulfate proteoglycan binding and endocytic packaging. Once internalized, heparan is degraded by heparanases, releasing R9 which leaks into the cytoplasm (Deshayes et al., Cell Mol Life Sci. 2005 62(16): 1839-49). Studies have recently shown that derivatives of polyarginine can deliver a full length p53 protein to oral cancer cells, suppressing their growth and metastasis, defining polyarginine as a potent cell penetrating peptide (Takenobu et al., Mol Cancer Ther. 2002 1(12):1043-9).

Thus, the provided polypeptide can comprise a cellular internalization transporter or sequence. The cellular internalization sequence can be any internalization sequence known or newly discovered in the art, or conservative variants thereof. Non-limiting examples of cellular internalization transporters and sequences include Polyarginine (e.g., R9), Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol).

In an aspect, a CT20 peptide administered as part of a therapeutic regimen can interact directly with CCT. In an aspect, direct interaction of the CT20 peptide and CCT can comprise hydrophobic interactions. For example, in an aspect, the CT20 peptide can comprise a biotin label. In an aspect, the CT20 peptide can comprise a fluorescent label or a label known to the art. In an aspect, CCT can be bound by the biotin-labeled CT20 peptide. The CT20 peptide, when bound to TCP, disrupts or inhibits one or more functions of CCT.

A disclosed method of treating a cancer can comprise comparing the amount of CCT in the sample to the amount of CCT in a sample obtained from one or more other subjects. In an aspect, the one or more other subjects can comprise subjects having been diagnosed with metastatic cancer and subjects without metastatic cancer.

A disclosed method of treating a cancer can comprise comparing the amount of CCT in the sample to a pre-determined range of CCT amounts, or a pre-determined CCT threshold level. In an aspect, the pre-determined range of CCT amounts or can comprise CCT amounts obtained from subjects having been diagnosed with metastatic cancer and from subjects without metastatic cancer. For example, the range can represent a continuum of CCT values from all types of subjects. In one aspect, a pre-determined CCT threshold level may be determined by comparing CCT levels from patients with metastatic cancer to those without metastatic cancer.

A disclosed method of treating a cancer can comprise comparing the amount of CCT in the sample to the pre-determined CCT threshold level. If the amount of CCT in the sample is above the pre-determined CCT threshold, a therapeutic regimen may be initiated. The therapeutic regimen may include administering a therapeutic composition, an anti-cancer agent, a chemotherapeutic agent, a radiosensitizer, or an anti-neoplastic agent. In some aspects, the therapeutic regimen may include administration of mitotoxic peptides, anti-metastatic agents, or anti-androgenic agents In some embodiments, the CT20 peptide causes immunogenic cell death of the cancer, effectively cause the cancer to become a cancer vaccine. Therefore, the methods may also include administering an immunotherapy regimen to promote a cancer vaccine response. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rittman, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some aspects, the therapeutic regimen may include administering a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. A list of immune-checkpoint targeting antibodies in clinical trials is provided in Table 1.

TABLE 1

Clinically evaluated immune-checkpoint blocking antibodies

| Target | Antibody |
|---|---|
| CTLA-4 | Ipilimumab (MDX-010) |
| | Tremelimumab (CP-675, 206) |
| PD1 | Nivolumab (BMS-936558 or MDX1106) |
| | CT-011 |
| | MK-3475 |
| PDL1 | MDX-1105 (BMS-936559) |
| | MPDL3280A |
| | MSB0010718C |
| PDL2 | rHIgM12B7 |
| B7-H3 | MGA271 |
| LAG3 | BMS-986016 |

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies. In some embodiments, the therapeutic regimen may include a functional nucleic acid to inhibit the expression or activity of CCT. For example, functional nucleic acids may be used to inhibit the expression of any gene encoding the expression of any CCT subunit, such as CCTα, CCTβ, CCTγ, CCTε, CCTζ, CCTη, CCTθ, CCT1-8, or a combination thereof.

Functional nucleic include antisense molecules, aptamers, ribozymes, triplex forming molecules, RNAi, and external guide sequences.

Functional nucleic acid molecules can interact with any macromolecule, such as DNA, RNA, polypeptides, or carbohydrate chains. Thus, functional nucleic acids can interact with the mRNA of CCT or the genomic DNA of CCT or they can interact with the polypeptide CCT. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$. A representative sample of methods and techniques which aid in the design and use of antisense molecules can be found in U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $K_d$'s from the target molecule of less than 10-12 M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule (U.S. Pat. No. 5,543,293). It is preferred that the aptamer have a $K_d$ with the target molecule at least 10, 100, 1000, 10,000, or 100,000 fold lower than the $K_d$ with a background binding molecule. It is preferred when doing the comparison for a polypeptide for example, that the background molecule be a different polypeptide. Representative examples of how to make and use aptamers to bind a variety of different target molecules can be found in U.S. Pat. Nos. 5,476,766, 5,503, 978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (U.S. Pat. Nos. 5,334,711, 5,436,330, 5,616,466, 5,633,133, 5,646, 020, 5,652,094, 5,712,384, 5,770,715, 5,856,463, 5,861,288, 5,891,683, 5,891,684, 5,985,621, 5,989,908, 5,998,193, 5,998,203; International Patent Application Nos. WO 9858058 by Ludwig and Sproat, WO 9858057 by Ludwig and Sproat, and WO 9718312 by Ludwig and Sproat) hairpin ribozymes (for example, U.S. Pat. Nos. 5,631,115, 5,646,031, 5,683,902, 5,712,384, 5,856,188, 5,866,701, 5,869,339, and 6,022,962), and tetrahymena ribozymes (for example, U.S. Pat. Nos. 5,595,873 and 5,652,107). There are also a number of ribozymes that are not found in natural systems, but which have been engineered to catalyze specific reactions de novo (for example, U.S. Pat. Nos. 5,580, 967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than 10-6, 10-8, 10-10, or 10-12. Representative examples of how to make and use triplex forming molecules to bind a variety of different target molecules can be found in U.S. Pat. Nos. 5,176,996, 5,645, 985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, Science 238:407-409 (1990)).

Similarly, eukaryotic EGS/RNAse P-directed cleavage of RNA can be utilized to cleave desired targets within eukarotic cells. (Yuan et al., Proc. Natl. Acad. Sci. USA 89:8006-8010 (1992); WO 93/22434 by Yale; WO 95/24489 by Yale; Yuan and Altman, EMBO J 14:159-168 (1995), and Carrara et al., Proc. Natl. Acad. Sci. (USA) 92:2627-2631 (1995)). Representative examples of how to make and use EGS molecules to facilitate cleavage of a variety of different target molecules be found in U.S. Pat. Nos. 5,168,053, 5,624,824, 5,683,873, 5,728,521, 5,869,248, and 5,877,162.

Gene expression can also be effectively silenced in a highly specific manner through RNA interference (RNAi). This silencing was originally observed with the addition of double stranded RNA (dsRNA) (Fire, A., et al. (1998) Nature, 391:806-11; Napoli, C., et al. (1990) Plant Cell 2:279-89; Hannon, G. J. (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Texas), ChemGenes (Ashland, Massachusetts), Dharmacon (Lafayette, Colorado), Glen Research (Sterling, Virginia), MWB Biotech (Esbersberg, Germany), Proligo (Boulder, Colorado), and Qiagen (Vento, The Netherlands). siRNA can also be synthesized in vitro using kits such as Ambion's SILENCER® siRNA Construction Kit. Disclosed herein are any siRNA designed as described above based on the sequences for CCT.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. Disclosed herein are any shRNA designed as described above based on the sequences for the herein disclosed inflammatory mediators.

In some aspects, the therapeutic regimen may comprise delivery of a therapeutic composition, including a CT20 peptide or variants thereof. The therapeutic regimen may be administered systemically, directly to the cancer cells, or a combination thereof. The cancer treated may be a primary tumor or a secondary tumor. The treatment may induce death of cancer cells and may prevent cancer cell metastases. In some aspects, non-cancerous cells are not killed by the therapeutic regimen.

Methods of Assing Circulating Tumor Cells

Molecular chaperones are often upregulated during oncogenesis; however, their use as diagnostic targets in cancer is underdeveloped. One example of molecular chaperones extensively studied in cancer is the heat shock proteins (HSPs). The activities of HSPs in protein folding, regulating immune responses, and preventing apoptosis are in demand during oncogenesis and led to the concept that cancer cells are subject to "chaperone addiction". Expression of HSPs inversely correlates with prognosis in several cancers, directly correlates with increased chemoresistance, and therefore are potential cancer drug targets as is being evaluated in cancer clinical trials. The use of HSPs for diagnostic purposes is supported by the fact that elevated expression of these chaperones occurs in multiple cancerous tissues and could be used as biomarkers for carcinogenesis. While the assessment of HSPs in tumor tissue in tandem with other tumor markers is being considered, the diagnostic use of chaperones for monitoring cancer is mainly focused on the detection of HSPs as serum markers. However, serum levels of HSPs can also be increased under non-cancer conditions like rheumatoid arthritis, glaucoma, and cardiovascular diseases. Hence, the use of HSPs as serum markers for cancer diagnosis cannot provide a direct correlate to tumor status and development. What is needed are methods for assessing biomarkers in circulation for diagnosing cancers and monitoring cancer recurrence and metastasis.

Current methods for assessing circulating tumor cells (CTC) in blood focus on capture and enumeration with epithelial markers that provide little information about the aggressive and invasive potential of CTC. As a result, valuable knowledge that enables monitoring of cancer recurrence and metastasis is lacking. To provide actionable information on CTC, a CTC identification method is disclosed herein based on detection of the subunit of Chaperonin Containing TCP1 (CCT). CCT is a macromolecular protein folding complex composed of eight subunits (CCT1-8) that drives expression of many tumorigenic factors. Bioinformatic analysis in multiple cancers, such as breast cancer, revealed increased gene expression in tumor tissue compared to normal tissue for CCT1-8 ($p<0.0001$), with the largest differences observed in CCT2 and CCT3. To determine whether CCT2 can be used to detect CTC, antibodies to CCT2 were validated for use in the CellSearch system (CSS), currently the only FDA approved CTC enrichment platform, and tested with breast cancer cells spiked into healthy human blood. Recovery using CCT2 for identification led to collection of 1-6% of spiked cancer cells that would have been lost by standard CTC classification through detection of cytokeratin (CK).

Accordingly, disclosed herein is a method for capturing a circulating tumor cell from a liquid biological sample, comprising a) contacting the liquid biological sample with one or more CCT-targeting affinity reagents, and b) capturing the cells retained in step a) thereby capturing the circulating tumor cell from the sample.

Chaperonin Containing TCP-1 (CCT), otherwise known as T-complex protein Ring Complex (TRiC), is a multiprotein complex and the chaperonin of eukaryotic cells. The structure of CCT consists of a double-ringed barrel composed of eight subunits (CCT1-8, or known as CCTα, CCTβ, CCTγ, CCTε, CCTζ, CCTη, and CCTθ).

Accordingly, the CCT targeting affinity reagent disclosed herein can be a CCT1 targeting affinity reagent, a CCT2 targeting affinity reagent, a CCT3 targeting affinity reagent, a CCT4 targeting affinity reagent, a CCT5 targeting affinity reagent, a CCT6 targeting affinity reagent, a CCT7 (NCBI Entrez Gene: 10574) targeting affinity reagent, or a CCT8 targeting affinity reagent. In some embodiments, the CCT targeting affinity reagent is a CCT2 targeting reagent.

In some embodiments, the CCT subunits disclosed herein can be those identified in the publicly available database: CCT1 (NCBI Entrez Gene: 6950), CCT2 (NCBI Entrez Gene: 10576), CCT3 (NCBI Entrez Gene: 7203), CCT4 (NCBI Entrez Gene: 10575), CCT5 (NCBI Entrez Gene: 22948), CCT6 (NCBI Entrez Gene: 908 for CCT6A and NCBI Entrez Gene: 10693 for CCT6B), CCT7 (NCBI Entrez Gene: 10574), and CCT8 (NCBI Entrez Gene: 10694).

In some embodiments, the CCT-targeting affinity reagent is an antibody or a functional fragment thereof. The term "antibodies" is used herein in a broad sense and includes both polyclonal 5 and monoclonal antibodies. As used herein, the term "antibody" encompasses, but is not limited to, whole immunoglobulin (i.e., an intact antibody) of any class. In addition to intact immunoglobulin molecules, also included in the term "antibodies" are fragments or polymers of those immunoglobulin molecules, and human or humanized versions of immunoglobulin molecules or fragments thereof. It should be understood that the "antibody" can be monoclonal antibodies, polyclonal antibodies, chimeric antibodies, bi-specific antibodies (diabody), or tri-specific antibody (triabody).

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces mono clonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody or fragments thereof" encompasses chimeric antibodies and hybrid antibodies, with dual or multiple antigen or epitope specificities, and fragments, such as F(ab')2, Fab', Fab, Fv, scFv, and the like, including hybrid fragments. Thus, fragments of the antibodies that retain the ability to bind their specific antigens are provided. For example, fragments of antibodies which maintain Annexin A2 binding activity are included within the meaning of the term "antibody or fragment thereof" Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual*. Cold Spring Harbor Publications, New York, (1988)).

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

In a complete antibody, typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant (C(H)) domains. Each light chain has a variable domain at one end (V(L)) and a constant(C(L)) domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively. In some embodiments, the antibody is of IgG1 isotype. In some embodiments, the antibody is of IgG2 isotype. In some embodiments, the antibody is of IgG3 isotype. In some embodiments, the antibody is of IgG4 isotype. In some embodiments, the antibody is of IgM isotype. In some embodiments, the antibody is of IgA isotype.

The methods disclosed herein can capture circulating tumor cells independent of their expression of mesenchymal-epithelial biomarker. Therefore, the methods provided herein can increase the recovery of circulating tumor cells using CCT2 for identification, collecting circulating tumor cells that would have been lost by standard CTC classification through detection of mesenchymal-epithelial biomarker. In some examples, the circulating tumor cell of any preceding aspect does not have an increased level of a mesenchymal-epithelial biomarker. In some examples, the circulating tumor cell of any preceding aspect has an increased level of one or more mesenchymal-epithelial biomarkers. In some examples, the one or more mesenchymal-epithelial biomarkers are selected from the group consisting of vimentin, HER2, EpCAM, E-cadherin, N-cadherin, cytokeratin(CK)5, CK6, CK7, CK8, CK14, CK18, and CK19.

In some embodiments, the method further comprises a step of detecting one or more mesenchymal-epithelial biomarkers in the circulating tumor cell. In some embodiments, the one or more mesenchymal-epithelial biomarkers are selected from the group consisting of vimentin, HER2, EpCAM, E-cadherin, N-cadherin, cytokeratin(CK)5, CK6, CK7, CK8, CK14, CK18, and CK19.

In some examples, the method further comprises a step of detecting one or more markers such as CD44 and/or CD45. It should be understood and herein contemplated that CD45 is a marker for immune cells like leukocytes and is used to exclude while blood cells. CD44 is a multi-function marker and used as a marker for cancer stem cells.

The method provided herein can further comprises contacting the liquid biological sample with one or more affinity reagents targeting one or more mesenchymal-epithelial biomarkers. Accordingly, in some aspects, disclosed herein is a method for capturing a circulating tumor cell from a liquid biological sample, comprising a) contacting the liquid biological sample with one or more CCT-targeting affinity reagents and one or more affinity reagents targeting one or more mesenchymal-epithelial biomarkers, and
b) capturing the cells retained in step a) thereby capturing the circulating tumor cell from the sample.

In some embodiments, the one or more mesenchymal-epithelial biomarkers are selected from the group consisting of vimentin, HER2, EpCAM, E-cadherin, N-cadherin, cytokeratin(CK)5, CK6, CK7, CK8, CK14, CK18, and CK19.

In some embodiments, the biomarkers disclosed herein are those identified in the publicly available database: vimentin (NCBI Entrez Gene: 7431), HER2 (NCBI Entrez Gene: 2064), EpCAM (NCBI Entrez Gene: 4072), E-cadherin (NCBI Entrez Gene: 999), N-cadherin (NCBI Entrez Gene: 1000), CD45 (NCBI Entrez Gene: 5788), CK5 (NCBI Entrez Gene: 3852), CK6 (NCBI Entrez Gene: 3853), CK7 (NCBI Entrez Gene: 3855), CK8 (NCBI Entrez Gene: 3856), CK14 (NCBI Entrez Gene: 3861), CK18 (NCBI Entrez Gene: 3875), CK19 (NCBI Entrez Gene: 3880), and CD44 (NCBI Entrez Gene: 960).

The liquid biological sample of any preceding aspect can be a whole blood sample, a urine sample, a plasma sample, a serum sample, or a lymphatic fluid sample.

The methods provided herein increases the number of captured circulating tumor cells from a liquid biological sample in comparison to standard methods through detection of cytokeratin (CK). These results show that the addition of CCT2 staining to a CTC detection protocol has positive implications for enumeration of CTC from blood, such as detecting CTC with low expression of epithelial markers. The combined bioinformatics, histologic and experimental results indicate that identification of CCT2-expressing CTC can be incorporated into CTC detection platforms (e.g., ACCEPT (Automated CTC Classification, Enumeration and PhenoTyping)) to monitor cancer treatment outcomes and identify those patients with a heightened risk for cancer recurrence or metastasis.

Accordingly, disclosed herein is a method of diagnosing a metastatic cancer in a subject comprising a) obtaining a liquid biological sample from the subject,
b) capturing cells from the liquid biological sample of step a) using the method of any preceding aspect; and
c) determining if the captured cells of step b) comprise circulating tumor cells; and
d) determining that the subject as having a metastatic cancer if two or more circulating tumor cells are captured.

In some embodiments, the method further comprises administering to the subject a therapeutically effective amount of a cancer therapeutic agent if more than four circulating tumor cells (including, for example, more than five, more than six, more than seven, more than eight, more than nine, more than 10, more than 11, more than 12, more than 13, more than 14, more than 15, more than 16, more than 20, more than 25, more than 30, more than 40, more than 50, or more than 100 circulating tumor cells) are captured. In some examples, the liquid biological sample has a volume of about 1 ml, 2 ml, 4 ml, 5 ml, 5.5 ml, 6 ml, 6.5 ml, 7 ml, 7.5 ml, 8 ml, 9 ml, 10 ml, 20 ml, 50 ml, or 100 ml.

Also disclosed herein is a method of treating a cancer in a subject, comprising a) obtaining a liquid biological sample from the subject,
b) contacting the blood sample with one or more CCT-targeting affinity reagents thereby capturing the cells bound by the one or more CCT-targeting affinity reagents,
c) determining if the captured cells of step b) comprise circulating tumor cells, and
d) administering to the subject a therapeutically effective amount of a cancer therapeutic agent if two or more (including, for example, three or more, four or more, five or more, six or more, seven or more, eight or more, nine or more, 10 or more, 11 or more, 12 or more, 13 or more, 14 or more, 15 or more, 16 or more, 20 or more, 25 or more, 30 or more, 40 or more, 50 or more, or 100 or more circulating tumor cells) circulating tumor cells are captured.

In some examples, the liquid biological sample has a volume of about 1 ml, 2 ml, 4 ml, 5 ml, 5.5 ml, 6 ml, 6.5 ml, 7 ml, 7.5 ml, 8 ml, 9 ml, 10 ml, 20 ml, 50 ml, or 100 ml.

In some examples, administering to the subject a therapeutically effective amount of a cancer therapeutic agent if two or more circulating tumor cells are captured from a liquid biological sample having a volume of 7.5 ml. In some embodiments, the liquid biological samples is a blood sample.

The method provided herein can further comprises contacting the liquid biological sample with one or more affinity reagents targeting one or more mesenchymal-epithelial biomarkers. Accordingly, in some aspects, disclosed herein is a method of treating a cancer in a subject, comprising a) obtaining a liquid biological sample from the subject,
b) contacting the liquid biological sample with one or more CCT-targeting affinity reagents and one or more affinity reagents targeting one or more mesenchymal-epithelial biomarkers,
c) capturing the cells retained in step b) thereby capturing the circulating tumor cell from the liquid biological sample, and
d) administering to the subject a therapeutically effective amount of a cancer therapeutic agent if two or more (including, for example, three or more, four or more, five or more, six or more, seven or more, eight or more, nine or more, 10 or more, 11 or more, 12 or more, 13 or more, 14 or more, 15 or more, 16 or more, 20 or more, 25 or more, 30 or more, 40 or more, 50 or more, or 100 or more circulating tumor cells) circulating tumor cells are captured.

In some examples, the liquid biological sample has a volume of about 1 ml, 2 ml, 4 ml, 5 ml, 5.5 ml, 6 ml, 6.5 ml, 7 ml, 7.5 ml, 8 ml, 9 ml, 10 ml, 20 ml, 50 ml, or 100 ml.

In some embodiments, the one or more mesenchymal-epithelial biomarkers are selected from the group consisting of vimentin, HER2, EpCAM, E-cadherin, N-cadherin, cytokeratin(CK)5, CK6, CK7, CK8, CK14, CK18, and CK19.

In some examples, the method further comprises a step of detecting one or more markers such as CD44 and/or CD45.

The CCT targeting affinity reagent disclosed herein can be a CCT1 targeting affinity reagent, a CCT2 targeting affinity reagent, a CCT3 targeting affinity reagent, a CCT4 targeting affinity reagent, a CCT5 targeting affinity reagent, a CCT6 targeting affinity reagent, a CCT7 (NCBI Entrez Gene: 10574) targeting affinity reagent, or a CCT8 targeting affinity reagent. In some embodiments, the CCT targeting affinity reagent is a CCT2 targeting reagent. In some embodiments, the CCT targeting affinity reagent is a CCT2 targeting reagent. In some embodiments, the CCT-targeting affinity reagent is an antibody or a functional fragment thereof.

In some embodiments, the CCT subunits disclosed herein can be those identified in the publicly available database: CCT1 (NCBI Entrez Gene: 6950), CCT2 (NCBI Entrez Gene: 10576), CCT3 (NCBI Entrez Gene: 7203), CCT4 (NCBI Entrez Gene: 10575), CCT5 (NCBI Entrez Gene: 22948), CCT6 (NCBI Entrez Gene: 908 for CCT6A and NCBI Entrez Gene: 10693 for CCT6B), CCT7 (NCBI Entrez Gene: 10574), and CCT8 (NCBI Entrez Gene: 10694).

It should be understood and herein contemplated that CTCs shed from the active edges of tumors into the peripheral circulation and typically have short half-lives (for example, about 1.0-2.4 hours). CTCs, therefore, provide current information about a patient's tumor status. Accordingly, in some examples, the method of any preceding aspect further comprises determining the level of CCT2 expression in the captured circulating tumor cell. In some examples, the method further comprises determining the cancer as a metastatic cancer if the level of CCT2 is increased in comparison to a reference control. In some embodiments, the level of CCT2 in the capture circulating tumor cells has an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level so long as the increase is statistically significant.

In some examples, the method of any preceding aspect further comprises staining a CCT2 polypeptide in the captured cell with one or more affinity reagents targeting the CCT2 polypeptide. In some examples, the method of any preceding aspect further comprises contacting the captured cells with a stain that binds DNA. In some embodiments, an increased level of CCT2 in the nucleus of the captured cell indicates that the captured cell is a circulating tumor cell. Accordingly, in some embodiments, detection of a fully or partially overlap (e.g., at least about 50%, 60%, 70%, 80%, 90%, 95%, 99% overlap) between the nucleus of the capture cell (e.g., as indicted by DNA staining) and the CCT2 polypeptide (e.g., as indicated by CCT2 staining) indicates that the captured cells are circulating tumor cells. In some embodiments, staining of the CCT2 polypeptide in the capture cells has no overlap or minimal overlap (e.g., less than about 50%, 40%, 30%, 20%, 10%, 5%, or 1% overlap) with the staining of CD45.

In some embodiments, the methods disclosed herein further comprise determining a level of one or more cancer biomarkers. In some embodiments, the one or more cancer biomarker are selected from, but not limited to, HER2, estrogen receptors (ER), progesterone receptor (PR), α-fetoprotein (AFP), prostate-specific antigen (PSA), cancer antigen 125 (CA125), human epididymis protein 4 (HE4), apolipoprotein A1, preablbumin, HE4, cancer antigen 15-3 (CA15-3), cancer antigen 27-29 (CA27-29), cancer antigen 19-9 (CA19-9), carcinoembryonic antigen (CEA), thyroglobulin (Tg), and human chorionic gonadotropin (hCG). In some embodiments, the cancer biomarkers include those disclosed in international publication No. WO2013/062515, incorporated by reference herein in its entirety.

The methods disclosed herein can capture circulating tumor cells independent of their expression of mesenchymal-epithelial biomarker. Therefore, the methods provided herein can increase the recovery of circulating tumor cells using CCT2 for identification, collecting circulating tumor cells that would have been lost by standard CTC classification through detection of mesenchymal-epithelial biomarker. In some examples, the circulating tumor cell of any preceding aspect does not have an increased level of a mesenchymal-epithelial biomarker. In some examples, the circulating tumor cell of any preceding aspect has an increased level of one or more mesenchymal-epithelial biomarkers. In some examples, the one or more mesenchymal-epithelial biomarkers are selected from the group consisting of vimentin, HER2, EpCAM, E-cadherin, N-cadherin, cytokeratin(CK)5, CK6, CK7, CK8, CK14, CK18, and CK19.

In some embodiments, the method further comprises a step of detecting one or more mesenchymal-epithelial biomarkers in the circulating tumor cell. In some embodiments, the one or more mesenchymal-epithelial biomarkers are selected from the group consisting of vimentin, HER2, EpCAM, E-cadherin, N-cadherin, cytokeratin(CK)5, CK6, CK7, CK8, CK14, CK18, and CK19.

The cancer cell can be a cell from any type of cancer including, but not limited to, cancer of the head and neck cancer, esophagus, stomach, pancreas, kidney, bladder, bone, brain, and cervix. In an aspect, the cancer can be breast cancer. In an aspect, the cancer can be colorectal cancer. In an aspect, the cancer can be lung cancer. In an aspect, the cancer can be liver cancer. In an aspect, the cancer can be prostate cancer. In an aspect, the cancer can be melanoma. In an aspect, the cancer can be lymphoma. In an aspect, the cancer can be a drug resistant cancer. In an aspect, the cancer cell can be a drug resistant cancer cell. In some examples, the cancer is selected from the group consisting of breast cancer, lung cancer, melanoma, pancreatic cancer, brain cancer, and colon cancer.

It should be understood that CCT2 expression does not correlate with ER or PR status and therefore can be used with different types of breast cancers including TNBC. Accordingly, disclosed herein is a method of treating a breast cancer in a subject, comprising a) obtaining a liquid biological sample from the subject,
b) contacting the liquid biological sample with one or more CCT-targeting affinity reagents,
c) capturing the cells retained in step b) thereby capturing the circulating tumor cell from the liquid biological sample, and
d) administering to the subject a therapeutically effective amount of a cancer therapeutic agent if two or more (including, for example, three or more, four or more, five or more, six or more, seven or more, eight or more, nine or more, 10 or more, 11 or more, 12 or more, 13 or more, 14 or more, 15 or more, 16 or more, 20 or more, 25 or more, 30 or more, 40 or more, 50 or more, or 100 or more circulating tumor cells) circulating tumor cells are captured The methods can be used for treating a breast cancer, including, for example, luminal breast cancer, triple-negative breast cancer, or basal breast cancer. In some examples, CK 8, CK18, and CK19 are present in luminal breast cancers and basal breast cancers have a stronger correlation with CK 5, 6, and 14. Accordingly, in some embodiments, the method further comprises detecting levels of CK5, CK6, CK8, CK14, CK18, and/or CK19.

Also, disclosed herein is a method of monitoring recurrence of a cancer in a subject comprising a) obtaining a liquid biological sample from the subject, b) capturing circulating tumor cells from the liquid biological sample of step a) using the method of any preceding aspect; and c) determining that the subject has recurrence of the cancer if two or more circulating tumor cells are captured.

In some embodiments, the method further comprises administering to the subject a therapeutically effective amount of a cancer therapeutic agent if more than four circulating tumor cells (including, for example, more than five, more than six, more than seven, more than eight, more than nine, more than 10, more than 11, more than 12, more than 13, more than 14, more than 15, more than 16, more than 20, more than 25, more than 30, more than 40, more than 50, or more than 100 circulating tumor cells) are captured. In some examples, the liquid biological sample has a volume of about 1 ml, 2 ml, 4 ml, 5 ml, 5.5 ml, 6 ml, 6.5 ml, 7 ml, 7.5 ml, 8 ml, 9 ml, 10 ml, 20 ml, 50 ml, or 100 ml.

It is intended herein that the disclosed methods of inhibiting, reducing, and/or preventing cancer metastasis and/or recurrence can comprise the administration of a CT20 peptide or CT20. As used herein, "a CT20 peptide" or "CT20" may refer to one peptide or may refer one or more peptides (i.e., a C-terminal Bx peptide), such as molar concentrations of the peptide, as would be found in a composition. The CT20 peptide and the methods of using thereof are known in the art. See, e.g., U.S. Patent Publication No. 11,129,868, which is incorporated herein by reference in its entirety.

It is intended herein that the disclosed methods of inhibiting, reducing, and/or preventing cancer metastasis and/or recurrence can comprise the administration of any anti-cancer agent known in the art including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate). Also contemplated herein are chemotherapeutics that are PD1/PDL1 blockade inhibitors (such as, for example, lambrolizumab, nivolumab, pembrolizumab, pidilizumab, BMS-936559, Atezolizumab, Durvalumab, or Avelumab).

Disclosed are the components to be used to prepare a composition of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the disclosed embodiments.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Targeting the Chaperonin CCT with the CT20 Peptide Induces Cytoskeletal Disruption and Breast Cancer Cell Death Whether CCT is a strong candidate for the intracellular target of CT20 is examined. CCT exists in two conformations: an open, ATP-unbound form and a closed, ATP-induced state (Booth, C. R., et al. (2008) Nat. Struct. Mol. Biol. 15, 746-753). The closed form of CCT results from a built-in lid that seals the folding chamber upon hydrolysis of ATP (Meyer, A. S., et al. (2003) Cell 113, 369-381). How the conformations of CCT are regulated remains unknown, but altered signaling pathways that drive physiological and morphological changes (e.g., as a result of the EMT) in cancer cells could cause heightened CCT activity, promoting the open conformation that enables binding to CT20.

Materials and Methods

Cell culture and reagents: Human breast cancer MDA-MB-231 and MDA-MB-468 cells were cultured in Dulbecco's modified Eagle's medium (Cellgro) with 10% fetal bovine serum (Biowest) and 1% penicillin-streptomycin (Cellgro). MDA-MB-436 cells were cultured in Leibovitz's L-15 medium (Cellgro) with 20% fetal bovine serum and 1% penicillin-streptomycin. BT-549 cells were cultured in RPMI (Cellgro) with 8 ug/mL insulin (Santa Cruz), 10% fetal bovine serum, and 1% penicillin-streptomycin. Breast epithelial MCF-10A cells were cultured in Mammary Epithelial Cell Growth Media (Lonza) with 1% penicillin-streptomycin. All cell lines were obtained from ATCC and used for experiments prior to passage 10. CT20p (Ac-VTIFVAGVLTASLTIWKKMG-NH2) and biotin-tagged CT20p were commercially synthesized (Biopeptide Co., Inc) at >98% purity. Purified recombinant CCTβ derived from *E. coli* was obtained commercially (MyBioSource) at >90% purity.

Cellular adhesion assay: 96-well tissue culture plates were coated with 20 ug/mL fibronectin (Sigma) overnight at 4° C. Cells were then seeded in the plates at a density of 10,000 cells/well. Cells were treated with varying doses of CT20p for 48 hours. Plates were then shaken at 1400 rpm for 15 seconds, washed, and fixed with 10% neutral buffered formalin (Leica). Adhered cells were stained with 5 mg/mL crystal violet (Sigma) and absorbance at 595 nm was read on an EnVision plate reader (Perkin Elmer).

Measurement of cell viability: Cells at 60% confluency were treated with CT20p at a dose of 75 ug/mL for varying lengths of time. Following treatment, cells were collected and stained with Sytox AADvanced and F2N12S Violet Ratiometric Apoptosis kit (Invitrogen). Data was acquired by flow cytometry on a FACS Canto (BD Biosciences), and analyzed with FCSExpress software (DeNovo).

Measurement of oxygen consumption and extracellular acidification: 24-well culture plates for use with the Seahorse XFe24 analyzer were coated with Cell-Tak (BD Bioscience) at 3.5 ug/cm2. Cells were then seeded at 60,000 cells/well and allowed to adhere overnight. Measurements of oxygen consumption rate and extracellular acidification rate were obtained using a Seahorse XFe 24 analyzer (Seahorse Bioscience). To obtain mitochondrial metabolic profiles, injections of oligomycin (1 uM), FCCP (0.3 uM), rotenone (0.1 uM), and antimycin A (2 uM) were performed. The mitochondrial coupling efficiency was calculated as: [1−(minimum oligomycin response/final basal measurement)]×100. To obtain glycolytic metabolic profiles, injections of glucose (10 mM), oligomycin (1 uM), and 2-deoxy-D-glucose (100 mM) were performed. Glycolytic reserve capacity was calculated as: maximum oligomycin response−maximum glucose response. All reagents were obtained from Seahorse Bioscience. To test the effect of CT20p on metabolic processes, cells were treated with CT20p at a dose of 75 ug/mL for 24 hours post-seeding, and prior to running the assay. Metabolic capacity was defined as the maximum recorded measurement in both mitochondrial and glycolytic contexts. CT20p-treated results were calculated as a percentage of untreated results.

Immunoblotting: Cell lysates were obtained by mechanical douncing in fractionation buffer consisting of 210 mM sucrose, 70 mM mannitol, 10 mM HEPES, 1 mM EDTA, pH 7.4. Lysates were centrifuged at 1,000×g for 10 minutes at 4° C., and the supernatants were subjected to SDS-PAGE, followed by transfer to Immobilon-FL membranes (Millipore). Blots were probed with primary antibodies against CCTβ (Millipore), CCTΔ (Abcam), CCTε (Abcam), or p38 (Santa Cruz). Detection was performed by incubation with IRDye 800CW or IRDye 680CW secondary antibodies (LI-COR), followed by imaging on the Odyssey detection system (LI-COR). Quantification of Western blots was performed with Image Studio software (LI-COR). Proteins of interest were quantified relative to p38 loading controls, then normalized to the level in MCF-10A cells.

Quantification of gene expression: RNA was obtained from cells using Trizol (Invitrogen) according to the manufacturer's protocol. cDNA was synthesized from 2.5 μg RNA using the iScript Advanced cDNA Synthesis kit (Bio-Rad). Quantitative real-time PCR was performed on a 7900HT Fast Real-Type PCR system (Applied Biosystems). Reactions were prepared in triplicate using SSoAdvanced Universal SYBR Green Supermix (Bio-Rad) and PrimePCR Assays to the following proteins: CCT2, CCT4, CCT5, and GAPDH (Bio-Rad). Levels of CCT subunits were compared to the endogenous control GAPDH. Expression levels were calculated relative to the lowest expressed subunit: CCT4 in MCF-10A cells. Relative expression (RQ) values were calculated using the formulas: (1) ΔCT=CT of target gene (CCT)−CT of endogenous gene (GAPDH), (2) ΔΔCT=ΔCT−reference gene (MCF10A CCT4), (3) RQ $2^{-\Delta\Delta CT}$.

Pull down experiments: Lysate pull-downs were performed with 200 ug cell lysate, obtained by douncing as described above. Lysates were pre-cleared with streptavidin-agarose beads (Pierce), then incubated with bug of CT20-Biotin or biotin for 3 hours at room temperature, followed by overnight incubation at 4° C. with streptavidin-agarose beads. Beads were washed thoroughly with wash buffer (25 mM Tris, 150 mM NaCl, 0.1% NP40, pH7.4), then heated in 4× loading buffer (Invitrogen) for analysis by SDS-PAGE. Mass spectrometric analysis was performed by Moffit Cancer Center (Tampa, FL). Mass spectrometry results presented are of proteins with at least two unique peptides identified, and that were not recovered with biotin-only pull down. In-cell pull downs were performed by first delivering CT20p-Biotin encapsulated in nanoparticles to viable cells at a dose of 75 μg/mL for varying lengths of time. Following treatment, cells were collected and lysed by douncing. 200 ug of cell lysate were then incubated with streptavidin-agarose beads overnight at 4° C., and pull-down was completed as described above. For competition pull downs, 200 ug of pre-cleared cell lysate were first incubated with the competing peptide for 1 hour at room temperature, followed by incubation with the CT20p-Biotin for 1 hour at room temperature. The amounts of competing peptide and CT20p-Biotin were varied as described in the Results section. Samples were then incubated with streptavidin-agarose beads overnight at 4° C. Pull-downs with recombinant CCTβ were performed in 20 mM Tris-HCl buffer. 0.1 nmol of CCTβ was used for each pull down, and the amount of CT20p-Biotin was varied between 0.1 nmol and 4 nmol.

Migration assay: The Oris cell migration assembly kit (Platypus Technologies) was used. Cells were stained with CellTrace Violet (Life Technologies) according to manufacturer's protocol. Stoppers were placed in wells of a 96-well plate before cells were seeded at a density of 30,000 cells per well. For experiments involving CT20p treatment, treatments with CT20p were began 18 hours following seeding and allowed to continue for 24 hours. Treatments were done in quadruplicate. At the end of the treatment period, stoppers were removed to create an exclusion zone that the cells would migrate into. MDA-MB-231 cells were allowed to migrate for 10 hours. MCF-10A and MCF-10A EMT cells were allowed to migrate for 20 hours. Following the migration period, fluorescent images were obtained using a Plate Runner HD (Trophos). One set of wells had stoppers removed immediately before imaging and served as the control that provided the pre-migration area. Images were analyzed by ImageJ software (NIH) by using the wand tool to automatically define and measure the migration zone. % closure was calculated as [(pre migration area−migration area)/pre migration area]×100.

Fixed cell immunofluorescence: Cells were seeded on glass coverslips (Fisher) in a 6-well plate at a density of 150,000 cells/well. Cells at 60% confluency were treated with CT20p or left untreated for 24 hours. After CT20p treatment, cells were stained with Mitotracker Red CMXRos (Life Technologies) at a concentration of 200 nM for 30 minutes, before being fixed in ice cold methanol for 10 minutes at −20° C. Cells were then permeabilized in 0.1% Triton X-100 for 10 minutes at 37° C. Samples were blocked in 5% normal goat serum (Santa Cruz) for 30 minutes at 37° C., then incubated with primary antibody α-tubulin (DM1A) (Santa Cruz) for 3 hours at 37° C. Secondary antibody was goat α-mouse IgG-FITC (Santa Cruz) and was applied for 1 hour at room temperature. Coverslips were mounted in UltraCruz mounting media (Santa Cruz), which contains DAPI for nuclear staining. Images were obtained with a Zeiss LSM 710 microscope, using a Zeiss 63× Pan-Apochromat oil immersion lens and Zeiss Zen software. To determine average tubulin levels per cell, the amount of FITC fluorescence intensity per region of interest was divided by the number of cells in the field. At least four images containing between 5 and 12 cells were quantified for each condition. Image analysis was done using Volocity software (Perkin Elmer).

Overexpression of CCM MCF-10A cells were transiently transfected with CCTβ, expressed from a pcDNA 3.1 (+) vector (GenScript). Transfections were performed with LT1 reagent (Mints) according to the manufacturer's instructions. To assess protein expression, cells were harvested 24 hours following transfection and subjected to immunoblotting for CCTβ. To assess transfection efficiency, parallel transfections were carried out with GFP under the same conditions, and the percentage of GFP+ cells was determined using an Accuri C6 cytometer (BD Bioscience). For viability assessment, cells were treated with CT20p at a dose of 75 μg/mL for 24 hours. Treatments were started 24 hours after transfection.

Immunohistochemistry: Tissue arrays containing multiple samples of human breast cancer tissue were purchased from US Biomax. Catalog numbers for the specific arrays analyzed are as follows: BR1002a, BR10010b, and BR963a. Information about the tissue type, tumor grade, and receptor status were provided. Tissues were analyzed using anti-CCTβ primary antibody (LifeSpan Biosciences) diluted 1:100 in Antibody Diluent (Leica). Staining of tissue arrays was performed by a Bond-Max Immunostainer (Leica), with an epitope retrieval buffer of EDTA pH 9.0 (Leica). Polymer Refine Detection reagents (Leica) were used, which include a hematoxylin counterstain. Scoring of CCTβ staining was done by a pathologist based on staining intensity.

Statistical analysis: Experiments were replicated at least 3 times, with representative data presented in this report. For migration and microscopy experiments, data was analyzed using a student's t-test to compare treated and untreated results. For scoring of CCTβ staining in tissue samples, one-way ANOVA was used to compare staining between the various groups. Calculations were performed using GraphPad Prism software (GraphPad). Statistical significance was defined as $p<0.05$.

Therapeutic peptides are cost-effective to produce and can be designed for specific biological targets (Boohaker R J, et al. 2012). To this end, CT20 was discovered. CT20 is an amphipathic peptide based on the C-terminal α9 helix of Bax. To develop the therapeutic application of CT20, peptide variants were tested in which two C-terminal lysines were mutated (Boohaker R J, et al. 2012; Tatulian S A, et al. 2012; Garg P, et al. 2013). These studies resulted in the current composition of CT20. The mechanism of CT20-induced cell death is very different from the parent protein in that Bcl-2 overexpression and caspase inhibition minimally blocked it (Boohaker, R. J., et al. (2012) Mol. Pharm. 7, 2080-2093), suggesting that the peptide could kill cells with defects in the apoptotic machinery (e.g., cancer cells). However, CT20 is not membrane permeable and thus, requires a vehicle for delivery to cells.

Having a high hydrophobic content, CT20 can be encapsulated in a nanoparticle made from hyperbranched polyester polymers (HBPE-NPs) (Santra, S., et al. (2010) Mol. Pharm. 7, 1209-1222; Santra, S., et al. (2010) Langmuir 26, 5364-5373). HBPE-NPs are ideal because these can be modified with tumor targeting ligands or imaging agents. HBPE-NPs protect CT20 while in circulation, releasing the peptide only in the acidic conditions of intracellular vesicles or by esterases found within cells (Santra, S., et al. (2010) Langmuir 26, 5364-5373). This has been demonstrated in previous studies, in which CT20 (N-terminal Rhodamine label) escaped from HBPE-NPs and entered the cytoplasm (Lee, M. W., et al. (2014) Cell Death Dis. 5). A schematic demonstrating the fabrication of HBPE-NPs can be found in FIG. 1.

Figure 2A:
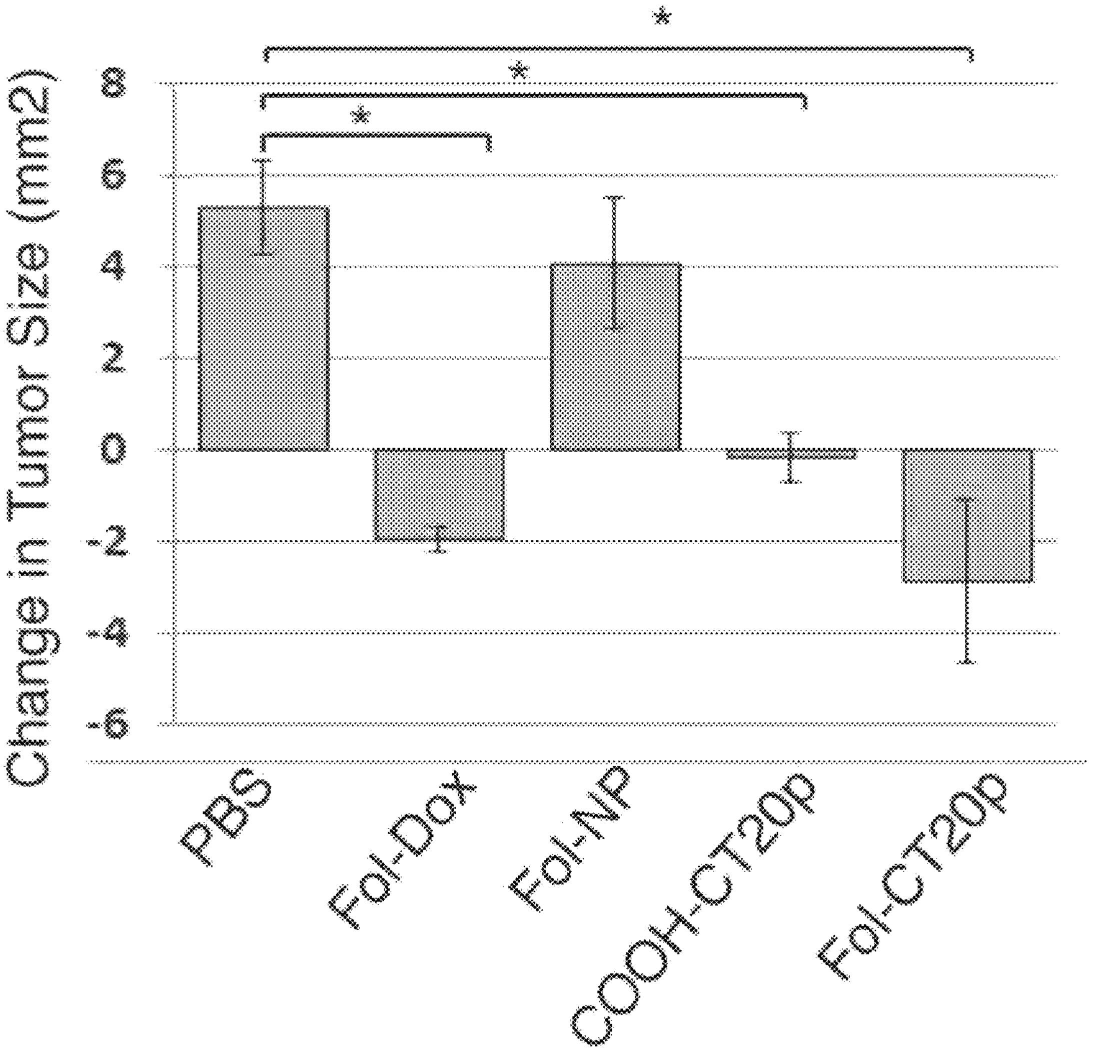
FIGS. 2A-2B show representative data demonstrating that CT20 caused tumor regression in mice.
Figure 2B:
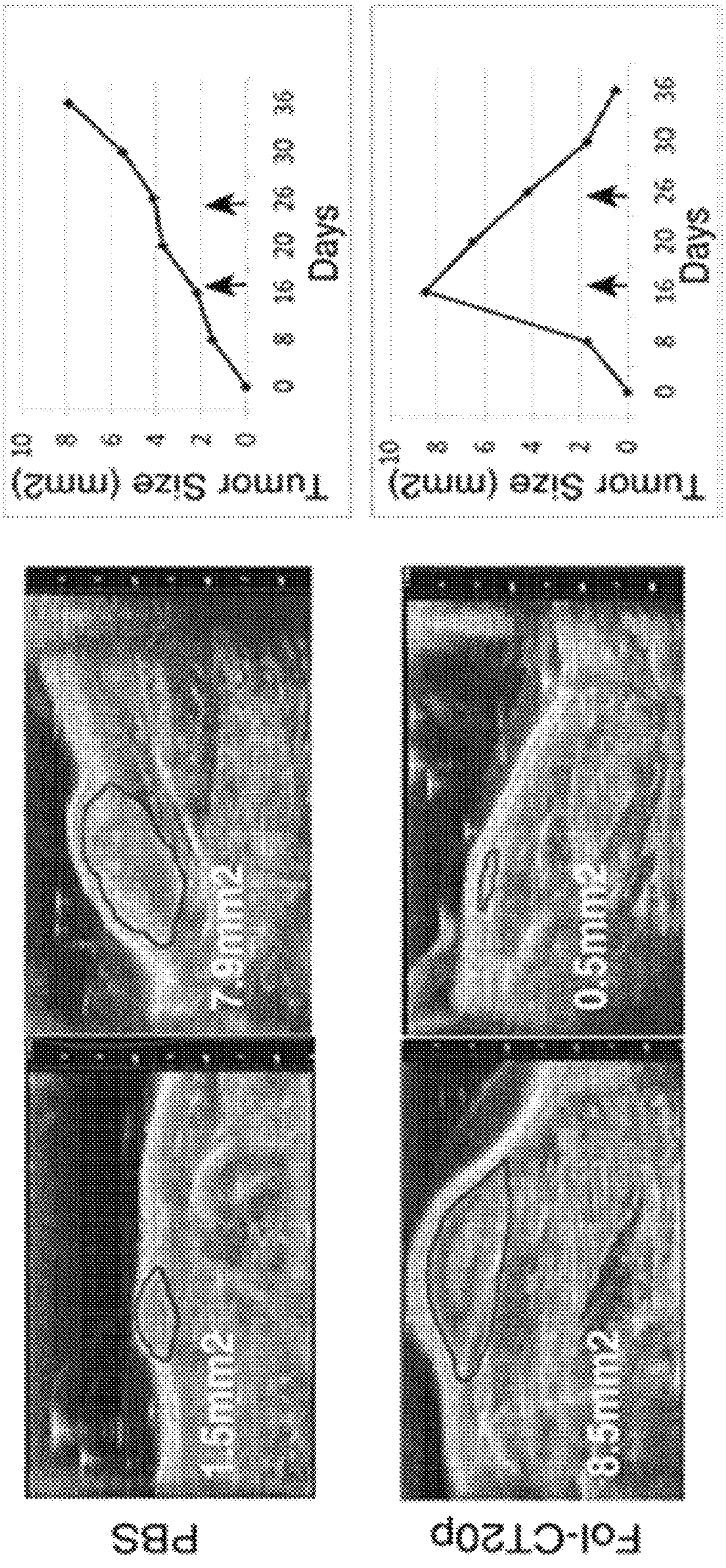

To test the ability of CT20 to inhibit tumor growth, HBPE-NPs were modified with folate (FOL) to target the folate receptor (FR) (Boohaker, R. J., et al. (2012) Mol. Pharm. 7, 2080-2093; Lee, M. W., et al. (2014) *Cell Death Dis.* 5). FR targeting enabled concentration of the HBPE-NPs in murine tumors during systemic delivery. FIG. 2 is a representative animal experiment in which MDA-MB-231 cells were used to form subcutaneous tumors. Mice (n=5) were treated with two subcutaneous injections of nanoparticles (2 mg/kg/dose) over a five week period. In the graph (FIG. 2A) and ultrasound images (FIG. 2B), FOL-CT20 is shown to effectively inhibit tumor growth, as well as untargeted COOH-CT20, to a lesser extent. Without wishing to be bound by theory, these data suggest that CT20 delivered in HBPE-NPs can be as effective, if not more, than drugs such as Doxorubicin (Dox) (FIG. 2A), without the side effects of conventional treatments (Lee, M. W., et al. (2014) Cell Death Dis. 5). Referring to FIG. 2B, representative ultrasound data is shown from mice treated with PBS or FOL-CT20-NPs. Arrows indicate treatment times. $^{*}p<0.05$.

Figure 3D:
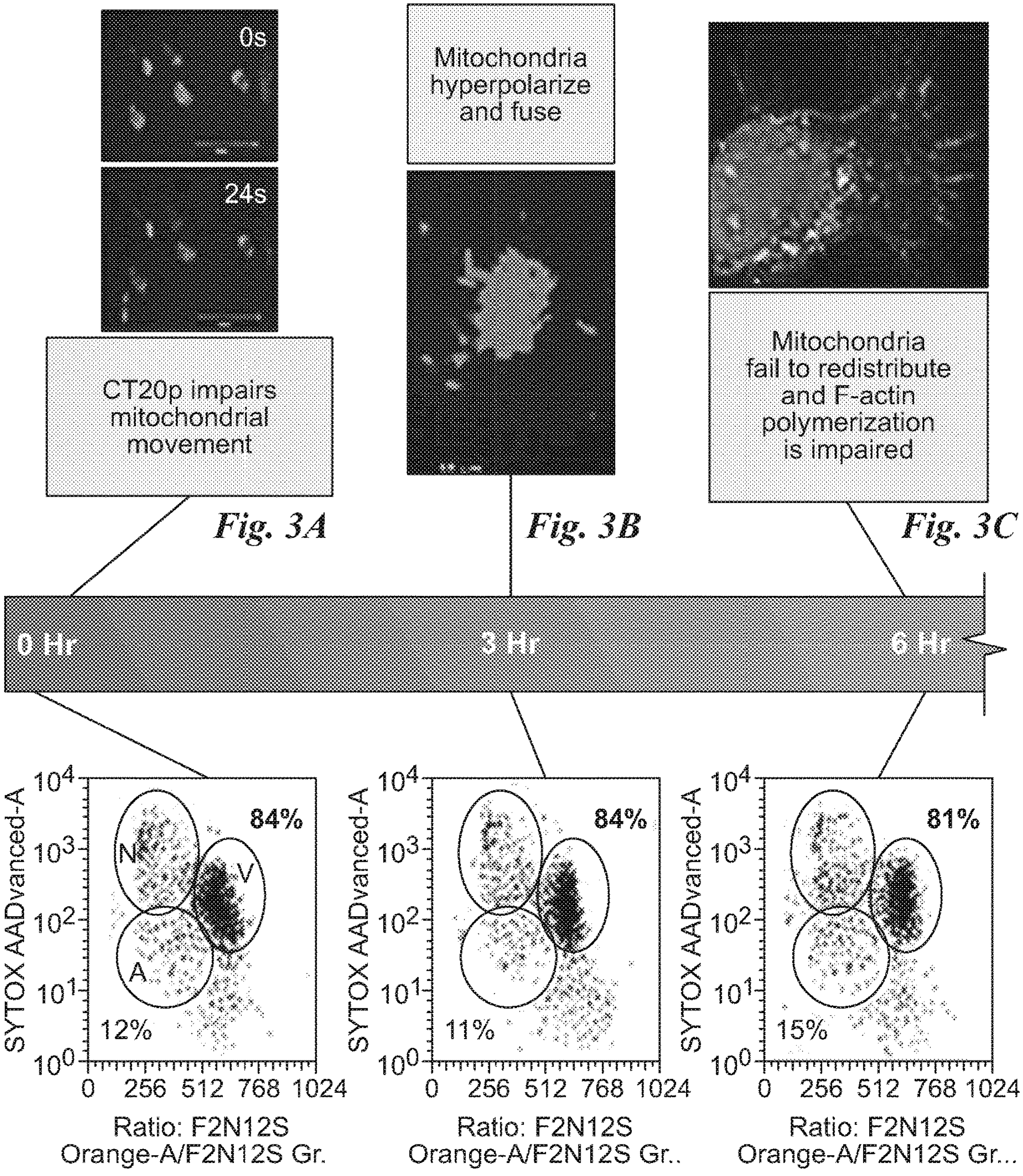
Figure 3E:
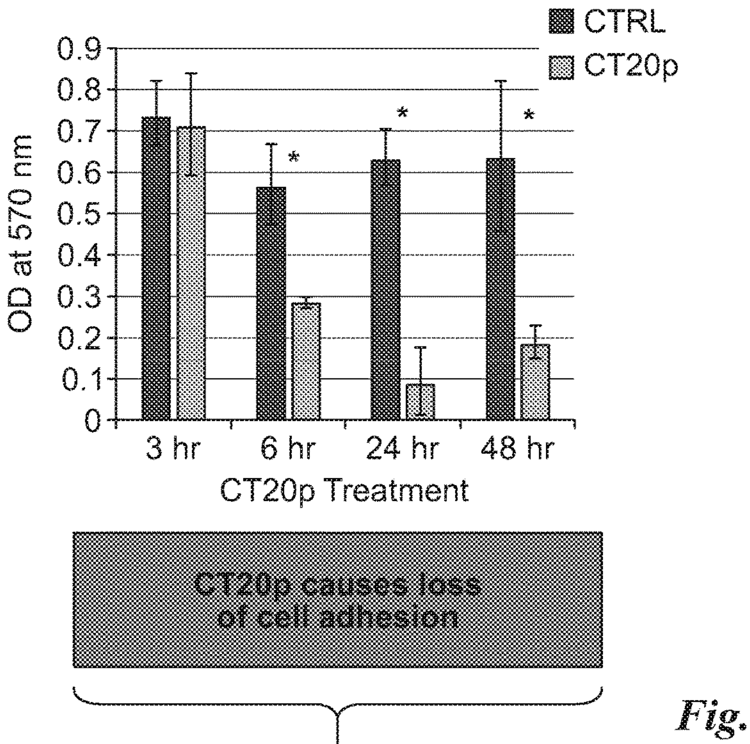
Figure 3F:
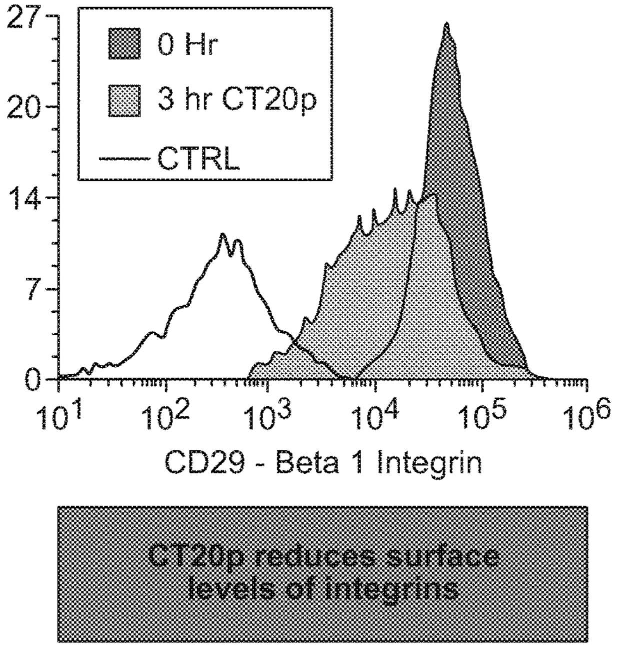
Figure 3H:
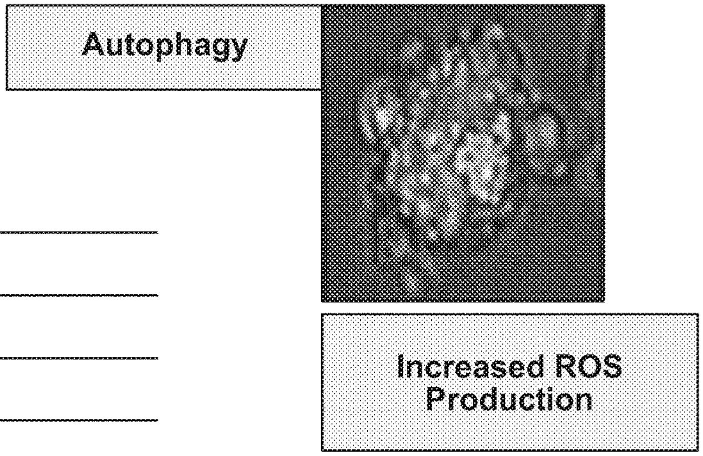
Figure 3G:
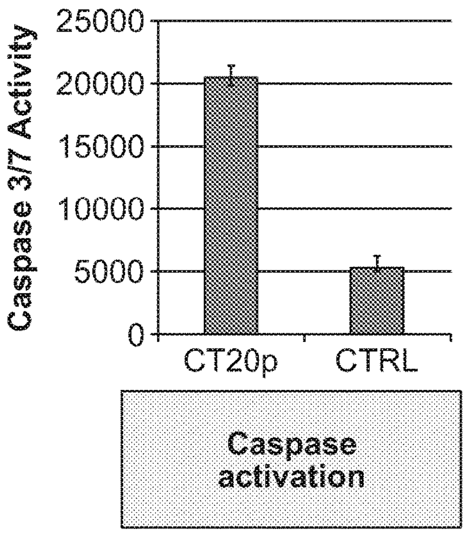
Figure 3I:
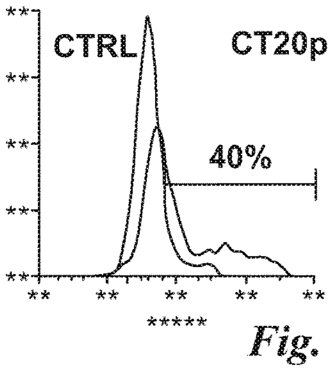
Figure 3J:
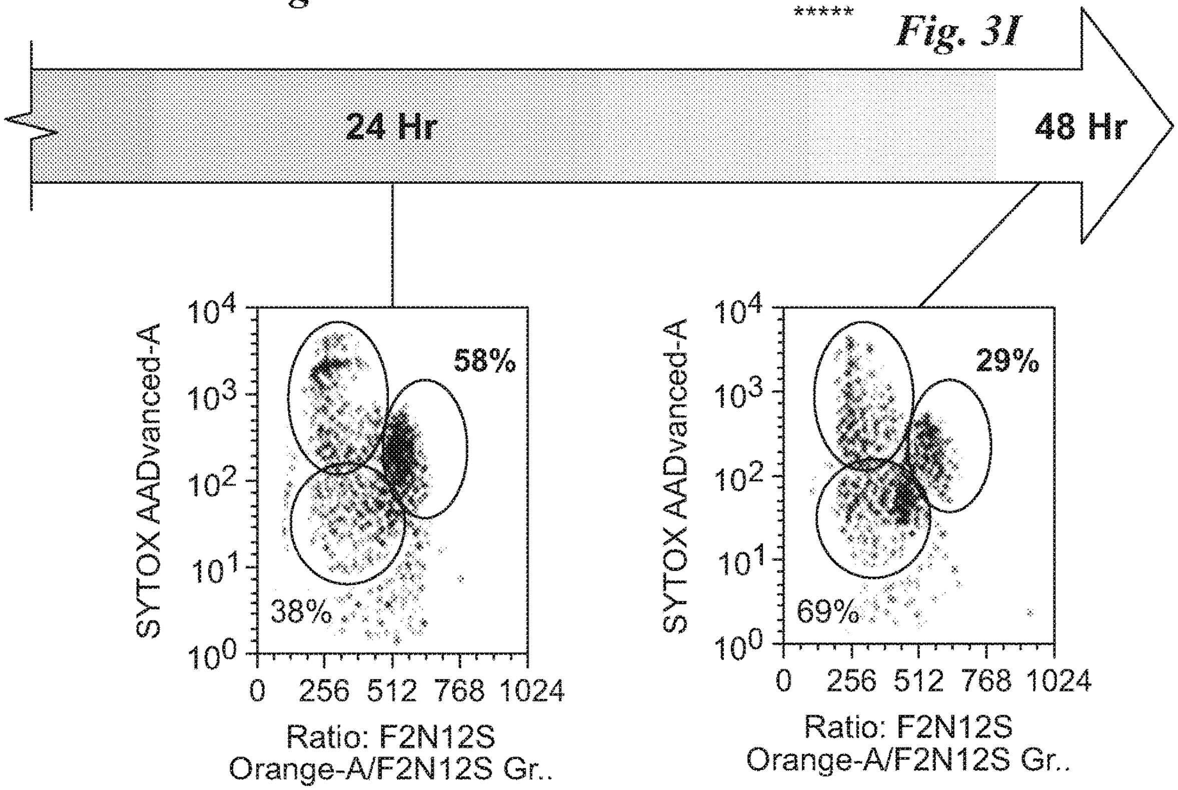
Figure 4B:
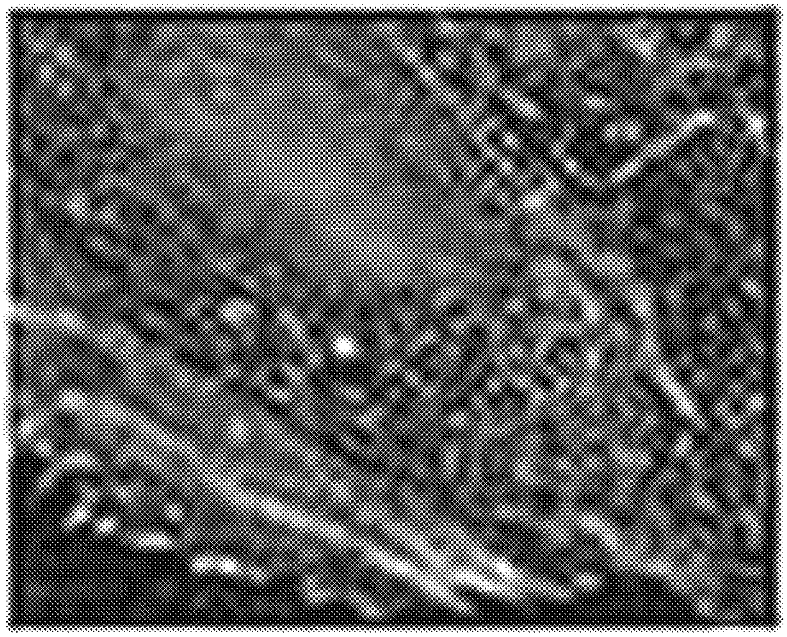
FIGS. 4A-4C show representative data demonstrating that normal cells were minimally affected by CT20 peptide. CT20 peptide did not cause mitochondrial clustering (FIG. 4A) or loss of F-actin (B4).
Figure 4A:
Figure 4C:
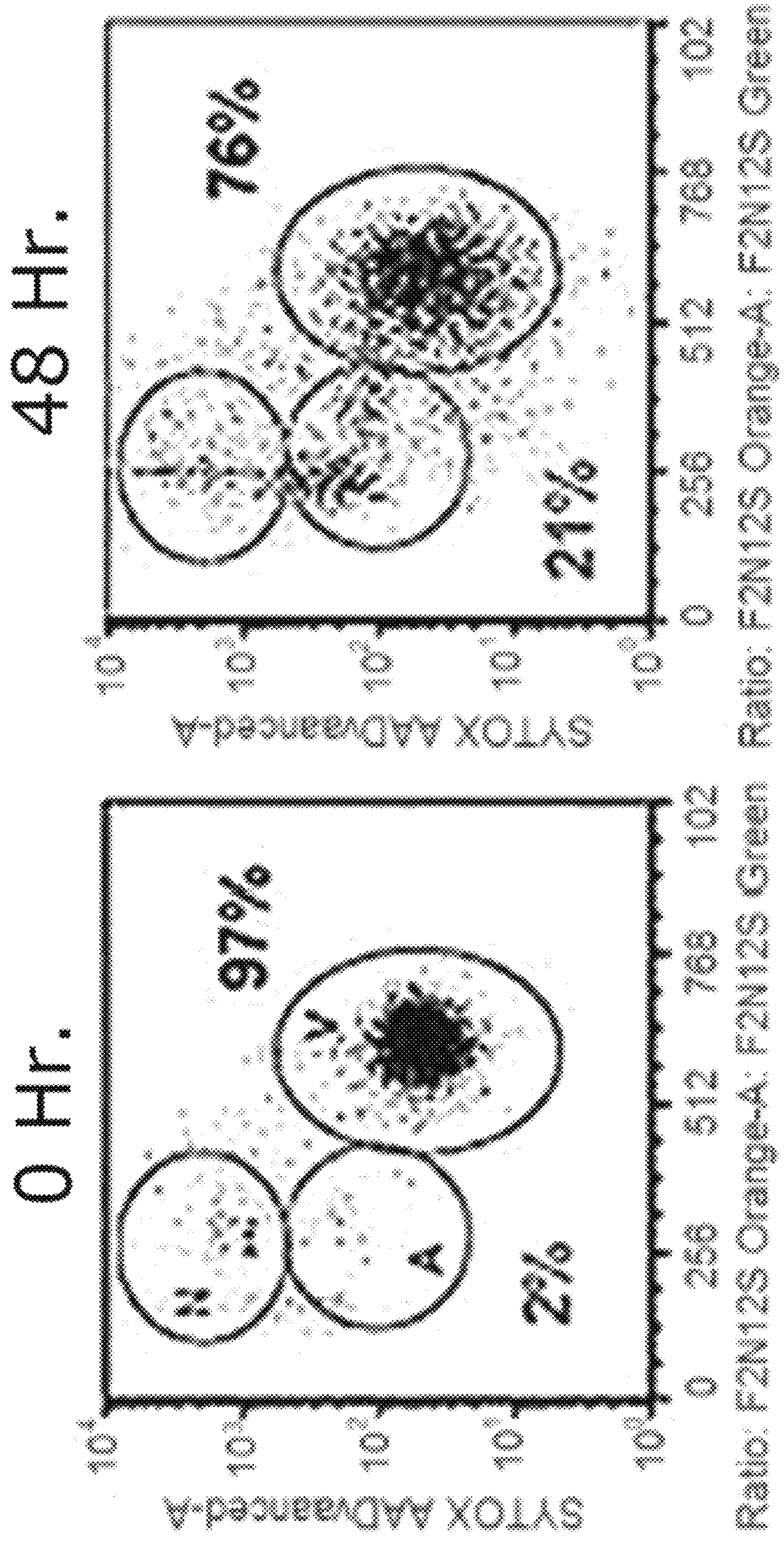

To understand how CT20 caused tumor regression, the biological effects of CT20 was examined in breast cancer cells (MDA-MB-231) compared to normal cells (MCF-10A). Using CT20 (~3.4 nM) in HBPE-NPs as above, reduced movement of mitochondria was observed (FIG. 3A), decreased four-fold compared to controls (Lee, M. W., et al. (2014) Cell Death Dis. 5). This triggered hyperpolarization of the mitochondrial membrane and fusion-like aggregation (FIG. 3B) that impaired mitochondrial redistribution, ATP production, and F-actin polymerization (FIG. 3C). Cells remained viable during these "initiating events" (FIG. 3D). However, at 6 hours post-CT20 treatment, cells began detaching from the substrate (fibronectin) (FIG. 3E). This was preceded by decreased expression of integrins (β1 integrin is shown; FIG. 3F). By 24 hours post-CT20 treatment, "effector events" caused by peptide-induced detachment were detected, including the activation of caspases (FIG. 3G), the induction of autophagy (FIG. 3H), and increased ROS production (FIG. 3I). Cell death (anoikis), indicated by membrane asymmetry, was detected in cancer cells by 48 hours (FIG. 3J). Importantly, similar results, such as cytoskeletal impairment and cell death, were not observed with the control epithelial cell line (FIG. 4), indicating that that the lethal activity of the peptide was cancer cell specific (Lee, M. W., et al. (2014) Cell Death Dis. 5). Without wishing to be bound by theory, these data suggest that CT20 may have the potential to impair cancer cell invasiveness through its actions on the cytoskeleton, which causes detachment-induced cell death.

Among the challenges of treating TNBC has been the vast heterogeneity of these cancers at a molecular level. Gene expression profiling has been employed broadly to better understand molecular drivers of breast cancer (Perou, Sorlie et al. 2000). Analysis of gene expression of triple negative tumors has led to definition of several subgroups based on differential expression patterns, including basal-like, mesenchymal-like, and mesenchymal stem-like subtypes (Lehmann, Bauer et al. 2011). Indeed, TNBC cell lines were variably sensitive to therapeutic agents in keeping with the genetic pathways upregulated in the different subtypes (Lehmann, Bauer et al. 2011). To obtain a representative sampling of TNBC subtypes for our studies, four TNBC cell lines were examined: MDA-MB-468 of the basal-like 1 subtype; BT-549 of the mesenchymal-like subtype; and MDA-MB-231 and MDA-MB-436 of the mesenchymal stem-like subtype. These were contrasted to the normal breast epithelial line MCF-10A.

To study CT20p as a therapeutic agent, an efficient delivery system was employed consisting of hyperbranched polyester nanoparticles (HBPE-NPs). The peptide is effectively sequestered upon formation of the nanoparticle, but low pH, such as that found in the endocytic environment of the cell, induces release of the cargo from the HBPE-NPs (Santra, Kaittanis et al. 2010; Boohaker, Zhang et al. 2012). Uptake of HBPE-NPs is comparable in MDA-MB-231 and MCF-10A cells using dye-loaded HBPE-NPs and rhodamine-labeled CT20p encapsulated in HBPE-NPs (Lee, Bassiouni et al. 2014). Therefore, all experiments involving CT20p delivery to cell lines were performed with HBPE-NPs.

Figure 5A:
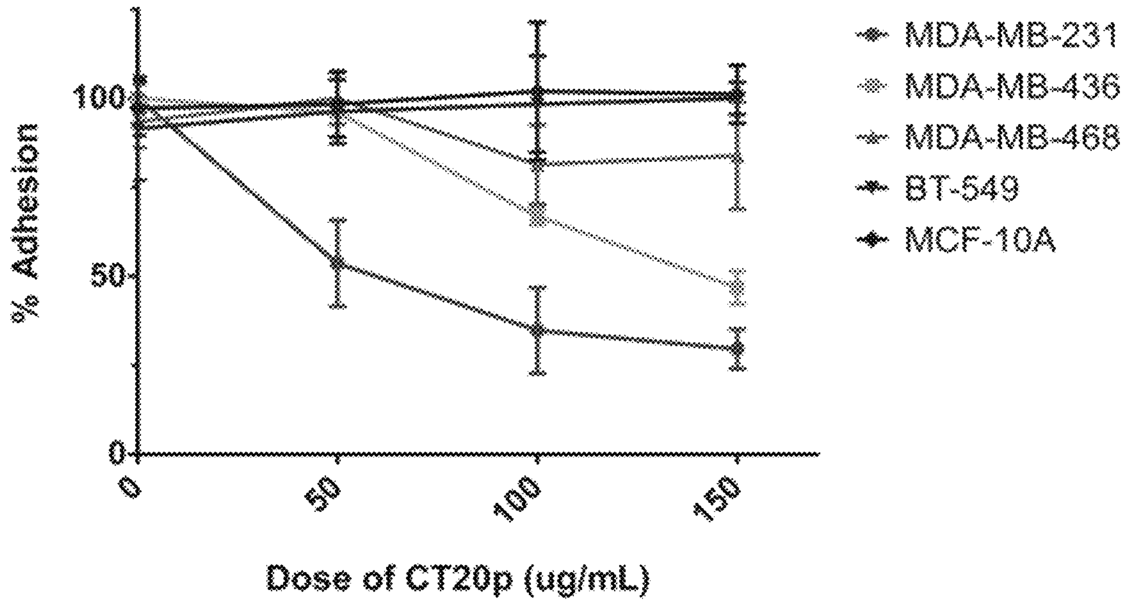
FIGS. 5A-5C show representative data demonstrating that CT20p has cytotoxic activity in TNBC cell lines.

The effect of CT20p was examined on a panel of cell lines by measuring the impact on cellular adhesion. Metastatic cells vary their adhesion patterns as dictated by their environment (Cheung and Ewald 2014), and targeting adhesion ability could mitigate metastasis. To examine the cell lines, plates were coated with fibronectin to provide an appropriate substrate for adhesion, and cells were treated with CT20p for 48 hours at varying doses (FIG. 5A). CT20p was found to cause a dose-dependent loss of adhesion, most notably in MDA-MB-231 and MDA-MB-436 cells. Interestingly, both of these cell lines fall into the mesenchymal stem-like (MSL) subtype of TNBC (Lehmann, Bauer et al. 2011). CT20p's effect varied among the cell lines, with MCF-10A and BT-549 cells being particularly unaffected by treatment. This data also led us to determine an effective working concentration of 75 μg nanoparticles per mL, which is equivalent to ~3.5 nM CT20p. Treating at this dose would allow us to observe the molecular effects of the peptide prior to cell death.

Figure 5C:
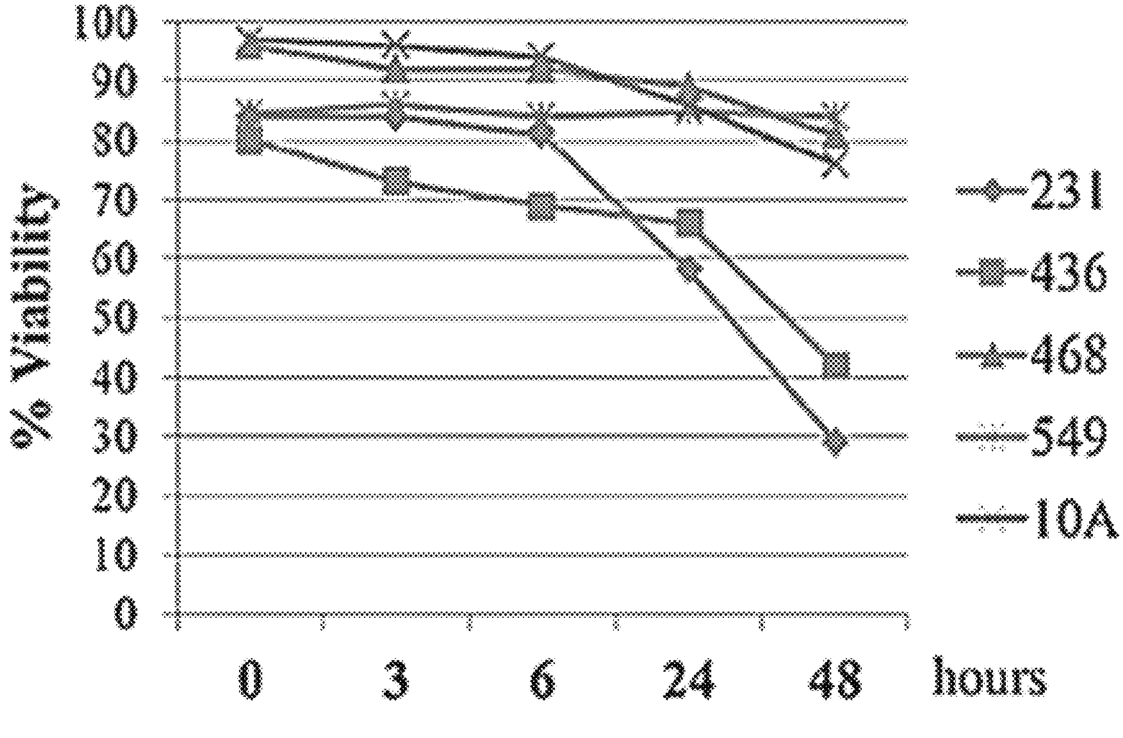
Figure 5B:
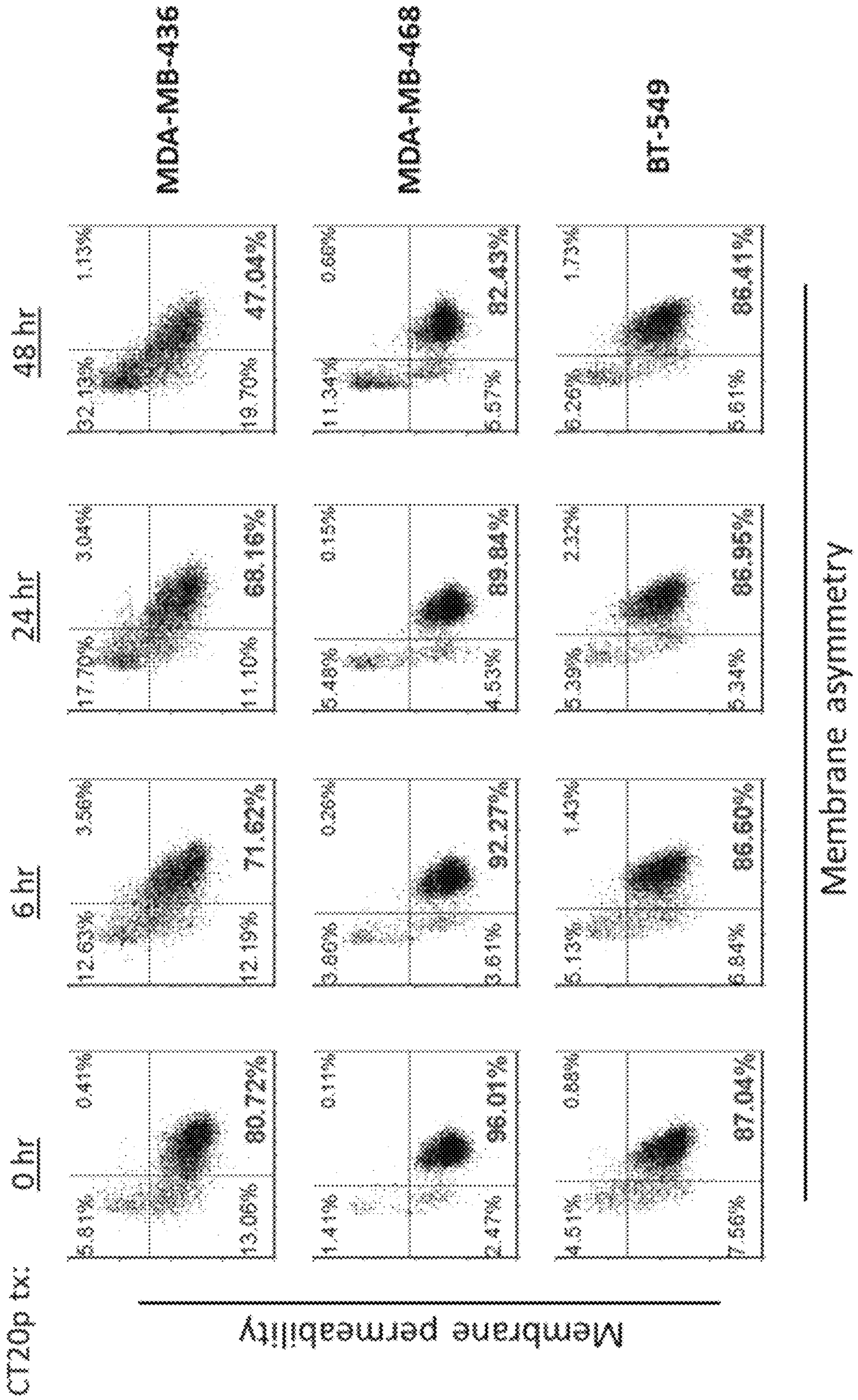

The cytotoxicity of CT20p to the cell lines was also assessed. To do this, cells were treated with the effective dose of CT20p in a time course-experiment, and membrane symmetry and permeability were examined by flow cytometry (FIG. 5B). The cell lines displayed varying susceptibilities to CT20p, with the degree of cytotoxicity correlating with the loss of adhesion observed in each cell line. MDA-MB-436 cells were most sensitive to CT20p, displaying characteristics of cell death as early as 6 hours of treatment. BT-549 cells, on the other hand, were resistant to the effects of the peptide. This supported the adhesion data indicating that MDA-MB-231 and MDA-MB-436 cells, those of the MSL subtype, are highly susceptible to the CT20p. FIG. 5C shows the viability of each of the cell lines over 48 hours, as measured by flow cytometry.

Therefore, the cytotoxic effect is varied among cancer cell lines. Hence, the target of CT20p's action that elicits a cell death response is likely a variable factor in cancer cells. This is supported by evidence in the literature showing that TNBC cells respond variably to a variety of chemotherapeutic drugs (Lehmann, Bauer et al. 2011; Masuda, Baggerly et al. 2013).

In an effort to understand the varying efficacy of the cytotoxic mechanism of CT20p, intracellular environment was examined. The subtypes of TNBC vary in their utilization of various metabolic processes, and their reliance on signaling pathways, such as EGF signaling, that may influence metabolism (Lehmann, Bauer et al. 2011). Because a portion of the CT20p delivered to the cell localizes to mitochondria (Lee, Bassiouni et al. 2014), it was examined whether the cell's metabolic environment was a driver of CT20p's effect. To characterize the metabolic phenotype of the TNBC cell lines, both mitochondrial oxidative respiration and glycolytic flux was measured.

Figure 6A:
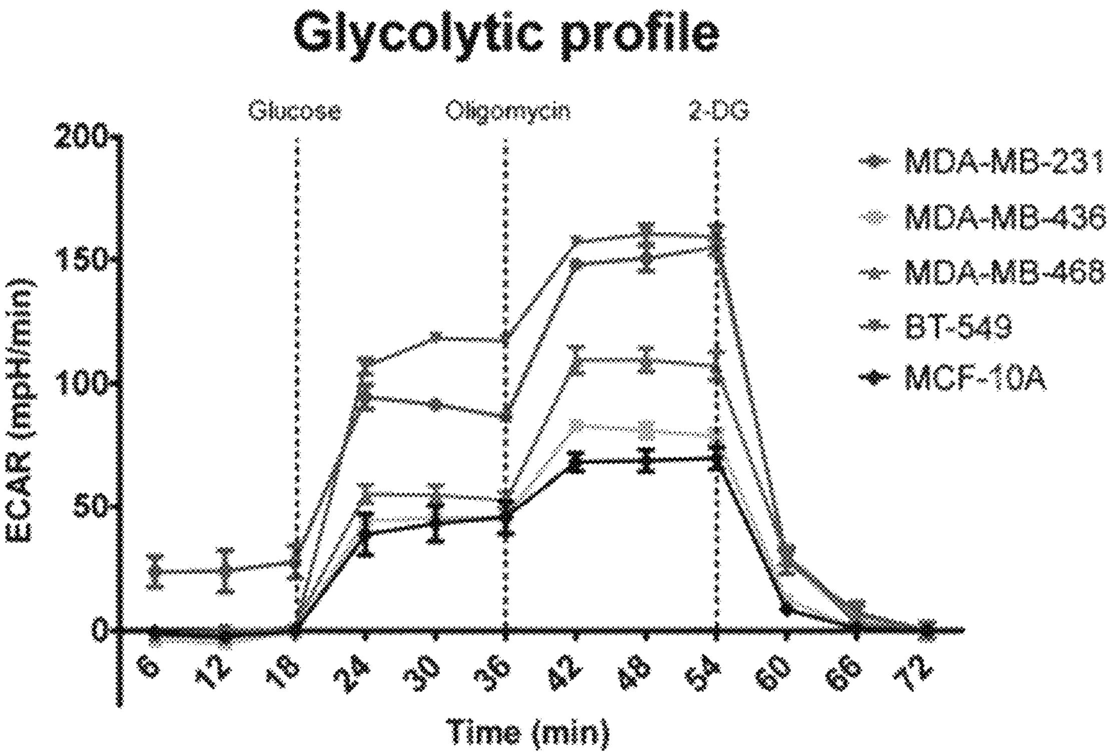
FIGS. 6A-6F show representative data showing that CT20p cytotoxicity does not correlate with metabolism.
Figure 6B:
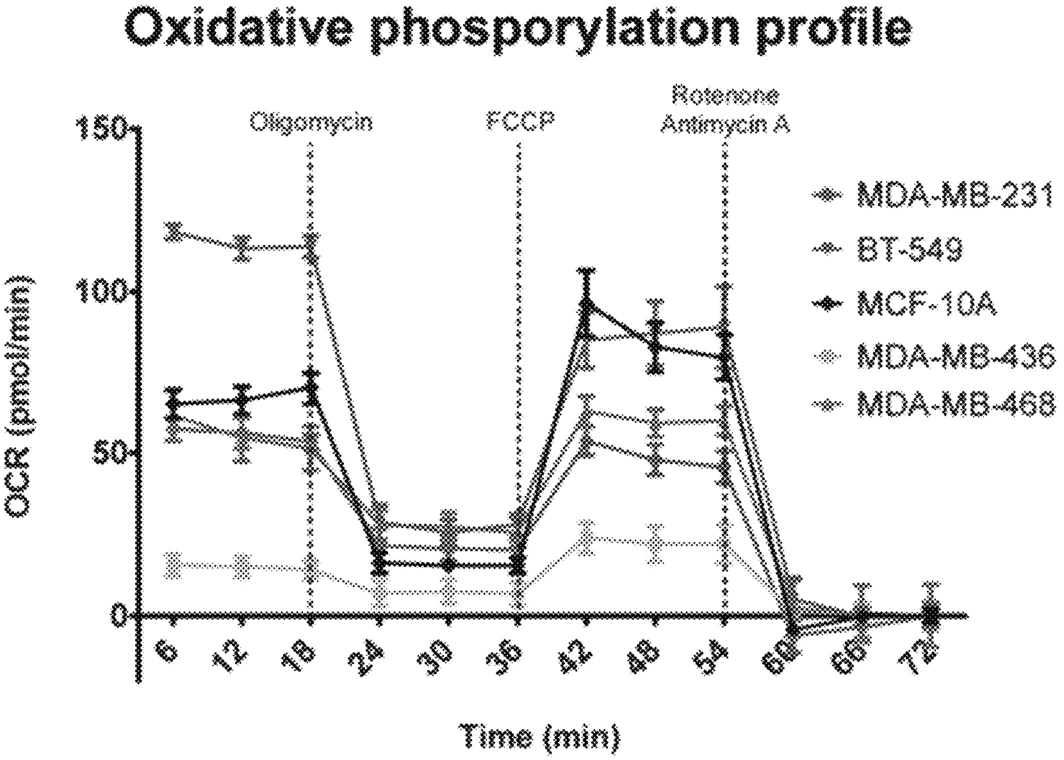

To gain a full understanding of the cell's metabolic responses, inhibitors and stimulators were applied over the course of the assay. By introducing glucose, oligomycin, and 2-deoxyglucose (2-DG) in sequence, glycolysis was first activate before complete inhibition. Glycolytic profiles, displayed as extracellular acidification rate (ECAR), were inherently varied among the cell lines (FIG. 6A). Glycolytic reserve capacity, which represents the difference between the maximum glycolytic flux induced by oligomycin and the basal flux induced by glucose, also varied (FIG. 6B).

Figure 6C:
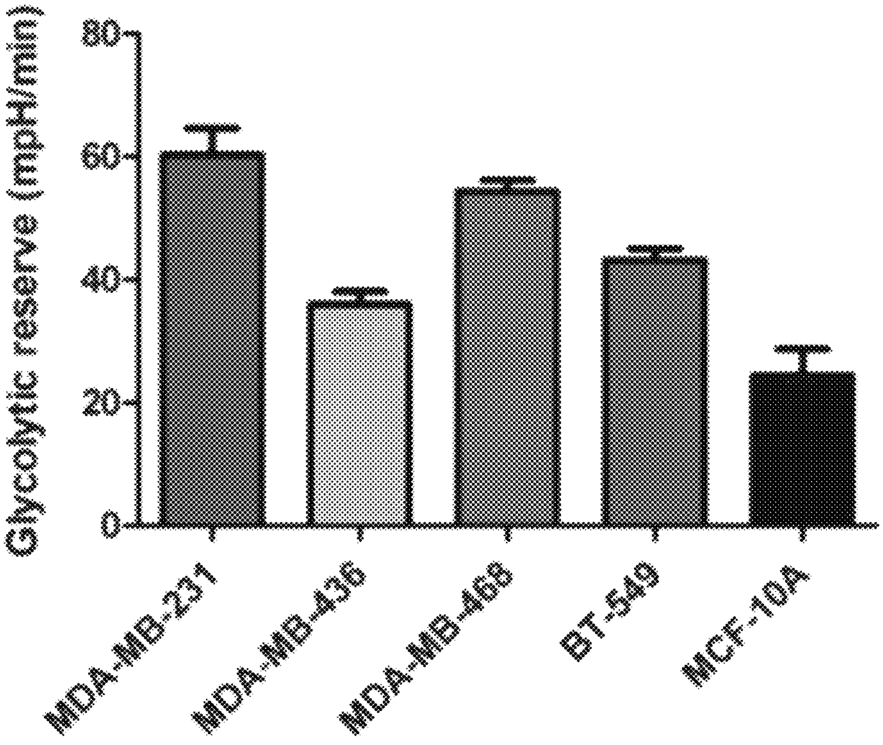
Figure 6D:
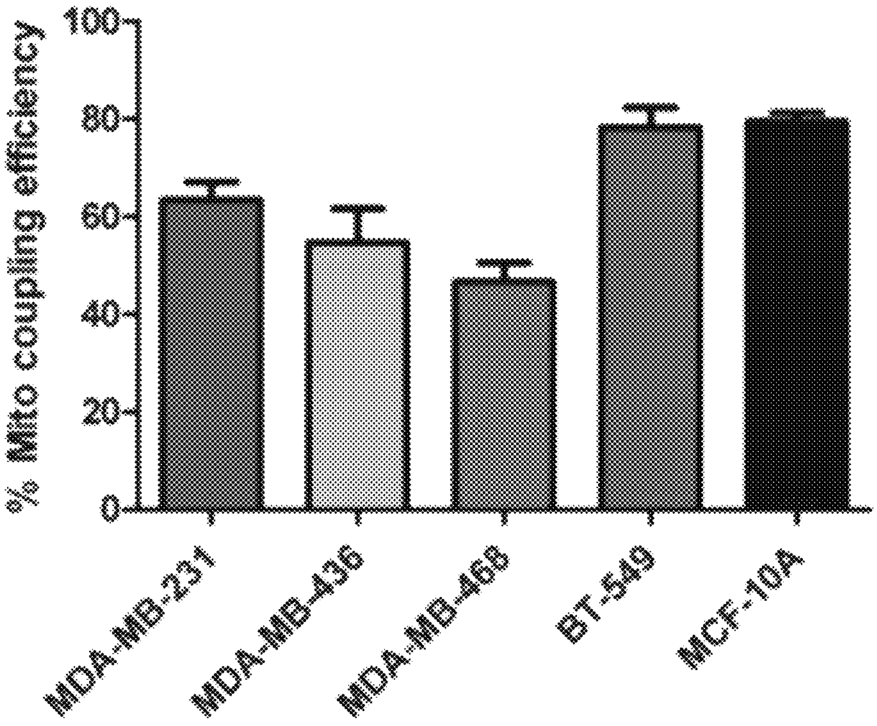
Figure 6E:
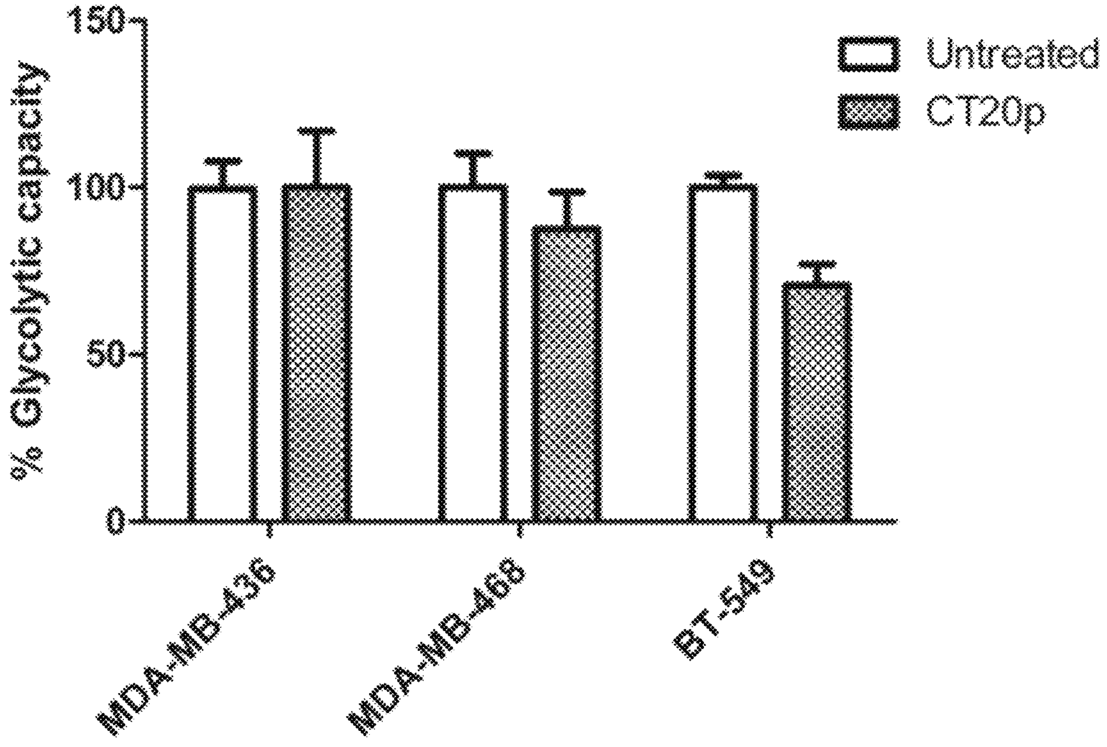

To create an oxidative phosphorylation profile, oligomycin, FCCP, rotenone, and antimycin A were used to induce both down regulation and upregulation of respiration, represented by oxygen consumption rate (OCR). As with glycolysis, the cell lines varied in their reliance on oxidative phosphorylation (FIG. 6D). This was also represented by the mitochondrial coupling efficiency. Coupling efficiency provides a measure of how efficiently the cell couples electron transport to energy generation, and is elucidated by the response to oligomycin, inhibitor of the F1FO ATPase. As expected, normal breast epithelial MCF-10A cells are reliant on oxidative phosphorylation, while the cancer cells tend to be more glycolytic. Even so, heterogeneity exists among the various cancer cell lines in their metabolic phenotypes. The metabolic pattern did not correlate with the susceptibility of the cells to CT20p, leading us to believe that the cells' metabolic state does not drive the effects of the peptide.

Figure 6F:
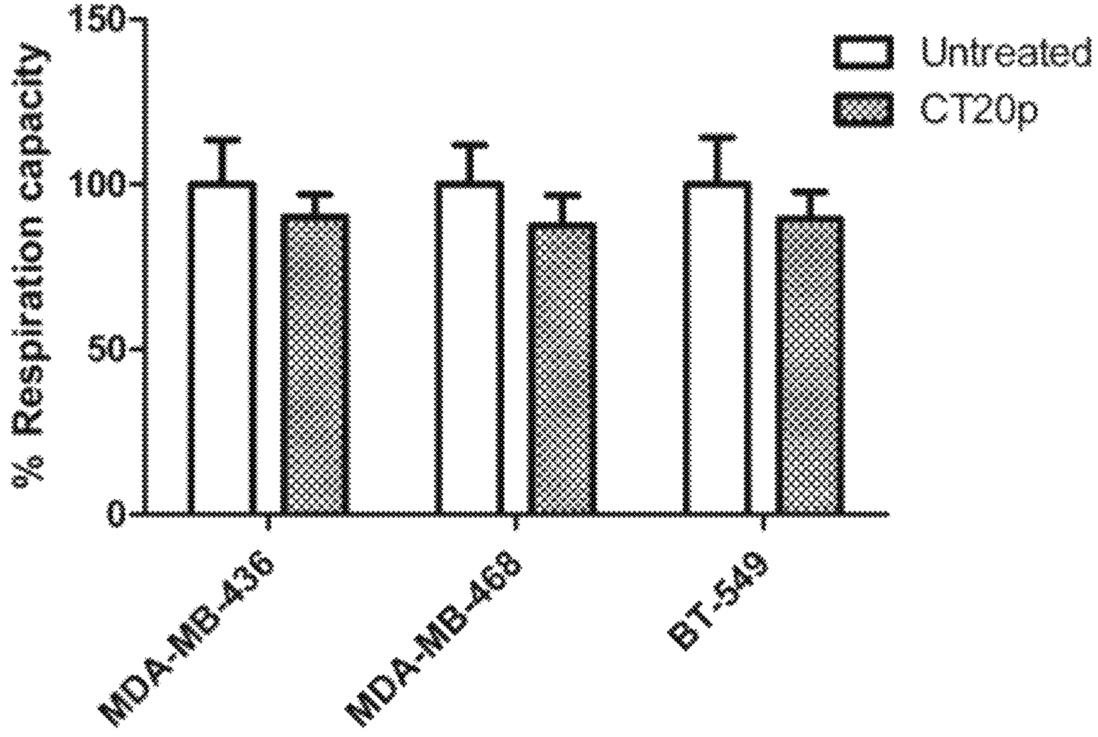

The effect of CT20p on cellular metabolism was also examined by pre-treating the cells with CT20p prior to running metabolic stress tests. Glycolytic capacity (FIG. 6C) and respiration capacity (FIG. 6F) were calculated for treated cells with respect to untreated cells. None of the cell lines displayed metabolic responses to CT20p that could explain the cytotoxicity pattern.

Figure 7:
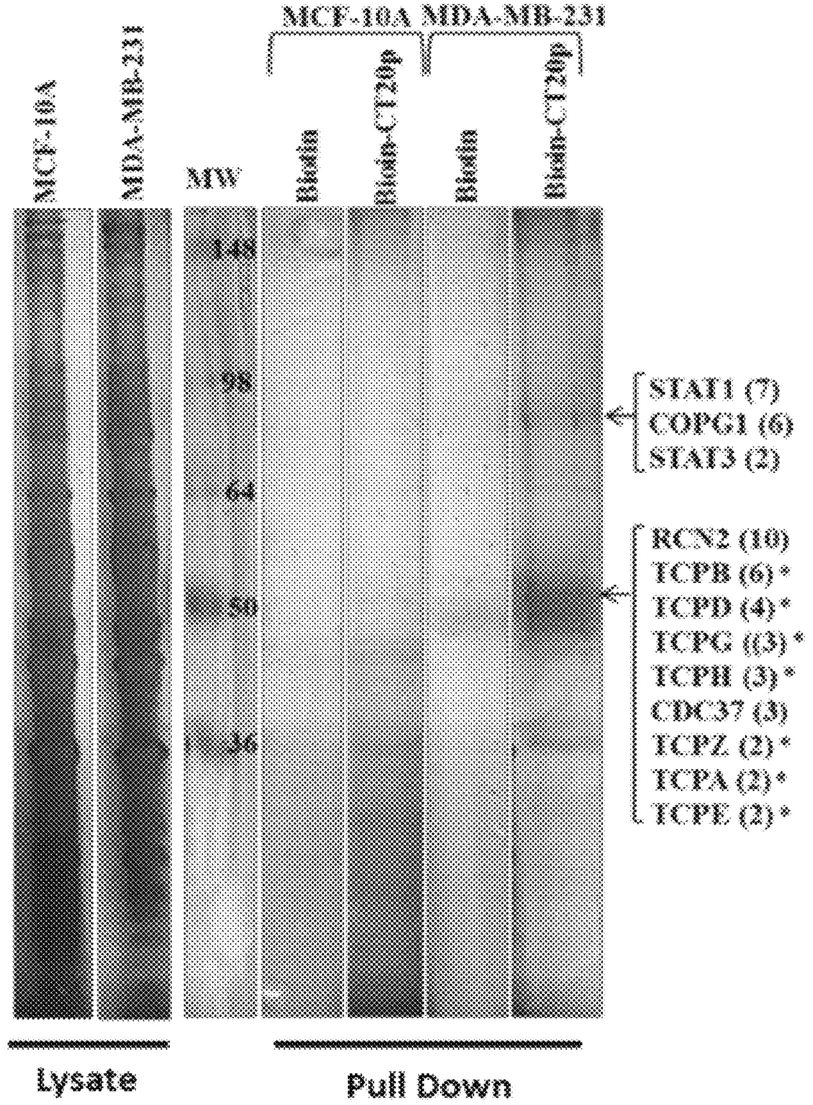
FIG. 7 shows representative data demonstrating that biotin-tagged CT20p was used to pull-down interacting proteins in MCF-10A and MDA-MB-231 cells. The gel was silver stained, and the two indicated bands that were present in the MDA-MB-231 pull down were excised and evaluated by mass spectrometry. A selected list of proteins present in each band is shown, with the number of identified peptides indicated in parentheses. More information on these proteins can be found in Table 2.

Despite being derived from the C-terminal of the Bax protein, the CT20 peptide does not induce effects similar to the parent protein. For example, it does not induce mitochondrial pore formation to initiate apoptosis (Boohaker, Zhang et al. 2012; Lee, Bassiouni et al. 2014). The possibility that CT20p could interact with targets outside the mitochondria was therefore explored. To identify cellular targets of CT20p, a pull-down was performed using biotin-tagged CT20p to probe for interacting proteins in MDA-MB-231 and MCF-10A cell lysates. N-terminal additions do not impair the intracellular localization or cytotoxicity of CT20p (Lee, Bassiouni et al. 2014). CT20p pulled down groups of proteins unique to MDA-MB-231 cells and not found in MCF-10A cells. Bands from the gel containing the unique proteins were excised and analyzed by mass spectrometry (FIG. 7).

A number of proteins that interacted with CT20p were identified. Of particular interest were proteins that were involved with the cytoskeleton, as CT20p causes impaired adhesion and inhibition of actin polymerization (FIG. 3C-D). A sample of relevant findings is shown in Table 2. Biotin-CT20p directly pulled down seven of the eight subunits of the T-complex protein 1 (TCP1), also known as the CCT (chaperonin containing TCP1) complex. This complex is a type II chaperonin, composed of eight individual subunits denoted as alpha, beta, gamma, delta, epsilon, eta, theta, and zeta, and is principally responsible for the folding of actin and tubulin into their native forms (Gao, Thomas et al. 1992; Yaffe, Farr et al. 1992; Kubota 2002). Inhibition of CCT causes the accumulation of unfolded proteins, leading to growth arrest, changes in cell morphology and loss of motility (Grantham, J., et al. (2006) Exp. Cell Res. 312, 2309-2324), which correlates with the observed effects of CT20 (FIG. 3C-D). In addition to CCT, our pull down identified many other interactors with CT20p (Table 3), and many of these, including STAT3, p53, and huntingtin, are known to be clients of CCT (Kitamura, Kubota et al. 2006; Trinidad, Muller et al. 2013; Kasembeli, Lau et al. 2014).

Figure 8A:
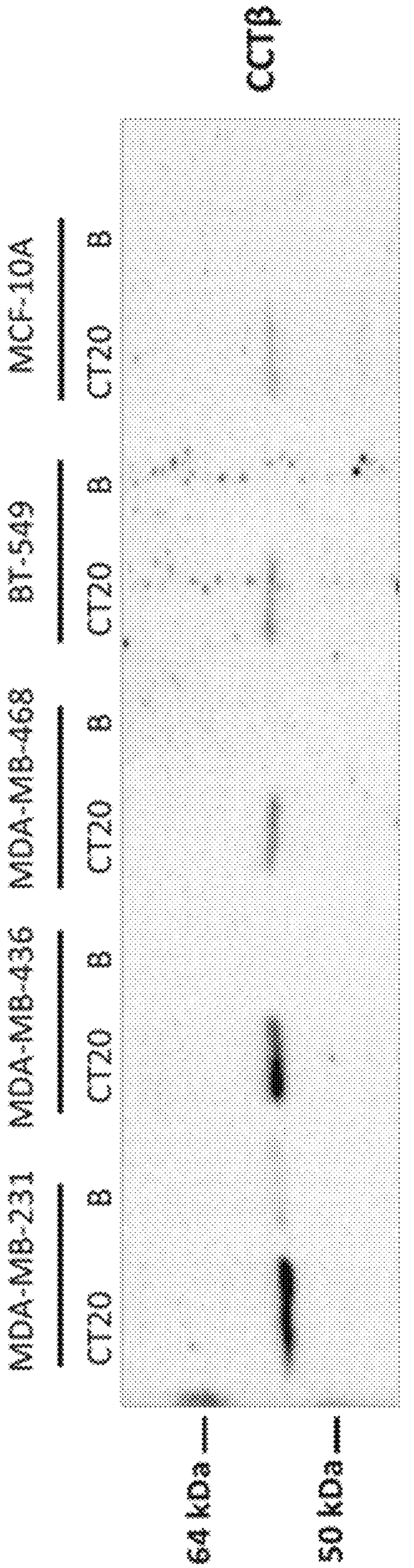
FIGS. 8A-8C show representative data showing that CT20p binds CCTβ in the cellular environment.

To confirm that CCT is an intracellular target of CCT, several experiments were performed. We first confirmed the results of our mass spectrometry experiment by probing lysates from the TNBC cell lines and MCF-10A cells with CT20p-biotin. Proteins pulled down by CT20p-biotin were then recovered and analyzed by blotting for the beta subunit of CCT (CCM (FIG. 8A). This subunit was chosen because it was the most highly recovered and identified by mass spectrometry, with 6 unique peptides identified. CT20p was able to interact with CCTβ in all cell lines, more so in the MSL subtypes, indicating that the peptide-CCT interaction is variable to some degree across cell lines (FIG. 8A). Biotin only was used as a negative control, and did not result in pull-down of CCT.

Figure 8B:
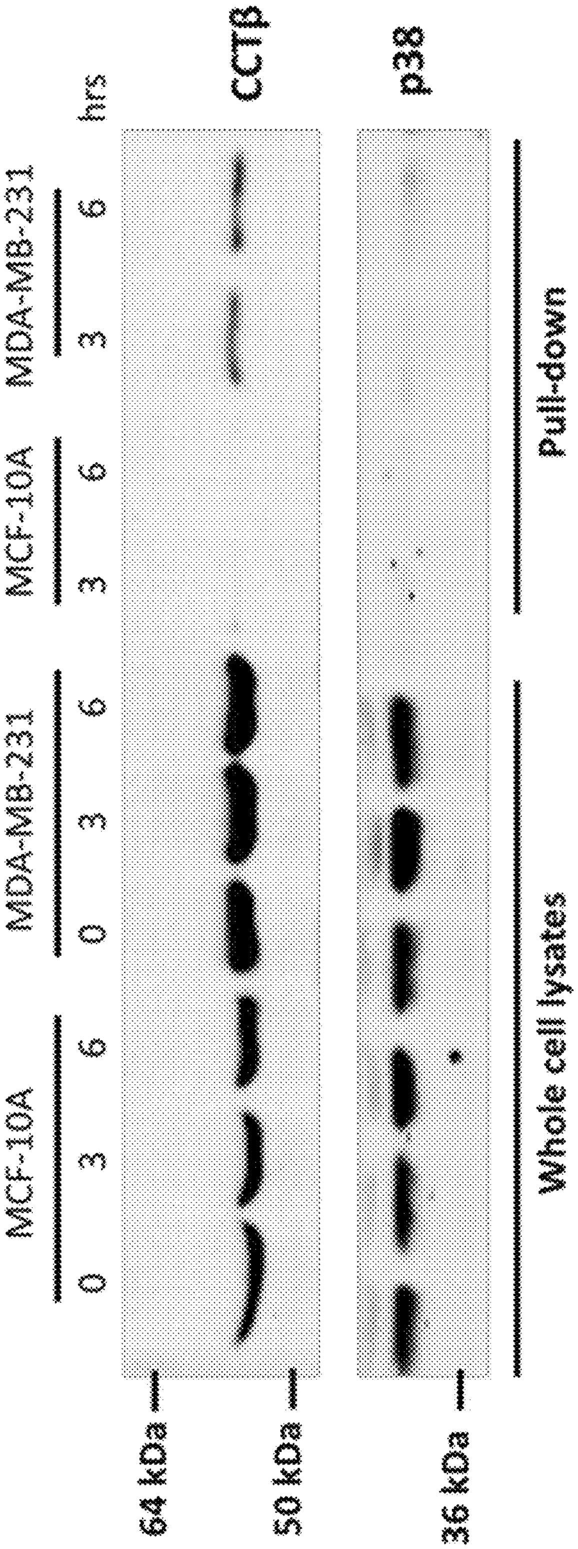
Figure 8C:
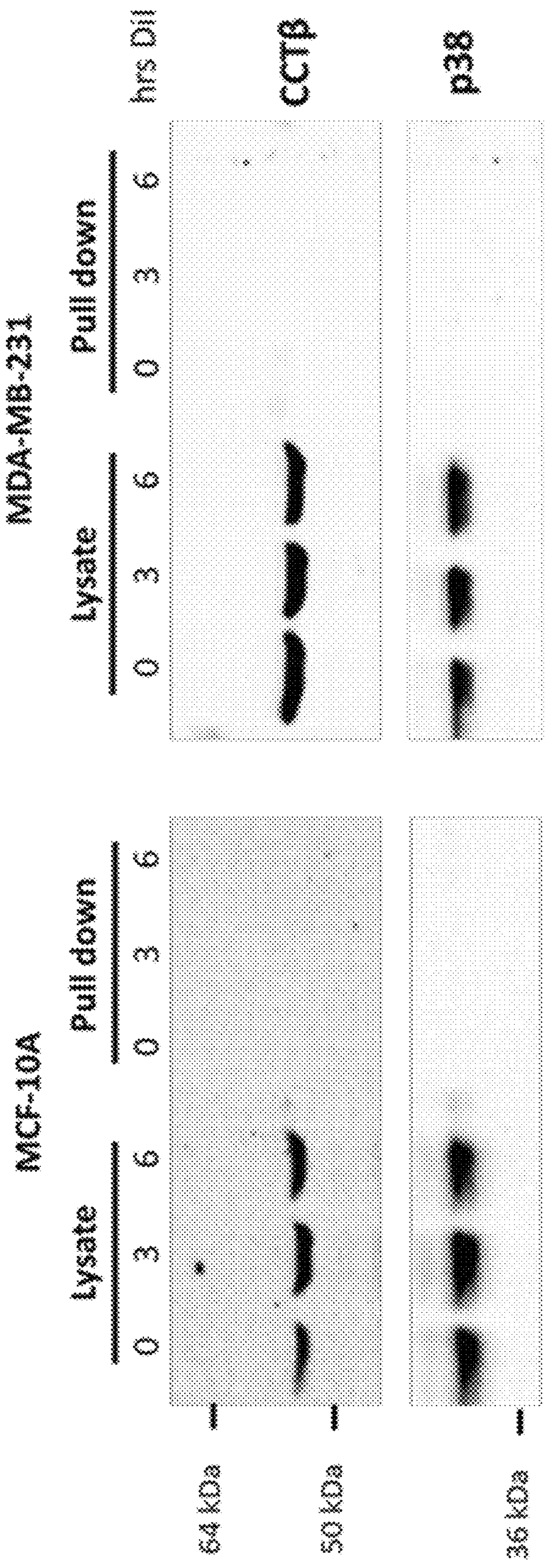

Because pull downs performed in cell lysates may emphasize non-specific protein interactions, we designed an in-cell pull down assay to better reflect interactions in the intracellular environment. To do this, biotin-tagged CT20p was encapsulated in HBPE-nanoparticles and delivered to viable MDA-MB-231 and MCF-10A cells, followed by gentle cell lysis and recovery of CT20p-biotin and its binding partners. Blotting for CCTβ revealed that the CT20p-CCT interaction does occur intracellularly, and is detectable as soon as 3 hours after treatment in MDA-MB-231 cells, but not in MCF-10A cells (FIG. 8B). However, CT20p treatment does not affect total CCTβ protein levels in either cell line, as shown by examining whole cell lysates. Because biotin's hydrophilic nature prevents it from being encapsulated in nanoparticles, nanoparticles containing DiI were used as a control to exclude the possibility that the interaction may be a nanoparticle effect, and therefore an artifact of the delivery mechanism (FIG. 8C). Indeed, no pull down was detected with DiI-loaded nanoparticles.

TABLE 2

| Number | Identified protein | Accession number | MW (kDa) | No. of unique peptides |
|---|---|---|---|---|
| 1 | Reticulocalbin-2 | RCN2_HUMAN | 37 | 10 |
| 2 | Signal transducer and activator of transcription 1-alpha/beta | STAT1_HUMAN | 87 | 7 |
| 3 | Coatomer subunit gamma-1 | COPG1_HUMAN | 98 | 6 |
| 4 | Coatomer subunit beta | COPB2_HUMAN | 102 | 6 |
| 5 | T-complex protein 1 subunit beta | TCPB_HUMAN | 57 | 6 |
| 6 | T-complex protein 1 subunit delta | TCPD_HUMAN | 58 | 4 |
| 7 | T-complex protein 1 subunit gamma | TCPG_HUMAN | 61 | 3 |
| 8 | T-complex protein 1 subunit eta | TCPH_HUMAN | 59 | 3 |
| 9 | T-complex protein 1 subunit zeta | TCPZ_HUMAN | 58 | 2 |
| 10 | T-complex protein 1 subunit alpha | TCPA_HUMAN | 60 | 2 |
| 11 | T-complex protein 1 subunit epsilon | TCPE_HUMAN | 60 | 2 |
| 12 | Signal transducer and activator of transcription 3 | STAT3_HUMAN | 88 | 2 |
| 13 | Hsp90 co-chaperone Cdc37 | CDC37_HUMAN | 44 | 2 |
| 14 | Cellular tumor antigen p53 | P53_HUMAN | 44 | 1 |
| 15 | Huntingtin | HD_HUMAN | 348 | 1 |

In addition to confirming the CT20p-CCT interaction, the in-cell pull down validates that CT20p delivered via HBPE-nanoparticles is able to access the cytosolic compartment. It also confirms that that CT20p is able to access and bind to CCTβ even when the entire CCT complex is assembled, and that the interaction is stable and detectable for several hours. The lack of binding of CT20p to CCTβ in MCF-10A cells may account for the decreased susceptibility of these cells to CT20p.

The nature of the interaction between CT20p and the CCT complex was next explored. One pressing question was whether CT20p interacted directly with any of the subunits, or whether the recovery of CCT in the pull down was due to indirect interaction through an alternate primary binding partner. Because the beta subunit of CCT (CCM was recovered with the greatest number of peptides in the mass spectroscopy results, it was examined whether CT20p formed a direct interaction with this subunit. Purified recombinant CCTβ was obtained commercially, and biotin-tagged CT20p was used to confirm an interaction through pull-down (FIG. 9).

Figure 9:
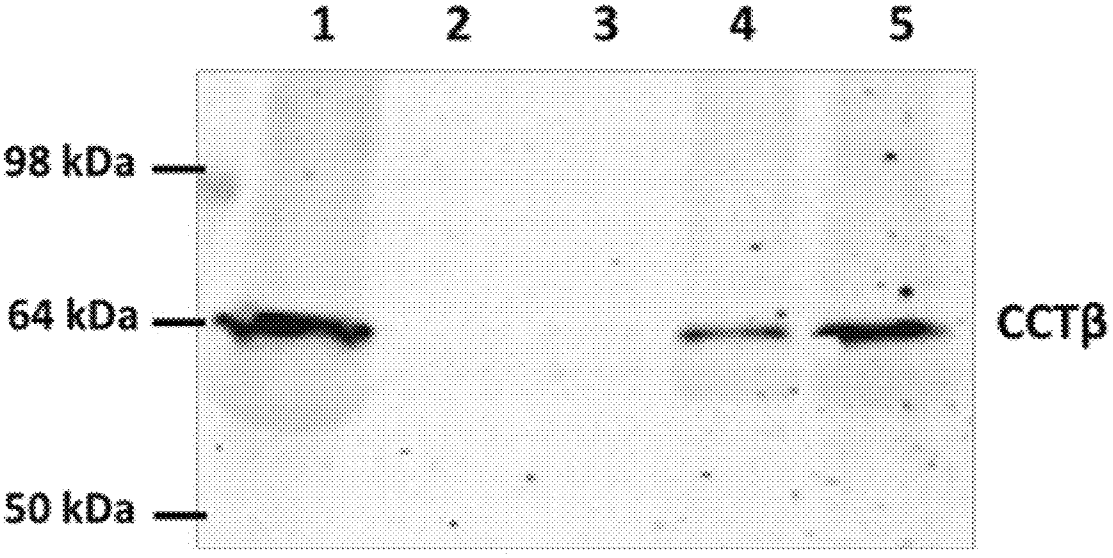
FIG. 9 is representative data showing that CT20p binds directly to CCTβ. Purified recombinant CCTβ was tested for interaction with CT20p as described in Materials and Methods. Biotin-tagged CT20p was able to pull down CCTβ in a concentration-dependent manner (lanes 3-5). Biotin alone (lane 2) did not pull down CCTβ.

By varying the molar ratio of CT20p to CCTβ, it was determine that while CT20p does interact directly with CCTβ, efficient pull down is best achieved at ratios greater than 1:1 (FIG. 9). However, this does not exclude the possibility of CT20p binding directly to multiple subunits of the CCT complex, thereby increasing the efficiency of pull-down when the entire complex is present. The results of the in-cell pull down (FIG. 8B) indicate that the reverse is not true—the quaternary structure of the CCT complex does not mask CT20p binding sites.

Figure 10A:
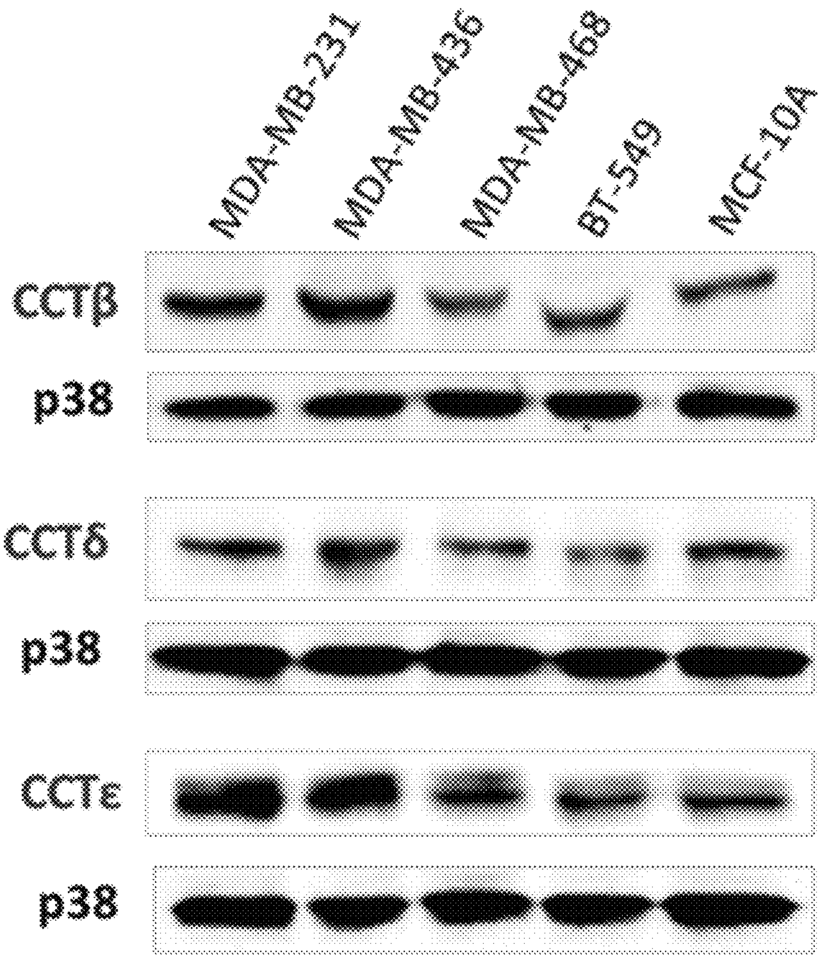
FIGS. 10A-10C show representative data demonstrating that CCT expression varies across TNBC cell lines.
Figure 10B:
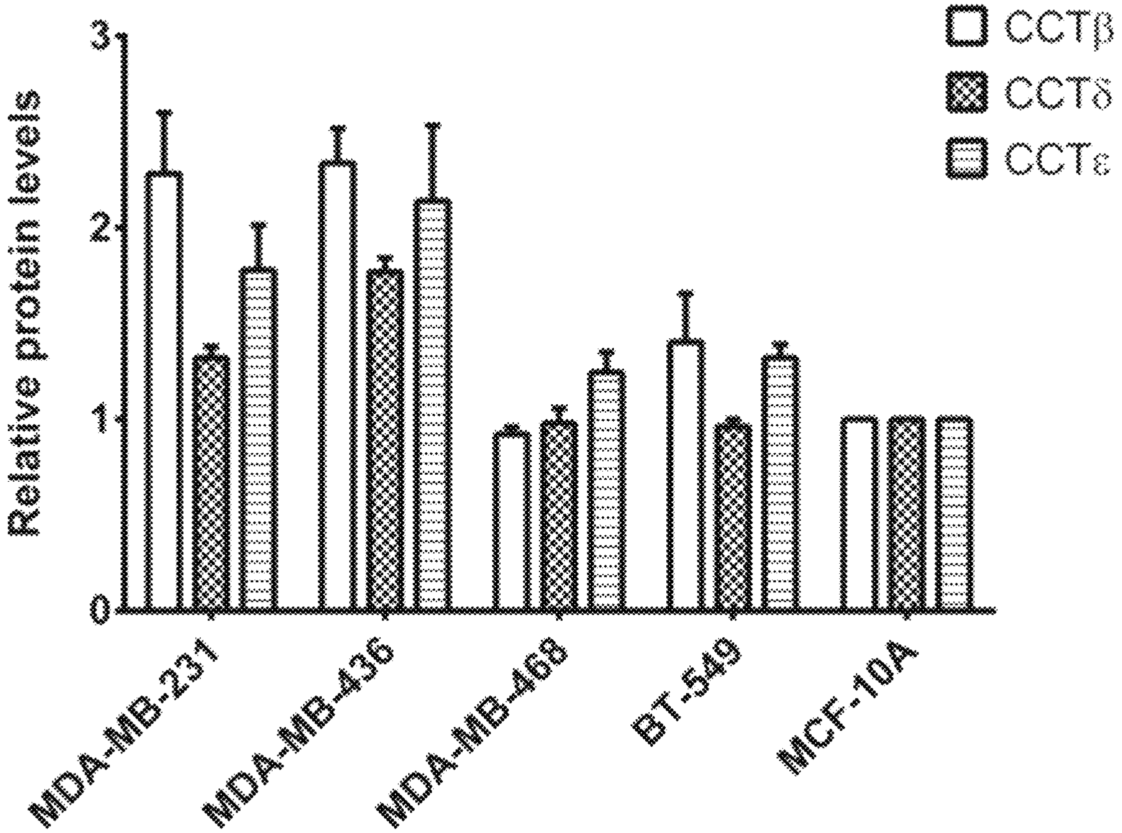

After establishing that CT20p binds directly to CCTβ, it was next determined whether CCTβ was the intracellular target of CT20p that potentiated the cytotoxic properties of the peptide. Because the susceptibility of TNBC cell lines to CT20p (FIG. 5) was previously studied, baseline levels of CCT was examined in each of the cell lines. CCT protein levels were examined by assaying for three CCT subunits: beta (13), epsilon(c), and delta (A), which are known to make direct contact with actin (Llorca, McCormack et al. 1999) (FIG. 10A). Quantification of the relative protein levels revealed that MDA-MB-231 and MDA-MB-436 cells contained the highest amounts of the CCT subunits (FIG. 10B). These two cell lines are also the most sensitive to the cytotoxicity of CT20p, suggesting a possible correlation between CCT protein levels and CT20p's effect, and supporting the hypothesis that CT20p may be targeting the CCT complex.

Figure 10C:
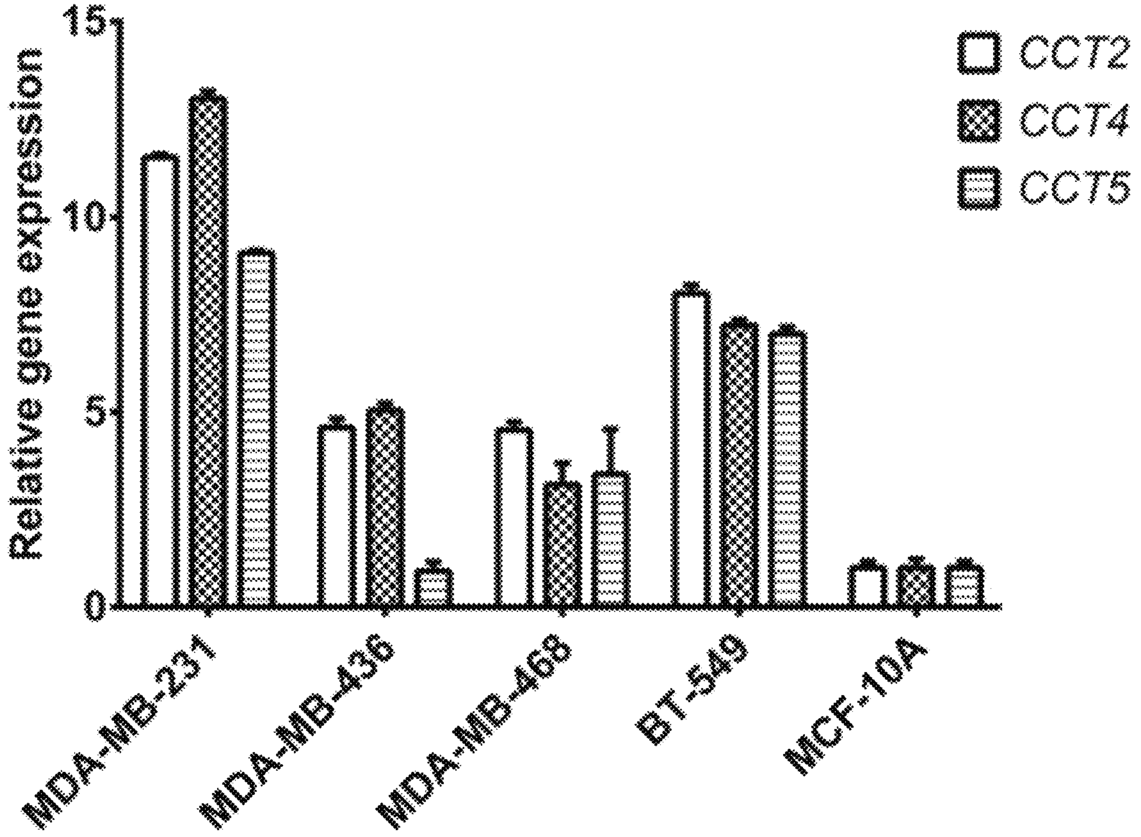

CCT gene expression levels was also examined in these cell lines. As shown in FIG. 10C, gene expression of the three subunits varied among cell lines. MDA-MB-231 cells displayed the highest level of both protein and gene expression levels, while MCF10A cells displayed the lowest. In fact, all the TNBC cell lines expressed higher levels of the CCT subunits than the MCF-10A cells. However, relative gene expression did not always correlate with relative protein expression, most notably in the case of BT-549 cells. However, expression levels of CCT do not always correlate with activity levels (Boudiaf-Benmammar, Cresteil et al. 2013). Regulation of the CCT complex at the protein level, rather than the transcript level, may therefore be a more important factor in its activity.

Figure 11A:
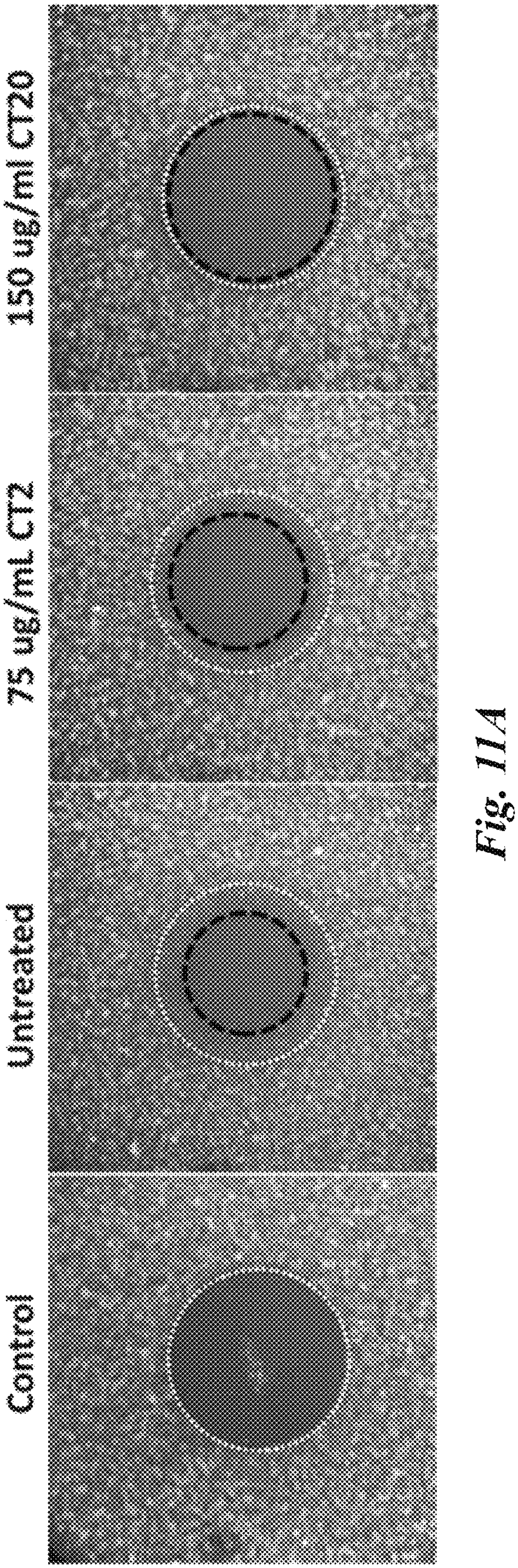
FIGS. 11A-11F show representative data demonstrating that the consequences of CT20p treatment include loss of migration ability and tubulin architecture.
Figure 11B:
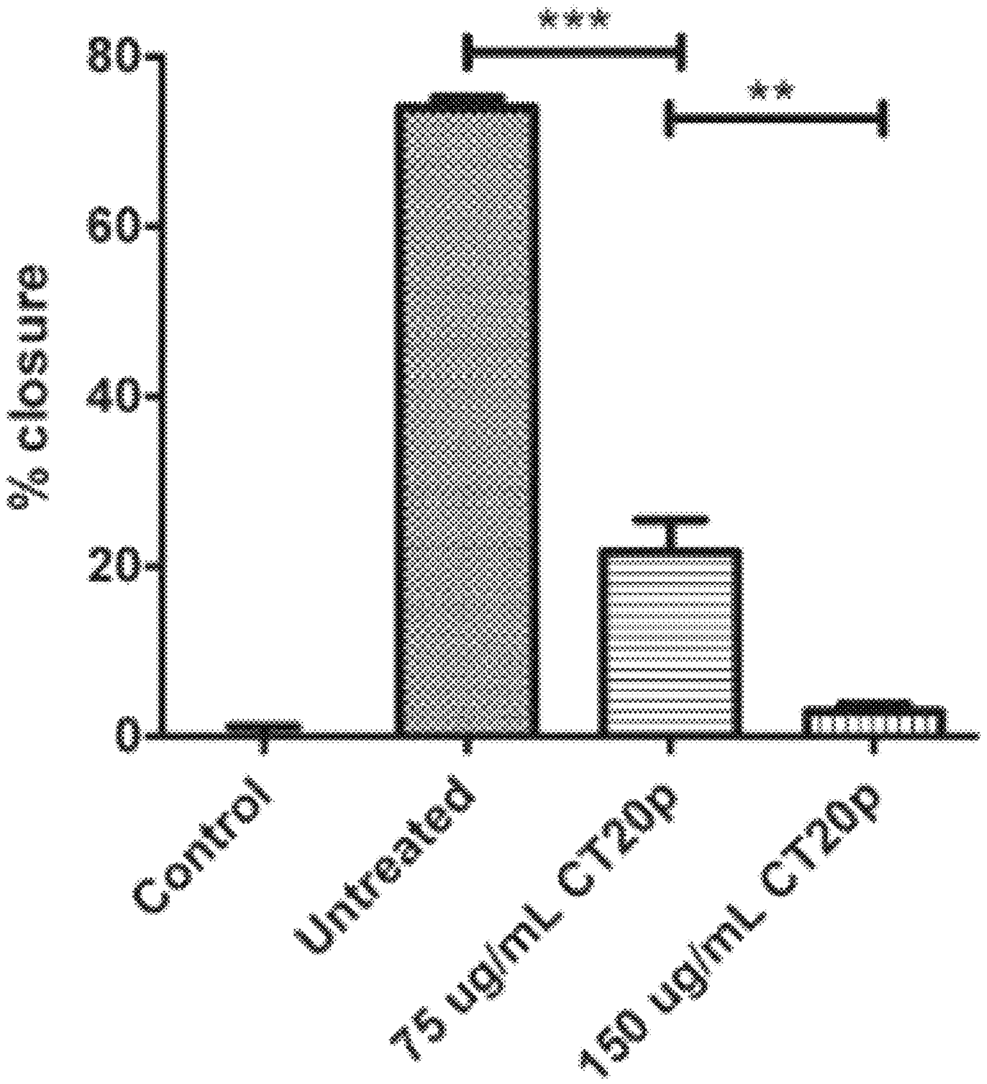

Observations on the effects of CT20p on breast cancer cells include loss of actin distribution throughout the cell, especially in the filapodia (FIG. 3C). As actin dynamics are necessary for cellular migration, and therefore metastasis, the effect of CT20p on the motility of MDA-MB-231 cells was examined. By using stoppers at the time of cell seeding, an exclusion zone was created that cells would later migrate into. Immediately following removal of the stoppers, the pre-migration area can be determined. After allowing migration for 10 hours, the migration area of untreated cells was compared to cells treated with CT20p at two different doses for 24 hours (FIG. 11A). The pre-migration area, based on the control, is defined by a white circle, while the migration area is outlined in red. After quantification of the areas as described in Materials & Methods, % closure was calculated for each condition (FIG. 11B). CT20p significantly impaired movement even at a dose of 75 μg/mL, and migration was nearly eliminated at 150 μg/mL. At this dose, after 24 hours of treatment, cells have not yet undergone detachment and death, as evidenced by the consistent cell densities in FIG. 11A. Therefore, loss of ability to migrate horizontally is an early consequence, consistent with previous data showing loss of actin architecture (FIG. 3C).

Figure 11C:
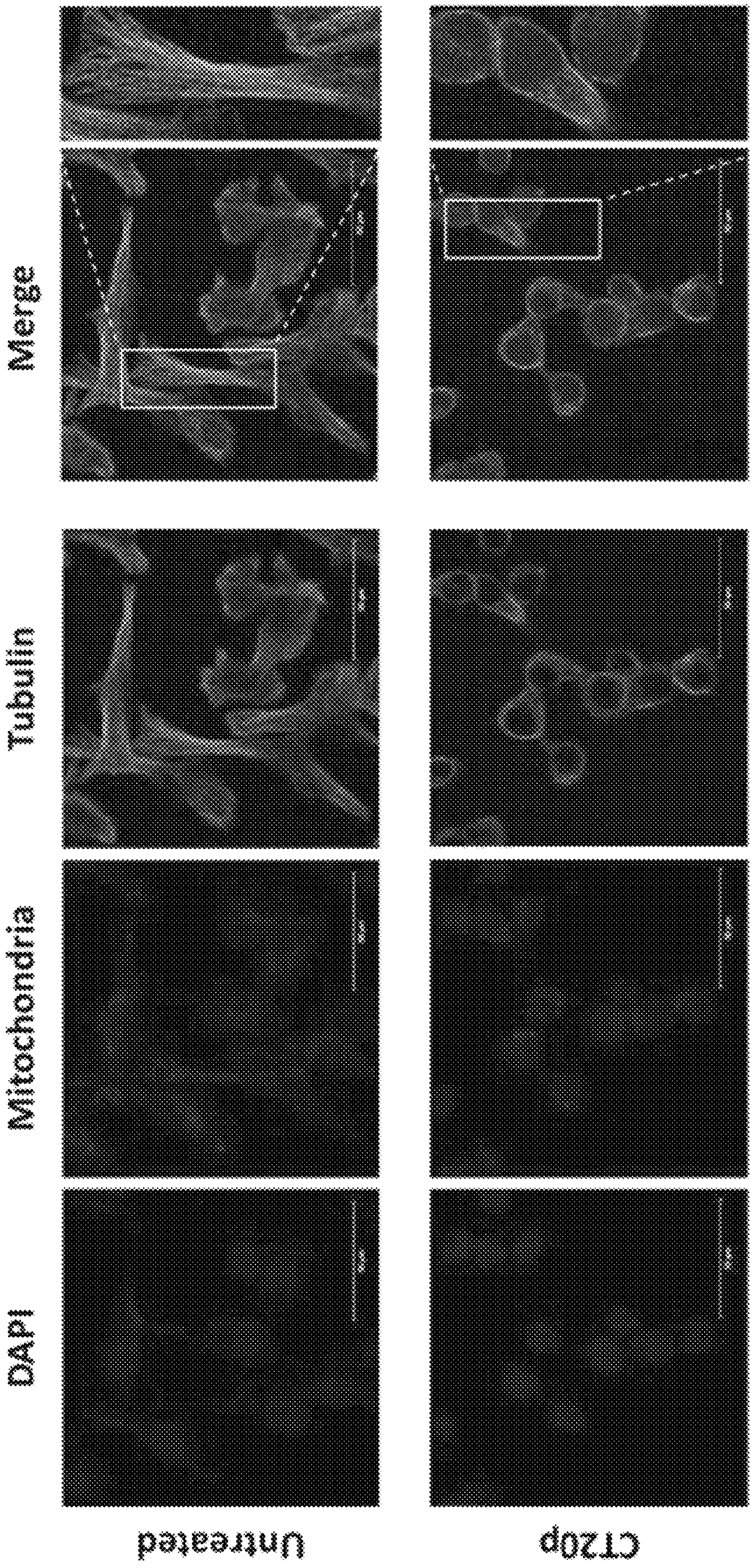
Figure 11D:
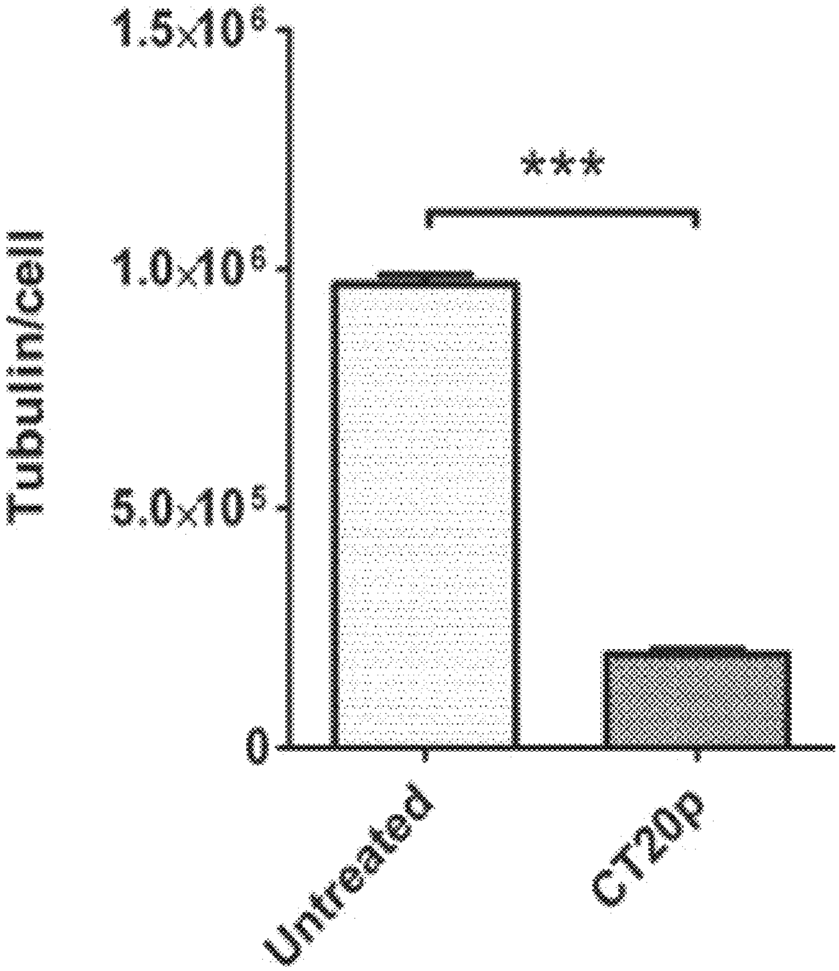

CT20p's effect on the other main client of CCT, tubulin, was also examined. Fixed cell immunofluorescence was employed to visualize tubulin in MDA-MB-231 cells before and after 24 hours of CT20p treatment. Cells were stained with α-DM1A antibody specific to tubulin (pseudo-colored green), Mitotracker Red, and the nuclear stain DAPI (pseudo-colored blue), and images were obtained by confocal microscopy. Immediately apparent was the significant loss of tubulin architecture in CT20p treated cells compared to untreated cells (FIG. 11C). Upon closer examination, loss of mitochondrial distribution throughout the cell is also observed. This is not unexpected, as mitochondria traffic along the tubulin network for proper distribution. Quantification of the amount of tubulin per cell confirms a significant decrease after CT20p treatment (FIG. 11D).

Figure 11E:
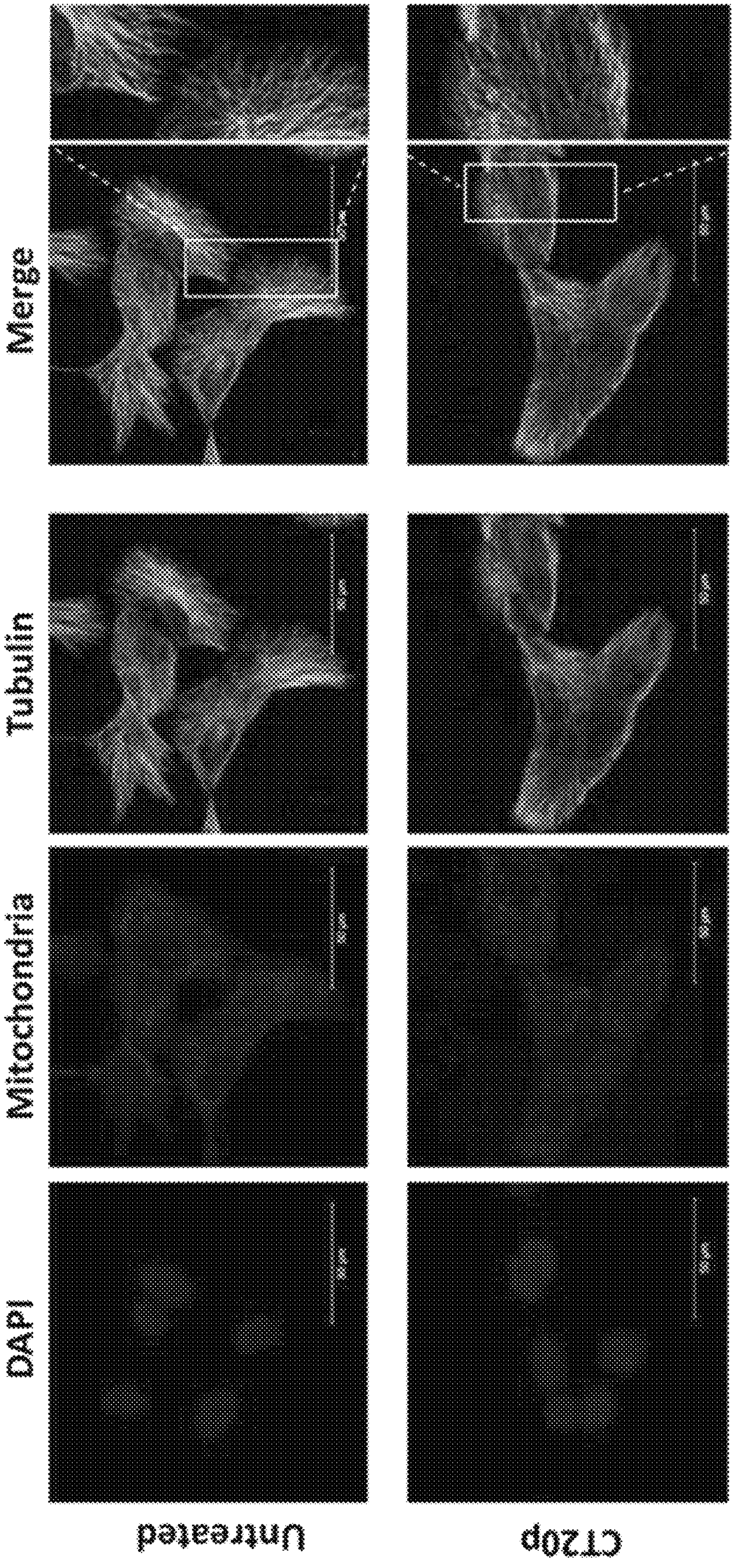
Figure 11F:
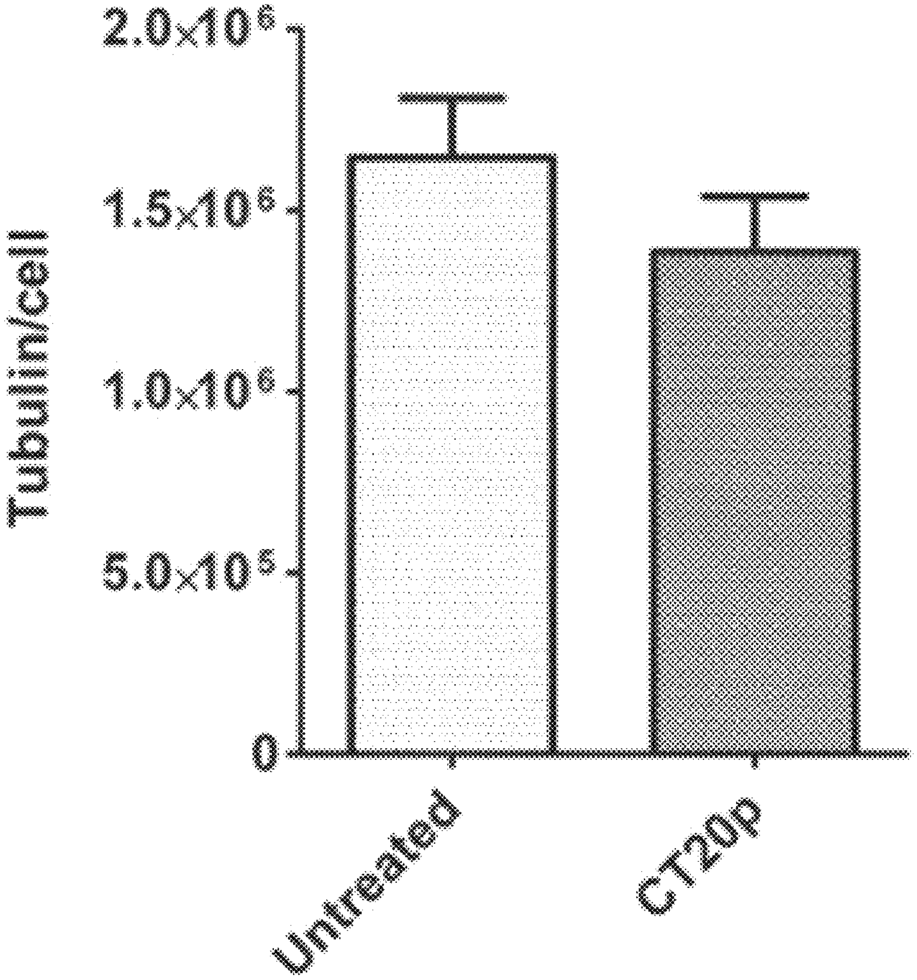
Figure 12A:
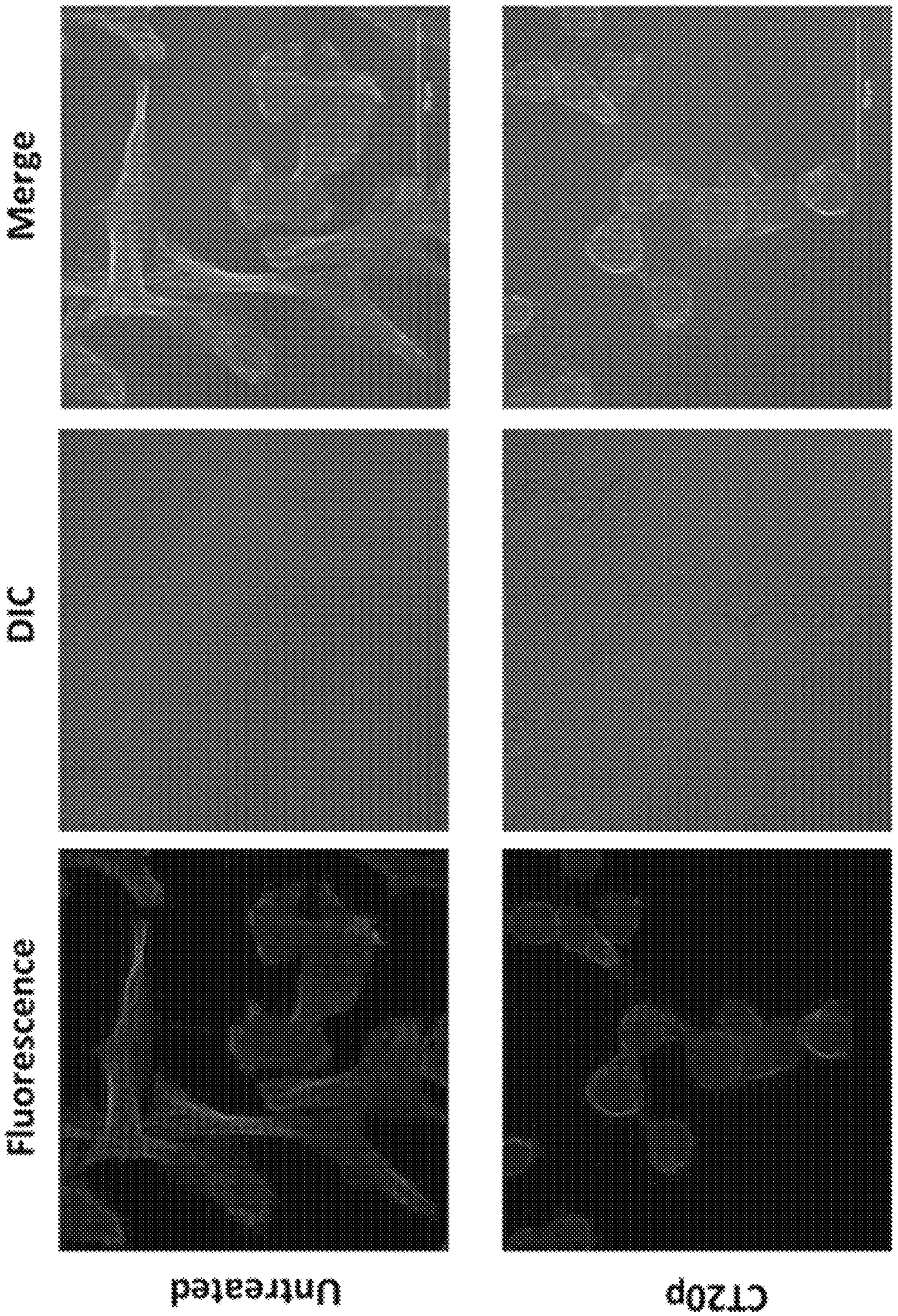
FIGS. 12A-12B show DIC images accompanying immunofluorescent staining of tubulin. MDA-MB-231 cells (in panel A) and MCF-10A cells (in panel B) were stained with DAPI (blue), Mitotracker Red (red) and α-DM1a antibody to tubulin (green). Untreated cells were compared to cells that had been treated with CT20p for 24 hours. Fluorescent images and DIC images were obtained. Scale bars are shown on the merge image and represent 50 μm.
Figure 12B:
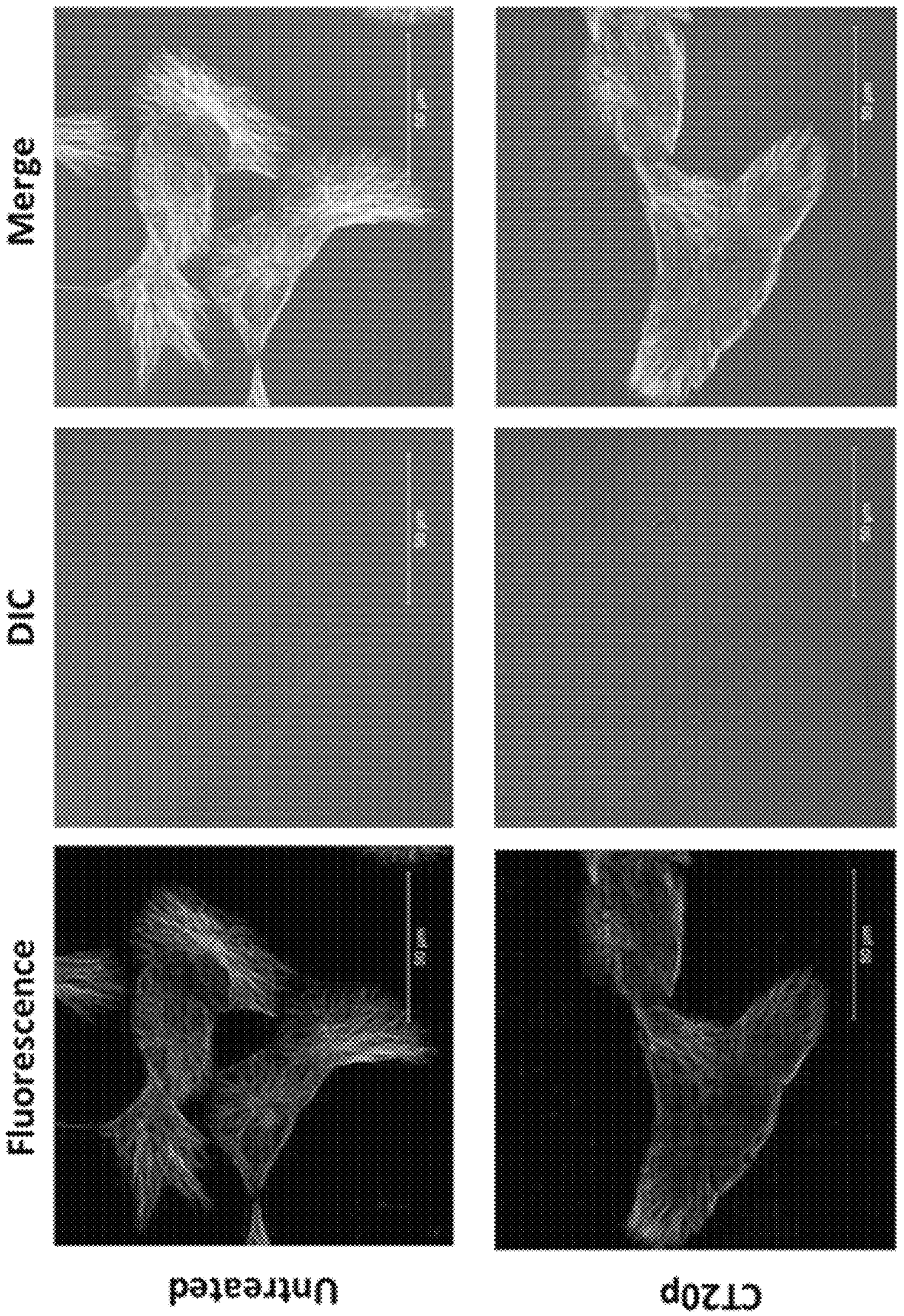

As a comparison to the effect of CT20p on MDA-MB-231 cells, the tubulin architecture of MCF-10A cells was also examined after peptide treatment (FIG. 11E). Unlike MDA-MB-231 cells, there was no significant loss of tubulin per cell in MCF-10A cells (FIG. 11F). Additionally, microscopy reveals that overall cell shape and mitochondrial distribution remain unchanged in MCF-10A cells upon CT20p treatment (FIG. 11E). Corresponding DIC images for both MDA-MB-231 and MCF-10A cells are provided in FIG. 12, and confirm cell attachment and overall cell shape.

MCF-10A cells do not display a loss of polymerized actin upon CT20p treatment (Lee, Bassiouni et al. 2014). As shown in FIG. 5A, a treatment of 75 μg/mL of CT20p does not cause detachment of MCF-10A cells. Together, this data supports the observation that the effect of CT20p varies in different cell lines, with a higher severity in MDA-MB-231 cells than in MCF-10A cells.

Having established that MCF-10A cells are less susceptible to CT20p cytotoxicity, it was examined whether manipulating the level of CCTβ in these cells changed susceptibility in response to CT20p. An attempt was made to increase CCTβ levels in MCF-10A cells in two distinct ways. First, MCF-10A cells were prompted to undergo epithelial-mesenchymal transition (EMT) by culturing them at low cell density. It has been shown that MCF-10A cells are highly sensitive to cell confluency, and that when grown too sparsely, they will spontaneously undergo an EMT-like process (Sarrio, Rodriguez-Pinilla et al. 2008). This includes phenotypic changes, as well as upregulation of classic mesenchymal markers such as vimentin and N-cadherin (Sarrio, Rodriguez-Pinilla et al. 2008).

Figure 13A:
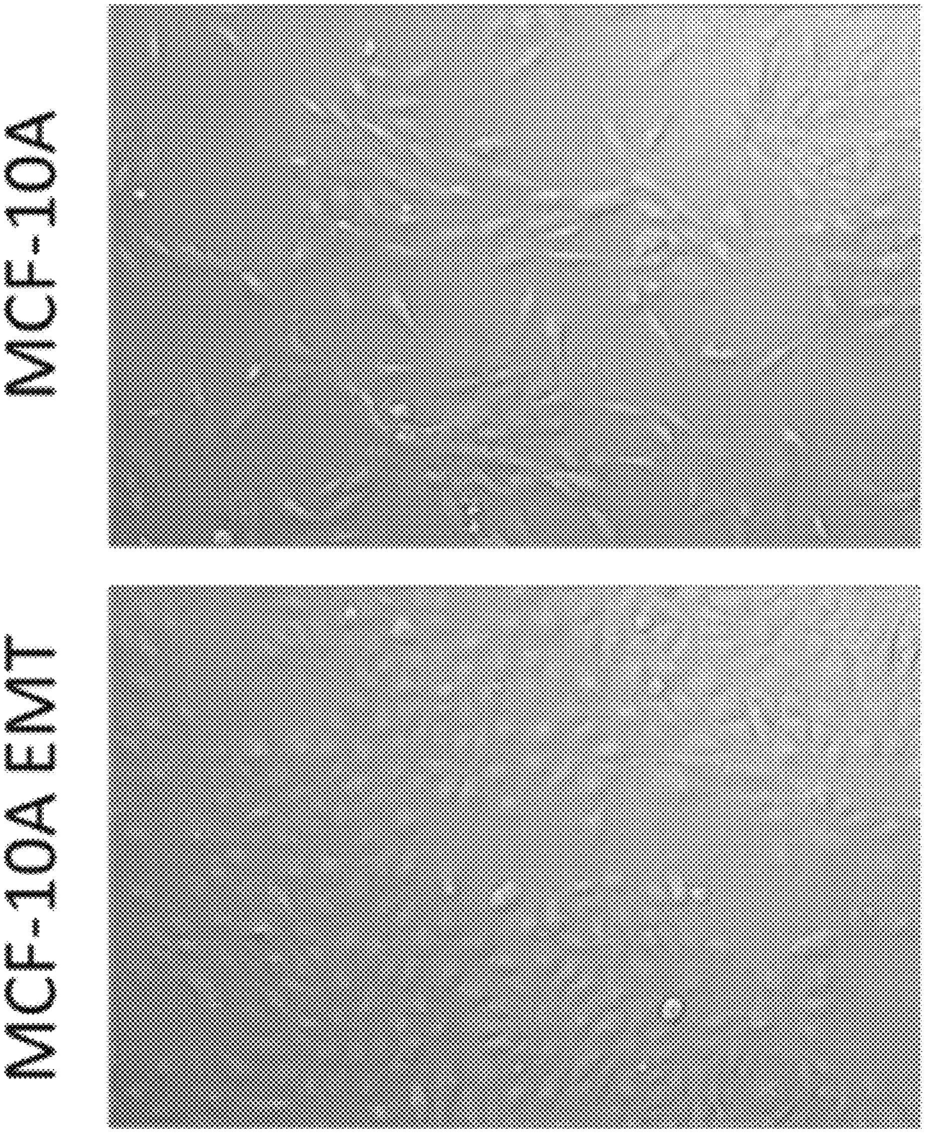
FIGS. 13A-13E show data demonstrating that CCT overexpression increases the susceptibility of MCF-10A cells to CT20p.
Figure 13B:
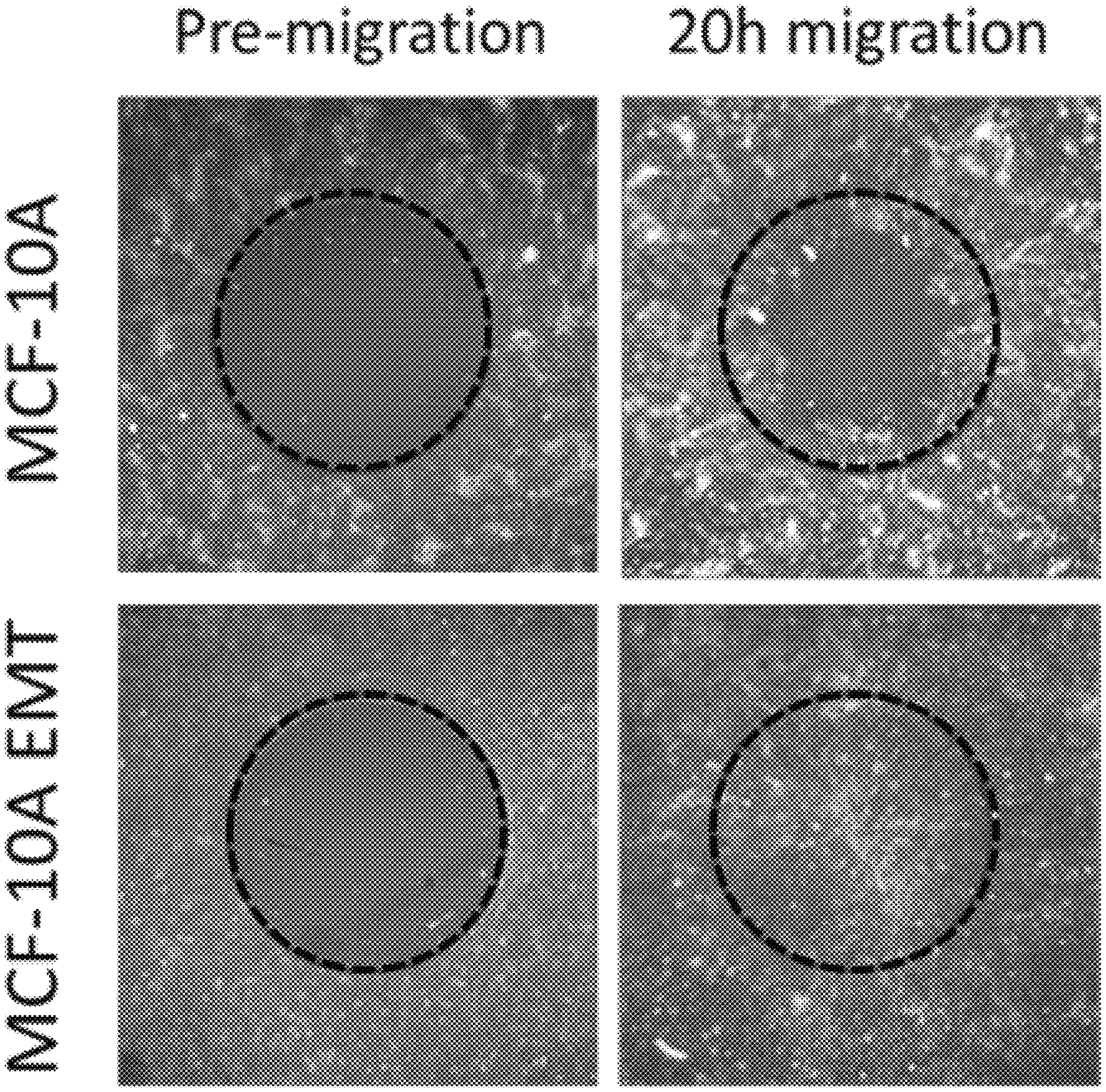

MCF-10A cells were therefore cultured at sub-optimal confluency until phenotypic changes were observed (FIG. 13A). The transitioned cells, referred to heretofore as MCF-10A EMT, also exhibited highly increased migration (FIG. 13B). After 20 hours of migration time, MCF-10A cells do not completely cover the exclusion zone, while MCF-10A EMT cells do. The increased potential for movement is supportive of the EMT the cells have undergone.

Figure 13C:
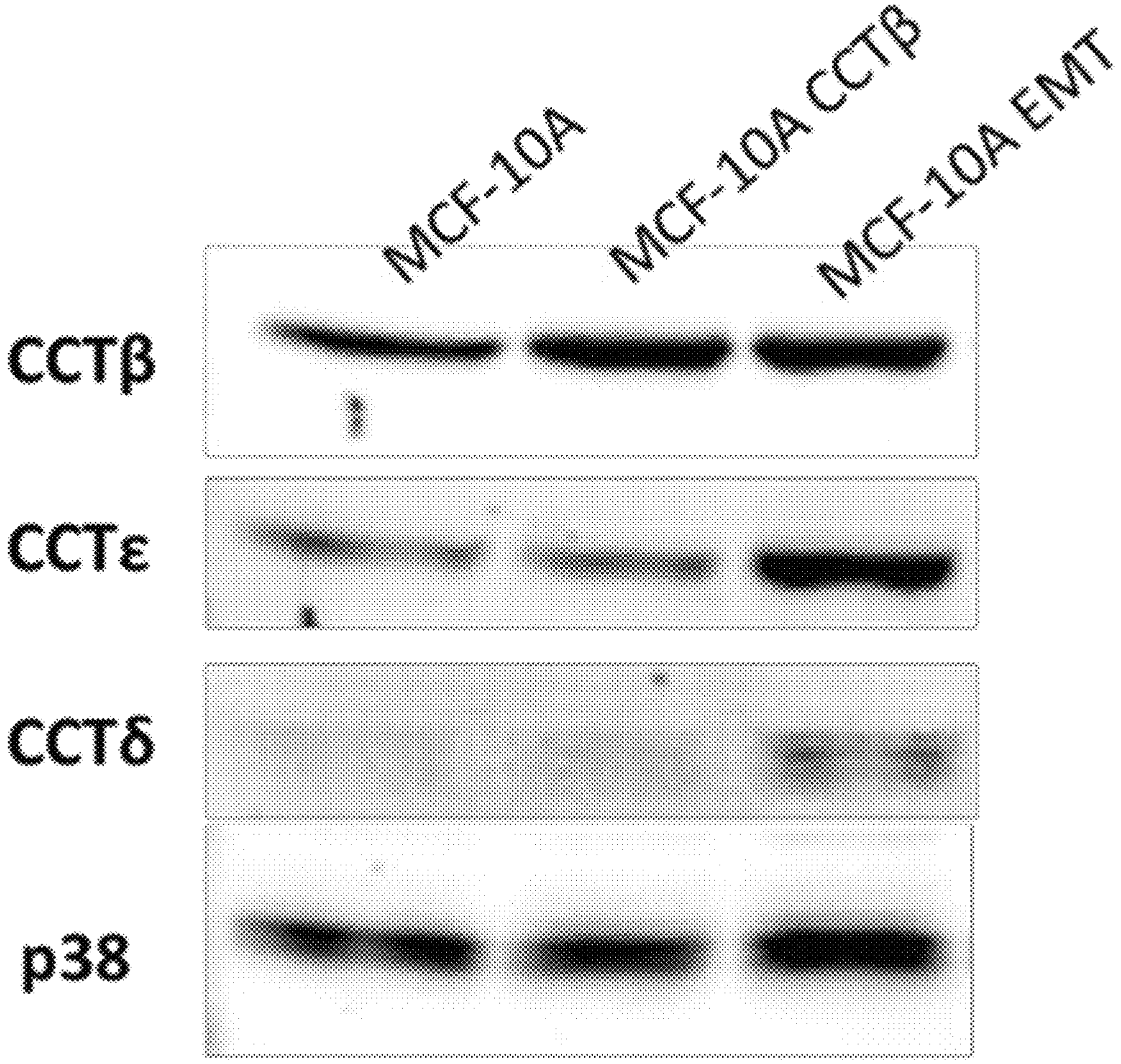
Figure 13D:
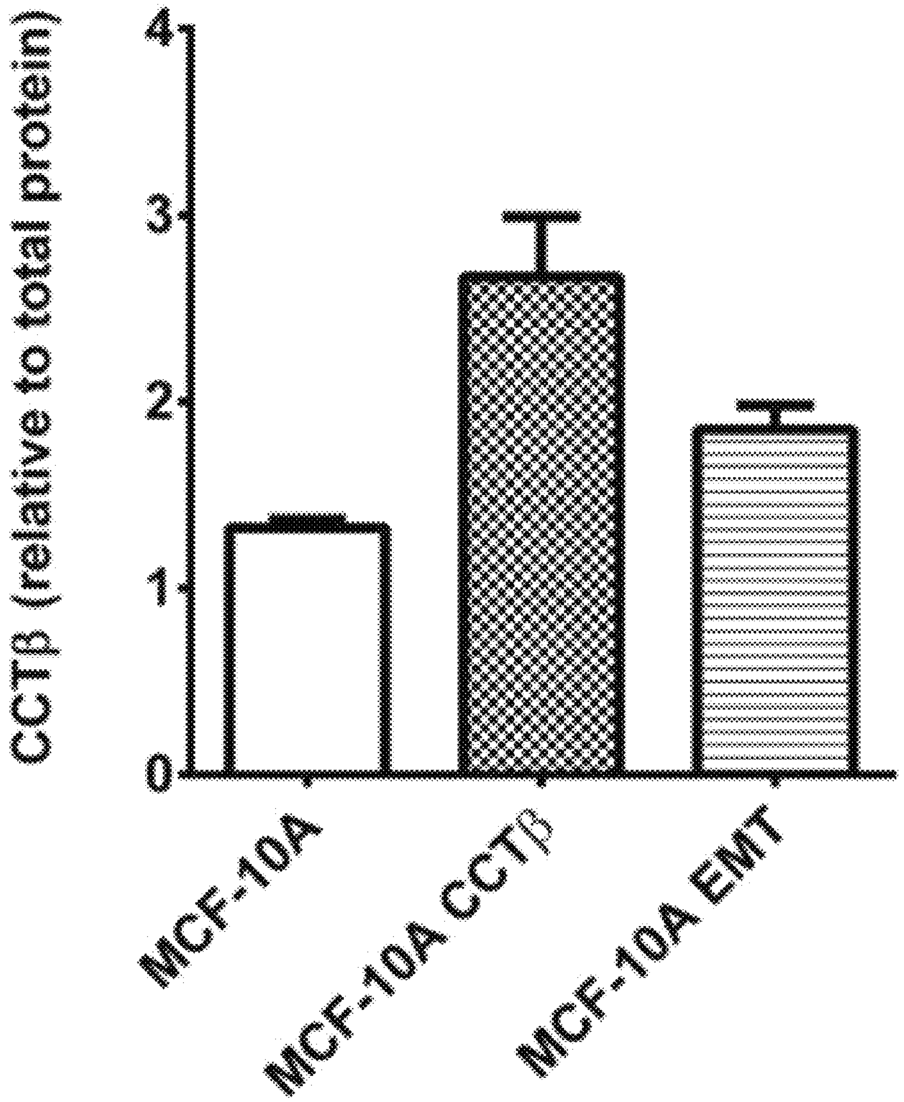

CCTβ was also overexpressed directly in MCF-10A cells by transient transfection. CCTβ protein levels increased in these cells, referred to as MCF-10A CCTβ (FIG. 13C, D). Interestingly, MCF-10A EMT cells also expressed higher levels of CCTβ than MCF-10A cells, demonstrating a direct link between EMT and need for CCT activity (FIG. 13C, D). The level of CCTδ and CCTε subunits was also examined in the three MCF-10A variants. Transfection of CCTβ alone did not prompt the cells to upregulate expression of other CCT subunits (FIG. 13C). However, the MCF-10A EMT cells contained high levels of all three CCT subunits, indicating that these cells have overexpressed the entire CCT complex (FIG. 13C). These three variants therefore provide models to study the effect of CT20p in three different conditions.

Figure 13E:
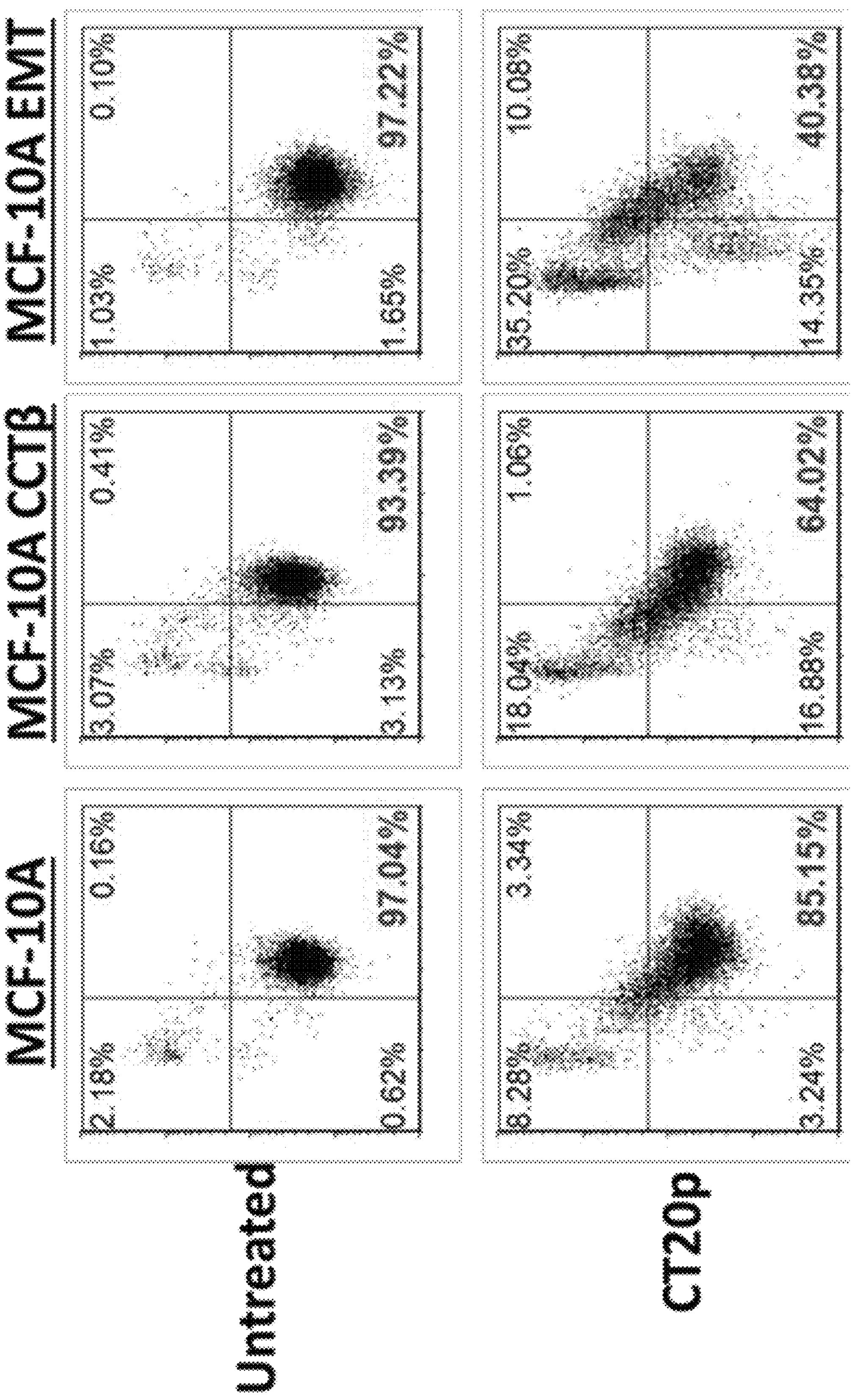

The three variants of MCF-10A cells were treated with CT20p at a dose of 75 μg/mL for 24 hours, then cell viability was examined by staining with Sytox AADvanced and F2N12S as described earlier. Normal MCF-10A cells exhibit a modest decrease in viability upon CT20p treatment (FIG. 13E), going from 97% to 85% viability. However, both MCF-10 CCTβ and MCF-10A EMT cells demonstrated markedly greater cell death, dropping to 64% and 40% viability, respectively.

Increasing CCTβ levels therefore directly increases susceptibility to CT20p. Additionally, the high level of cell death seen in MCF-10A EMT cells may indicate that CT20p is more cytotoxic when the entire CCT complex is present in high levels.

Figure 14A:
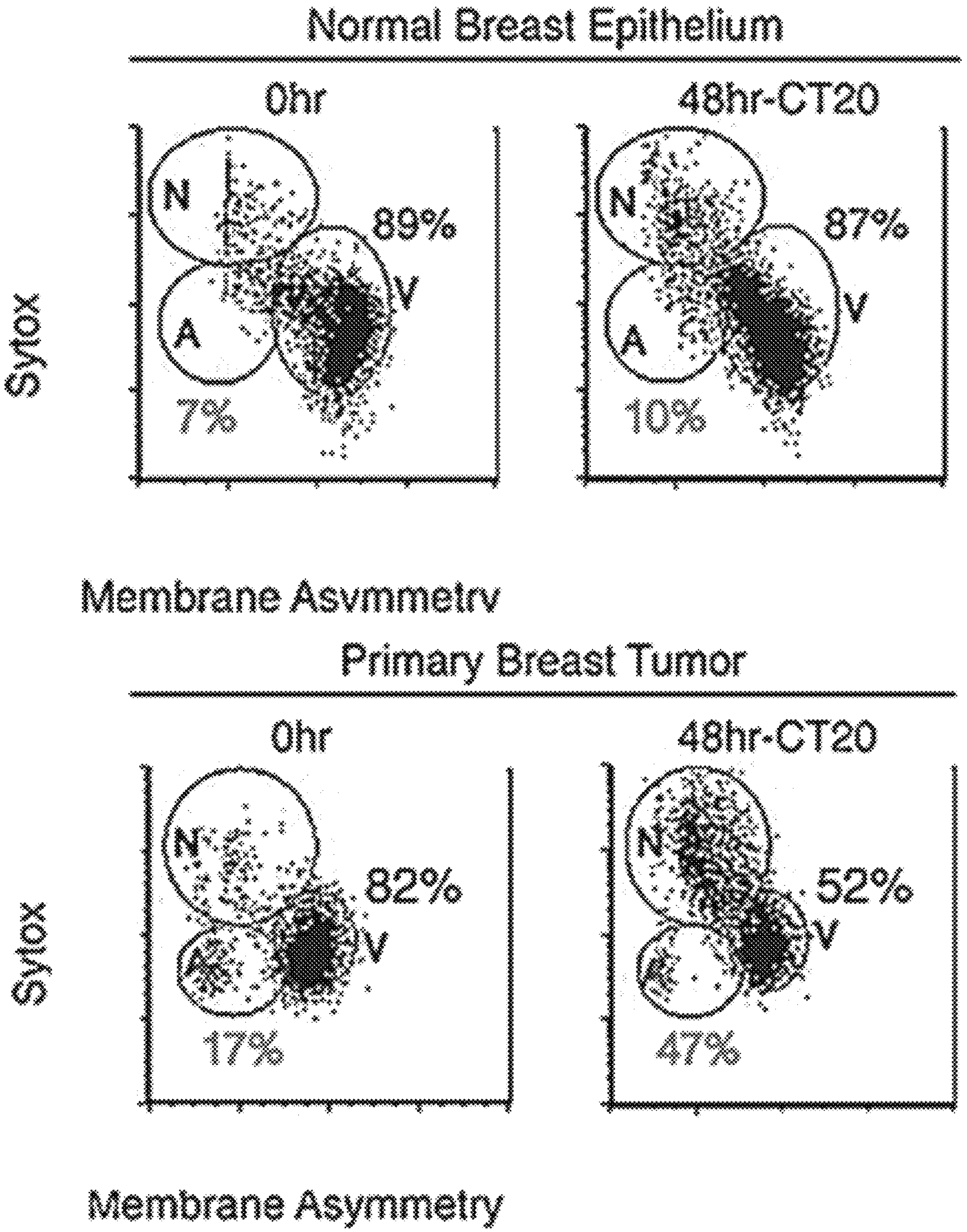
FIG. 14A shows the viability of cells isolated from normal versus cancerous patient tissue samples treated with CT20 peptide in HBPE-NPs.

The lethality of CT20 was also examined in cells isolated from primary breast tumors and paired normal tissue. CT20 killed the tumor cells but not the normal cells (FIG. 14A). Hence, CCT expression can be increased in breast cancer cells. To this end, the levels of CCTβ were examined in a pilot tissue array of breast cancer tissue cores by immunohistochemistry (IHC) and detected CCTβ in invasive breast cancer (FIG. 14B).

Figure 15:
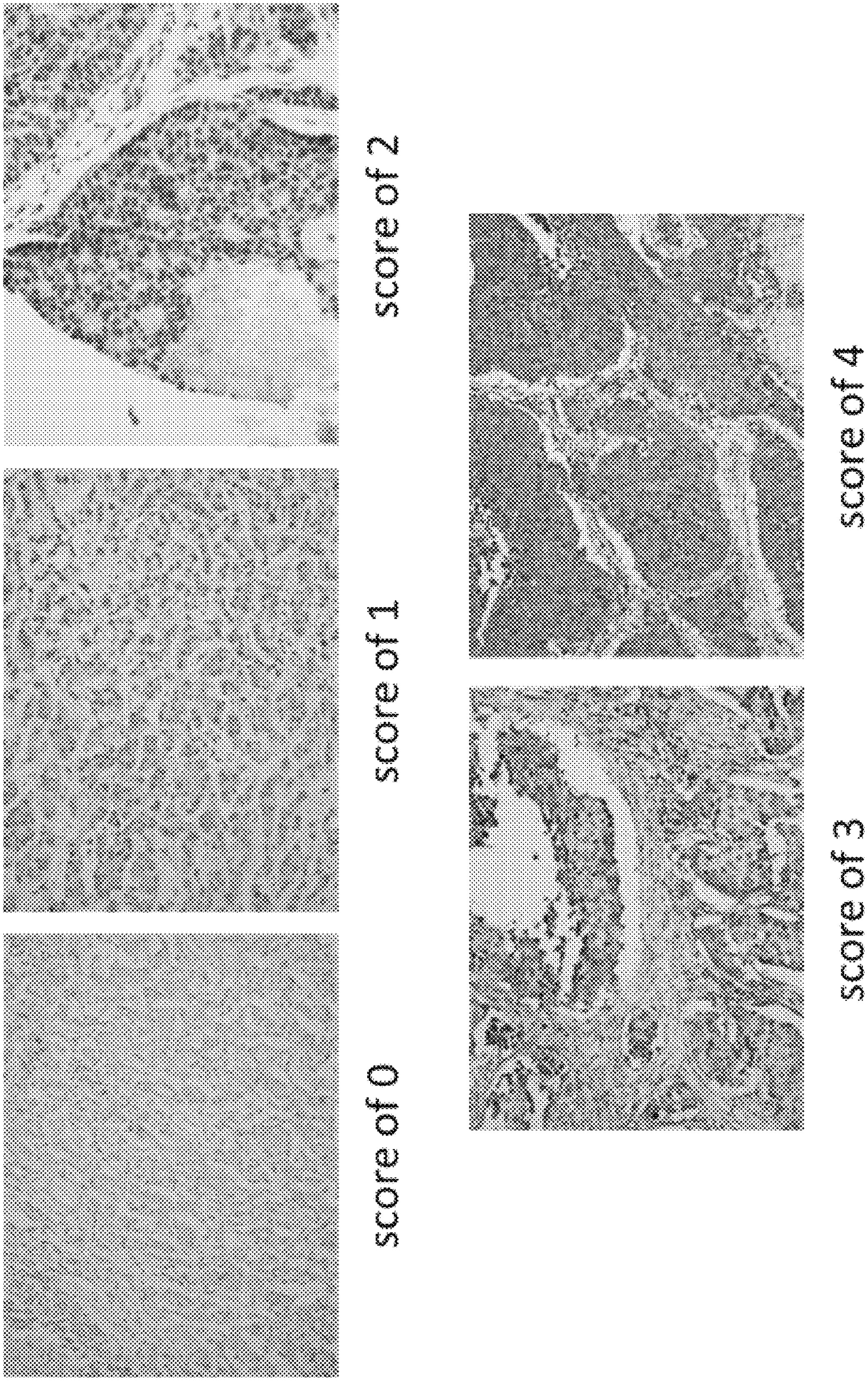
FIG. 15 shows representative images of CCTβ tissue scoring parameters. Human breast cancer tissue arrays were analyzed by immunohistochemistry for CCM Tissue cores were scored by a pathologist based on intensity of staining. The scoring ranged from 0 to 4. Presented here are representative images of the staining associated with each score. Images are at 200× total magnification. General guidelines for assigning a score are described as follows: Score of 0: no staining, Score of 1: faint, focal cytoplasmic staining, Score of 2: weak cytoplasmic staining throughout sample (not focal), Score of 3: intense staining that does not obscure nucleus, Score of 4: very intense staining, or intense staining that obscures nucleus.

The data indicated that not only is CT20p a viable agent for cancer therapy, the CCT complex may also be a promising target. Impairment of the CCT complex by CT20p results in catastrophic intracellular events that lead to cancer cell death. To gain an understanding of the clinical relevance of the correlation of CCT expression with disease, several breast cancer tissue arrays containing many individual tissue cores were examined for CCTβ expression by immunohistochemistry. Each core was then scored by a pathologist on a scale from 0 to 4 based on CCTβ staining intensity. FIG. 15 provides representative staining associated with each score, as well as guidelines for assigning a score to a sample.

Figure 16A:
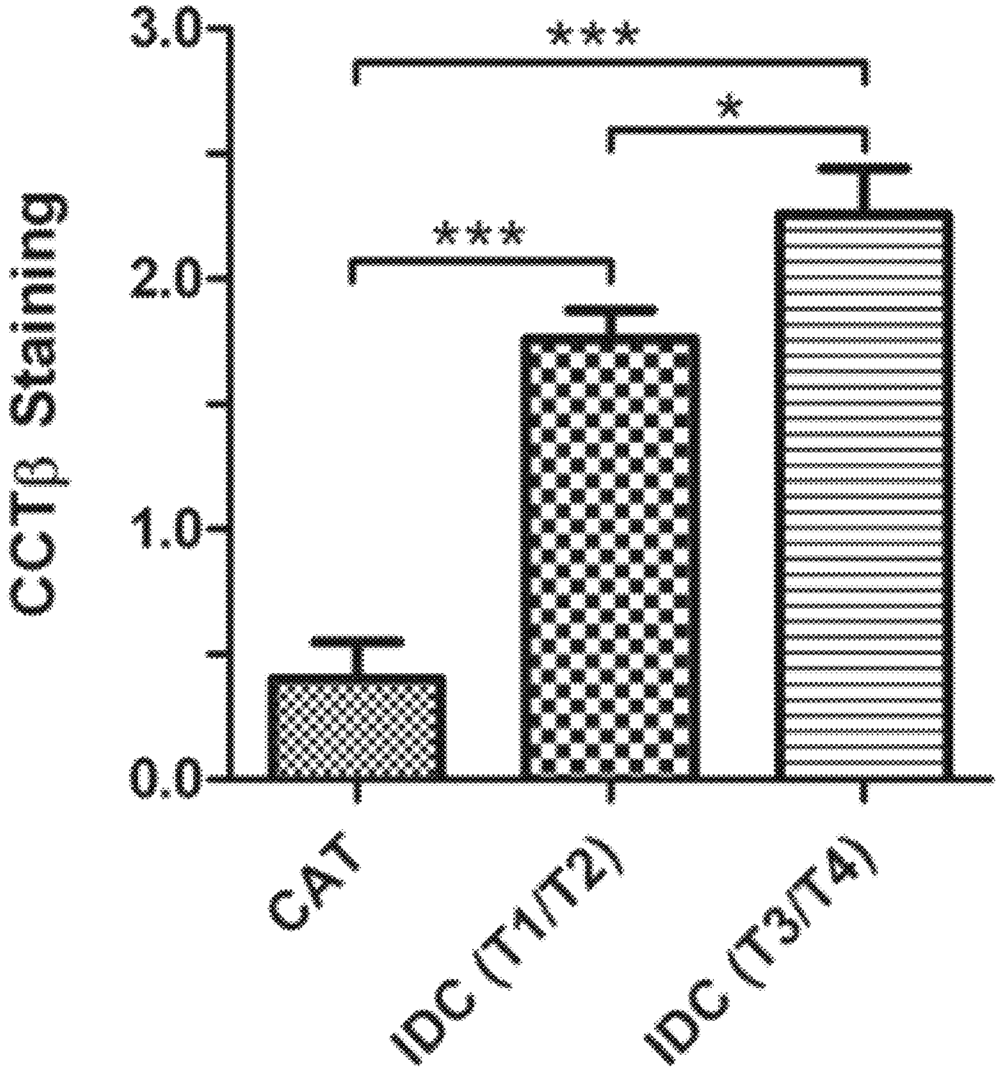
FIGS. 16A-16C show data and images that demonstrate that breast cancers express higher levels of CCTβ than normal tissue.
Figure 16B:
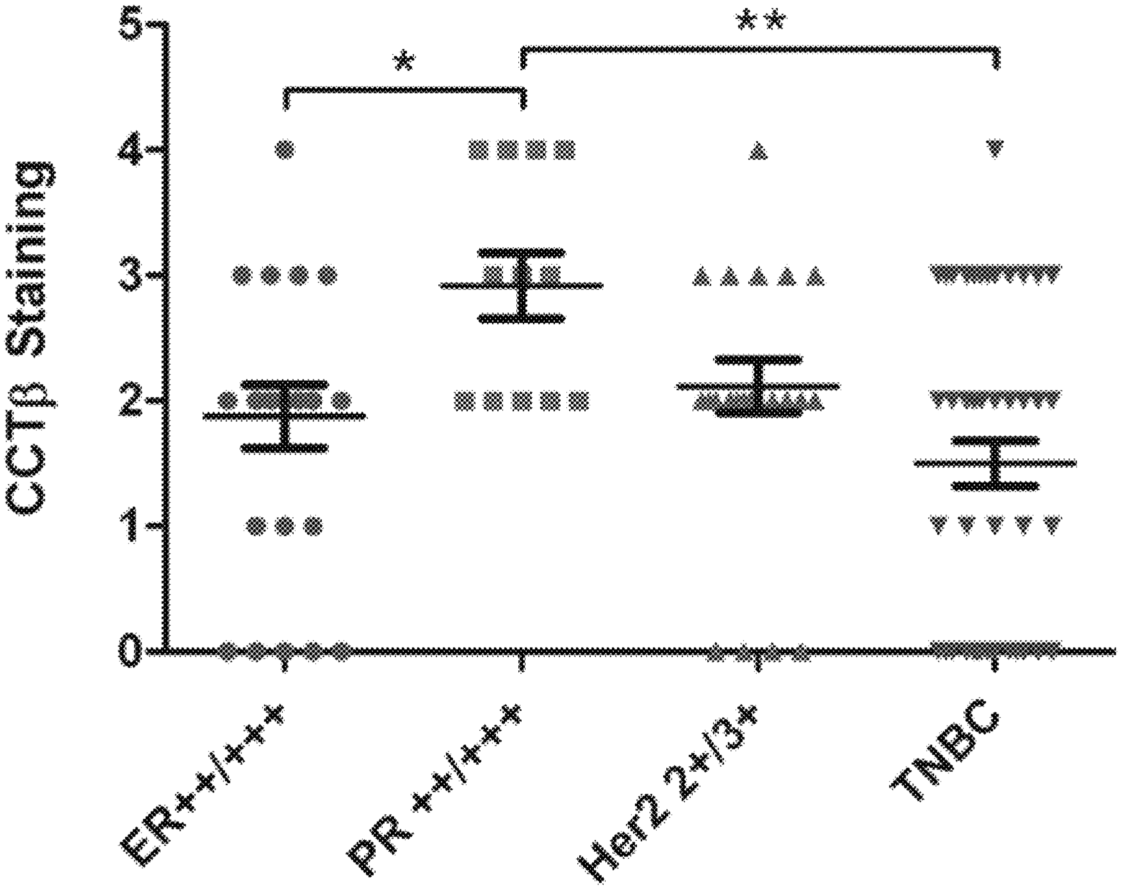
Figure 16C:
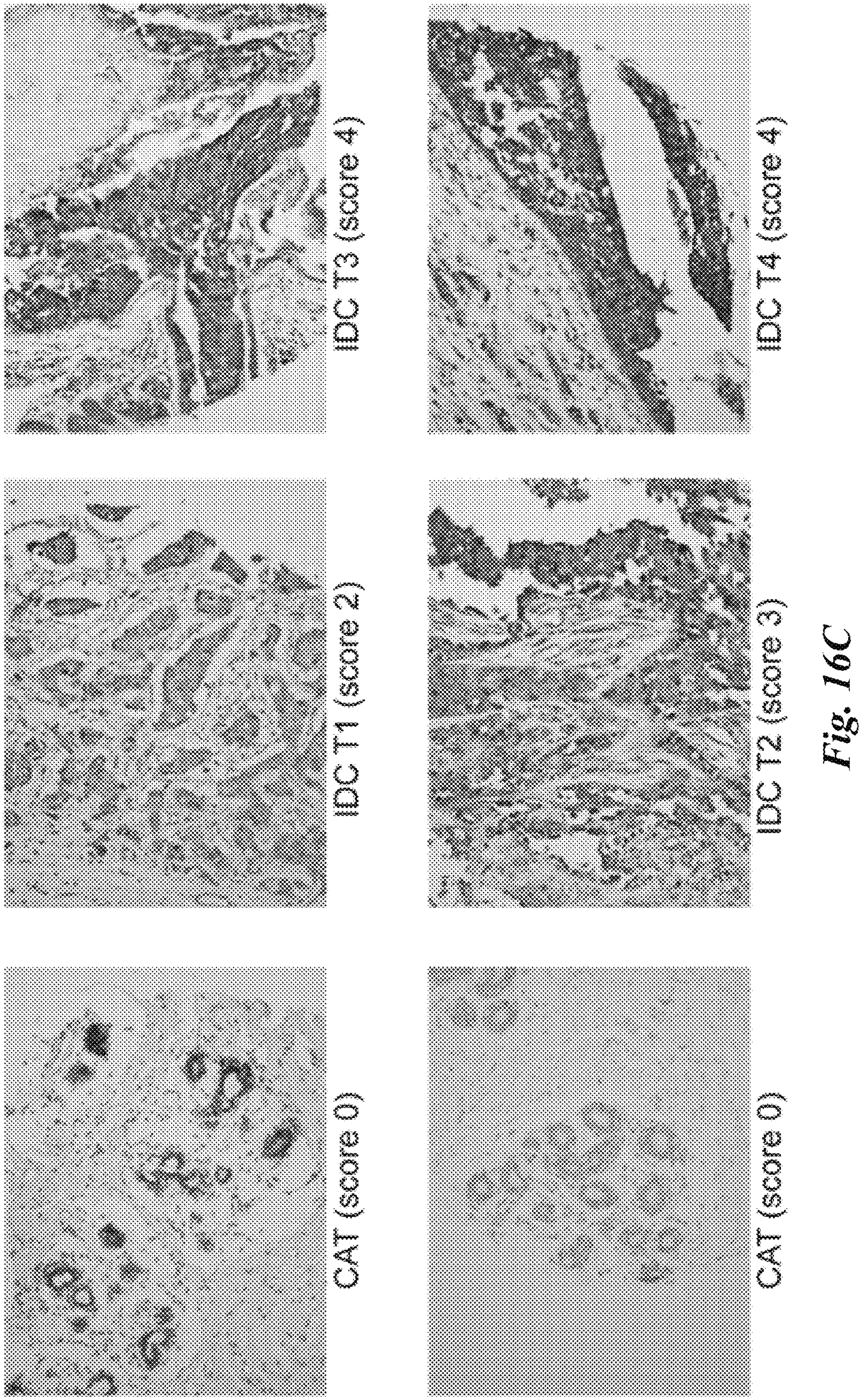

It was first examined whether cancer tissue expressed more CCTβ than healthy cancer-adjacent tissue. On average, invasive ductal carcinoma (IDC) displayed staining at least three times greater than cancer-adjacent tissue (CAT) (FIG. 16A). Additionally, CCTβ staining was significantly increased in more highly invasive primary tumors characterized as T3 or T4, than in those less invasive cancers characterized as T1 or T2 (FIG. 16A). The T score is a measurement of the invasiveness of the primary tumor and is a component of TNM grading, which is a commonly used clinical descriptor of breast cancers. Table 3 provides the number of cores analyzed, or the sample size, for each group. Representative images of CAT and IDC in FIG. 16C are provided to illustrate the increasing CCTβ staining intensity, correlating with increased disease severity.

TABLE 3

| Tissue type | Sample size |
|---|---|
| Cancer adjacent tissue (CAT) | 42 |
| Invasive ductal carcinoma, T1 and T2 (IDC T1/T2) | 109 |
| Invasive ductal carcinoma, T3 and T4 (IDC T3/T4) | 43 |
| Estrogen receptor, high expression (ER ++/+++) | 24 |
| Progesterone receptor, high expression (PR ++/+++) | 12 |
| Her2, high expression (Her2 2+/3+) | 26 |
| Triple negative breast cancer (TNBC) | 46 |

In an attempt to understand the molecular signaling pathways that may be driving the expression of CCT in breast cancer, the scored results were next analyzed by receptor status. Samples were compared that had high estrogen receptor (ER++/+++), progesterone receptor (PR++/+++), and Her2 (Her 2+/3+) expression levels, as detailed in the literature accompanying each tissue array. Samples that had no expression of any of these receptors were designated as triple negative breast cancer (TNBC). As seen in FIG. 16B, TNBC samples were highly variable in CCTβ expression, correlating with what we had previously seen in our TNBC cell lines (FIG. 10). No significant correlation was made with CCTβ staining and ER or HER2 expression, but PR++/+++ samples were uniformly high in staining (FIG. 16B). These findings suggest that the PR signaling pathway may be a driver of CCT expression, but that CCT may also be used as a clinical target for TNBC on a case-by-case basis.

Figure 17:
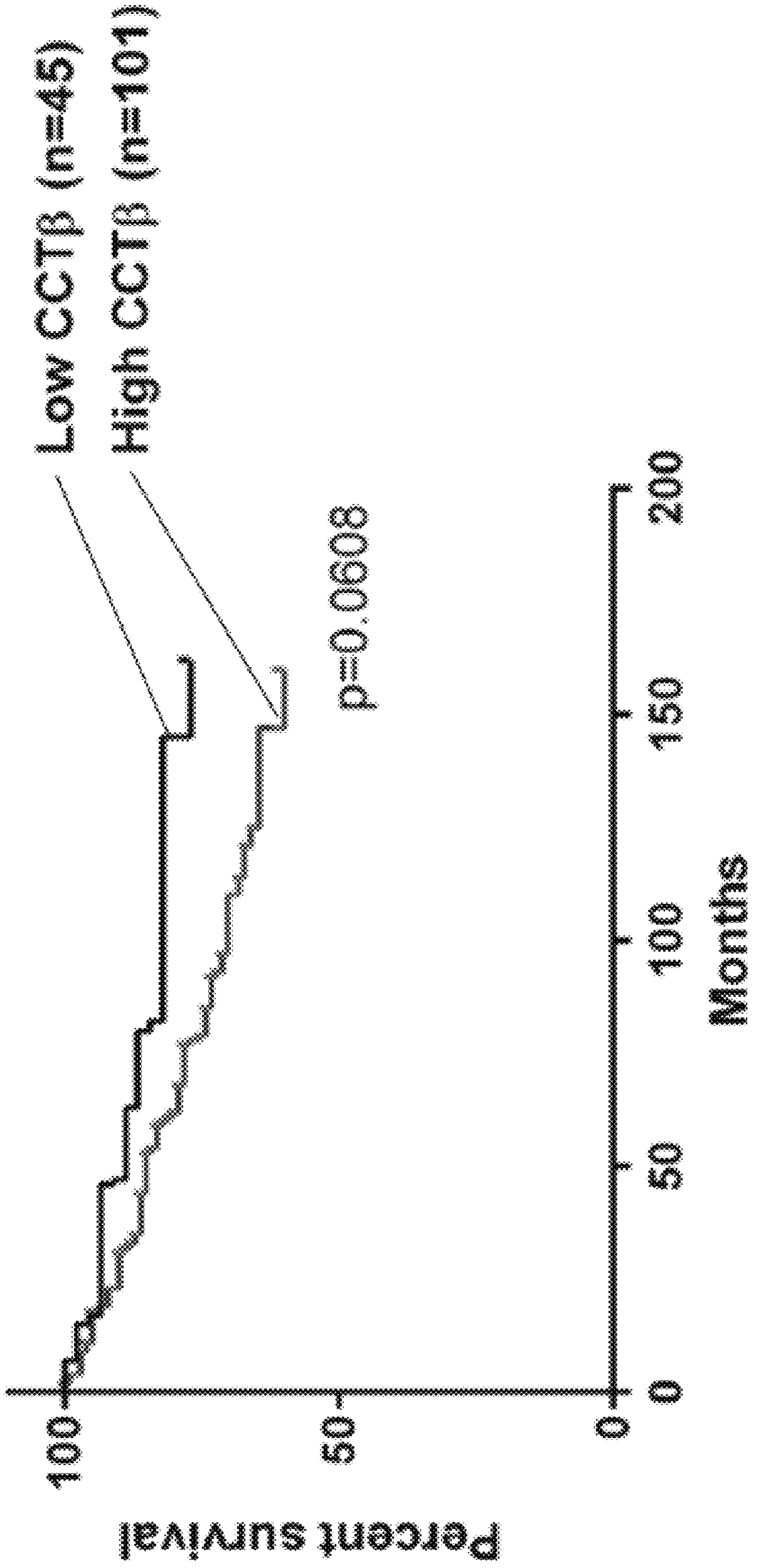
FIG. 17 shows data demonstrating that high levels of CCTβ are associated with a decreased survival rate of breast cancer patients. A human breast cancer tissue array containing samples of invasive ductal carcinoma from 146 patients was analyzed by immunohistochemistry for CCM Survival data, including survival/deceased status and duration of monitoring in months, was provided for each tissue sample. CCTβ staining intensity was scored as described in FIG. 21. Samples scoring 0, 1, and 2 were categorized as low CCTβ (n=45), while samples scoring 3 or higher were categorized as high CCTβ (n=101). Percent survival was compared between these two groups.

In addition to correlating CCTβ levels with tumor severity, survival rates of patients with invasive ductal carcinoma containing low and high levels of CCTβ were also examined. Tissue samples were scored as described in FIG. 15, and then grouped by CCTβ expression. Tissues with a score of 0, 1, and 2 were characterized as low CCTβ expressers, at the recommendation of a pathologist. Samples scoring 3 or higher were characterized as high CCTβ expressers. Using survival data provided with the tissue array, the percent survival over time was compared between the two groups (FIG. 17). Patients with tumors containing high CCTβ exhibited a poorer survival rate than those with tumors containing low CCTβ. The final survival percentage for the high CCTβ group was 59.98%, while the low CCTβ group had a more favorable survival percentage of 77.03% (FIG. 17). While the difference was not statistically significant, with a p-value of 0.0608, the trend indicates that CCTβ levels may be higher in tumors that are likely to be life-threatening.

Discussion

Figure 18:
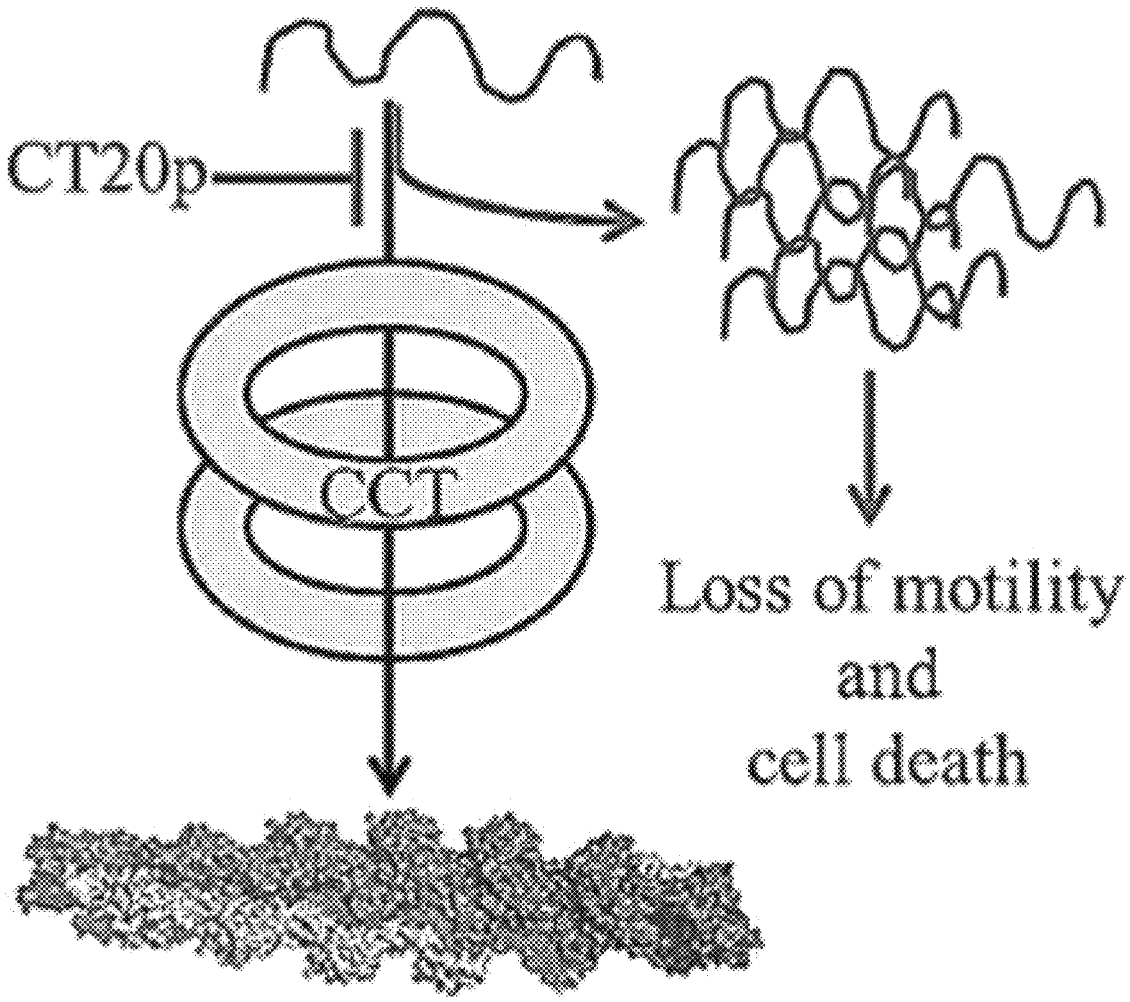
FIG. 18 shows a representative model for the interaction of CT20 peptide with CCT.

In this study, evidence is presented that CT20p, a peptide with cytotoxic effects in breast cancer cells, induces its actions by targeting the chaperonin CCT. CT20 impairs the invasiveness and survival of tumor-initiating and metastatic breast cancer cells by binding to and impeding the essential protein folding activities of CCT, which causes disassembly of the cytoskeleton (see the schematic of FIG. 18). Referring to FIG. 18, newly synthesized proteins are typically folded into the native form by CCT. CT20 inhibits this activity, causing unfolded proteins to accumulate, leading to cell death.

TNBC cell lines were found to have varying CCT levels that mirror their susceptibility to CT20p's cytotoxic actions. CT20p binds to CCT from all the cell lines, and makes at least one direct interaction with the CCTβ subunit. Among the consequences of CT20p treatment is loss of migration, due to loss of actin polymerization, and catastrophic loss of tubulin architecture. CT20 was directly linked to CCTβ by demonstrating increased susceptibility to the peptide upon overexpression of CCTβ in MCF-10A cells. Finally, a broad analysis of CCT expression in breast cancer tissue samples revealed that high CCT levels corresponded with higher disease severity.

Of great interest from these findings is that CCT may serve as a clinical biomarker of disease. Targeting CCT was also shown to be a viable strategy for treatment of cancer, particularly because cancer cells appear to express and rely on the chaperonin more heavily than normal cells.

Example 2: Potential of CCT as a Target in Various Human Cancers

Materials and Methods

Immunohistochemistry: Tissue arrays containing multiple samples of human cancer tissue were purchased from US Biomax. Catalog numbers for the specific arrays analyzed are as follows: BC041115a, BC03118, C0484A, EN801A, LC802A, LC726b, PR803b, PR631. Information about the tissue type, TNM, score, tumor grade, and stage were provided (when applicable). Tissues were analyzed using anti-CCTβ primary antibody (LifeSpan Biosciences) diluted 1:100 in Antibody Diluent (Leica). Staining of tissue arrays was performed by a Bond-Max Immunostainer (Leica), with an epitope retrieval buffer of EDTA pH 9.0 (Leica). Polymer Refine Detection reagents (Leica) were used, which include a hematoxylin counterstain. Scoring of CCTβ staining was done by a pathologist based on staining intensity. The sample sizes of each of these groups are presented in Table 4.

Statistical analysis: One-way ANOVA was used to compare mean scoring between the different groups defined by various tissue parameters. Tukey's multiple comparison test was used to compare significance between individual groups. Calculations were performed with GraphPad Prism software (GraphPad). Statistical significance was defined as $p<0.05$.

TABLE 4

| | Tissue type | Sample size |
|---|---|---|
| Colon tissue | Normal colon tissue | 7 |
| Liver tissue | Adenocarcinoma | 23 |
| | Mucinous adenocarcinoma | 8 |
| | Signet cell ring carcinoma | 7 |
| | Grade 1 tumor | 12 |
| | Grade 2 tumor | 6 |
| | Grade 3 tumor | 12 |
| | Normal hepatic tissue | 20 |
| | Cholangiocellular carcinoma | 30 |
| | Hepatocellular carcinoma | 147 |
| | HCC—grade 1 | 19 |
| | HCC—grade 2 | 111 |
| | HCC—grade 3 | 12 |
| | HCC-T2 | 68 |
| | HCC-T3 | 71 |
| Prostate tissue | Normal prostate tissue | 9 |
| | Adenocarcinoma | 131 |
| | Adenocarcinoma—T2 | 38 |
| | Adenocarcinoma—T3 | 21 |
| | Adenocarcinoma—T4 | 8 |
| | Adenocarcinoma—Stage II | 33 |
| | Adenocarcinoma—Stage III | 10 |
| | Adenocarcinoma—Stage IV | 27 |
| | Gleason grade 3 | 35 |
| | Gleason grade 4 | 34 |
| | Gleason grade 5 | 37 |
| lung tissue | Normal lung tissue | 20 |
| | Adenocarcinoma | 63 |
| | Squamous cell carcinoma | 67 |
| | Atypical carcinoid | 35 |
| | Smail cell carcinoma | 82 |
| | Carcinoid | 9 |
| | SqCLCT1/T2 | 52 |
| | SqCLCT3/T4 | 15 |
| | SCLCT1 | 15 |
| | SCLCT2 | 50 |
| | SCLCT3/T4 | 15 |

A colonic carcinoma tissue microarray was examined for CCTβ expression by immunohistochemistry. Normal colon tissue was compared to three subtypes of carcinomas: adenocarcinoma, mucinous adenocarcinoma, and signet-ring cell carcinoma (SRCC). Of these, SRCC is most aggressive, with significantly reduced survival rates compared to the other two subtypes (Thota, Fang et al. 2014).

Figure 19A:
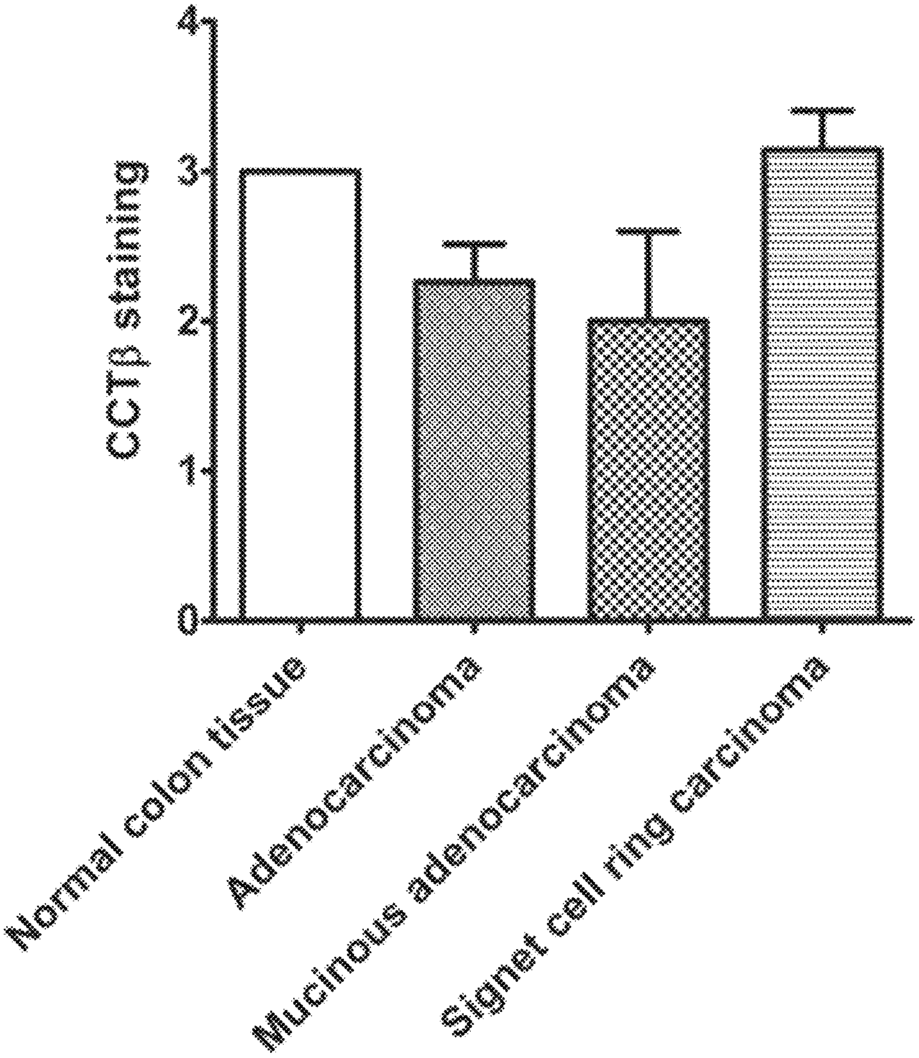
FIGS. 19A-19B show data representing the analysis of CCTβ staining in colon tumor tissue.

While our analysis did indicate that SRCC contained higher CCTβ than adenocarcinoma and mucinous adenocarcinoma, the difference was not statistically significant (FIG. 19A). Additionally, normal colonic tissue stained highly for CCTβ, indicating that this tissue may present a high background of CCTβ expression.

Figure 19B:
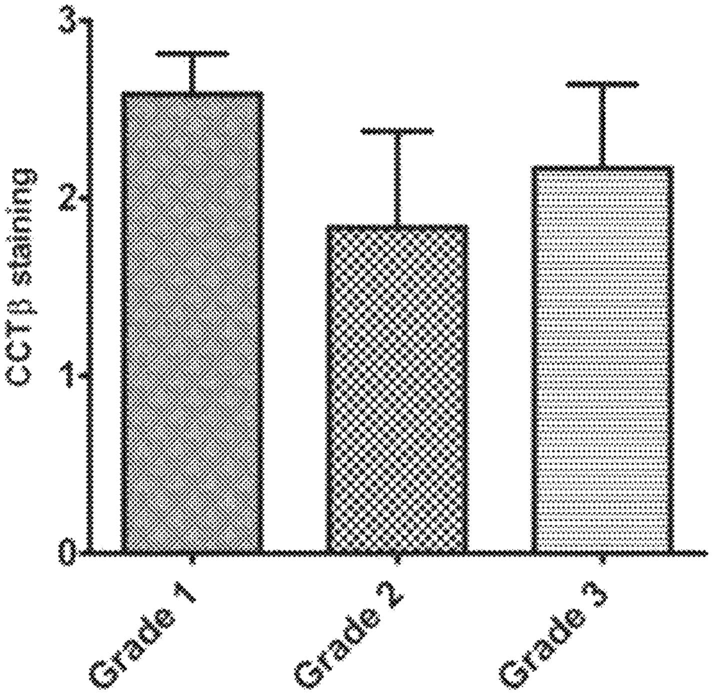

The correlation of CCTβ with tumor grade, which is an indication of cellular differentiation, was also examined. Grade 1 indicates well-differentiated cells that appear normal, while grade 3 indicates poorly differentiated cells that grow abnormally and aggressively. However, due to the morphological characteristics of SRCC, these cannot be assigned a grade. The analysis was therefore limited to adenocarcinoma and mucious adenocarcinoma. No correlation of grade with CCTβ was determined in these subtypes (FIG. 19B). CCTβ is therefore not likely involved in the dedifferentiation process of these carcinomas.

Because colorectal cancer patients often do not present with symptoms until the disease has become more advanced, detection of late-stage disease is common. The carcinoma samples present on the tissue microarray were all classified as T3 or T4, indicating high invasiveness of the primary tumor. CCTβ levels in T1/T2 tumors and T3/T4 tumors could not be compared (FIG. 16).

Using tumor tissue microarrays, CCTβ levels were examined in normal hepatic tissue and two subtypes of hepatic carcimona: hepatocellular carcinoma (HCC) and cholangiocellular carcinoma. HCC arises from transformed hepatocytes and accounts for approximately 80% of primary liver cancers (McGlynn, Petrick et al. 2015). Cholangiocellular carcinoma arises in the bile ducts, and while less common, is associated with therapeutic resistance and poor prognosis and survival rates (Razumilava and Gores 2014).

Figure 20A:
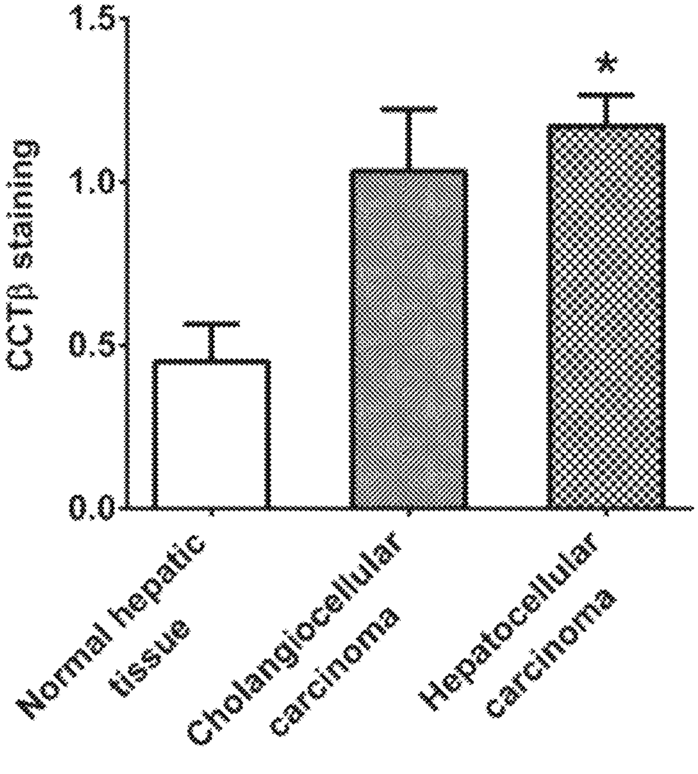
FIGS. 20A-20D show data representing the analysis of CCTβ staining in liver tumor tissue.
Figure 20B:
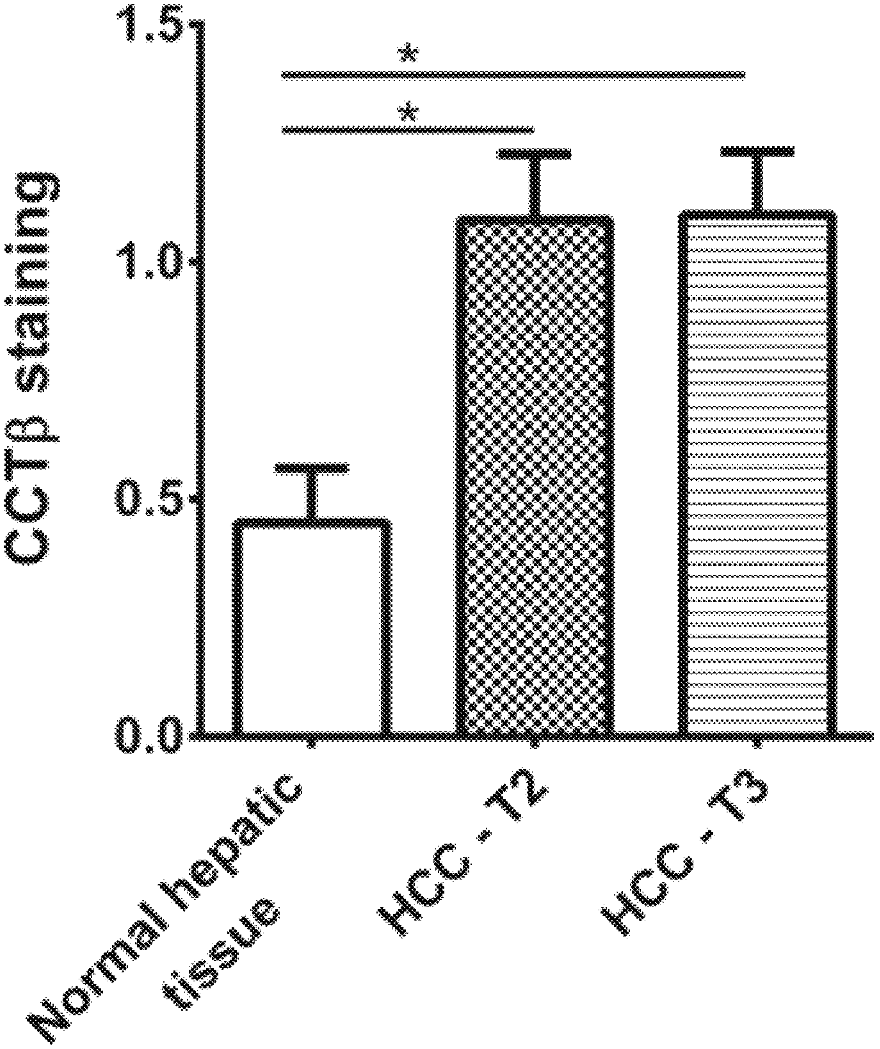

CCTβ was found to be expressed more highly in both HCC and cholangiocellular carcinoma when compared to normal hepatic tissue (FIG. 20A). However, this difference was only statistically significant ($p<0.05$) in HCC. HCC samples were further divided based on TNM score. The T score is a measure of primary tumor invasiveness (Lauwers et al. 2002). T1 refers to a single tumor that has not invaded the vasculature, while T2 may refer to a single tumor with vascular invasion, or multiple small tumors less than 5 cm. T3 tumors may be larger than 5 cm, and invade a major branch of the portal or hepatic veins. Finally, T4 tumors have invaded nearby organs (Lauwers et al. 2011). Experiments were therefore conducted to see whether CCTβ staining correlated with tumor invasiveness. Due to limited T1 and T4 sample size, only T2 and T3 HCC samples were examined. In HCC samples, both T2 and T3 samples expressed significantly more CCTβ than normal hepatic tissue (FIG. 20B). However, there was no difference between T2 and T3 samples.

Figure 20C:
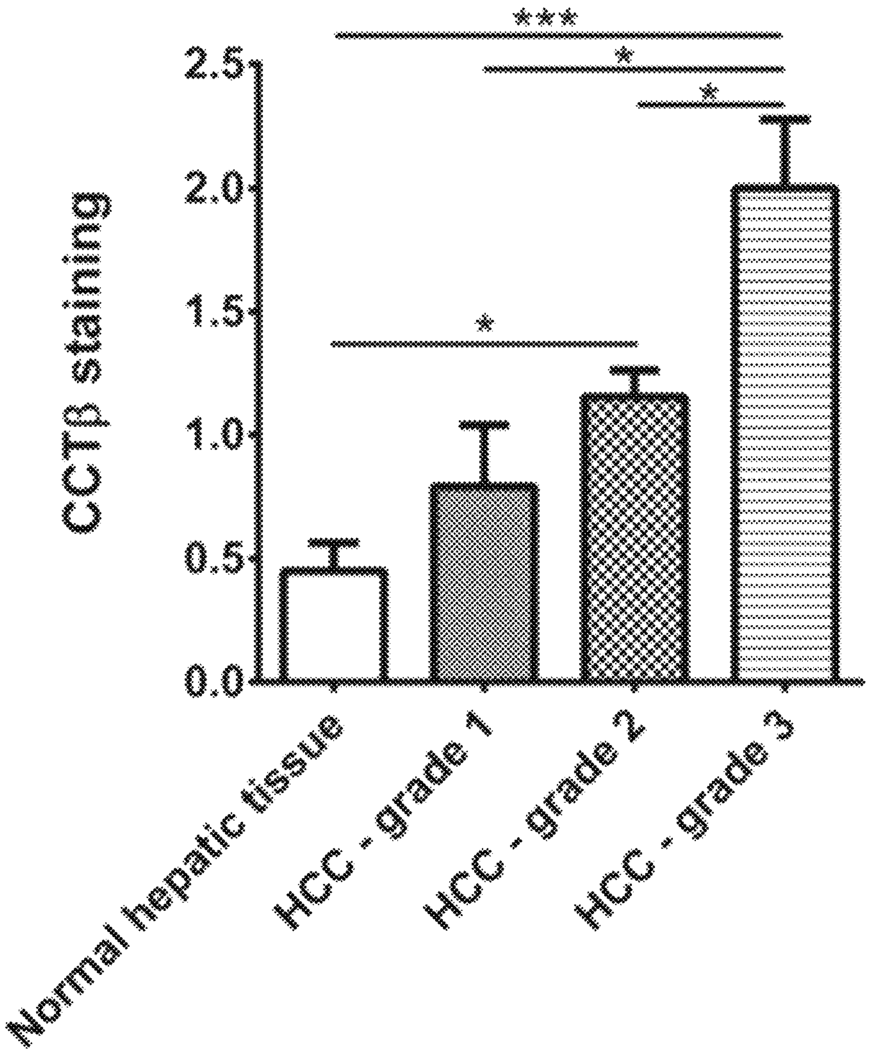
Figure 20D:
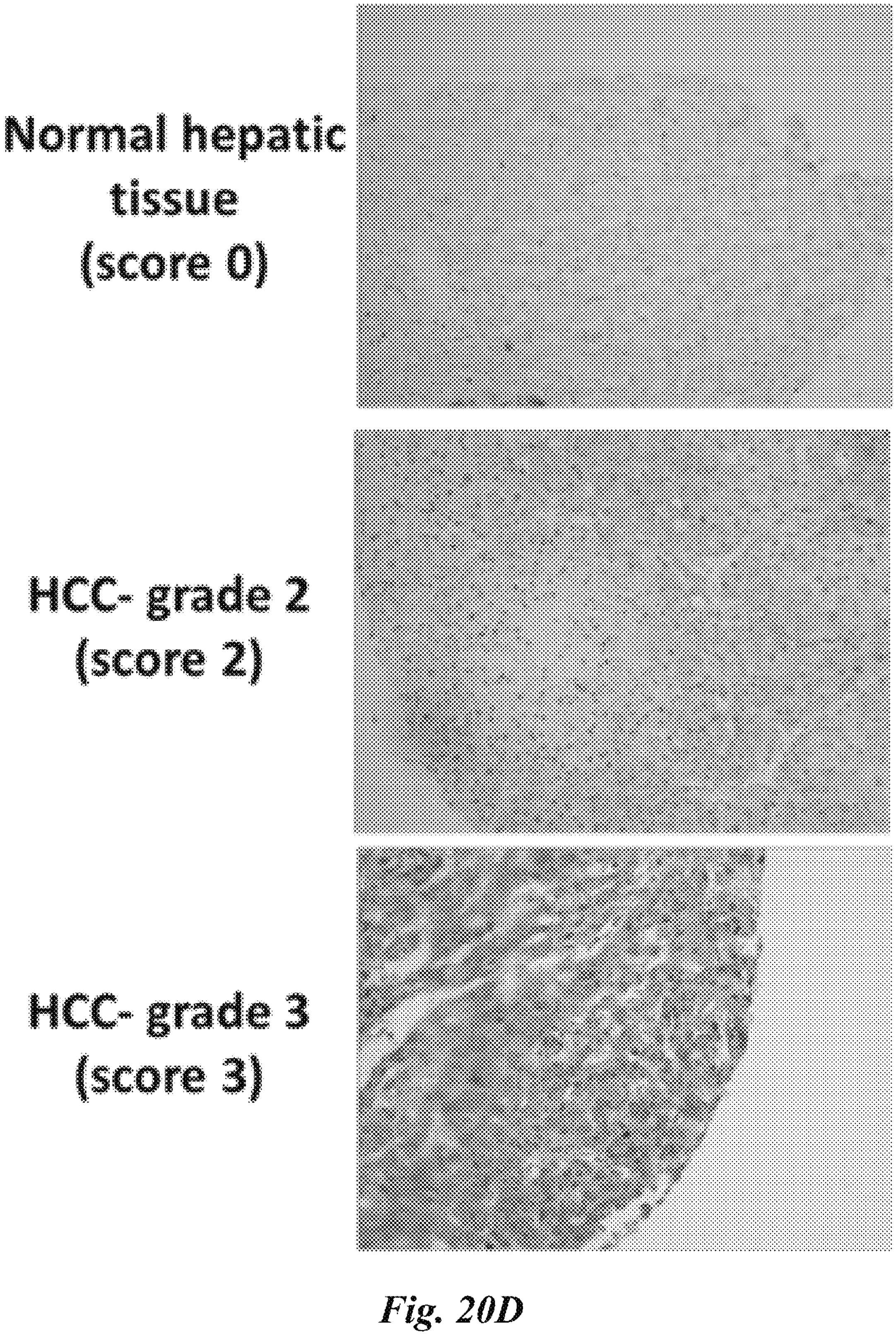

The HCC samples were also divided by grade, a measure of cell differentiation. As grade increases from 1 to 3, cell borders become less distinct, and nuclei become hyperchromatic and occupy a large percentage of the cell (Lauwers et al. 2011). Moreover, high grade HCC has been shown have poorer prognosis (Lauwers, Terris et al. 2002). A progressive increase in CCTβ staining was seen with increasing grade (FIG. 20C). Grade 3 HCC, characterized by poor differentiation and aggressive growth, expressed significantly higher levels of CCTβ than the other grades and normal hepatic tissue. Representative images are provided to illustrate the increase in CCTβ staining when comparing normal hepatic tissue to low-grade HCC and high-grade HCC (FIG. 20D).

In order to understand the expression pattern of CCTβ in various cancers, carcinomas that have not been previously described in the literature in this context were also examined. To this end, additional cancers that are impactful to society were examined. Prostate cancer is the most commonly diagnosed cancer in men, and the second leading cause of death in men after lung cancer (American Cancer Society. 2015). The most common form of prostate cancer is adenocarcinoma, which originates from the gland cells that secrete prostate fluid.

Figure 21A:
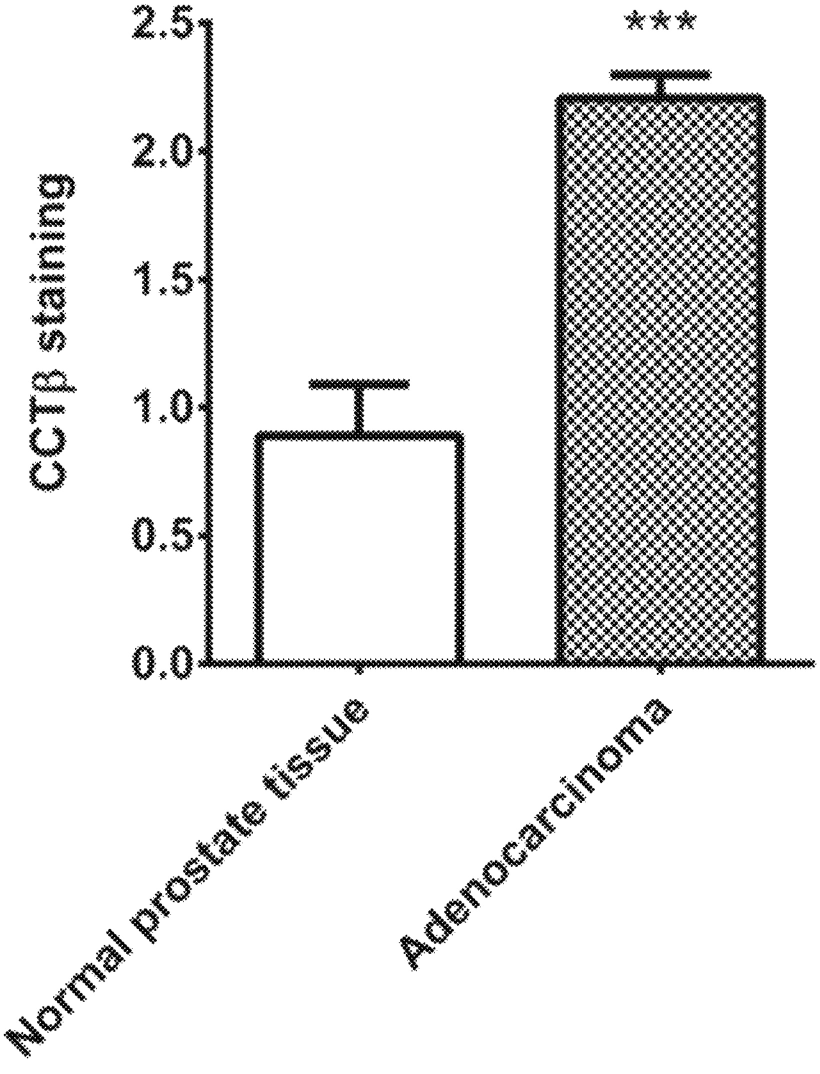
FIGS. 21A-21D show data representing the analysis of CCTβ staining in prostate cancer tissue.
Figure 21B:
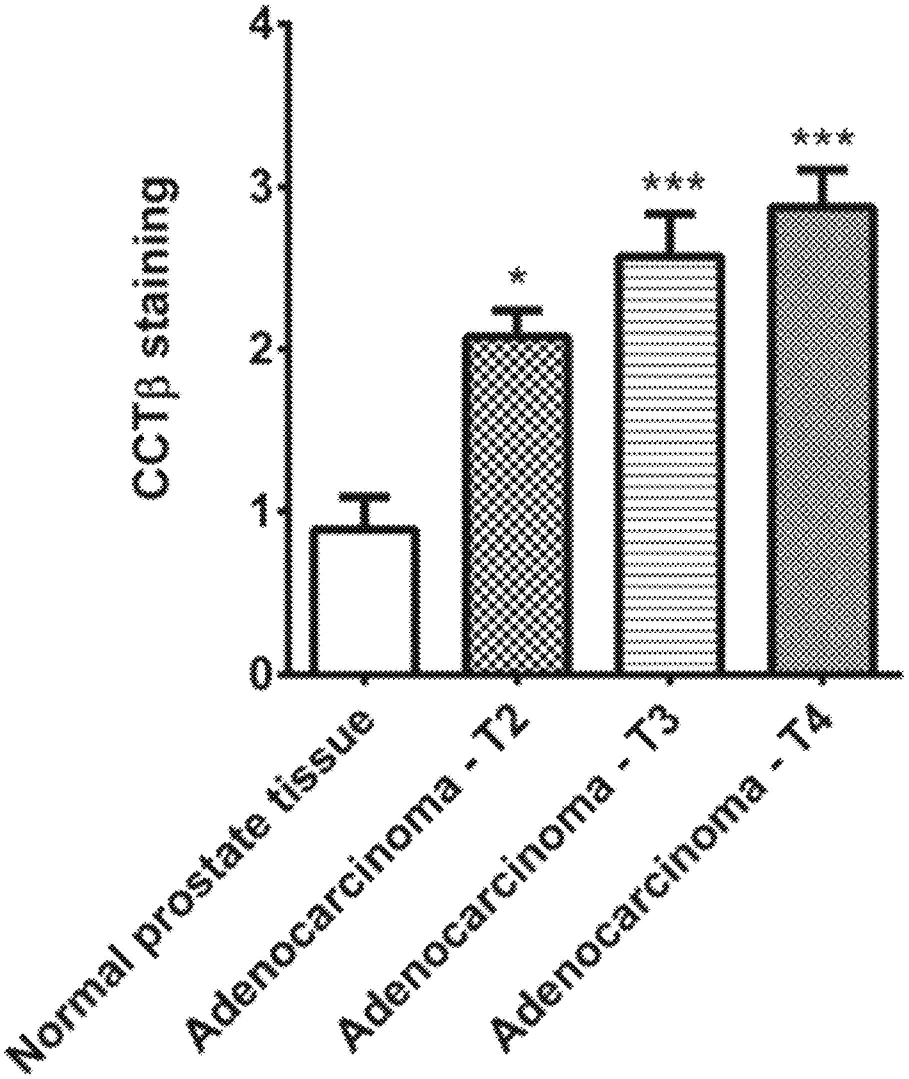

The levels of CCTβ staining was examined in prostate adenocarcinoma and levels found to be significantly increased when compared to normal prostate tissue (FIG. 21A). This supports the trend seen in breast cancer and liver cancer subtypes that express more CCTβ than normal tissue. Adenocarcinoma samples were then grouped by TNM score, into T2, T3, and T4 group. According to the College of American Pathologists, T2 tumors are confined within the prostate, T3 tumors have extended beyond the prostate capsule, and T4 tumors have invaded into adjacent tissues (College of American Pathologists. 2012). Increasing T score therefore indicates spread and invasiveness of the primary tumor. A trend of increasing CCTβ staining was detected as T score increased from T2 to T4 (FIG. 21B).

Figure 21C:
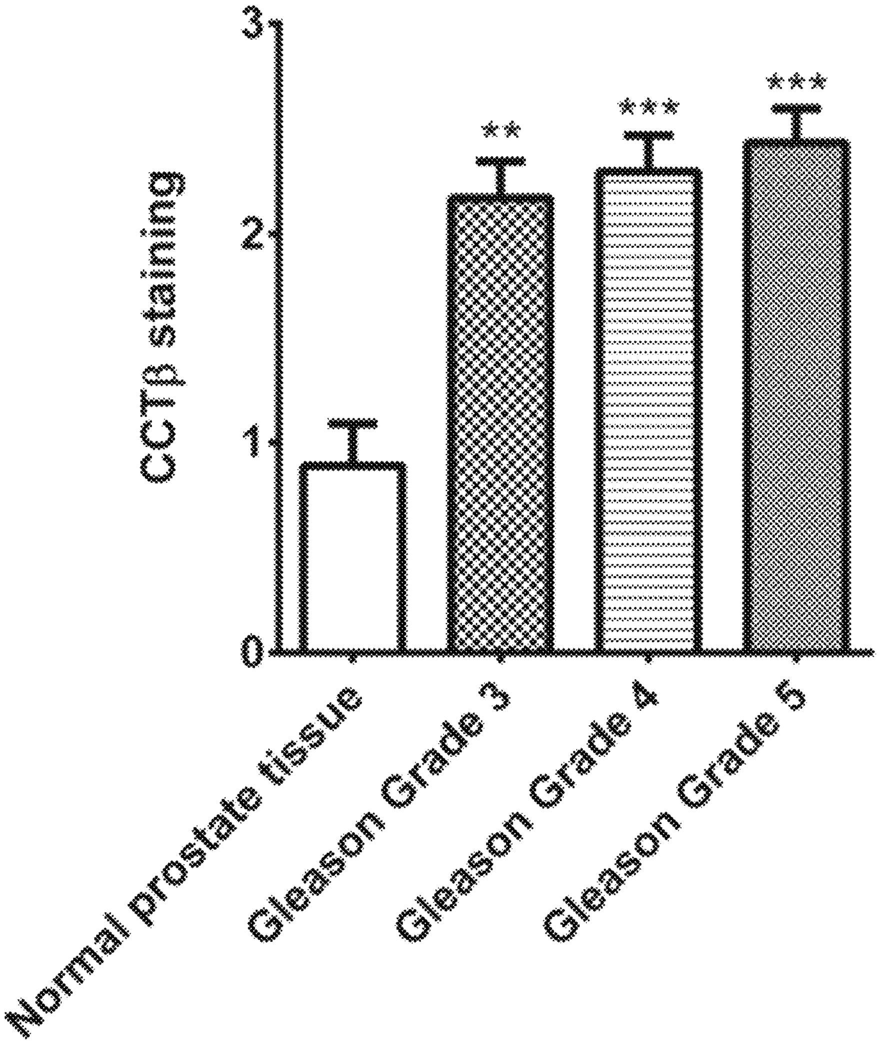

The correlation between CCTβ and Gleason grade was also examined. As a measure, the Gleason grade takes into account histological architecture and cellular differentiation. As Gleason grade increases, cellular appear less differentiated and there is a loss of normal prostate gland architecture (Epstein, Allsbrook et al. 2005). It is therefore reflective of aggressiveness and malignancy. Gleason scores 1 and 2 still resemble normal prostate tissue, and are therefore rarely assigned. When we examined Gleason grades 3 through 5, a very slight trend was seen in CCTβ staining with increased grade (FIG. 21C), but it was not as pronounced as that seen with T score (FIG. 21B).

Figure 21D:
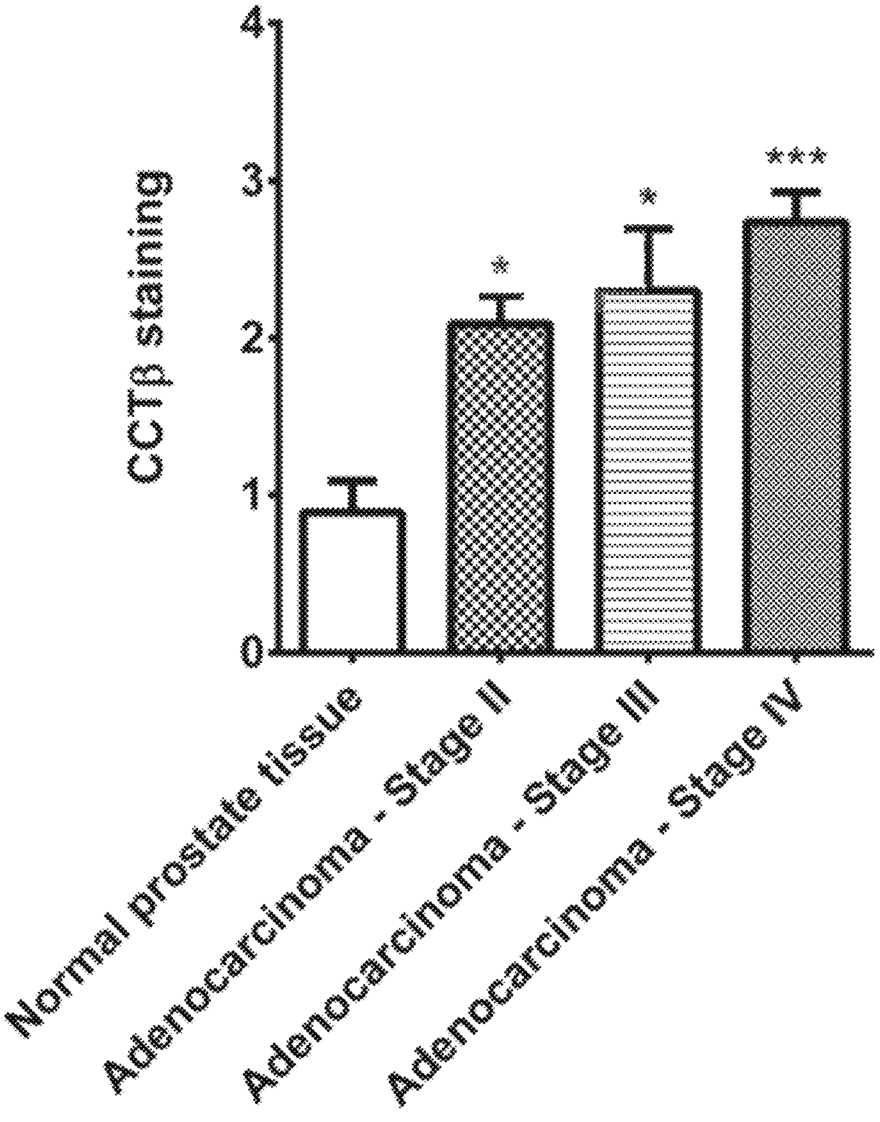

The tissue samples were finally grouped by stage. Staging in prostate cancer takes into account both the TNM score and the Gleason grade to assign a stage to the patient, which then determines prognosis and drives treatment decisions. Increased stage indicates higher severity of disease and poorer prognosis. Again, a trend of increasing CCTβ staining was seen with increasing stage (FIG. 21D). Overall, the data suggests that as severity of the prostate cancer increases, regardless of the measure used to represent this, CCTβ expression also increases.

Lung cancer, the deadliest cancer in the United States, was next studied. Although it is not the most commonly diagnosed cancer in neither men nor women—those are prostate cancer and breast cancer, respectively—lung cancer is responsible for the most deaths in both genders (American Cancer Society. 2015). In fact, estimates for 2015 indicate that lung and bronchus cancer will be responsible for more than a quarter of total cancer deaths—more than prostate, breast, and colorectal cancers combined (American Cancer Society. 2015).

The 5-year survival rate of lung cancer is only 17.8%, which is much lower than the 90.5% and 99.6% survival rates for breast and prostate cancer, respectively (Howlader N based on November 2014 SEER data submission, posted to the SEER web site, April 2015). Contributing to the severity of the disease is the fact that symptoms often do not appear until an advanced stage. More than 50% of lung cancers are diagnosed after the cancer has metastasized from the primary site, and these are associated with only a 4% 5-year survival rate (Howlader N based on November 2014 SEER data submission, posted to the SEER web site, April 2015). The extent of the disease cannot be understated, and research into treatments has become a priority.

Lung cancer is classified into three main broad classes. The first, non-small cell lung cancer (NSCLC), accounts for more than 80% of cases. NSCLC can be further divided into subtypes based on histological characteristics. These subtypes include adenocarcinoma and squamous cell carcinoma. The second class of lung cancer is small cell lung cancer (SCLC), which accounts for 10 to 15% of cases. SCLC is more aggressive, faster spreading, and more likely to recur than NSCLC. It is associated with a 5-year survival rate of only 6%, compared to 21% for NSCLC (American Cancer Society. 2015). The final class of lung cancer is neuroendocrine carcinoma. This includes carcinoid and atypical carcinoid tumors. These cancers are rare and slow spreading, and have a better prognosis than other lung cancers.

Figure 22A:
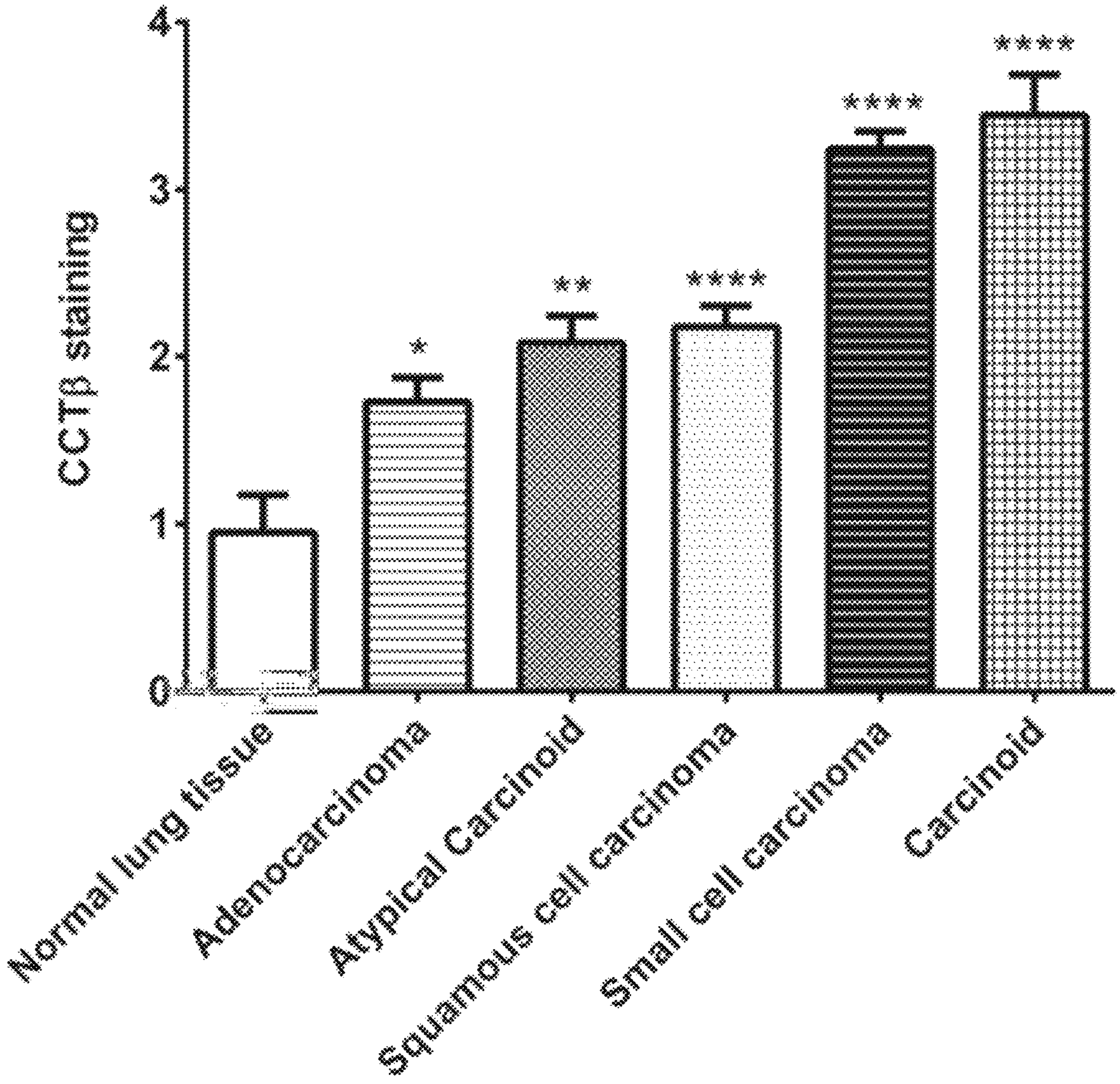
FIGS. 22A-22E show data representing the analysis of CCTβ staining in lung tumor tissue.

First examined was whether any subtype of lung cancer was associated with high levels of CCTβ staining. When compared to normal tissue, all lung cancer subtypes expressed significantly higher CCTβ (FIG. 22A). Noticeably, small cell carcinomas and carcinoid tumors stained consistently high, with CCTβ staining intensity more than three times that of normal lung tissue. These two subtypes were also statistically significant when compared to all other subtypes, with $p<0.001$ (not indicated on graph).

Figure 22B:
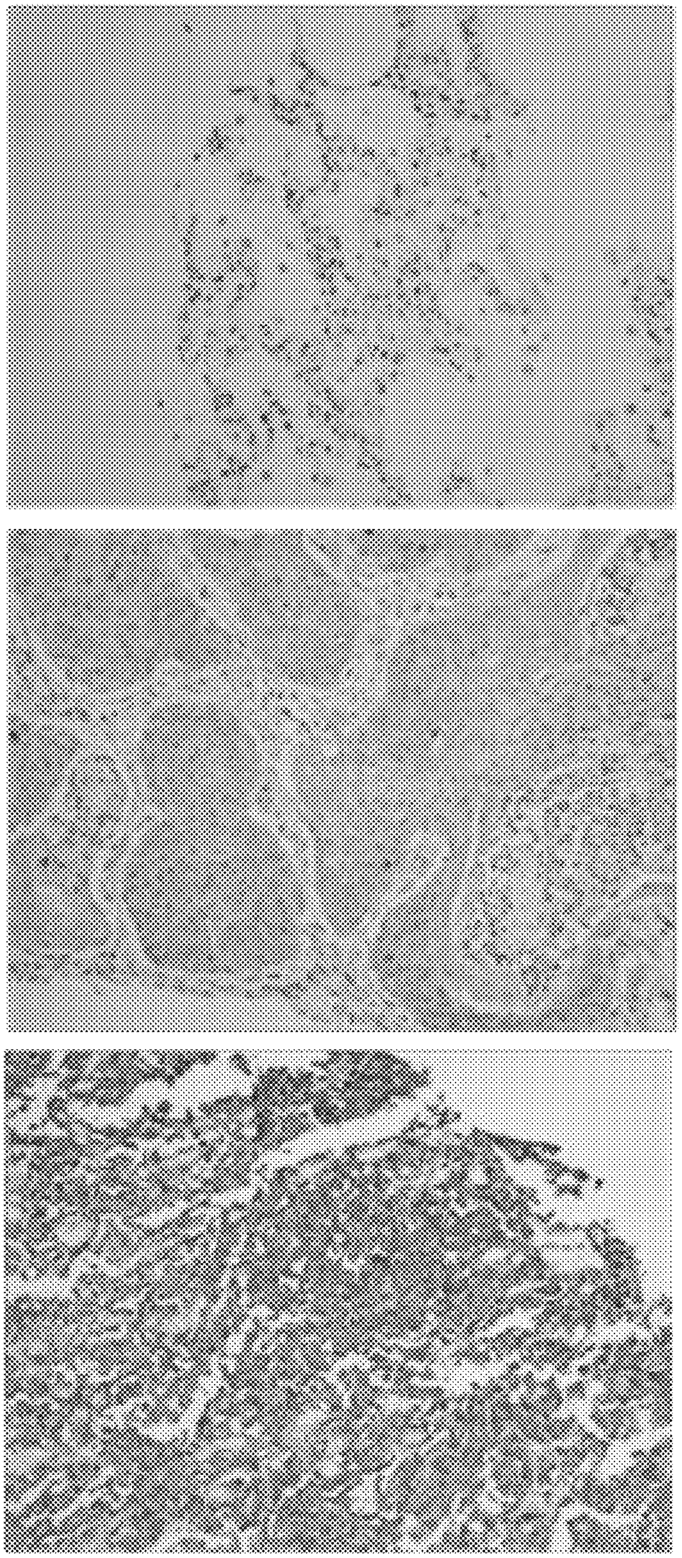
Figure 22C:
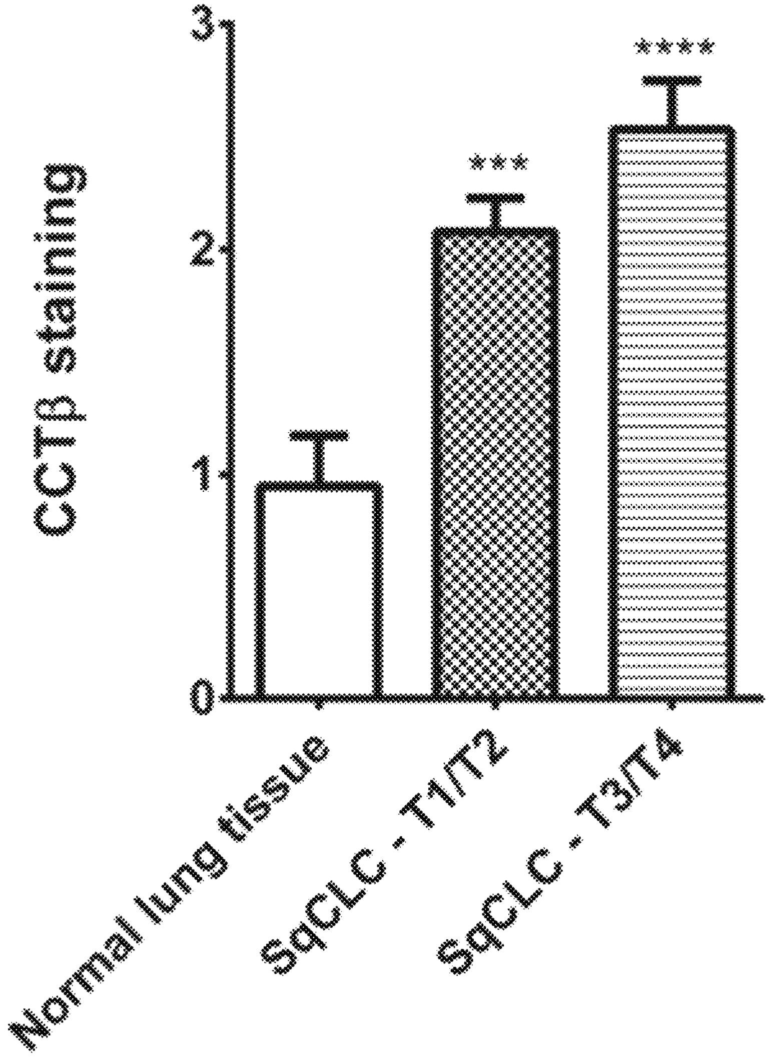
Figure 22D:
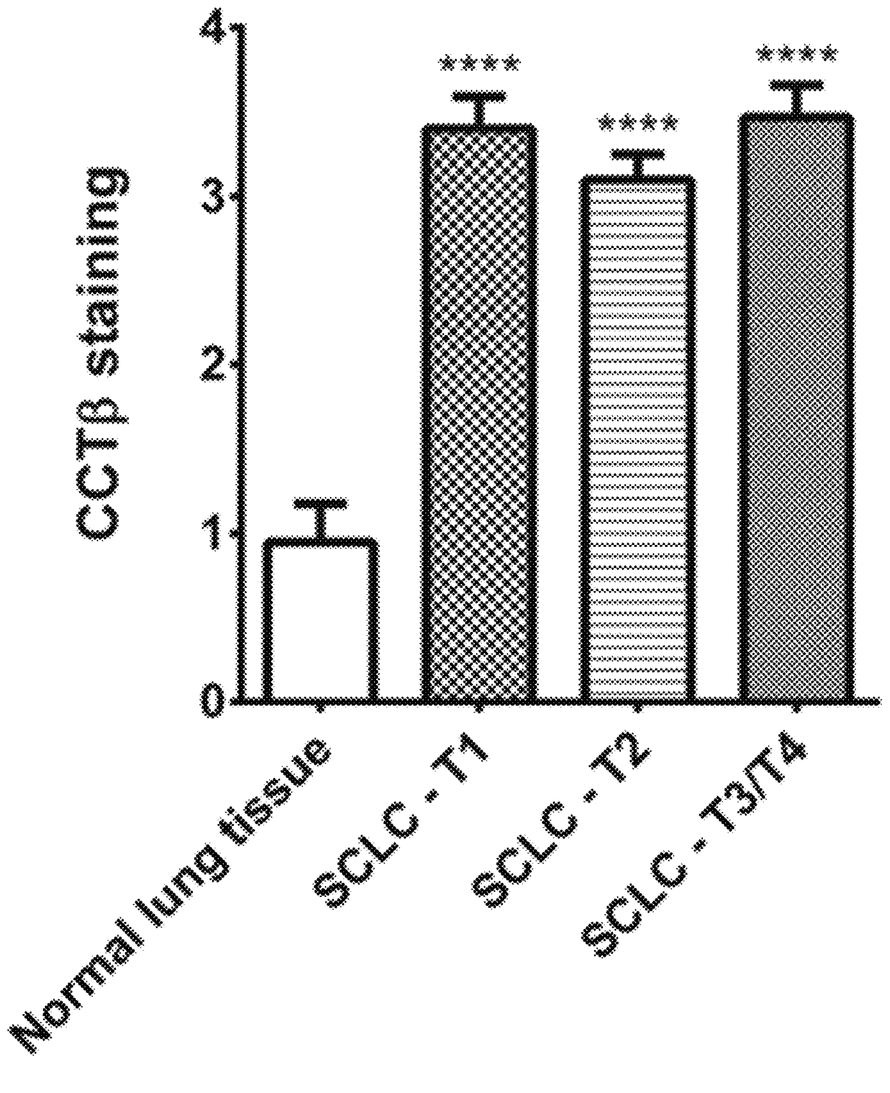
Figure 22E:
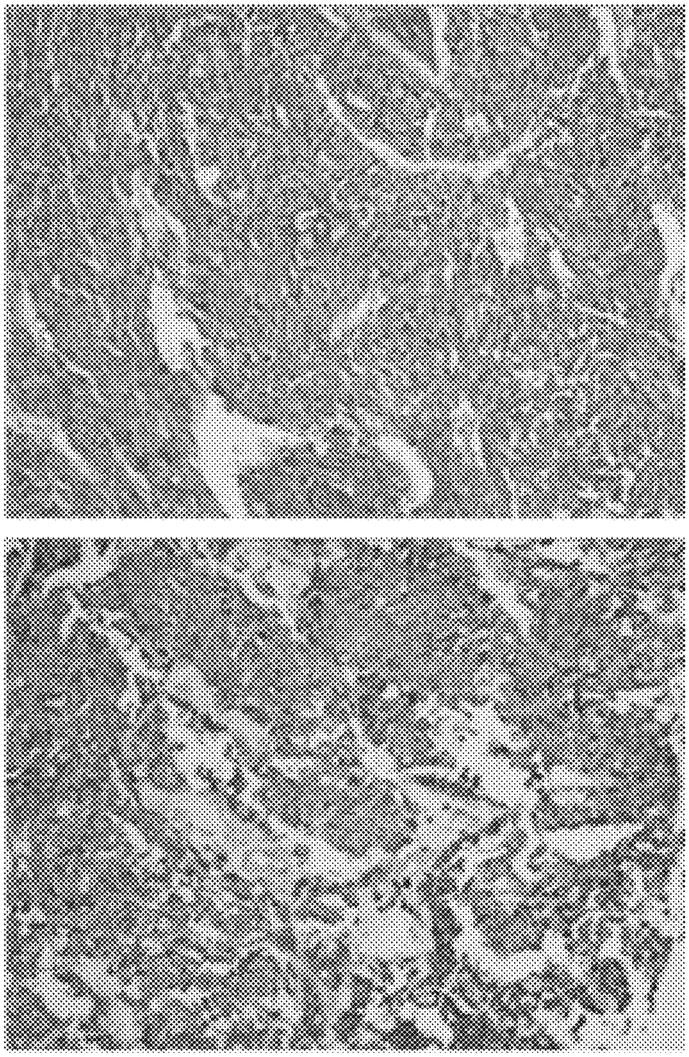

Squamous cell carcinoma also scored significantly higher than normal lung tissue. FIG. 22B provides images representative of staining in normal tissue, squamous cell carcinoma, and small cell carcinoma. Because these two subtypes contribute to a large proportion of lung cancer cases and are difficult to treat, we explored each of them in greater detail. In lung cancer, T score refers to the size and invasiveness of the primary tumor. When squamous cell lung carcinoma (SqCLC) was grouped by TNM score, a small increase in CCTβ staining was found in T3/T4 samples compared to T1/T2 samples (FIG. 22C). However, the difference was not statistically significant. When small cell lung carcinoma (SCLC) samples were examined in the same sway, CCTβ staining was uniformly high across TNM scores (FIG. 22D). Representative pictures of various TNM scores of SCLC illustrate the consistently high staining (FIG. 22E).

Discussion

In this study, tissue samples from various cancer and normal tissues were analyzed in an effort to characterize the potential of CCT as both a biomarker and a target in cancer treatment. Using tissue microarrays, CCTβ levels were studied by immunohistochemistry in a large amount of samples. This also had the benefit of providing cancers of a variety of stages, severities, and histological characteristics. a broad analysis of CCTβ levels was therefore conducted across colon, prostate, liver, and lung tissue specimens.

Analysis revealed that normal colon tissue contained high background levels of CCTβ, making it difficult to detect an increase in carcinoma samples.

Hepatocellular carcinoma was found to express higher levels of CCTβ than normal tissue. No correlation was found between CCTβ expression and TNM score. However, there was a strong positive correlation with tumor grade, with higher grade associated with high CCTβ staining. As tumor grade is a reflection of malignancy, it may be of note that CCTβ is expressed at high levels in poorly differentiated, highly aggressive hepatocellular carcinomas.

Prostate adenocarcinoma expressed significantly higher levels of CCTβ than normal prostate tissue. In prostate adenocarcinoma samples, there was a correlation between CCTβ staining and TNM score, Gleason grade, and disease stage.

Analysis of lung cancer samples revealed the highest scoring cancer subtypes in this study: small cell lung carcinoma and lung carcinoid tumor. Further analysis revealed that small cell carcinoma expressed high CCTβ regardless of TNM or tumor severity. As this is a particularly deadly form of lung cancer, identifying a target that is consistently present at all stages of the disease would be very beneficial toward developing a treatment.

Example 3: Development of CT20 Variants for Optimized Delivery and Binding to CCT A set of CT20 variants has been synthesized, focusing on optimization of the hydrophobic content and charge distribution for encapsulation within polymeric nanoparticles and maximal binding to CCT. These variants may be used to target cancer cells. The list can be found in Table 5.

TABLE 5

| Name | Sequence | MW | # of AA | Attributes | Gravy* |
|---|---|---|---|---|---|
| CT20 | VTIFVAGVLTASLT IWKKMG (SEQ ID NO: 1) | 2135.6 | 20 | basic | 1.258 |
| CT20-V1 | ASLTIWKKMG (SEQ ID NO: 2) | 1134.41 | 10 | basic | 0.140 |
| CT20-V2 | VTIFVAGVLT (SEQ ID NO: 3) | 1019.25 | 10 | neutral | 2.370 |
| CT20-V3 | VTIFVAG (SEQ ID NO: 4) | 705.85 | 7 | neutral | 2.343 |
| CT20-V4 | IFVAG (SEQ ID NO: 5) | 505.62 | 5 | neutral | 2.580 |
| CT20-V5 | IWKKMG (SEQ ID NO: 6) | 761.99 | 6 | basic | -0.450 |
| Control 1- Actin binding | GRPRHQGVMVGMGQ K (SEQ ID NO: 7) | 1637.96 | 15 | basic | -0.940 |
| Control 2- Actin non-binding | DNGSGMCKAGFAGD D (SEQ ID NO: 8) | 1444.53 | 15 | acidic | -0.633 |
| Control 3- Ir-relevant | ATAAAAAAATASLT IQDDMG (SEQ ID NO: 9) | 1821 | 20 | acidic | 0.630 |

*Grand average of hydropathicity.

1. Example 4: Methods

Collection of data from online bioinformatics and histology databases: Data was collected from UCSC Xena at xena.ucsc.edu using the combined cohort of "TCGA, TARGET, and GTEx samples" dataset. From the 19,131 available samples, 734 samples were excluded because they were childhood cancers (TARGET), and 1,197 samples were excluded due to missing information/"null" in either the main category or gene expression. This left us with 17,200 from TCGA and GTEX to be used for analysis. The initial analysis examined CCT subunits (CCT1-CCT8) RSEM expected count (DESeq2 standardized) expression between normal tissue (GTEx) and primary cancer (TCGA) in overall cancer, and then in brain, breast, colon, and lung cancer separately. Secondary analysis of UCSC Xena focused on the expression of the CCT2 gene and the CK genes KRT8, KRT18, and KRT19. From the 19,131 samples in the "TCGA, TARGET, GTEx samples" dataset, the phenotype/sample types that were included were: "Metastatic", "Normal tissue", "Primary tumor", and "Solid tissue normal", leaving 17,722 samples. This data was downloaded and analyzed through R software for dataset mean and standard deviation (SD). Data for the KMplots was collected at kmplot.com using an mRNA gene chip for breast cancer and lung cancer. Genes used were CCT2 (201946_s_at) and "mean expression of multiple genes" for CK (KRT8:

209008_x_at; KRT18: 201596_x_at; and KRT19: 201650_at). Hazard ratios and Longrank p values were calculated by kmplot.com software. mRNAseq data of breast cancer cell lines from the Broad Institute Cancer Cell Encyclopedia (CCLE) were collected by searching for E-cadherin (CDH1), N-cadherin (CDH2), EpCAM, and vimentin (VIM) expression in breast cancer. Histology data was collected from the Human Protein Atlas (HPA) under the "tissue atlas" and "pathology atlas" tabs. These tissue images had been stained with the CCT2 antibody HPA003198.

Collection of patient blood samples. For the metastatic breast cancer (MBC) study, participants included 38 female patients aged 18 years or older, diagnosed with MBC arising from a prior stage 1, 2, or 3 of disease with a tissue block available to produce slides for histology. Patients with de novo MBC were excluded. Our study size met the parameters established in a sample size estimation based a range of Pearson correlation (R) using the wp.correlation function in the R package (WebPower). If R is >=0.5 (medium effect), then CCT2 expression in CTCs is as clinically relevant as in tumor tissue for prognosis prediction. To detect such a level of effect size (power 0.8, alpha 0.05), we would need 28 patients. If R is >=0.6 (medium-large effect), we would need 18 patients. The study was conducted observing the human subject protection criteria for the Orlando Regional Medical Center (ORMC) and the University of Central Florida (UCF) and was approved by separate Institutional Review Board (IRB) committees at ORMC and UCF. Informed consent agreements were obtained from all participating subjects. Patients received standard treatments and follow-up at ORMC for breast cancer, at which time two 10 mLs of blood in CellSave tubes (Menarini) were drawn and four slides of tissue were obtained from the pathology department at ORMC. Deidentified samples and data on diagnosis, treatment, and recurrence were acquired and processed by the lab at UCF following the Federal Privacy Regulations for protected health information. For the SCLC study, deidentified patient blood from four participants, 7.5-10 mLs of blood in CellSave tubes, was acquired from a commercial source (BioIVT).

Recruitment of MBC study participants and their CTC collection: Participants included 38 female patients aged 18 years or older, diagnosed with MBC arising from a prior stage 1, 2, or 3 of disease with a tissue block available to produce slides for histology. Patients with de novo MBC were excluded. The study met human subject protection criteria for the Orlando Regional Medical Center (ORMC) and the University of Central Florida (UCF) and was approved by separate Institutional Review Board (IRB) committees at ORMC and UCF. Informed consent agreements were obtained from all participating subjects. Patients received standard treatments and follow-up at ORMC for breast cancer, at which time two 10 mL vials of blood in CellSave vials (Menarini) were drawn and four slides of tissue were obtained from the pathology department at ORMC. Deidentified samples and data on diagnosis, treatment, and recurrence were acquired and processed by the lab at UCF following the Federal Privacy Regulations for protected health information. Blood samples in CellSave vials (Menarini) were stored at room temperature and run in CSS according to the manufacturer's protocol for CSS CTC Kit (Menarini) for CTC analysis within 96 hours of blood draw. CTCs were selected based on the standard CSS criteria for CTC, which is met if the cell is 1) DAPI positive, 2) CK positive and the CK stain overlaps with 50% of the DAPI stain, and 3) CD45 negative. Tissue slides were stained as described below.

Protocol for standard CTC capture and enumeration. Blood samples in CellSave vials (Menarini) were stored at room temperature and run in CSS according to the manufacturer's protocol for the CSS CTC Kit (Menarini) for CTC analysis within 96 hours of blood draw. CTCs were selected based on the standard CSS criteria for CTC, which is met if the cell is 1) positive for DAPI (4',6-diamidino-2-phenylindole) staining, 2) positive for CK-FLU (Cytokeratin-fluorescein-conjugated (green)) staining and the CK-FLU stain overlaps with 50% of the DAPI stain, and 3) negative for cluster of differentiation 45 (CD45) staining.

Immunohistochemistry staining of tissue slides: Slides with formalin-fixed paraffin-embedded (FFPE) tissues were received from four sites. 1) US Biomax Inc: normal breast tissue microarray (TMA) BRN801b. 2) ORMC: MBC patients from the pilot study described above. 3) AdventHealth: surgical breast cancer archival tissues TMA (>10 yrs) from 28 patients with G1-G3 invasive ductal carcinoma arrayed under IRBNet #748165. 4) BioIVT: lung cancer case numbers were 30453 and 32648 for normal tissue; 30171, 63381, and 66835 for adenocarcinoma; 63454 and 63526 for squamous cell carcinoma; and 63087 for small cell carcinoma. Slides were baked at 60° C. for 60 min and stained using Bond-Max Immunostainer (Leica). Anti-CCTβ antibody [amino acids 277 and 473 of Human TCP1 beta] from LifeSpan Biosciences, was diluted at 1:100, in antibody diluent (Leica). STAT3 antibody [E121-21] from Abcam, was diluted at 1:100, in antibody diluent (Leica). Epitope retrieval buffer of EDTA pH 9.0 (Leica) for 10 min (anti-CCTβ) or 20 mins (STAT3). Polymer Refine Detection reagents (Leica) were used, which include a hematoxylin counterstain. Slides were stained and scored for the CCT2 stain intensity twice, and supported by an independent and identification-blinded pathologist, as described previously (Bassiouni et al., 2016). Images were taken using the BZ-X800 Keyence.

Cell lines and culture conditions: MDA-MB-231 cells (ATCC® HTB-26™) were cultured in Dulbecco's Modified Eagle's Medium (DMEM) (Corning) and supplemented with 10% fetal bovine serum (FBS) (Gemini) and 1% Penicillin-Streptomycin (P/S) (Corning). T47D cells (ATCC® HTB-133™) were transfected with a lentiviral plasmid to express CCT2-FLAG, as previously described (Showalter et al., 2020). T47D cells were cultured in RPMI-1640 (Corning) supplemented with 10% FBS (Gemini), 1% P/S (Corning), and 0.2 units/mL human recombinant insulin (Santa Cruz). 0.5 μg/mL puromycin dihydrochloride (ThermoFisher) was added to maintain plasmids. NCI-H1882 [H1882] (ATCC® CRL-5903™) and NCI-H1048 [H1048] (ATCC® CRL-5853™) were cultured in DMEM:F12 Medium (Corning) supplemented with 1× Insulin/Transferrin/Sodium selenite (ITS) (Lonza) [final concentrations were 0.005 mg/mL Insulin/0.01 mg/mL Transferrin/30 nM Sodium selenite], 10 nM Hydrocortisone (Sigma Aldrich), 10 nM Beta-Estradiol (Sigma Aldrich), 2 nM L-Glutamine (Corning), 5% FBS (Gemini) and 1% P/S (Corning). All cells were low passage numbers and grown at 37° C. in a 5% carbon dioxide atmosphere.

Flow cytometry experiments for EMT protein expression and CCT2 antibody optimization: Cells were collected, stained, and measured with a BD Cytoflex S flow cytometer as follows. Isotype controls and antibody concentrations were used per the manufacturer's instructions. EpCAM-PE: [VU-1D9] (Abcam) and isotype control [MOPC-21] (BD Pharmingen). E-cadherin-PE: CD324 [DECMA-1] BioLegend) and isotype control [A95-1] (BD Pharmingen). N-cadherin-APC: CD325 [8C11] (BioLegend) and isotype control [27-35] (BD Pharmingen). Cells were stained for 30 mins (EpCAM) and 20 mins (E-cadherin and N-cadherin) in a 50 μL final volume and measured with the BD Cytoflex S. CCT2-PE: [NP_006422] (LSBio) and the isotype control [MOPC-21] (LSBio) were also used following the manufacturer's recommendations. Permeabilization and fixation protocol was adapted from the ThermoFisher Scientific protocol A: two-step protocol: intracellular (cytoplasmic) proteins. Antibody incubation was 20 min to match CSS Autoprep automated conditions and compared to a 70 min incubation for long-term exposure. Analysis was performed using De Novo FCS Express 6 software.

Reverse transcription-polymerase chain reaction (RT-PCR) for gene expression of EMT markers: RNA was isolated from cells using TRIzol™ (Invitrogen) following the manufacturer's standard protocol for RNA extraction. RNA was quantified using a Nanodrop. cDNA was synthesized using the iScript™ cDNA Synthesis Kit (Bio-Rad) following the manufacturer's protocol. cDNA was diluted 1:5 and mixed with a Fast SYBR™ Green Master Mix (Applied Biosystems) according to manufacturer's recommendations and then run in the Quantstudio PCR for 40 cycles at 95° C. for 3 sec, and 62° C. for 30 sec. Primers were designed using the NCBI nucleotide database, Table 11.

Buffer/Manual CSS experiments for optimization of CCT2 antibody in CSS: Protocol was adapted from. In brief, for enrichment CSS reagents from the CSS CXC kit (Menarini) were used: dilution buffer (450 μL), anti-EpCAM ferrofluid (25 μL), and capture enhancement reagent (25 μL). Samples were incubated for 15 min and then added to a magnet holder and incubated for an additional 10 min. The supernatant was removed and discarded. Samples were then stained with the following CSS CXC kit (Menarini) reagents: nucleic acid dye (50 μL), staining reagent (51.5 μL), and permeabilization reagent (100 μL). Anti-CCT2-PE (5 μL) (LSBio: LS-C649415) was added and the sample was incubated for 20 min. After incubation, dilution buffer (500 μL) was added, and the sample was placed in a magnet holder for an additional 10 min. The supernatant was discarded. Samples were re-suspended in dilution buffer (350 μL) and transferred into CSS magnets cartridges and run in CSS Analyzer II. Using the CSS Analyzer II's Setup tab, the magnets could be reconfigured with the format sample button. The magnets can then be labeled for the CXC kit algorithm and the exposure time can be adjusted as described in (Lowes et al., 2014).

Cancer cells spiked into healthy human blood: Healthy human blood was collected in CellSave vials (Menarini) by BioIVT and shipped overnight. Cancer cells were collected from tissue culture in 5% FBS/PBS buffer at the desired concentration and then spiked into the CellSave blood vials. After overnight incubation at room temperature, the samples were run in the CSS using the CSS CXC kit according to the staining protocol for CCT2 listed below. Viability of cells after addition to CellSave vials, under blood-free conditions, was measured using Trypan blue (Gibco) according to the manufacturer's protocol.

Incorporating the CCT2 stain in the CTC detection protocol and selection of CCT2 positive cancer cells. To incorporate the anti-CCT2-PE antibody into the CSS protocol, the study used the Veridex PDF "Guidelines for user-defined markers in CSS". The PDF can be found at www.cellsearchruo.com/sites/default/files/Guideline-for-Use-and-Optimization-of-User-Defined-Markers.pdf. For blood containing spiked cancer cells, anti-CCT2-PE antibody (LSBio) was added at 8 μg/mL using the Veridex PDF recommendations for the staining protocol associated with the CSS CXC kit (Menarini). Lower concentrations (1 ug/mL-4 ug/mL) were also tested with SCLC cell lines. For analysis, the spiked cancer cells were reviewed first using the CSS definition for CTCs which is based on using CK in the Fluorescein isothiocyanate (FITC) channel for identification, and second by the positive expression for CCT2 which is read in the PE channel. Criteria for the CCT2 positive analysis were as follows: 1) round positive signal in the PE channel, 2) PE signal that shows overlap with the DAPI signal, and 3) PE signal that did not show overlap with a CD45 signal if a CD45 signal was present. Cells with faint signal in CD45 channel that could be explained by bleed from the PE channel were not counted as CD45 positive. Cells with pixelated images or streaks in the PE channel were selected if there was a definitive outline between the stained cell and the background. Cells with punctate staining in the PE channel were selected only when the cell outline had a definitive difference from the background. Overlap with CK signal was not a requirement for CCT2 positive cell selection. For the pilot study of SCLC patients, samples were collected and processed according to the "Protocol for standard CTC capture and enumeration" mentioned above. Anti-CCT2 antibody was added at either 12 ug/mL or 24 ug/mL. The same criteria for selection of CTC and CCT2 positive CTC were used as mentioned previously in this section.

Staining for CCT2 in CSS and selection of CCT2' spiked cancer cells: Staining protocol was adapted from Veridex PDF "Guidelines for user-defined markers in CSS". The PDF can be found at www.cellsearchruo.com/sites/default/files/Guideline-for-Use-and-Optimization-of-User-Defined-Markers.pdf. Anti-CCT2-PE antibody (LSBio) was added at 8 μg/mL using the Veridex PDF recommendations for the staining protocol associated with the CSS CXC kit (Menarini). For analysis, the spiked cancer cells were reviewed first using the CSS definition for CTCs which is based on using CK in the FITC channel for identification, and second by the positive expression for CCT2 which is read in the PE channel. Criteria for the $CCT2^{hi}$ analysis were as follows: 1) round positive signal in the PE channel, 2) PE signal that shows overlap with the DAPI signal, and 3) PE signal that did not show overlap with a CD45 signal if a CD45 signal was present. Cells with pixelated images or streaks in the PE channel were selected if there was a definitive outline between the stained cell and the background. Cells with punctate staining in the PE channel were selected only when the cell outline had a definitive difference from the background. Overlap with CK signal was not a requirement for $CCT2^{hi}$ cell selection.

Staining blood spiked CCT2' breast cancer cells post CSS for CD44: In order to measure breast cancer cells enriched after processing in the CSS for flow cytometry analysis, the CSS CXC kit (Menarini) was used in the CSS Autoprep with the adaptation that the DAPI reagent was removed before the CSS Autoprep cycle began and replaced with PBS. After recovering cells from the CSS magnets, the cells were stained for CD44 with BV421 mouse anti-human CD44 [G44-26] (BD Horizon) or the isotype control [KPL-1] (BD Horizon). The positive control was MDA-MB-231 cells alone (not in blood). The negative control was blood cells alone (not spiked with MDA-MB-331 cells). After staining for 20 min, the samples were measured in the BD Cytoflex S and analyzed using De Novo FCS Express 6 software.

Operator independent analysis using the ACCEPT (Automated CTC Classification Enumeration and PhenoTyping) software: ACCEPT is an open software program that can be downloaded from github.com/LeonieZ/ACCEPT. The ACCEPT Manual is found on the same website or in Zeune, 2019. Analyzer II images were archived onto CD drives and downloaded onto a computer that had the ACCEPT program. ACCEPT has several modes for detection including marker characterization (MC) and full detection (FD), which can be selected from the top dropdown menu. The MC mode was used to process the spiked breast cancer cells. Once processed, the files turn from red to green and can be individually selected for visualization. The window's right side shows a gating options panel based on stain intensity, which is similar to those seen in flow cytometry. On the top left of the screen, under the "multiple gates" button, a series of channel-specific gates can be created. For this experiment, gates were set to identify $CK^{hi}$ or $CCT2^{hi}$ cells. Gate settings were as follows: CK: Channel 3/DiOC: Mean Intensity >10, CCT2: Channel 4/PE: Mean Intensity >10.

Statistical analysis: T-test and one-way ANOVA statistical analysis was performed to compare gene expression differences between tumor and normal tissue, and among different cancer types. R software was used to calculate mean and SD for UCSC Xena-downloaded data. For RT-PCR analysis, relative gene expression was calculated by dividing a gene's expression in that sample by the average expression of this gene in control samples, i.e., $2^{-\Delta\Delta Ct}$/average ($2^{-\Delta\Delta Ct\ control\ sample}$) with T47D-lentiviral control (T47D-GFP) assigned as the control sample. A Log-rank test was used to compare cancer patient survival rates between high and low expression for CCT2 and CK. To investigate the association of CCT2 expression with CTC and active disease (time gap), Spearman's correlation analysis and multiple linear regression analysis were performed. For regression analysis, we incorporated time gap as a dependent variable and CCT2 as an independent variable, and controlled for CTCs, age, ER, PR, and HER2 status. All statistical analyses were performed using Stata MP 15 (StataCorp LLC, 2019) or GraphPad Prism 9 software. All statistical tests were two-tailed with a significance level of a (type I error)<0.05.

Surface markers and intracellular staining analysis by flow cytometry. Cells were collected, stained, and analyzed by flow cytometry (BD Cytoflex S flow cytometer) as follows. Staining for membrane surface molecules included use of the following antibodies: EpCAM-PE (phycoerythrin): [VU-1D9] (Abcam) and isotype control [MOPC-21] (BD Pharmingen); E-cadherin-PE: CD324 [DECMA-1] BioLegend) and isotype control [A95-1] (BD Pharmingen); and N-cadherin-APC (Allophycocyanin): CD325 [8C11] (BioLegend) and isotype control (BD Pharmingen). Staining was performed following standard methods. Cells were stained for 30 mins (EpCAM) and 20 mins (E-cadherin and N-cadherin). For intracellular staining of CCT2 we used the antibody CCT2-PE: [NP_006422] (LSBio) and the isotype control [MOPC-21] (LSBio), following the method in ThermoFisher Scientific's "Protocol A: two-step protocol: intracellular (cytoplasmic) proteins" and incubating the antibody for 70 mins. When optimizing the CCT2 intracellular stain for CSS Autoprep conditions, we adjusted the antibody staining protocol for CCT2-PE to match the 20 min in the CSS Autoprep automated conditions. All data was generated using FCS Express 6 software (De Novo).

2. Example 5. Results

Figures 30A, 30B, 30C, 30D, 30E:
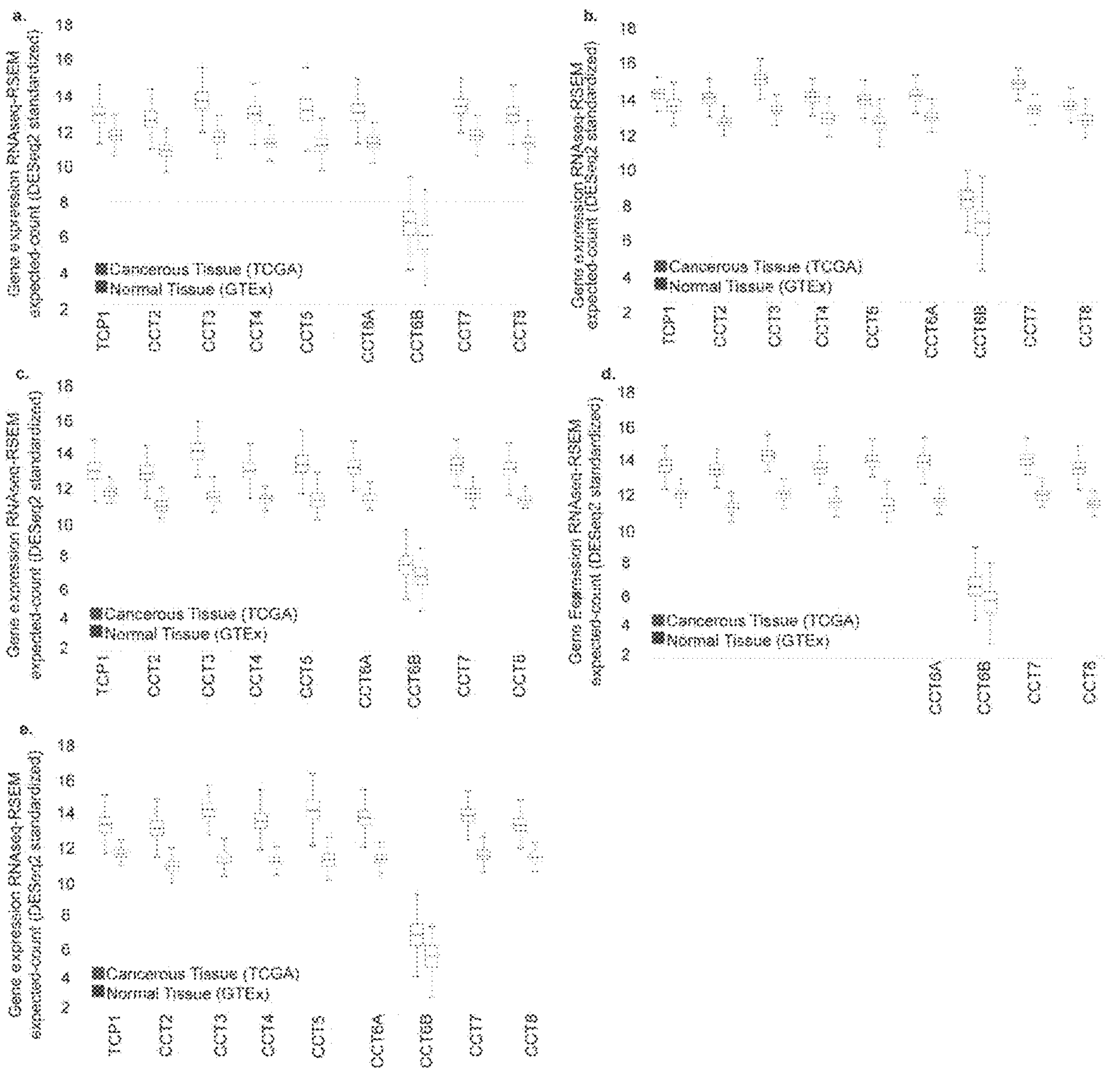
FIGS. 30*a*-30*e* show UCSC Xena database comparing all eight CCT subunits in normal (GTEx) vs. cancerous (TCGA) tissue.

Bioinformatics-based evaluations of CCT2 or CK/KRT gene expression in normal compared to cancer tissue. To evaluate CCT gene expression in tumor tissues compared to normal tissues, the eight CCT subunits (CCT1-8) were analyzed in the UCSC Xena Browser using the cohort of "TCGA, TARGET, and GTEx samples" dataset. All eight CCT subunits showed significant (p<0.0001) upregulation in RNAseq expression in cancer compared to normal tissue, with the strongest upregulation seen in CCT2 and CCT3, Online Resource FIG. 30*a*. These results were consistent when broken down by cancer type; brain, breast, colon, and lung, show in FIGS. 30*b*-30*e*. CK is a standard diagnostic marker for epithelial cancers and CK8, CK18, and CK19 are used in the CSS when visualizing for CTCs. Therefore, to evaluate CCT2 and CK/KRT gene expression correlations with tumors and normal tissue, the UCSC Xena dataset was used to focus on CCT2, KRT8, KRT18, and KRT19. The pair-wise comparison showed that the average CCT2 gene expression in primary tumor and metastatic tissue was significantly higher than in normal tissue and solid tissue normal (mean±SD: 12.42±0.76 and 12.51±0.72 compared to 11.51±0.62 and 11.86±0.42 respectively, p<0.0001 for all pairwise comparisons). Meanwhile, KRT8 and KRT19 gene expression in metastatic tissue showed significant downregulation compared to normal tissue (mean±SD: 8.51±2.78 vs 9.68±3.51, p<0.0001, and 4.19±3.77 vs 8.47±3.53, p<0.0001) for KRT8 and KRT19 respectively, FIG. 23*a*. CCT2 also demonstrated the lowest variance of the four markers. Full statistical analysis is shown in Table 13. To determine how CCT2 and CK/KRT correlated with overall survival (OS), KMplotter was used to assess these relationships for breast cancer (FIG. 23*b*) and lung cancer (FIG. 23*c*). Results showed statistically significant inverse correlations between $CCT2^{hi}$ and OS in both breast cancer (p=6.4e−05) and lung cancer (p=9.6e−10). High KRT8/18/19 expression also demonstrated an inverse correlation with patient OS in both cancers, but only lung cancer was statistically significant (p=7.2e−09). These findings support that CCT2 expression is upregulated in cancer and metastatic tissues compared to normal tissue, while KRT8/19 showed downregulation in metastatic tissue, and that CCT2 expression correlated inversely with patient OS.

1. Detection of CCT2 in tumor tissues using breast cancer patient cohorts. To confirm the trend of high CCT2 gene expression correlating with tumor progression observed in the bioinformatics data, the prevalence of the CCT2 protein was examined in normal tissue compared to breast cancer tissues. A breast tissue microarray (TMA) (TMABRN801b) was stained. The TMA contained 70 patient samples of normal, adjacent normal, and cancer-adjacent tissue (CAT), and ten samples of invasive ductal carcinoma (IDC) for CCT2. Normal tissue was from breast tissue in patients without cancer, while adjacent normal tissue was from normal breast tissue that was distal to the patient's cancerous tissue. CAT was from breast tissue that was next to the cancerous tissue. A previous report shows CCT2 tissue staining scale from 0 to 4 that was created by a pathologist based on light and dark cytoplasmic and nuclear staining. The tissue data present results as CCT2neg, (score of 0), CCT2lo (score of 1 to 2), and CCT2hi staining (score of 3-4), FIG. 24A. Normal breast tissues mostly showed minimal to low CCT2 staining, FIG. 24A. Early-stage IDC tumor samples also showed minimal to low CCT2 staining. A pilot study was next run to evaluate CCT2 protein levels in different stages of breast cancer. A TMA was created using archived patient specimens from ductal and lobular breast cancers of various grades. This TMA was stained for CCT2 and one of its client proteins, STAT3 (FIG. 31B and FIG. 31C) and contained 13 $CCT2^{lo}$ specimens and 11 $CCT2^{hi}$ specimens that correlated with the corresponding levels of STAT3 staining, Table 12. Moreover, $CCT2^{hi}$ staining positively correlated with higher cancer stage in both ductal and lobular carcinoma which is consistent with data previously reported.

Figures 24A, 24B, 24C:
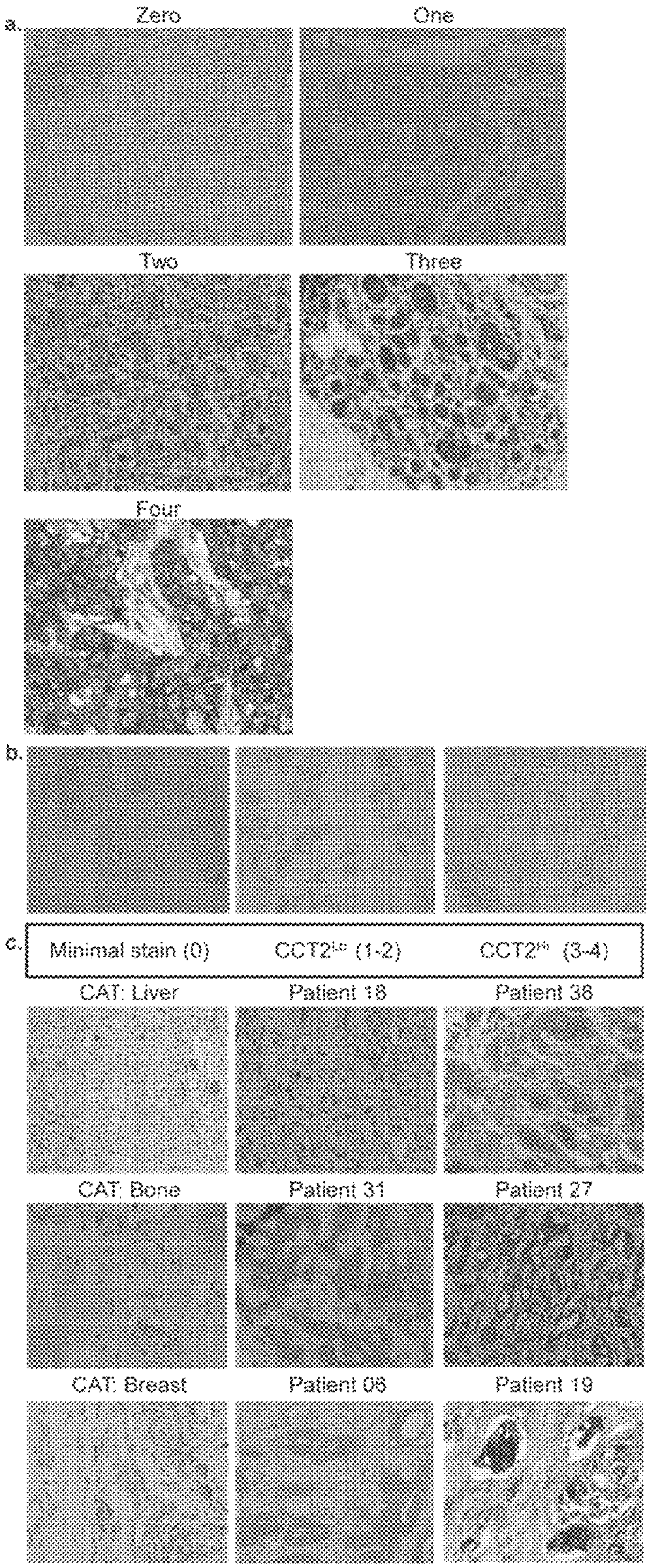
FIGS. 24*a*-24*c* show histological analysis of CCT2 in normal tissue vs. metastatic breast cancer (MBC) patients. (a) Representative images of breast cancer tissue at each CCT2 tumor stain score. Zero represents no stain present (e.g., TMABRN801b sample E1); One represents light staining of the cytoplasm (e.g., patient 25); Two represents light staining of the cytoplasm with darker staining throughout (e.g., patient 08); Three represents dark staining of the cytoplasm (e.g., patient 33); Four represents dark staining of the cytoplasm and staining of the nucleus (e.g., patient 37). (b) Representative images from normal tissue in microarray of breast tissue stained for CCT2 from sections A2, D7, and J4. (c) Representative images from a cohort of MBC patient tissues stained for CCT2. The images are—left column: cancer adjacent tissue (CAT) that had minimal staining, compared to middle column: CCT2$^{lo}$ tissue, which was classified as a score of one or two, and the right column: CCT2$^{hi}$ tissue, which was classified as a score of three or four
Figures 32A, 32B, 32C:
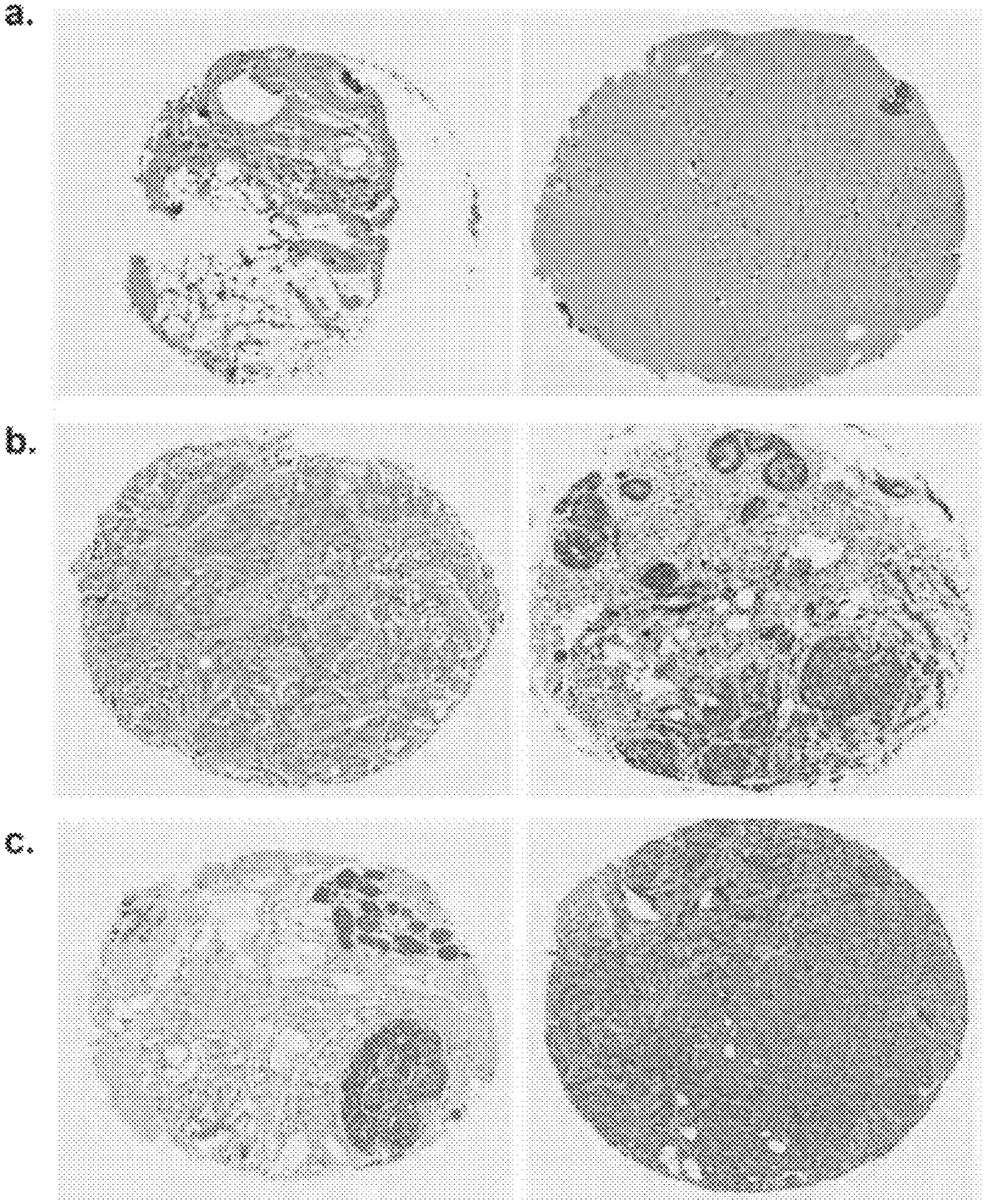
FIGS. 32*a*-32*c* show human Protein Atlas staining for CCT2 in normal and cancerous breast tissue. All tissues were stained with the HPA003198 antibody.

The levels of CCT2 in MBC was examined by staining tumor specimens from 38 MBC patients, shown in Table 14. Fifteen specimens were excluded due to failed screening (n=4) or inadequate samples (n=11). Tumor source (primary or metastatic) is listed in Table 14. CCT2 score ($CCT2^{lo}$ or $CCT2^{hi}$) is listed in Table 6 and representative images are shown in FIG. 24c. All tumor samples were positive for CCT2 staining, with 14 cases of $CCT2^{lo}$ (score one or two) and 9 cases of $CCT2^{hi}$ (score three or four). To confirm these observations with patient tumor tissues, the HPA for CCT2 levels in breast tissue were analyzed and it was found that cancerous tissue showed increased levels compared to normal tissue. The tissue images show darker and more abundant staining in cancerous tissue compared to normal tissue, shown in FIG. 32. Together, these findings further corroborate CCT2 levels being lower in normal breast (and other normal tissues) and increased in cancerous tissue in a manner that could be dependent on cancer stage and metastasis.

Evaluation of CCT2 tumor score and CTCs enumerated in a cohort of MBC patients. Having found that gene expression and tumor levels of CCT2 correlated with breast cancer, next experiment was performed to investigate how CCT2 tumor levels compared with tumor lineage markers as well as CTCs enumerated using standard epithelial markers. Blood samples were collected from 23 of the MBC patients (Table 14) and CTC analysis was run according to the FDA-approved standard CSS protocol, Table 6. Although all 23 patients were diagnosed with MBC, only three met the CTC threshold established by CSS for poor prognosis (>5 CTC/7.5 mL of blood). To determine how the CCT2 tumor score compared to CTC counts with patient outcomes, a Spearman correlation analysis was run. As a surrogate for active disease, the time gap between the date of the most recent tumor tissue biopsy and the date of our blood draw for CTC analysis was used, Table 6. A larger gap can indicate a less active disease state, while a shorter time gap could indicate increased patient monitoring and a more active disease state. The result of the Spearman correlation showed that the $CCT2^{hi}$ tumor score had a statistically significant (p=0.007) inverse correlation with the time gap, while other parameters like CTCs did not, Table 7. A multiple linear regression analysis to determine the impact of CCT2 tumor score on time gap when accounting for other variables: age, CTCs, ER, PR, and HER2 status, Table 8. The CCT2 tumor score demonstrated statistically significant (p=0.009) inverse correlations with the time gap. In comparison, ER status demonstrated statistically significant (p=0.010) positive correlations with the time gap indicating that this marker is linked to treatment outcomes. Additional trends were noted from the data in Table 6. For example, a $CCT2^{lo}$ score correlated with a longer period of time since the metastatic diagnosis. Also, three out of the five patients with 4-5 CTCs had $CCT2^{hi}$ tumor scores. When $CCT2^{hi}$ tumor scores did not correlate with high CTC counts, it can be due to differences in the quality of the tumor biopsy as well as treatment effects or it can be from undercounted CTCs due to the reliance on epithelial markers.

Figures 25A, 25B, 25C, 25D:
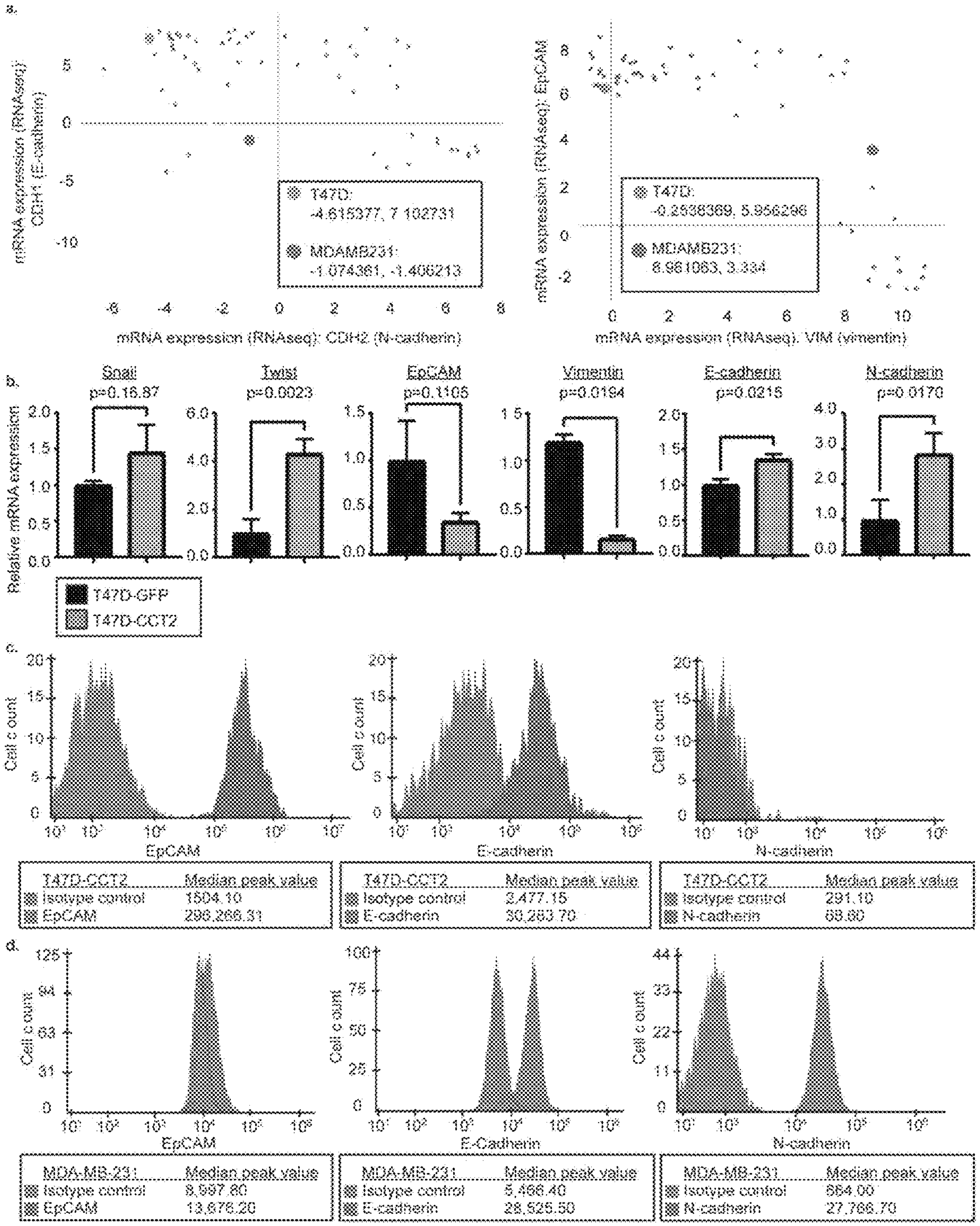
FIGS. 25*a*-25*d* show EpCAM, vimentin, E-cadherin, and N-cadherin expression in MDA-MB-231 and T47D cells. (a) Broad Institute Cancer Cell Line Encyclopedia (CCLE) RNAseq expression data in breast cancer cell lines (purple dots) with a focus on T47D (green dot) and MDA-MB-231 (red dot) cell lines for CDH1 (E-cadherin) vs. CDH2 (N-cadherin), and EpCAM vs VIM (vimentin). (b) RT-PCR data comparing lentiviral control (T47D-GFP) (black) with T47D-CCT2 (grey) for expression of epithelial to mesenchymal transition (EMT) genetic markers: SNAIL and TWIST, epithelial markers: EpCAM and E-cadherin, and mesenchymal markers: vimentin and N-cadherin. P-values are shown on the graph. (c) EpCAM, E-cadherin, and N-cadherin expression in T47D-CCT2 (green) with isotype controls (grey). (d) EpCAM, E-cadherin, and N-cadherin expression in MDA-MB-231 (red) with isotype controls (grey). All experiments were performed in duplicate FIGS. 26A-26C. Breast cancer cells spiked in blood can be detected based on CCT2 staining using the CSS. Representative images of (FIG. 26A) whole healthy human blood without spiked cancer cells processed through the CSS and stained for CCT2, and (FIGS. 26B-26C) Representative images of MDA-MB-231 (FIG. 26B) or T47D-CCT2 (FIG. 26C) cells spiked into human blood, processed through the CSS, and stained for CCT2. Light blue arrows: Leukocyte that is CCT2 positive. Red arrows: cells with dim CK signal and CCT2 positive signal. Yellow arrows: Leukocytes that have dim CCT2 signal. Dark blue arrow: doublet of spiked cancer cells with different CCT2 staining intensities. Grey arrows: cells with dim CCT2 signal. CK-FLU (Cytokeratin-fluorescein-conjugated). This data is representative of ten experiments.

Optimization of CCT2 staining in the CSS. Bioinformatic and tumor histology data support that CCT2 can be a marker for cancer and is associated with metastasis, indicating that CCT2 can be used for CTC identification to improve enumeration and analysis. Therefore, a CCT2 antibody (anti-CCT2-PE) for staining in the CSS platform was optimized. For this study, breast cancer cell lines displaying a range of epithelial and mesenchymal characteristics were chosen. According to the online database CCLE, RNAseq expression of EMT markers showed that luminal A T47D breast cancer cells are more epithelial-like, and TNBC MDA-MB-231 breast cancer cells are more mesenchymal-like, FIG. 25a. T47D cells were transfected with a lentiviral plasmid that overexpressed CCT2-FLAG (T47D-CCT2). These cells were assessed for SNAIL, TWIST, EpCAM, vimentin, E-cadherin, and N-cadherin mRNA expression, FIG. 25b. Statistically significant increases in TWIST (p=0.0023), N-cadherin (p=0.0170), and E-cadherin (p=0.0215) mRNA were present in the T47D-CCT2 cells compared to the lentiviral control cells, with a significant decrease in vimentin (p=0.0194) mRNA. Therefore, CCT2 overexpression led to increases in some mesenchymal characteristics without loss of epithelial ones. To determine if EMT-related T47D-CCT2 and MDA-MB-231 mRNA expression correlated with membrane protein levels, surface levels of EpCAM, E-cadherin, and N-cadherin were measured by flow cytometry, FIGS. 25b and 25c. T47D-CCT2 cells were EpCAM and E-cadherin positive, while the N-cadherin was negative, FIG. 25b. The lack of N-cadherin expression on the surface despite mRNA expression demonstrates the complexity of membrane protein expression pathways including, post-translational regulations, receptor internalization, etc. MDA-MB-231 were N-cadherin positive with a slightly lower expression of EpCAM and E-cadherin, FIG. 25d. These data demonstrate that these two cell lines represent a range of epithelial and mesenchymal features.

Figures 33A, 33B, 33C, 33D:
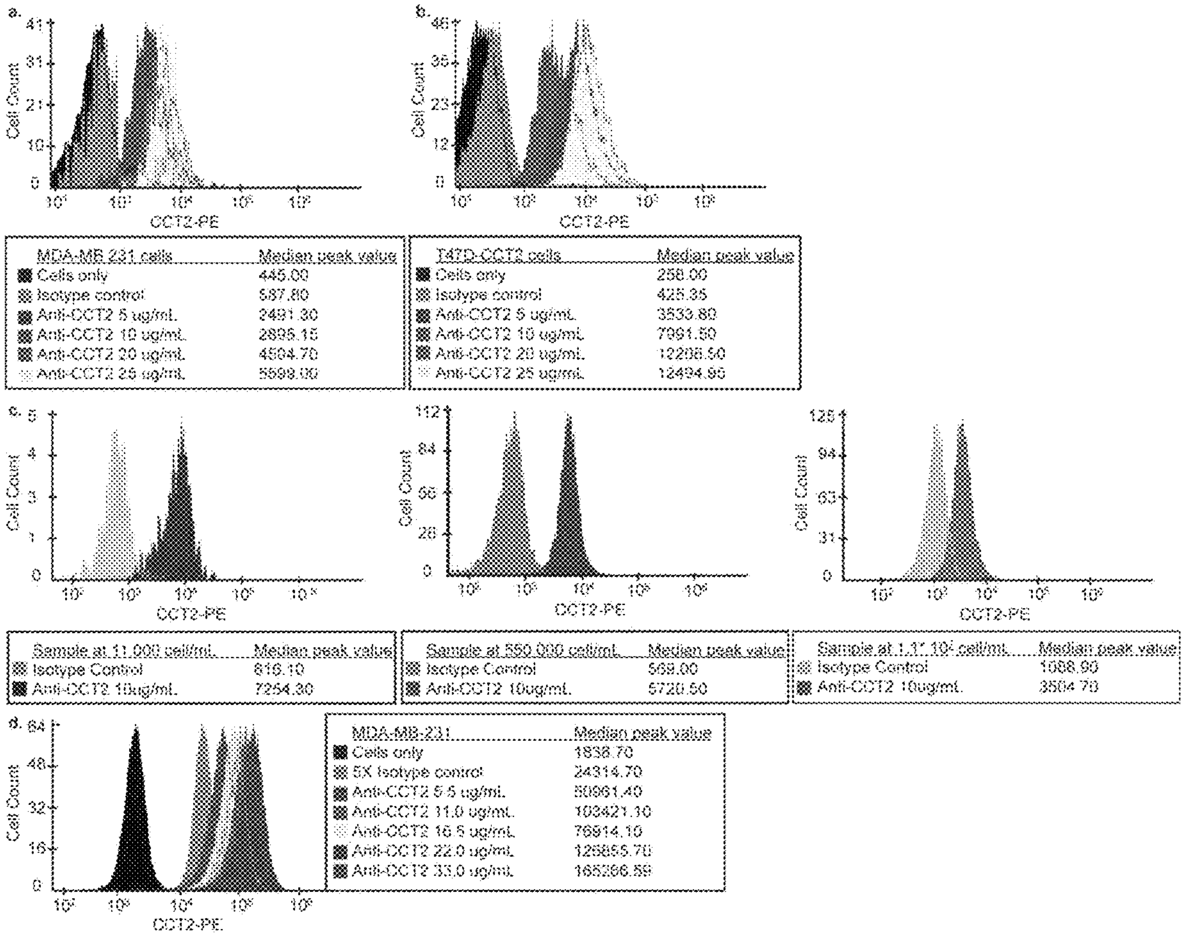
FIGS. 33*a*-33*d* show anti-CCT2-PE validated with PE-isotype control under different conditions.
Figures 34A, 34B:
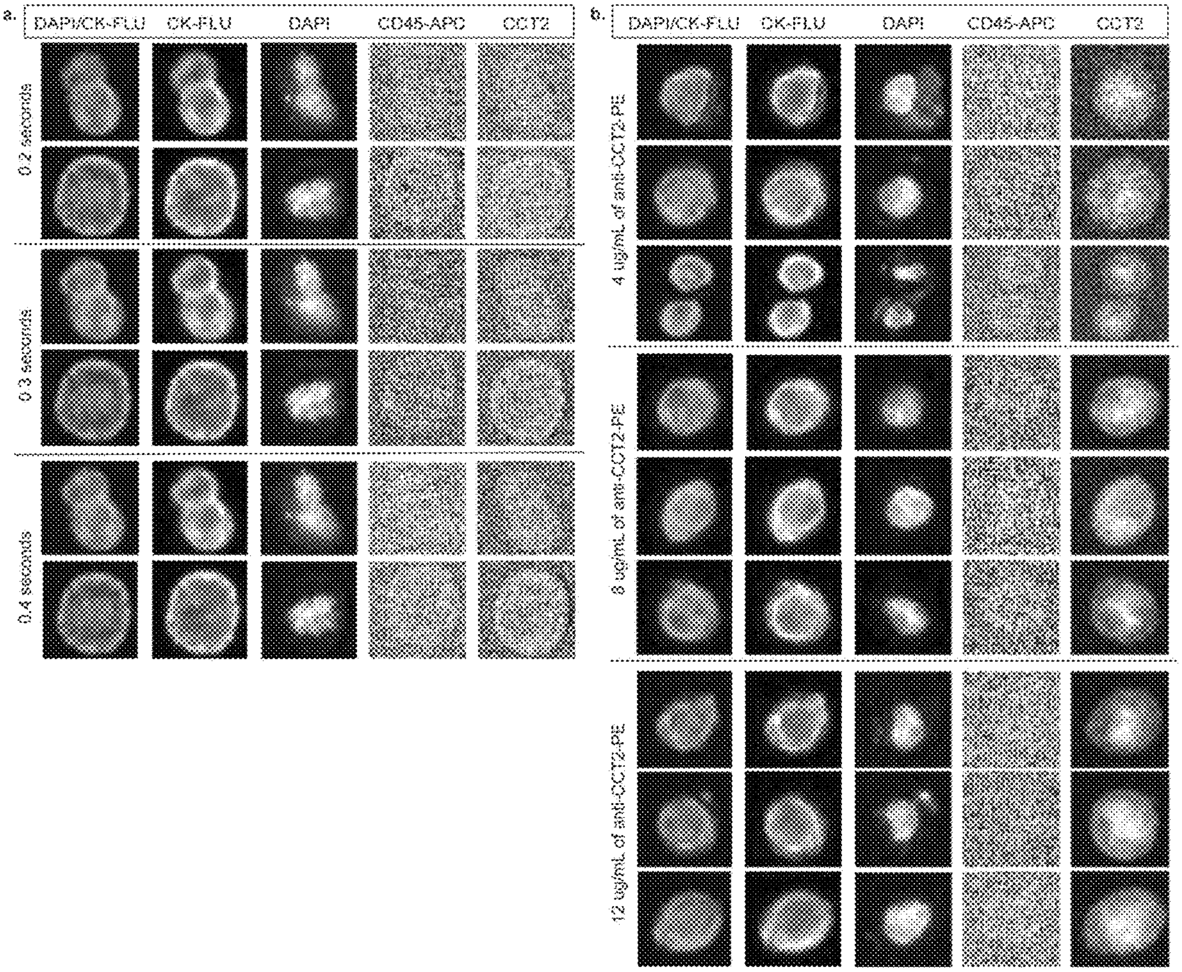
FIGS. 34*a*-34*b* show that anti-CCT2-PE was tested in CellSearch® System (CSS) Analyzer II to determine exposure times and antibody concentrations that would minimize background interference.

To validate the CCT2 antibody staining, the detection of the intracellular signal by flow cytometry was used to test various antibody concentrations in MDA-MB-231 cells and T47D-CCT2 cells. The CCT2 antibody differentiated between specific and non-specific binding within a range of cell concentrations that approached conditions occurring during automated CTC collection with the CSS. Saturation of the response was achieved around 20 μg/mL, FIG. 33. To optimize the cell-based signal from the intracellular stain of the CCT2 antibody in the CSS Analyzer II, cells were manually stained and the exposure time and the antibody concentration were adjusted. The 0.2 second exposure time showed the least background noise, while both 8 μg/mL and 12 μg/mL of anti-CCT2-PE resulted in a clear positive signal, FIG. 34. 8 μg/mL was chosen as the anti-CCT2 antibody concentration moving forward.

Figures 26A, 26B:
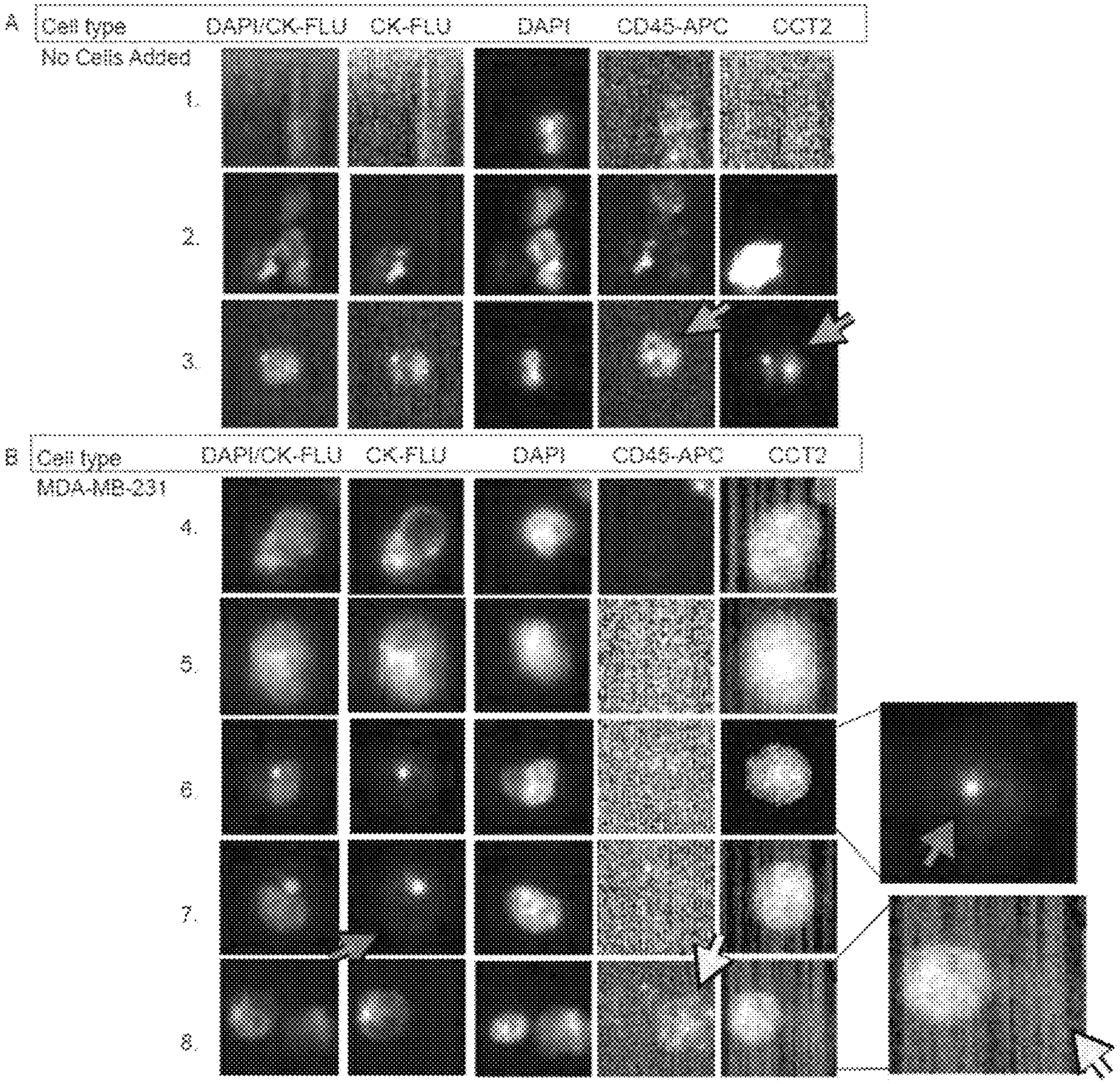
Figure 26C:
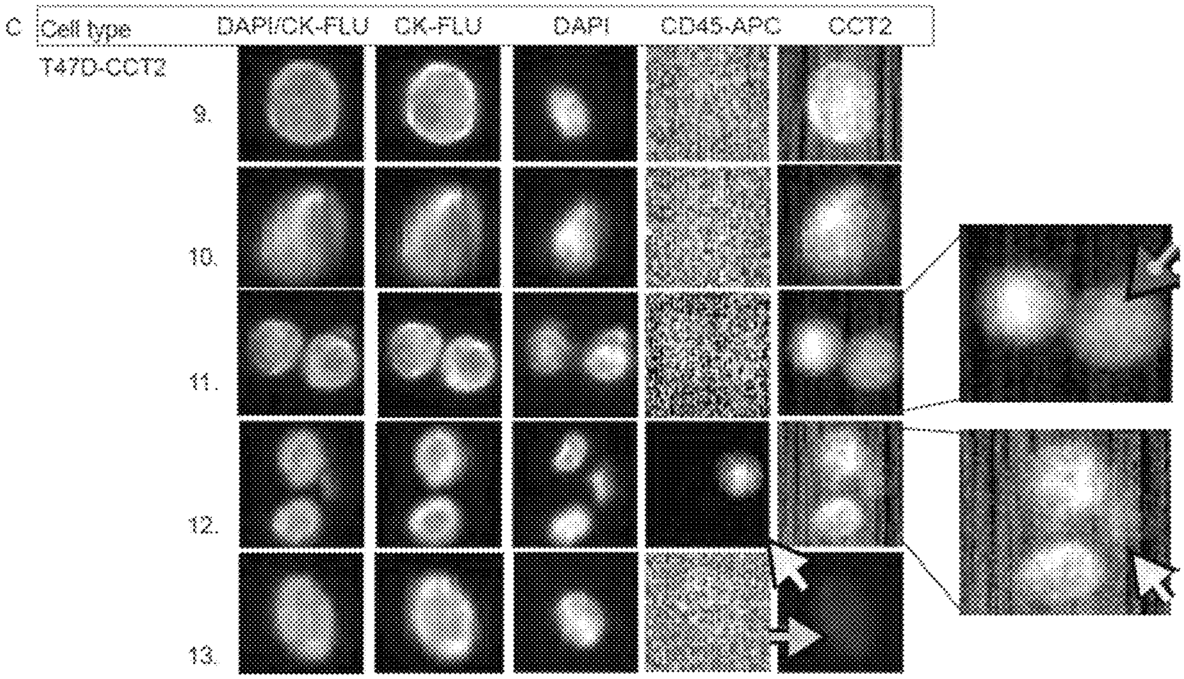

Detection of $CCT2^{hi}$ breast tumor cells spiked in blood. To investigate how CCT2 staining impacts CTC visualization, a known number of cancer cells were spiked into a vial of freshly collected blood from healthy individuals. This method helped evaluate and validate the CTC detection protocol that incorporates the CCT2 signal under conditions that are controlled but also similar to the conditions encountered during patient blood processing. 1,000 cells from either the MDA-MB-231 or the T47D-CCT2 cell lines were spiked into 10 mL of healthy human blood. The standard FDA-approved protocol for CTC detection uses the CSS CTC kit in which the signal for CK is read in the PE channel. Because this study wanted to do a comparative analysis of PE channels, the CSS CXC kit was used in which the PE channel is available for customization of the CCT2 signal and CK is read in the FITC channel. A representative page from the CSS Analyzer II readout is shown in FIG. 25. Images were sorted and selected for spiked cancer cells by the operator according to the CXC kit definition for CTCs and additionally, the cells were selected for a $CCT2^{hi}$ signal in the PE channel. Select images of cells are shown in FIG. 26. CXC classification for CTCs includes 1) a DAPI positive signal, 2) a CK-FITC positive signal that overlaps with 50% of the DAPI signal, and 3) a negative CD45 signal. Normal healthy human blood does not contain CTCs and therefore the machine picks up random signals of CK and DAPI that are near to each other. Examples of this are seen in FIG. 26A, rows 1 and 2. It is also common to see leukocytes that are CK positive as seen in row 3. None of these cells in rows 1-3 are CTCs, based on the CXC kit definition. For this study, 1,000 cells from either the MDA-MB-231 or the T47D-CCT2 cell lines were spiked into 10 mL of healthy human blood. An operator then sorted through the CSS Analyzer II events to select spiked cancer cells based on 1) CTC criteria from the CXC kit and 2) positive signal in the PE channel (column five), which was for CCT2 antibody staining intensity as described in the methods. FIGS. 26A and 26B, show that CCT2 was detected in MDA-MB-231 and T47D-CCT2 cells with minimal background inference in the column five. Rows 4, 5, 9, and 10 show typical spiked cancer cells that were CK positive and CCT2 positive. Rows 6 and 7 show examples of spiked cancer cells that were CK dim, as indicated by the red arrows, but were CCT2 positive and CD45 negative. These non-leukocytic cells would have been missed by the classical definition for CTC. Images in FIG. 26 also showed that spiked cancer cells have variations in CCT2 staining intensity. This is seen by the doublet in row 11, where the blue arrow points to a cell with a slightly lower CCT2 intensity than its partner in the same frame and by the cell in row 13 which has dim CCT2 staining, as shown by the grey arrow. The doublet finding is especially significant since it demonstrates that variations in the CCT staining intensity (dim vs bright) are detectable in the CSS or other similar CTC detection systems. Finally, it is important to note that while some leukocytes are CCT2 positive (light blue arrow in row 3), this is not always the case (yellow arrows in rows 8 and 12). Furthermore, leukocytes are ruled out as cancer cells due to positive CD45 signal.

Figure 27:
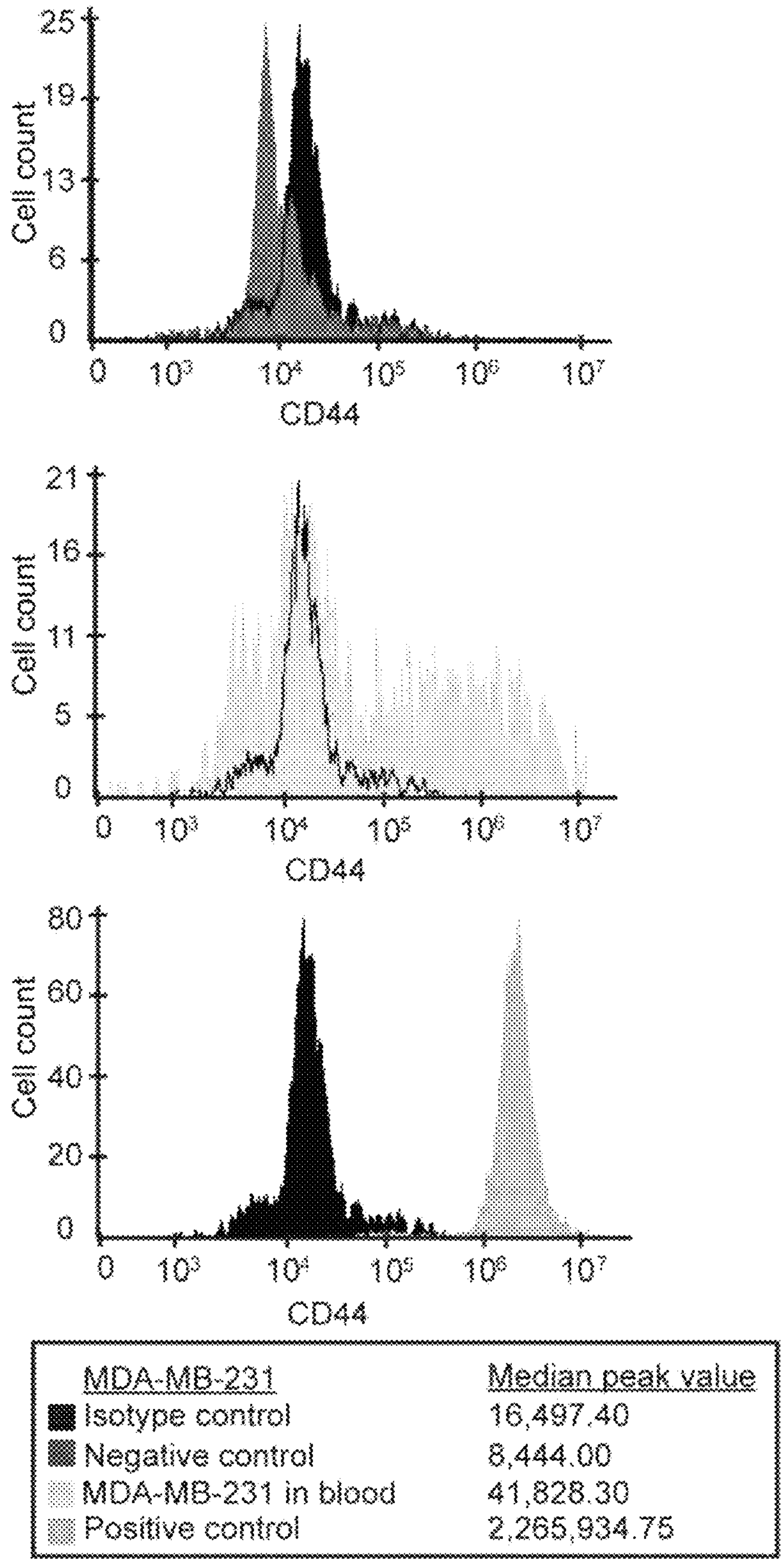
FIG. 27 shows that recovered breast cancer cells that are CK'° and CCT2$^{hi}$ also express CD44. MDA-MB-231 cells recovered from the spike in blood were stained and measured for CD44 expression in CCT2$^{hi}$ cells. Alexa-405 served as the isotype control (black). The top panel shows the negative control which was healthy blood cells only stained for CD44 (dark green). The middle panel shows the CCT2$^{hi}$ spiked cancer cells stained for CD44 (yellow). The bottom panel shows the positive control which was MDA-MB-231 cells (not spiked in blood) stained for CD44 (light green)

The goal of the CTC enumeration equipment is to determine if patients meet a threshold. Therefore, instead of trying to capture every CTC in the blood, the technology tends to underestimate the number of CTCs in a vial of blood. With such low thresholds of 3 or 5 CTC per 7.5 mL of blood, ways to improve recovery and detection of CTCs would be beneficial. The standard CSS CTC kit is around 81% efficient at recovering cells spiked into CSS Autoprep tubes and immediately analyzed by CSS. For this study, the CSS CXC kit was used, which is estimated to have a 10-18% lower recovery than the CSS CTC kit. The blood spiked cancer cell experiment was quantitatively evaluated after processing through the CSS. It was found that cells stored in CellSave vials for ~22 hours, resulted in about 30% of cell death. This timeframe was chosen to resemble the processing of patient blood specimens. Using the modified CTC definition for CK' and CCT2' cells described herein, the average recovery was 62% for MDA-MB-231 and 64% for T47D-CCT2 (Table 9). This shows around 92%-94% recovery when accounting for the loss of cell viability during storage overnight in the CellSave vial. Visually, the MDA-MB-231 cells showed reduced epithelial expression with multiple cells that had CK'° fluorescence. Therefore, the $CK^{lo}/CCT2^{hi}$ population of cells were analyzed and it was found that this population included 5.6% of the MDA-MB-231 cells and 1.3% of the T47D-CCT2 cells. This numerically demonstrates that CCT2 staining was beneficial for detecting cells that displayed mesenchymal features. To confirm that the $CK^{lo}$)/$CCT2^{hi}$ cells detected in this analysis were the cancer cells that were originally spiked and not a random blood cell, CD44 was stained, a marker associated with MDA-MB-231 cells. Flow cytometry results showed that the recovered $CK^{lo}/CCT2^{hi}$ cells also expressed CD44, FIG. 27. These CD44 positive cells were absent in the blood-alone control lacking MDA-MB-231 cells, confirming the results from the CSS Analyzer II where the CCT2 stain was used to detect spiked cancer cells.

Figure 35:
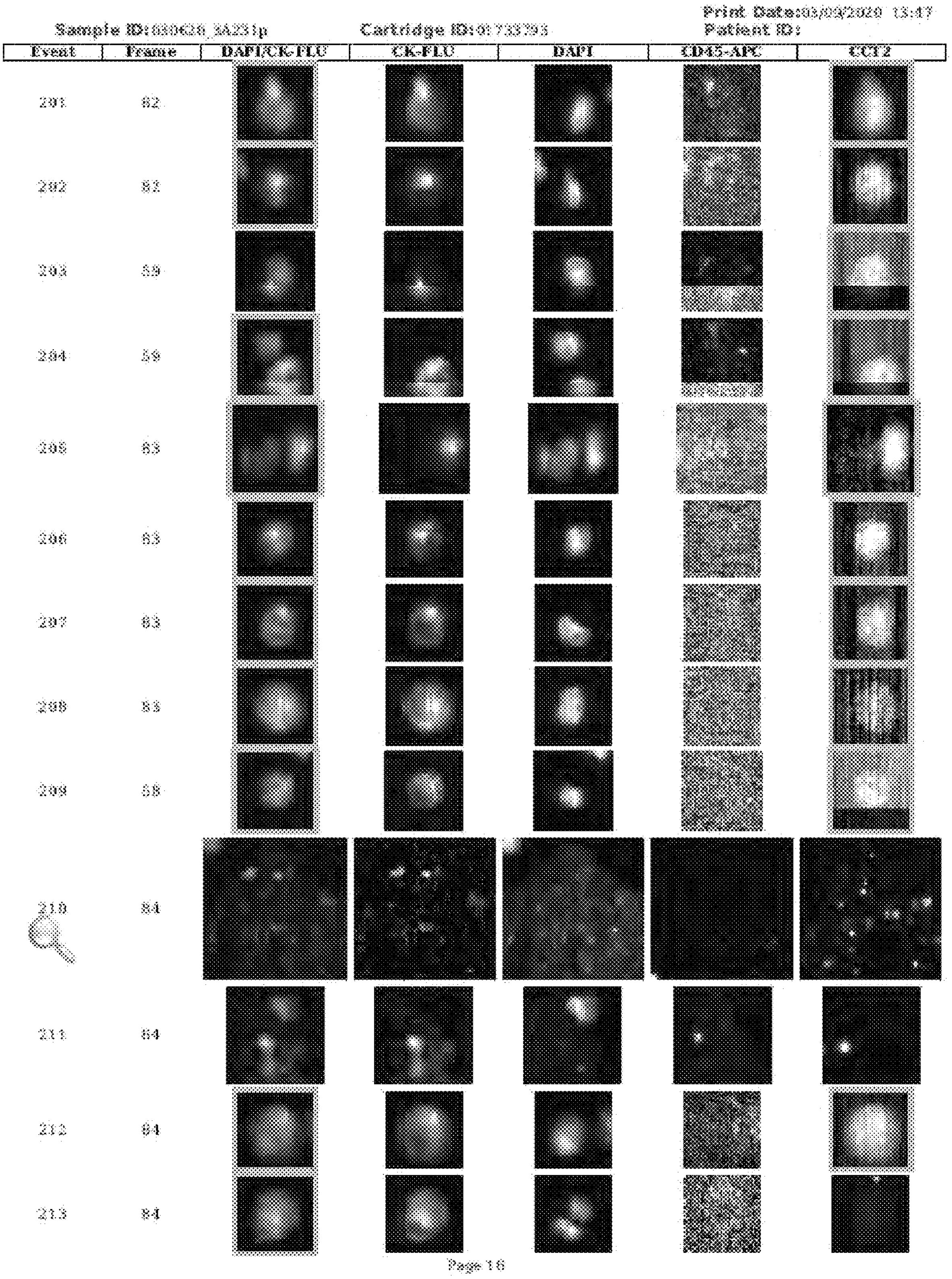
FIG. 35 shows representative page from CellSearch (CSS) Analyzer II showing events from the MDA-MB-231 cell spike into blood that need to be examined by an operator. The orange box indicates an event that was selected by the operator as a spiked cancer cell or $CCT2^{hi}$ cell. Column one: overlay of columns two and three. Column two: CK-FITC signal. Column three: DAPI signal. Column four: CD45-APC signal. Column five/"extra channel". This column was used to stain for anti-CCT2-PE. The experiment was completed in duplicate.
Figures 36A, 36B, 36C:
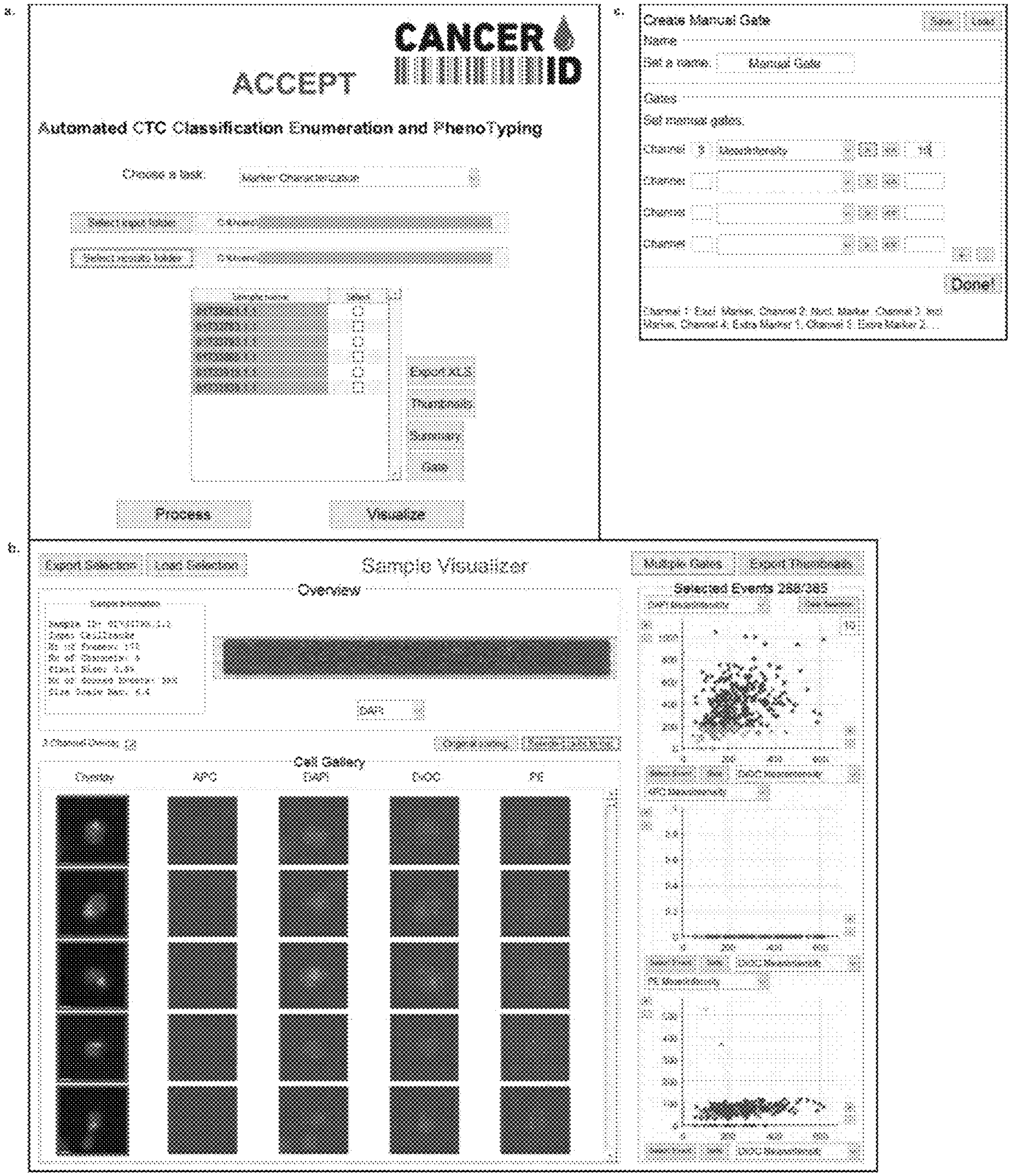
FIGS. 36*a*-36*c* show representative images showing the process of moving data from CellSearch® System (CSS) Analyzer II into ACCEPT (Automated CTC Classification Enumeration and PhenoTyping) software.

CTC detection can involve the automation of specimen analysis to minimize operator error. An open software program called ACCEPT was developed to start the process of automating CTC selection. To determine if CCT2 staining can be applied to this technology, the CSS Analyzer II image files (FIG. 26 and FIG. 35) from the spiked blood experiment were run in the ACCEPT program, FIG. 36. ACCEPT has several different ways to analyze the images, with the two most common modes being MC and FD. MC mode has the program re-analyze the CTCs the operator has selected and quantifies the intensities for each stain in each cell. The FD mode is similar but rescans the entire sample to create its own "cell-events". While FD mode can be ideal for a fully automated process, this mode is still limited in recognizing CTC on its own since the computer focuses on the intensity of the signal instead of considering cell structure and shape. The present study circumvented this problem by using the MC mode. With the computer focused on the spiked cancer cells selected by the operator, thresholds were created that allowed the computer to confirm these cells as $CK^{hi}$ or $CCT2^{hi}$, replicating a version of an automated process, FIGS. 36*b* and 36*c*. The results are shown in Table 10. 97% of MDA-MB-231 and 91% of T47D-CCT2 were $CK^{hi}$. Based on the CCT2 staining detected, an average of 89% of MDA-MB-231 and 81% T47D-CCT2 cells were $CCT2^{hi}$, demonstrating CCT2 can be used in this automated system. Additionally, the CCT2 signal in blood samples lacking spiked cells (negative control) was examined and minimal expression was found. These results with ACCEPT demonstrate that CCT2 can be a discriminating biomarker between cancer cells and blood cells and that CCT2 could be used as a marker in automated software for CTC identification.

Figures 28A, 28B, 28C, 28D, 28E, 28F:
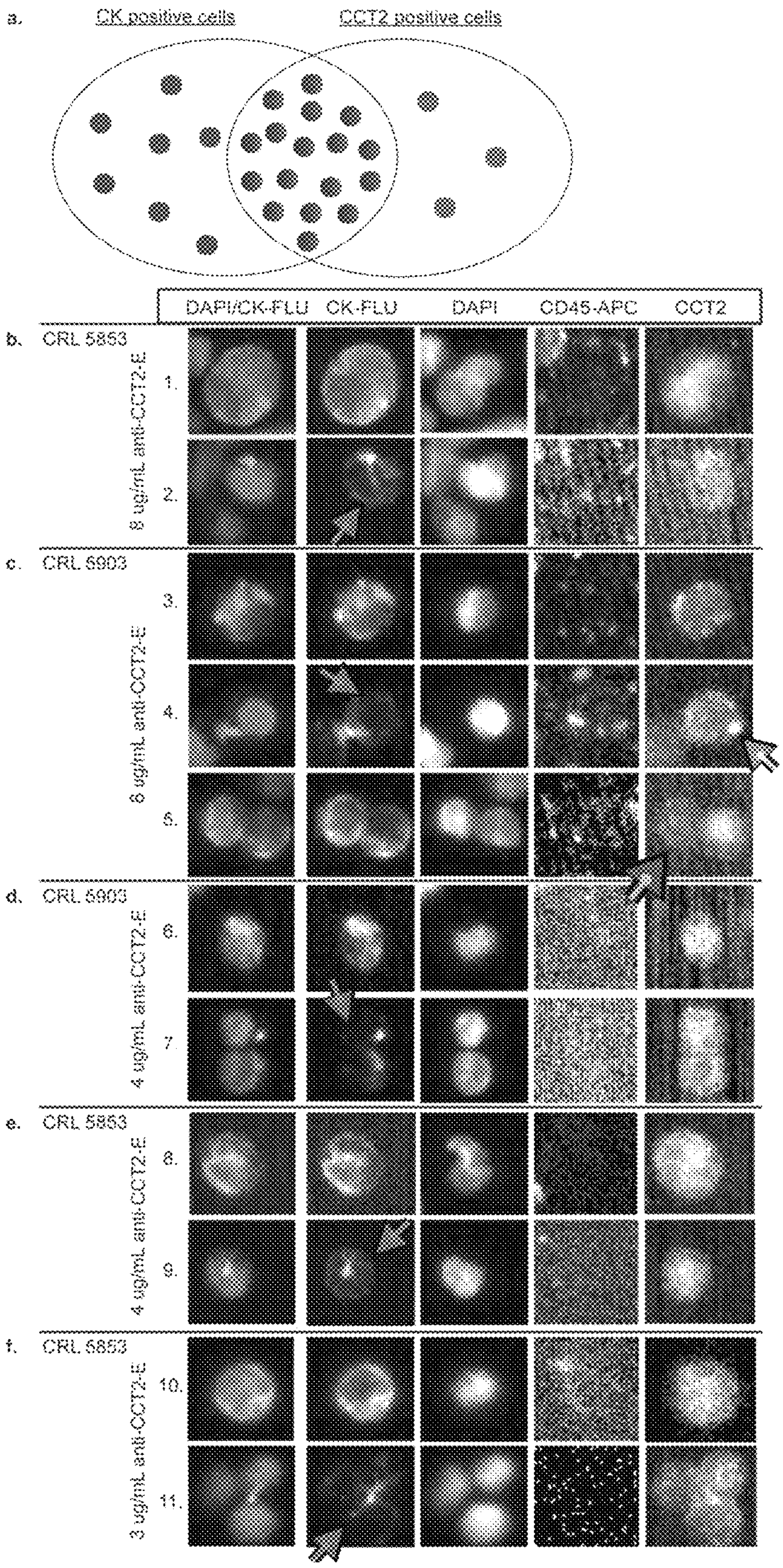
FIGS. 28*a*-28*f* show cancer cell populations and CCT2 staining in lung cancer cell lines. (a) Venn diagram showing theoretical CK$^{hi}$/CCT2$^{lo}$, CK$^{hi}$/CCT2$^{hi}$, and CK$^{lo}$/CCT2$^{hi}$ cancer cell populations. (b-c) Representative images from CellSearch Analyzer II showing small cell carcinoma cell lines recovered from being spiked in healthy human blood and stained with 8 ug/mL of anti-CCT2-PE (b) CRL 5853 and (c) CRL 5903. Red arrows: cells that are CK'° and CCT2$^{hi}$. Green arrows: cells with punctate staining for CCT2. Blue arrows: doublet of spiked cancer cells with different CCT2 staining intensities. The experiment was completed in duplicate. (d-f) Representative images of lung cancer cells (d) CRL 5903 and (e-f) CRL 5853, stained with 4 μg/mL of CCT2 antibody or 3 μg/mL of CCT2 antibody, as indicated. Red arrows: cells with $CK^{lo}$ and $CCT2^{hi}$ expression
Figures 29A, 29B, 29C, 29D:
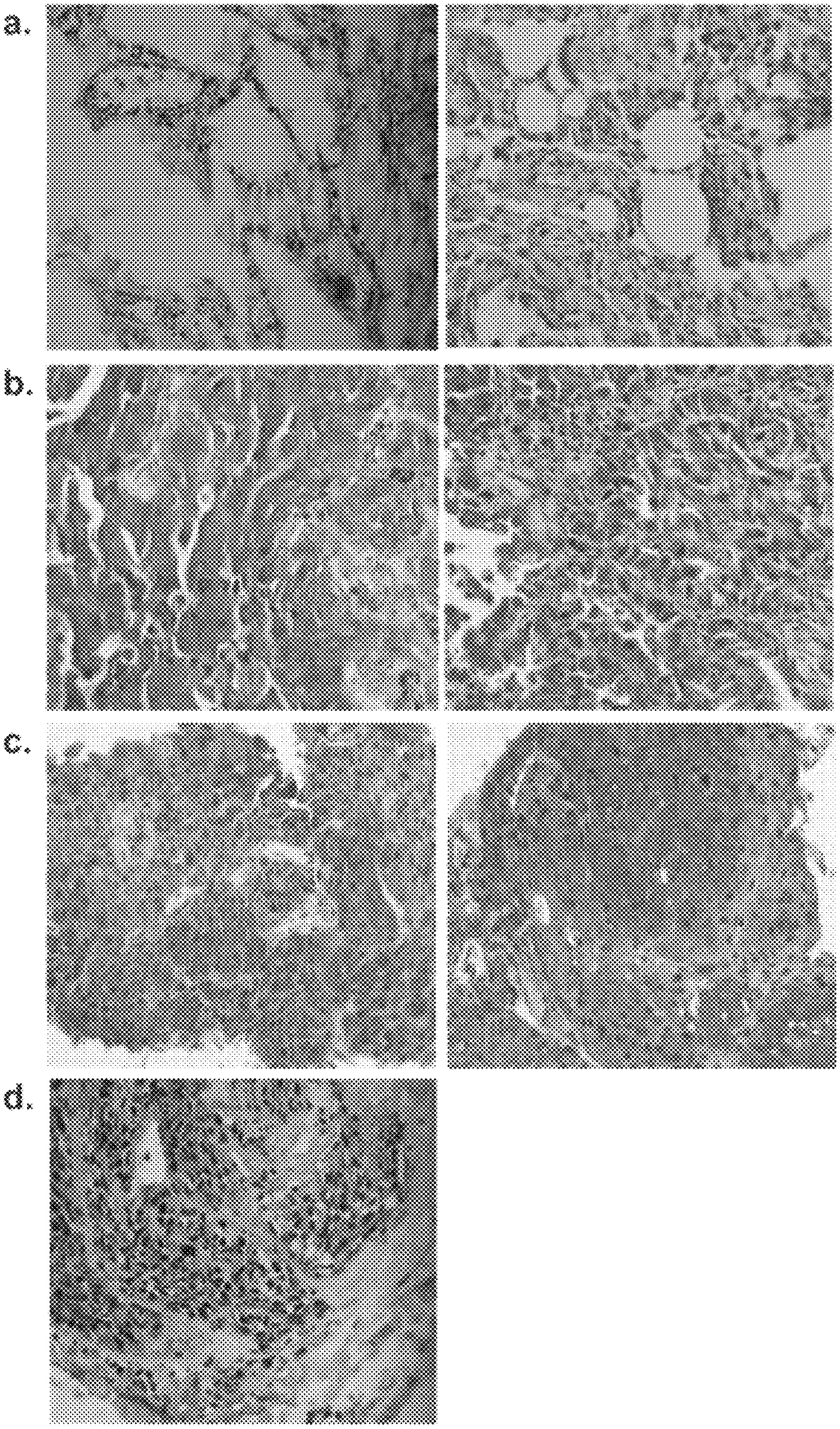
FIGS. 29*a*-29*d* show histological staining of normal lung tissue vs cancerous lung tissue for CCT2.

Applications for CCT2 staining when CTC detection is challenging. Using the modified CTC definition, the data provided herein revealed three cancer cell populations; $CK^{hi}/CCT2^{lo}$; $CK^{hi}/CCT2^{hi}$; $CK^{lo}/CCT2^{hi}$ as shown in the Venn diagram in FIG. 28*a*. Current CTC detection methods recover cells from the first two populations and have found prognostic clinical significance in CTC counts above certain thresholds. The bioinformatics and histological data support that the third population of cells ($CK^{lo}$)/$CCT2^{hi}$) can have similar clinical significance, due to CCT2's association with metastatic tissue and patient OS. While this population is small, it can help establish CTC thresholds in cancers beyond the three approved by CSS enumeration (breast, prostate, and colon). In particular, cancers with more mesenchymal characteristics, like lung cancer, have had more difficulty in establishing CTC prognostic thresholds. To determine if CCT2 staining can be used to assist with CTC detection in cancers like lung cancer, CRL5853 and CRL5903 small cell carcinoma cell lines were spiked into healthy blood and CCT2 staining was performed in the CSS platform. Select images representing different recovered spiked cancer cells are shown in FIGS. 28*b* and 28*c*. Both cell lines showed positive CCT2 staining with similar trends to what was seen in breast cancer. Typical spiked cancer cells that were both $CK^{hi}$ and $CCT2^{hi}$ are seen in rows 1, 3, and 5. Red arrows designate $CK^{lo}/CCT2^{hi}$ spiked cancer cells in rows 2 and 4. A cell with punctate CCT2$^{hi}$ staining is shown in row 4 (green arrow) and a doublet of cells with different staining intensities for CCT2 is L shown in row 5 (blue arrow). lower CCT2 antibody concentrations were also tested in the spiked lung cancer cells and still saw strong staining, FIGS. 28*d*, 28*e*, and 28*f* Most notably, several cells were CK'$^{o}$ or had CK that was blocked by DAPI staining while remaining CCT2$^{hi}$ (rows 7, 9, and 11). One population that has an increased risk of being underdiagnosed for lung cancer is the African American population. To determine if this population can benefit from a CCT2-based diagnostic as described herein, lung tumor tissue for CCT2 from African Americans that had both smoking and non-smoking status was stained and was compared to normal lung tissues. These samples included one patient with small cell carcinoma, three patients with adenocarcinoma, two patients with squamous cell carcinoma, and two patients with normal lung tissue. Additional patient information is listed in Table 15. Results were minimal CCT2 staining in normal lung tissue (FIG. 29*a*) and a positive CCT2 stain for all cancerous tissues, FIG. 29*b*. These data indicate that CCT2 staining for detection of CTCs can be applicable for lung cancer diagnostics and can address issues with health disparity in lung cancer by providing a parameter to detect CTCs that are missed or CK'$^{o}$ and would not have been counted with current liquid biopsy technology.

Figures 37A, 37B:
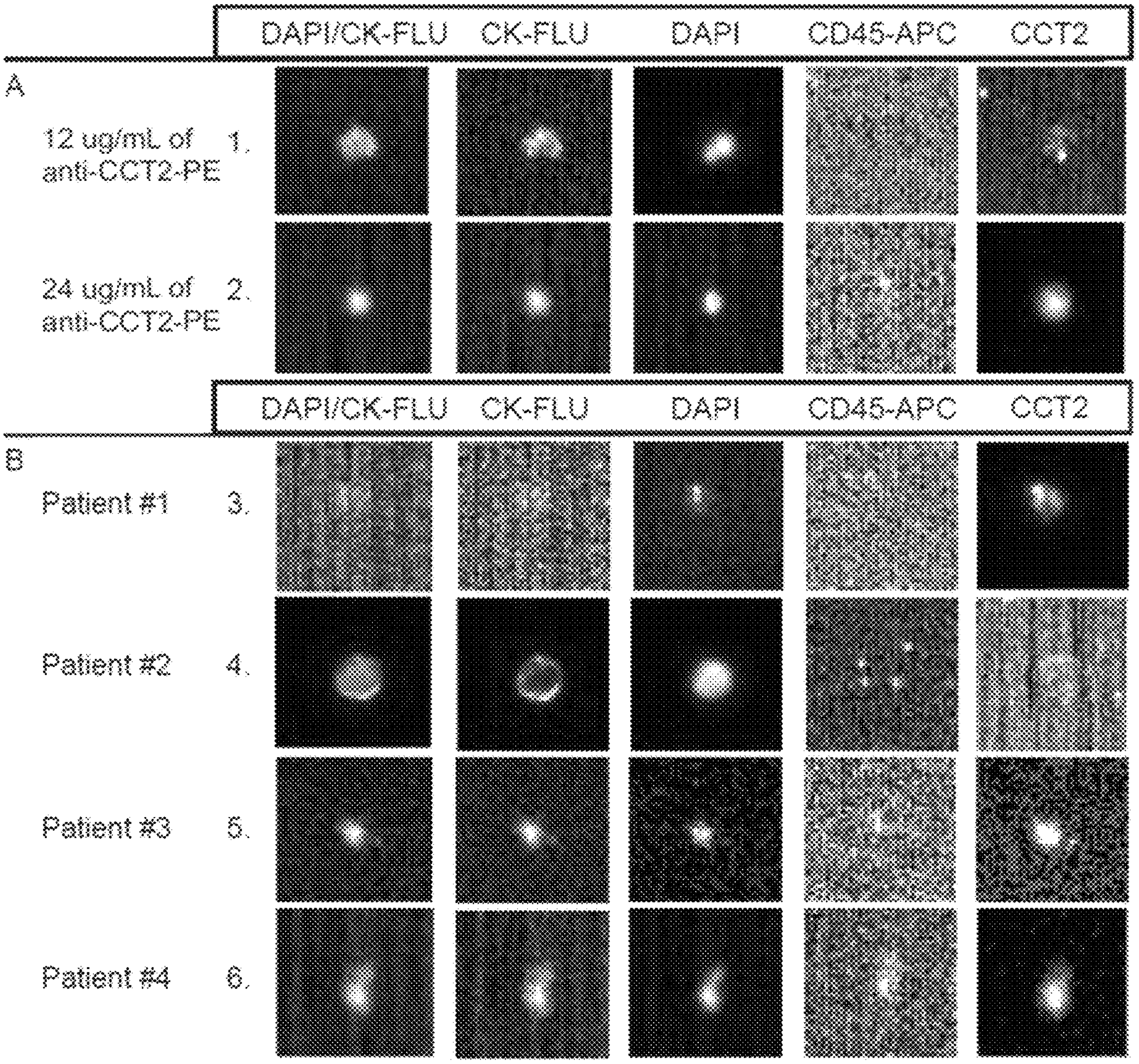
FIGS. 37A-37C show representative images from SCLC CTCs stained for CCT2.
Figure 37C:
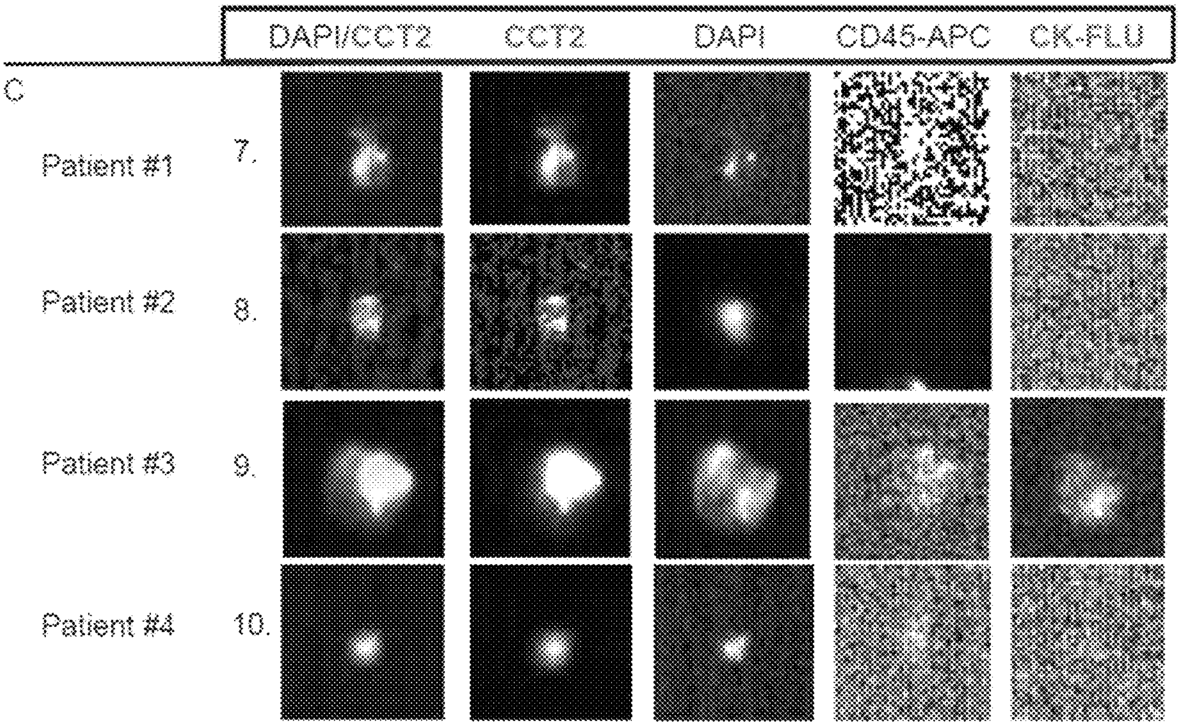

CCT2 staining of CTC tested with blood from SCLC patients. Having shown that CCT2 staining works in a standard CTC detection protocol using cancer cells spiked into blood, this study performed a small pilot study using blood from SCLC patients to determine if CCT2 staining could detect CTCs released into blood in these patients. This study chose SCLC, since such patients typically have greater number of CTCs compared to other cancer types. The results confirm that CCT2 staining can be observed in CTCs detected in SCLC patient blood and that a range of detection is possible based on the saturating amounts on anti-CCT2 antibody used, FIG. 37A. Three patterns of CCT2 staining of CTCs were noted. In patient 1, no CTCs based on standard criteria (>50% overlap of DAPI and CK staining, while CD45 negative) were noted, but dim CCT2 staining in some cells was observed; in patient 2, numerous CTCs were found that had dim or negative CCT2 staining; and patients 3 and 4, most CTCs detected were both CK positive and CCT2 positive, FIG. 37B. To determine whether CCT2 could be used to detect CTCs in place of CK, we used a different algorithm for analysis of CTC from the CSS analyzer, based on a >50% overlap of DAPI and CCT2, while CD45 negative. This study detected any more CTCs that were CCT2 positive and CK negative in all four patient samples, FIG. 37C. These results indicate that the use of CCT2 as a marker for CTCs is feasible with the current CTC technology, as exemplified by the CSS, and that in cancers like SCLC, could provide an additional discriminatory marker to improve enumeration as well as provide biological data that could be relevant to the invasive nature of the CTCs being detected.

3. Example 6. Summary

This study shows that CCT2 expression is increased in primary cancer and metastatic tissue compared to normal tissue, and this is inversely correlated with patient OS. CCT2 protein levels were minimal in normal breast and lung tissues and increased in cancerous tissue. Meanwhile, in an MBC patient cohort, CCT2$^{hi}$ tumor scores correlated inversely with active disease. The addition of CCT2 staining to the CSS led to improved recovery of breast cancer cells spiked into blood, including those with mesenchymal features, providing visual differences that could help classify CTCs. This was most notable in spiked cancer cells with CK$^{lo}$ and CCT2$^{hi}$ expression, as was also seen in the spiked lung cancer cells. CCT2 staining was also applicable for use in the automated ACCEPT program, which can advance emerging technologies that can exploit variations in CCT2 stain intensity of CTCs. Optimization of CCT2 staining for clinical use can further improve this sensitivity and provide the details that help explain how the localization of CCT2 staining (cytosolic vs nuclear) can be involved in promoting the generation of metastatic producing CTCs. The CK$^{lo}$/CCT2$^{hi}$ cell population is of interest since it can provide information on tumor progression that has implications for patient stratification. Correlations of CCT2$^{hi}$ CTCs with patient outcomes can help determine the significance of these CTCs and provide actionable diagnostic information to physicians.

Chaperones are evolutionarily conserved and central components of multiple biological processes, potentially making these informative markers during oncogenesis. In current diagnostic applications for cancer, serum protein levels of chaperones like HSP27, HSP70, or HSP90 are used. However, the serum levels of HSPs are nonspecific as these chaperones are known to increase in several diseases. Unlike tissue biopsy, liquid biopsy provides a minimally invasive option to evaluate chaperone expression in tumor cells. One study that used chaperones for the enrichment of CTCs is Breuninger et al. In this study they used an antibody against membrane HSP70 (mHSP70) to enrich for CTCs in head and neck cancer or lung cancer patients. This study examined mHSP70 in several cancer cell lines (breast, lung, melanoma, pancreas, brain, colon, etc.) and found that it was consistently expressed post-EMT while EpCAM was decreased. Then in a small cohort of cancer patients with head and neck cancer or lung cancer, they tested CTC collection from blood with mHSP70 enrichment vs EpCAM enrichment and found that mHSP70 increased CTC collection. Since then, a clinical trial has been recruiting patients with various metastatic cancers to measure CTC levels when enriched with mHSP70 vs EpCAM (NCT04628806).

Another type of liquid biopsy involves detecting extracellular vesicles (EVs). In a recent review that discussed extracellular HSP and cancer, it was noted that although several studies had characterized the proteome of EVs through mass spectrum (MS) analysis, none of these studies had specifically examined the HSP expression profiles. Therefore, MS data of EVs were retrospectively evaluated from studies that had clinical cancer patient samples to measure the expression of HSP and their co-chaperones in the EVs. It was found that the HSP profiles varied depending upon cancer type and the type of fluid the EVs were collected from (urine, plasma, lymphatic, etc.). This study concluded by remarking that EVs from urine and NK cells can provide sources for identifying cancer-specific biomarkers if coupled with machine learning statistics to determine the patterns of HSP expression in different cancers as well as in healthy patients.

While most CTC enrichment technologies focus on either physical or biological properties, staining for CCT2 to identify CTCs can have a wide application that is particularly beneficial for tumor heterogeneity. In study shown herein, the CSS platform was used as a starting point to evaluate CCT2 as a marker for CTCs because it is an FDA-approved CTC enumeration technique whose use can advance clinical applications. The CSS employs EpCAM-based isolation methods, and therefore CSS can miss EpCAM negative CTCs as these undergo EMT. CSS addresses this concern with a capture enhancement reagent that enables controlled EpCAM-ferrofluid nanoparticle aggregation so that even cells with low EpCAM levels are recovered. Additionally, some studies found no correlation between CTCs with low EpCAM expression and patient OS. Nevertheless, it is a limitation in the study described herein that any EpCAM negative and $CCT2^{hi}$ cells potentially could have been missed. Post-CTC enrichment, CSS uses the epithelial marker CK for staining and CTC visualization. The bioinformatics data provided herein shows that CK levels are low in metastatic tissue, which indicates that using CK for CTC discrimination can overlook more invasive-prone CTCs. Additionally, studies show that while CK 8, 18, and 19 are present in luminal breast cancers, basal breast cancers have a stronger correlation with CK 5, 6, and 14. Researchers have started addressing this concern by adapting CSS with additional antibody markers, including vimentin, HER2, and CD44, among others. The following summarizes the outcome of such experiments.

Vimentin: Pro—it is a mesenchymal marker. A study showed increased recovery of CTCs for prostate cancer patients using cell-surface vimentin. Con—it is present on leukocytes and other mesenchymal cells making it difficult to isolate from other blood cells. It is important to note that there is a difference between intracellular vimentin and extracellular vimentin and that these have different functions. Membrane expression of vimentin is increased in some tumor cells, although most cancer research has focused on the intracellular functions of vimentin. Clarifying the differences between intracellular and extracellular forms will be important for determining the significance of increases, and their roles in pathogenesis because of the multiple interactions with other cells that vimentin can be involved in.

HER2: Pro—it is an established breast cancer marker and tied to treatment options. Con—heterogeneous tumors can result in a mix of CTCs that are $HER2^{hi}$ and $HER2^{lo}$. Additionally, it is mainly found in breast cancer and not in other cancers.

CD44: Pro—it is a cancer stem cell marker, and it is expressed in multiple cancer types. Con—it is an extracellular marker, and it has a role in hematopoiesis where the loss of function in mice led to abnormalities in bone-marrow colonization and migration of lymphocytes.

Research on these markers for in vitro diagnostic (IVD) has been ongoing since 2006, but none of these have been approved for clinical use. It is important to note that most of the markers studied are proteins expressed on the cell membrane, which is fluid and can results in variable expression of membrane proteins due to receptor internalization. In contrast, CCT2 is an intracellular protein that is not subject to the variability of plasma membrane protein detection. CCT2 has the added benefit of increased expression in multiple cancers giving it a potentially broader application. CCT2 expression does not correlate with ER or PR status and therefore can be used with different types of breast cancer including TNBC. This demonstrates that CCT2 as a biomarker can bring a unique solution to the problem of tumor heterogeneity.

The study herein demonstrates that chaperones have novel applications in liquid biopsy for cancer diagnostics. A specific area of research benefit from chaperone-based liquid biopsy methods is clinical drug trials. While clinical trials testing HSP90 inhibitors like Ganetespib (STA-9090) and Onalespib (AT13387) or HSP27 inhibitors like Apatorsen (OGX-427) have achieved varying degrees of success, there has yet to be one that demonstrated sustained clinical efficacy. Researchers in such studies concluded that future research directions should focus on "establishing predictors of response" and "pharmacodynamic markers of anticancer activity" specific to these types of drugs. Assessing for $CCT2^{hi}$ CTCs can advance these drug studies by 1) Adding a minimally invasive outcome, amenable to frequently sampling, to measure disease status and progression related to trial therapies 2) Stratifying patients that can receive the most benefit from novel treatment such as chaperone inhibitors and 3) Improve the number of recovered of CTCs in studies that do use CTC analysis. Most clinical trials use common endpoints such as OS or progression free survival (PFS) or the RECIST criteria of complete response, partial response, or stable disease. Often this involves monitoring the disease status through radiologic imaging, which exposes patients to radiation. For example, one study tested the use of Apatorsen in pancreatic cancer patients and concluded that although the drug did not show improvement in OS and PFS from RECIST criteria, there was a trend of increased PFS and OS in patients that had high baseline serum HSP27, indicating possible subgroup benefits. This study can have benefited from an outcome measure like CCT2-based CTC analysis that can enable frequent monitoring and additional time points (4 weeks) without radiation exposure and be directly correlated to disease response to treatments targeting chaperones. Similarly, when Apatorsen was tested in non-squamous-NSCLC, PFS showed an increase from 6.0 months to 4.9 months but was not statistically significant. When the patients were grouped into high (>9.3 ng/mL) baseline serum levels of HSP27, patients that received OGX-427 had a median PFS of 10.8 months compared to 4.8 months in the patients that received the placebo. This data demonstrates that determining which patients have high expression of HSP27 helped with the study design to optimize outcomes. The presented findings on developing a CTC detection protocol by incorporating identification of $CCT2^{hi}$ shed tumor cells align with these needs to improve patient stratification and clinical trials assessments. With further optimization, the use of CCT2 as a parameter for detection of CTCs in liquid biopsy can lead to new patient monitoring regimes for cancers, like lung cancer, that can benefit from frequent diagnostic sampling and demonstrates how molecular chaperones like CCT are adept and viable targets for therapeutic and diagnostic development in cancer.

TABLE 6

List of metastatic breast cancer (MCB) patients with their circulating tumor cells (CTCs) count in blood, the intensity of CCT2 staining in their tumor tissue, receptor status, and time gap information. A 38 MBC patient cohort was assessed for CTCs in blood and CCT2 staining was scored from tumor tissue biopsies. Samples 005, 007, 009, and 010 failed the screening. Samples 001, 002, 003, 004, 011, 015, 016, 022, 024, 026, and 029 were inadequate for either CTC processing or CCT2 staining. Grey highlights indicate patient specimens with five years or more time gap. The "time gap" is defined as the number of years between blood draw and a patient's tumor biopsy. Abbreviations: NG, information not given. Y, yes. N, no.

| Patient Number | Number of CTCs in Blood | CCT2 Score: Low (1-2), High (3-4) | ER Status | PR Status | HER2 Status | Patient Age | Number of yrs. since biopsy "Time Gap" | Number of yrs. since metastatic diagnosis |
|---|---|---|---|---|---|---|---|---|
| 20 | 1 | High | Y | N | N | 61 | 0 | 0 |
| 8 | 2 | Low | Y | Y | N | 75 | 1 | 1 |
| 12 | >5 | Low | N | N | N | 69 | 1 | 1 |
| 13 | 5 | High | Y | N | N | 71 | 1 | 11 |
| 27 | 1 | High | Y | Y | N | 48 | 1 | 1 |
| 32 | 0 | High | Y | Y | N | 51 | 1 | 1 |
| 36 | 2 | Low | N | N | Y | 40 | 1 | 1 |
| 37 | 4 | High | Y | Y | N | 57 | 1 | 0 |
| 38 | 0 | High | Y | Y | N | 70 | 1 | 1 |
| 34 | >5 | High | Y | Y | N | 62 | 2 | 1 |
| 14 | 2 | Low | N | N | N | 63 | 3 | 3 |
| 21 | 0 | Low | Y | Y | N | 57 | 3 | 3 |
| 30 | 0 | Low | Y | Y | N | 80 | 3 | 3 |
| 31 | 0 | Low | N | N | Y | 69 | 3 | 3 |
| 33 | 2 | High | Y | Y | N | 53 | 3 | 1 |
| 17 | 1 | Low | Y | Y | N | 55 | 4 | 0 |
| 19 | 1 | High | Y | Y | N | 68 | 4 | 4 |
| 23 | 4 | Low | Y | Y | N | 66 | 4 | 4 |
| 35 | 1 | Low | Y | Y | N | 50 | 5 | 0 |
| 25 | 0 | Low | NG | NG | NG | 64 | 7 | 1 |
| 18 | 1 | Low | Y | Y | N | 55 | 8 | 3 |
| 28 | 3 | Low | Y | N | Y | 33 | 9 | 4 |
| 6 | 0 | Low | Y | N | Y | 70 | 10 | 4 |

TABLE 7

Summary of Spearman correlation statistical analysis of metastatic breast cancer patients' CCT2 tumor score, circulating tumor cell (CTC) count, and time gap.

| | CTC | CCT2 tumor stain Score |
|---|---|---|
| CCT2 Tumor stain Score | 0.138(p = 0.531) | NA |
| Time gap | −0.232(p = 0.287) | −0.545(p = 0.007) |

TABLE 8

Multiple linear regression statistical analysis of metastatic breast cancer patients' CCT2 tumor stain score, (circulating tumor cell) CTC count, ER, PR, HER2, age, and time gap.

| | Coefficient | SE | 95% C.I. (low) | 95% C.I. (high) | P-value |
|---|---|---|---|---|---|
| CTC | 0.005 | 0.251 | −0.530 | 0.539 | 0.986 |
| CCT2 | −3.063 | 1.026 | −5.251 | −0.876 | 0.009 |
| ER | 4.505 | 1.524 | 1.256 | 7.753 | 0.010 |
| PR | −0.669 | 1.462 | −3.784 | 2.447 | 0.654 |

TABLE 8-continued

Multiple linear regression statistical analysis of metastatic breast cancer patients' CCT2 tumor stain score, (circulating tumor cell) CTC count, ER, PR, HER2, age, and time gap.

| | Coefficient | SE | 95% C.I. (low) | 95% C.I. (high) | P-value |
|---|---|---|---|---|---|
| HER2 | 2.734 | 1.734 | −0.963 | 6.430 | 0.136 |
| Age | −0.019 | 0.042 | −0.108 | 0.070 | 0.657 |

TABLE 9

Recovery of breast cancer cells spiked in blood and analyzed with the CellSearch Analyzer II.

| | PERCENT FROM CELL SPIKE: (1,000 CELLS/10 mL blood) | |
|---|---|---|
| Cell Type | CKhi cells | CKhi and CCT2hi cells |
| MDA-MB-231 | 58.60% | 62.10% |
| T47D-CCT2 | 63.10% | 64.00% |
| | PERCENT FROM TOTAL CELL COUNT: CTC AND (CKlo/CCT2hi) | |
| Cell Type | CKhi/CCT2lo cells | CKlo/CCT2hi cells |
| MDA-MB-231 | 7.61% | 5.62% |
| T47D-CCT2 | 14.66% | 1.28% |

TABLE 10

Recovery of breast cancer cells spiked in blood analyzed with ACCEPT (Automated CTC Classification Enumeration and PhenoTyping) software.

| | MARKER CHARACTERIZATION PERCENT OF SELECTED CELLS WITH STAIN FOR: | |
|---|---|---|
| Cell Type | High DiOC (CKhi) | High PE (CCT2hi) |
| Control 1 (no cells) | 0% | 0% |
| Control 2 (no cells, plus antibody) | 0.5% | 0.5% |
| MDA-MB-231 | 97.26% | 88.95% |
| T47D-CCT2 | 91.16% | 81.39% |

TABLE 11

Primer sequences for a reverse transcription-polymerase chain reaction

| Primer Name | Sequence 5' to 3' |
|---|---|
| TWIST Forward | GGAGTCCGCAGTCTTACGAG (SEQ ID NO: 10) |
| TWIST Reverse | TCTGGAGGACCTGGTAGAGG (SEQ ID NO: 11) |
| SNAIL Forward | TCGGAAGCCTAACTACAGCGA (SEQ ID NO: 12) |
| SNAIL Reverse | AGATGAGCATTGGCAGCGAG (SEQ ID NO: 13) |
| Vimentin Forward | GTGAATCCAGATTAGTTTCCCTCA (SEQ ID NO: 14) |
| Vimentin Reverse | CAAGACCTGCTCAATGTTAAG (SEQ ID NO: 15) |
| E-Cadherin Forward | GTCTGTCATGGAAGGTGCTC (SEQ ID NO: 16) |
| E-Cadherin Reverse | CTGAGGATGGTGTAAGCGATG (SEQ ID NO: 17) |
| N-Cadherin Forward | GTTTGCCAGTGACTCCA (SEQ ID NO: 18) |
| N-Cadherin Reverse | CATACCACAAACATCAGCACAAG (SEQ ID NO: 19) |

TABLE 11-continued

Primer sequences for a reverse transcription-polymerase chain reaction

| Primer Name | Sequence 5' to 3' |
|---|---|
| EpCAM Forward | TGTTGCTGGAATTGTTGTGC (SEQ ID NO: 20) |
| EpCAM Reverse | CCTATGCATCTCACCCATCTC (SEQ ID NO: 21) |
| GAPDH Forward | GAAGGTGAAGGTCGGAGTCAAC (SEQ ID NO: 22) |
| GAPDH Reverse | TGGAAGATGGTGATGGGATTTC (SEQ ID NO: 23) |

TABLE 12

TMA core matrix IRBNet# 748165 tumor score results for CCT2 and STAT3.

| Patient # | Tumor Type | Grade | Stage | CCT Tumor Score Low (0-2) High (3-4) | STAT3 Tumor Score Low (0-2) High (3-4) |
|---|---|---|---|---|---|
| 12 | Ductal | G1 | IIB | Low | Low |
| 37 | Ductal | G2 | IA | Low | Low |
| 24 | Ductal | G2 | IIA | High | High |
| 16 | Ductal | G2 | IIA | Low | Low |
| 31 | Ductal | G2 | IIA | High | High |
| 29 | Ductal | G2 | IIA | Low | Low |
| 2 | Ductal | G2 | IIA | Low | Low |
| 9 | Ductal | G2 | IIB | High | High |
| 28 | Ductal | G3 | IA | High | High |
| 27 | Ductal | G3 | IA | High | High |
| 4 | Ductal | G3 | IA | Low | Low |
| 8 | Ductal | G3 | IIA | High | High |
| 15 | Ductal | G3 | IIA | Low | Low |
| 3 | Ductal | G3 | IIB | High | High |
| 14 | Ductal | G3 | IIB | High | High |
| 33 | Ductal | G3 | IIB | Low | Low |
| 5 | Ductal | G3 | IIB | Low | Low |
| 17 | Ductal | G3 | IIB | High | Low |
| 36 | Ductal | G3 | IIIA | Low | Low |
| 22 | Tubo-lobular | G1 | IIA | Low | High |
| 40 | Lobular | G2 | IIA | High | High |
| 20 | Tubo-lobular | G2 | IIA | High | High |
| 38 | Lobular | G3 | IIA | Low | High |
| 1 | Lobular | G3 | IIA | Low | Low |

TABLE 13

UCSC Xena statistics comparing CCT2, KRT8, KRT18, and KRT19 gene expression in TCGA and GTEx samples (n = 17,722)

| Tissue Type | Mean | SD | One-way ANOVA | | Pair-wise Comparison | | Adjusted P-value |
|---|---|---|---|---|---|---|---|
| CCT2 (log2 (norm_count + 1)) | | | | | | | |
| Metastatic (Met) | 12.51 | 0.72 | F-value | 2439 | NT | PT | 0.000000034 |
| Normal Tissue (NT) | 11.51 | 0.62 | DF | (3, 17718) | NT | Met | 0.000000034 |
| Primary Tumor (PT) | 12.42 | 0.76 | P-value | <2e-16 | STN | PT | 0.000000034 |
| Solid Tissue Normal (STN) | 11.86 | 0.42 | | | STN | Met | 0.000000034 |
| KRT8 (log2 (norm_count + 1)) | | | | | | | |
| Metastatic (Met) | 8.51 | 2.78 | F-value | 1678 | NT | PT | 0.000000034 |
| Normal Tissue (NT) | 9.68 | 3.51 | DF | (3, 17718) | NT | Met | 0.000000039 |
| Primary Tumor (PT) | 13.47 | 3.87 | P-value | <2e-16 | STN | PT | 0.001090000 |
| Solid Tissue Normal (STN) | 13.99 | 2.04 | | | STN | Met | 0.000000034 |

TABLE 13-continued

UCSC Xena statistics comparing CCT2, KRT8, KRT18, and KRT19 gene expression in TCGA and GTEx samples (n = 17,722)

| Tissue Type | Mean | SD | One-way ANOVA | | Pair-wise Comparison | | Adjusted P-value |
|---|---|---|---|---|---|---|---|
| KRT18 log2 (norm_count + 1)) | | | | | | | |
| Metastatic (Met) | 9.31 | 2.62 | F-value | 2321 | NT | PT | 0.000000034 |
| Normal Tissue (NT) | 9.3 | 2.92 | DF | (3, 17718) | NT | Met | 1.000000000 |
| Primary Tumor (PT) | 13.18 | 3.32 | P-value | <2e-16 | STN | PT | 0.266000000 |
| Solid Tissue Normal (STN) | 13.4 | 1.81 | | | STN | Met | 0.000000034 |
| KRT19 log2 (norm_count + 1)) | | | | | | | |
| Metastatic (Met) | 4.19 | 3.77 | F-value | 1505 | NT | PT | 0.000000034 |
| Normal Tissue (NT) | 8.47 | 3.53 | DF | (3, 17718) | NT | Met | 0.000000034 |
| Primary Tumor (PT) | 12.16 | 4.55 | P-value | <2e-16 | STN | PT | 0.025900000 |
| Solid Tissue Normal (STN) | 12.6 | 2.51 | | | STN | Met | 0.000000034 |

TABLE 14

Metastatic breast cancer patient information from the pilot study. NG: information not given, Y: yes, N: no.

| Patient # | Dignosis summary from the pathology report | Date of initial Diagnosis | Date of first finding metastatic disease | Date of Blood Draw | Tumor biopsy sample date | Tumor tissue location | ER status | PR Status | HER2 Status | Patient Age | Treatment Status |
|---|---|---|---|---|---|---|---|---|---|---|---|
| 001 | metastatic tumor | Feb. 26, 2016 | Dec. 4, 2017 | 20 Feb. 2018 | Dec. 4, 2017 | Metastatic | NG | NG | NG | 74 | Receiving Doxorubicin (Doxil) |
| 002 | metastatic tumor | Jan. 13, 2015 | 12.21 2017 | 12 Feb. 2018 | Dec. 21, 2017 | Metastatic | NG | NG | NG | 62 | Recently completed stereotactic body radiotherapy on 09 Feb. 2018 |
| 003 | metastatic tumor | Oct. 2, 2014 | 10.02 2014 | 21 Feb. 2018 | Mar. 11, 2015 | Breast tissue | NG | NG | NG | 39 | Receiving Palbociclib (Ibrance) and Letrozole (Femara), and Denosumab (Xgeva) |
| 004 | metastatic tumor | May 1, 2010 | 06.22 2015 | 27 Feb. 2018 | Dec. 16, 2010 | Breast tissue | NG | NG | NG | 54 | Receiving Trastuzumab (Herceptin), Capecitabine (Xeloda) and Tucatinib/placebo |
| 005 | | | | | | Failed Screening | | | | | |
| 006 | Invasive Ductal Carcinoma | Aug. 8 2008 | Oct. 15, 2014 | 12 Jun. 2018 | Aug. 28, 2008 | Breast tissue | Y | N | Y | 70 | Receiving Lapatinib (Tykerb), Capecitabine (Xeloda) and Denosumab (Xgeva) |
| 007 | Failed Screening | | | | | | | | | | |
| 008 | metastatic carcinoma | Dec. 11, 2012 | Jan. 19, 2017 | 4 Dec. 2018 | Jan. 19, 2017 | Metastatic | Y | Y | N | 75 | Receiving Letrozole (Femara), Palbociclib (Ibrance) and Denosumab (Xgeva) |
| 009 | | | | | | Failed Screening | | | | | |
| 010 | | | | | | Failed Screening | | | | | |
| Oil | metastatic tumor | Feb. 15, 2013 | Nov. 9, 2015 | 8 Jun. 2018 | Feb. 15, 2013 | Breast tissue | NG | NG | NG | 53 | Receiving Letrozole (Femara) and Palbociclib (Ibrance) |
| 012 | metastatic carcinoma | Apr. 17, 2012 | Mar. 1, 2017 | 2 Aug. 2018 | Mar. 1, 2017 | Metastatic | N | N | N | 69 | Receiving Vinorelbine (Navelbine) and Zoledronic acid (Zometa) |
| 013 | Invasive carcinoma | Oct. 21, 2004 | Feb. 2, 2007 | 20 Sep. 2018 | Feb. 2, 2017 | Metastatic | Y | N | N | 71 | Receiving Paclitaxel (Taxol) |
| 014 | metastatic carcinoma | Sep. 30, 2004 | Jan. 18, 2016 | 14 Mar. 2019 | Jan. 18, 2016 | Metastatic | N | N | N | 63 | Receiving Anastrozole (Arimidex) and Denosumab (Xgeva) |
| 015 | metastatic tumor | Jan. 25, 2017 | Aug. 9, 2018 | 18 Oct. 2018 | Aug. 09, 2018 | Metastatic | NG | NG | NG | 44 | Recently received whole brain radiation on 06Sep2018. Receiving Gemcitabine (Gemzar) |
| 016 | metastatic tumor | Jul. 31, 2012 | Nov. 15, 2016 | 22 Oct. 2018 | Sep. 04, 2012 | Breast tissue | NG | NG | NG | 45 | Receiving Doxorubicin (Doxil) and Denosumab (Xgeva) |
| 017 | Invasive Ductal Carcinoma | Sep. 9, 2014 | Aug. 29, 2018 | 1 Nov. 2018 | Oct. 15, 2014 | Breast tissue | Y | Y | N | 55 | Recently completed radiation to left sacrum on 100ct2018 Receiving Fulvestrant (Faslodex) and Ribociclib (Kisqali) |
| 018 | Invasive LubularCar cinoma | Apr. 1, 2010 | Jan. 27, 2015 | 15 Nov. 2018 | Oct. 8, 2010 | Breast tissue | Y | Y | N | 55 | Receiving Pertuzumab (Perjeta), Trastuzumab (Herceptin), Paclitaxel (Taxol), and Denosumab (Xgeva) |

TABLE 14-continued

Metastatic breast cancer patient information from the pilot study. NG: information not given, Y: yes, N: no.

| Patient # | Dignosis summary from the pathology report | Date of initial Diagnosis | Date of first finding metastatic disease | Date of Blood Draw | Tumor biopsy sample date | Tumor tissue location | ER status | PR Status | HER2 Status | Patient Age | Treatment Status |
|---|---|---|---|---|---|---|---|---|---|---|---|
| 019 | metastatic adenocarcinoma | Apr. 29 2004 | Jan. 14, 2015 | 13 Feb. 2019 | Jan. 14, 2015 | Metastatic | Y | Y | N | 68 | Receiving Anastrozole (Arimidex) and Denosumab (Xgeva) |
| 020 | metastatic adenocarcinoma | Oct. 30 2007 | Mar. 26, 2018 | 12 Dec. 2018 | Mar. 26, 2018 | Metastatic | Y | N | N | 61 | Receiving Fulvestrant (Faslodex), Palbociclib (Ibrance), and Denosumab (Xgeva) |
| 021 | lobular carcinoma | Mar. 13 2006 | Feb. 9, 2016 | 6 Feb. 2019 | Feb. 09, 2016 | Metastatic | Y | Y | N | 57 | Receiving Capecitabine (Xeloda) |
| 022 | Invasive Ductal Carcinoma | Aug. 12 2015 | Sep. 19, 2018 | 1 Feb. 2019 | Aug. 12, 2015 | Breast tissue | Y | Y | Y | 43 | Receiving Protein-bound Paclitaxel (Abraxane) and Denosumab (Xgeva) |
| 023 | metastatic mammary carcinoma | Apr. 8, 2004 | Feb. 6, 2015 | 24 Jan. 2019 | Feb. 06, 2015 | Metastatic | Y | Y | N | 66 | Receiving Letrozole (Femara) and Palbociclib (Ibrance) |
| 024 | metastatic carcinoma | Oct. 13, 1994 | Dec. 18, 2014 | 14 Jan. 2019 | Dec. 18, 2014 | Metastatic | N G | N G | N G | 72 | Receiving Fulvestrant (Faslodex), Ribociclib (Kisqali), and Denosumab (Xgeva) |
| 025 | mixed ductal and lobular carcinoma | Sep. 12, 2012 | Jul. 31, 2018 | 22 Apr. 2019 | Oct. 16, 2012 | Breast tissue | N G | N G | N G | 64 | Receiving Fulvestrant (Faslodex) |
| 026 | metastatic adenocarcinoma | Aug. 13 2009 | Dec. 29, 2017 | 2 Apr 2019 | Dec. 29, 2017 | Metastatic | Y | Y | Y | 80 | Receiving Fulvestrant (Faslodex) and Denosumab (Xgeva) |
| 027 | metastatic adenocarci noma | Sep. 9, 2011 | Apr. 12, 2018 | 28 Feb. 2019 | Apr. 12, 2018 | Metastatic | Y | Y | N | 48 | Receiving Letrozole (Femara) and Goserelin (Zoladex) |
| 028 | Invasive Ductal Carcinoma | May 26, 2010 | Dec. 4, 2015 | 26 Mar. 2019 | Jul. 16, 2010 | Breast tissue | Y | N | Y | 33 | Receiving Goserelin (Zoladex), Fulvestrant (Faslodex), Trastuzumab (Herceptin), and Abemaciclib (Verzenio). |
| 029 | metastatic tumor | Mar. 4, 2011 | Mar. 2, 2018 | 21 Mar. 2019 | Mar. 04, 2011 | Breast tissue | N G | N G | N G | 46 | Receiving Palbociclib (Ibrance), Letrozole (Femara) and Denosumab (Xgeva) |
| 030 | metastatic adenocarci noma | May 21, 2002 | Feb. 5, 2016 | 13 Mar. 2019 | Feb. 05, 2016 | Metastatic | Y | Y | N | 80 | Receiving Capecitabine (Xeloda) and Denosumab (Xgeva) |
| 031 | metastatic carcinoma | Nov. 23. 1998 | Oct. 24, 2016 | 8 Feb 2019 | Oct. 24, 2016 | Metastatic | N | N | Y | 69 | Receiving Ado-trastuzumab emtansine (Kadcyla) |
| 032 | metastatic carcinoma | Jan. 9. 2015 | Jun. 6, 2018 | 3 Jun 2019 | Nov. 13, 2018 | Metastatic | Y | Y | N | 51 | Receiving Abraxane (Protein-bound paclitaxel) and Atezolizumab (Tecentriq) |
| 033 | Invasive Ductal Carcinoma | Oct. 30 2015 | Jul. 16, 2018 | 16 May 2019 | May 20, 2016 | Breast tissue | Y | Y | N | 53 | Receiving Trastuzumab (Herceptin), Pertuzumab (Perjeta) and Denosumab (Xgeva) |
| 034 | Invasive Ductal Carcinoma | Oct. 27, 2016 | Apr. 6, 2018 | 13 May 2019 | Jul. 25, 2017 | Breast tissue | Y | Y | N | 62 | Receiving Vinorelbine (Navelbine), Trastuzumab (Herceptin), Xgeva (Denosumab) |
| 035 | Invasive Ductal Carcinoma | Jan. 13, 2014 | Mar. 19, 2019 | 14 May 2019 | Aug. 4, 2014 | Breast tissue | Y | Y | N | 50 | Receiving Fulvestrant (Faslodex), Ribociclib (Kisqali), Denosumab (Xgeva) |
| 036 | Invasive Ductal Carcinoma | Jul. 23, 2017 | Jun. 5, 2018 | 25 Apr. 2019 | Mar. 29, 2018 | Breast tissue | N | N | Y | 40 | Receiving Trastuzumab (Herceptin) |
| 037 | Invasive Ductal Carcinoma | Aug. 3, 2017 | Mar. 27, 2019 | 18 Jun. 2019 | Jan. 10, 2018 | Breast tissue | Y | Y | N | 57 | Receiving Protein-bound paclitaxel (Abraxane), Atezolizumab (Tecentriq), Denosumab (Xgeva) |
| 038 | metastatic adenocarcinoma | Sep. 1, 2015 | Feb. 20, 2018 | 17 Jun. 2019 | Feb. 20, 2018 | Metastatic | Y | Y | N | 70 | Receiving Fulvestrant (Faslodex), Palbociclib (Ibrance), and Denosumab (Xgeva) |

TABLE 15

Lung cancer histology slide patient information. NG: information was not given.

| Case ID | Tissue Notes | Biosample Diagnosis | Year of Excision | Age | Sex | Ethnicity | Smoking Status | Clinical Diagnosis |
|---|---|---|---|---|---|---|---|---|
| 30453 | Lung, Normal | Congestion: Edema | 2006 | 76 | M | NG | NG | Adeno |
| 32648 | Lung, Normal | NG | 2006 | 59 | M | Cau | Current | SqCC |
| 30171 | Lung | Adeno, acinar predominant | 1994 | 52 | M | B/AA | Current | Adeno |
| 63381 | Lung | Adeno | 1997 | 64 | M | B/AA | Unknown | Adeno |
| 66835 | Lung | Adeno | 1999 | 66 | M | B/AA | Current | Adeno, invasive |
| 63454 | Lung | SqCC | 1997 | 64 | F | B/AA | Current | SqCC |
| 63526 | Lung, Bronchus | SqCC | 1995 | 66 | M | B/AA | Previous | SqCC |
| 63087 | Lung, Tumor, Necrosis | SCC | 1994 | 72 | M | B/AA | Previous | SCC |

Adeno: Adenocarcinoma,
SqCC: Squamous cell carcinoma,
SCC: Small cell carcinoma,
F: Female,
M: Male,
Cau: Caucasian,
B/AA: Black/African American.

What is claimed is:

1. A method of treating a subject having breast cancer or lung cancer, the method comprising:

a) obtaining a blood sample from the subject;

b) measuring the amount of chaperonin containing TCP (CCT) in the blood sample;

c) determining that the subject has breast cancer or lung cancer if the amount of CCT in the blood sample is higher than an amount of CCT in a reference control of healthy blood; and d) initiating a therapeutic regime if the subject is determined as having breast cancer or lung cancer, wherein the therapeutic regimen comprises administering to the subject an effective amount of a composition comprising a CT20 peptide, wherein the CT20 peptide comprises the amino acid sequence of SEQ ID NO: 1.

2. The method of claim 1, wherein the blood sample comprises one or more circulating tumor cells.

3. The method of claim 1, wherein step b) further comprises b1) contacting the blood sample with one or more CCT-targeting affinity reagents; and b2) capturing the cells retained in step b1) thereby the capturing circulating tumor cells from the blood sample.

4. The method of claim 1, wherein measuring the amount of CCT in the sample comprises measuring the amount of one or more subunits of CCT.

5. The method of claim 4, wherein the one or more subunits of CCT comprise CCTα, CCTβ, CCTγ, CCTε, CCTζ, CCTη, or CCTθ.

6. The method of claim 1, wherein the therapeutic regimen further comprises administration of an anti-cancer agent, an anti-neoplastic agent, a radiosensitizer, or a chemotherapeutic agent.

7. The method of claim 1, further comprising administering to the subject an immune checkpoint inhibitor.

8. A method of treating breast cancer or lung cancer in a subject, comprising a) obtaining a blood sample from the subject, b) contacting the blood sample with one or more CCT-targeting affinity reagents thereby capturing the cells bound by the one or more CCT-targeting affinity reagents, c) determining if the captured cells of step b) comprise circulating tumor cells, and d) administering to the subject a therapeutically effective amount of a cancer therapeutic agent if two or more circulating tumor cells are captured wherein the therapeutic regimen comprises administering to the subject an effective amount of a composition comprising a CT20 peptide, wherein the CT20 peptide comprises the amino acid sequence of SEQ ID NO: 1.

9. The method of claim 8, wherein the CCT targeting affinity reagent is a CCT2 targeting reagent.

10. The method of claim 8, wherein the circulating tumor cell does not have an increased level of a mesenchymal-epithelial biomarker.

11. The method of claim 8, wherein the circulating tumor cell has an increased level of one or more mesenchymal-epithelial biomarkers.

12. The method of claim 8, further comprising contacting the blood sample with one or more affinity reagents targeting one or more mesenchymal-epithelial biomarkers.

13. The method of claim 11, wherein the one or more mesenchymal-epithelial biomarkers are selected from the group consisting of vimentin, HER2, EpCAM, CD146, CK5, CK6, CK7, CK8, CK14, CK18, and CK19.

14. The method of claim 8, further comprising contacting the blood sample with one or more affinity reagents targeting CD44 and/or CD45.

15. The method of claim 8, further comprising determining the level of CCT2 expression in the captured cells.

16. The method of claim 14, wherein an increased level of CCT2 in the nucleus of the captured cells indicates that the captured cells are circulating tumor cells.

17. The method of claim 8, further comprising contacting the captured cells with a stain that binds DNA.

18. The method of claim 8, wherein the blood sample has a volume of about 7.5 ml.

* * * * *